US012698273B2

(12) United States Patent
Lee et al.

(10) Patent No.: US 12,698,273 B2

(45) Date of Patent: Aug. 4, 2026

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Seungjae Lee, Suwon-si (KR); Jongwoo Won, Suwon-si (KR); Chang Ju Shin, Suwon-si (KR); Changwoo Kim, Suwon-si (KR); Youngkyoung Jo, Suwon-si (KR); Hyung Sun Kim, Suwon-si (KR); Sung-Hyun Jung, Suwon-si (KR); Il Geun Hong, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 986 days.

(21) Appl. No.: 17/951,299

(22) Filed: Sep. 23, 2022

(65) Prior Publication Data

US 2023/0138421 A1 May 4, 2023

(30) Foreign Application Priority Data

Sep. 24, 2021 (KR) ........................ 10-2021-0126582
Sep. 22, 2022 (KR) ........................ 10-2022-0120144

(51) Int. Cl.
*C07D 403/14* (2006.01)
*H10K 85/60* (2023.01)

(52) U.S. Cl.
CPC ......... *C07D 403/14* (2013.01); *H10K 85/654* (2023.02); *H10K 85/6572* (2023.02); *C07B 2200/05* (2013.01)

(58) Field of Classification Search
CPC ......................... H10K 85/654; H10K 85/6572
See application file for complete search history.

(56) References Cited

U.S. PATENT DOCUMENTS 5,061,569 A 10/1991 Vanslyke et al.
10,476,008 B2 11/2019 Kim et al.
(Continued)

FOREIGN PATENT DOCUMENTS

CN 113637006 A 11/2021
CN 115403569 A 11/2022
(Continued)

OTHER PUBLICATIONS

Chinese Office Action (including a search report) dated Jan. 29, 2024, of the corresponding Chinese Patent Application No. 202211167554.1.

(Continued)

*Primary Examiner* — Vu A Nguyen
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by Chemical Formula 1:

(Continued)

100

[Chemical Formula 1]

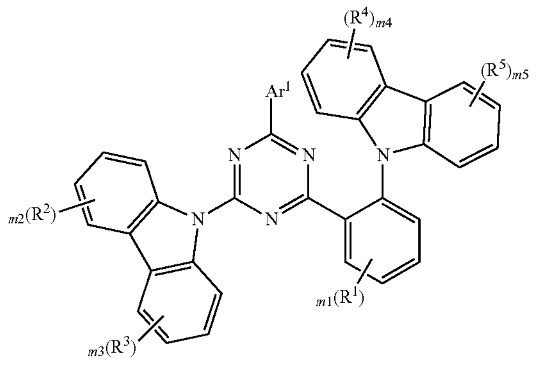

11 Claims, 1 Drawing Sheet

(56) References Cited

U.S. PATENT DOCUMENTS

| | | | | |
|---|---|---|---|---|
| 2019/0214570 | A1* | 7/2019 | Inayama | C07D 487/04 |
| 2020/0251670 | A1 | 8/2020 | Thompson et al. | |
| 2021/0359215 | A1* | 11/2021 | Um | H10K 85/6574 |
| 2021/0363132 | A1 | 11/2021 | Jung et al. | |
| 2022/0352476 | A1 | 11/2022 | Boudreault et al. | |
| 2023/0117383 | A1 | 4/2023 | Kim et al. | |
| 2023/0122972 | A1 | 4/2023 | Jo et al. | |
| 2023/0403931 | A1 | 12/2023 | Danz et al. | |

FOREIGN PATENT DOCUMENTS

| | | | |
|---|---|---|---|
| CN | 115785076 | A | 3/2023 |
| JP | 1993-009471 | A | 1/1993 |
| JP | 1995-126615 | A | 5/1995 |
| JP | 1998-095973 | A | 4/1998 |
| JP | 2006-143845 | A | 6/2006 |
| JP | 2019-023163 | A | 2/2019 |
| KR | 10-2012-0116282 | A | 10/2012 |
| KR | 10-2019-0004517 | A | 1/2019 |
| KR | 10-2019-0086347 | A | 7/2019 |
| KR | 10-2020-0063053 | A | 6/2020 |
| KR | 10-2020-0087020 | A | 7/2020 |
| KR | 10-2021-0110775 | A | 9/2021 |
| KR | 10-2021-0124922 | A | 10/2021 |
| WO | WO 1995/009147 | A1 | 4/1995 |
| WO | WO 2022/074122 | A2 | 4/2022 |

OTHER PUBLICATIONS

Korean Notice of Allowance dated Mar. 28, 2025.

* cited by examiner

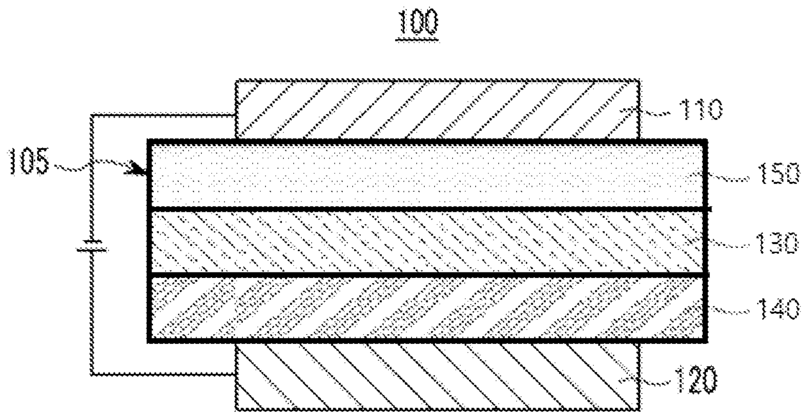
100
110
105
150
130
140
120

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

This application claims priority to and the benefit of Korean Patent Application No. 10-2021-0126582 filed in the Korean Intellectual Property Office on Sep. 24, 2021, and Korean Patent Application No. 10-2022-0120144 filed in the Korean Intellectual Property Office on Sep. 22, 2022, the entire contents of which are incorporated herein by reference.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., organic optoelectronic diode) is a device that converts electrical energy into photoenergy, and vice versa.

An organic optoelectronic device may be classified as follows in accordance with its driving principles. One is a photoelectric device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectronic device may include an organic photoelectric device, an organic light emitting diode, an organic solar cell, and an organic photo conductor drum.

Among them, the organic light emitting diode (OLED) has recently drawn attention due to an increase in demand for flat panel displays. The organic light emitting diode converts electrical energy into light, and the performance of organic light emitting diode is greatly influenced by the organic materials disposed between electrodes.

SUMMARY

The embodiments may be realized by providing a compound for an organic optoelectronic device, the compound being represented by Chemical Formula 1:

[Chemical Formula 1]

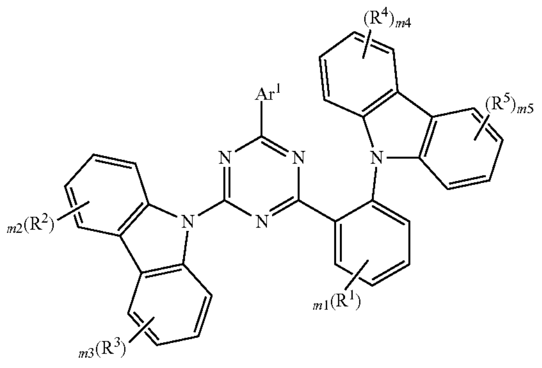

wherein, in Chemical Formula 1, $Ar^1$ is a substituted or unsubstituted C6 to C30 non-fused aryl group, each $R^1$ is independently hydrogen, deuterium, or an unsubstituted C6 to C12 aryl group, $R^2$ to $R^5$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and m1 to m5 are each independently an integer of 1 to 4.

The embodiments may be realized by providing a composition for an organic optoelectronic device, the composition including a first compound; and a second compound, wherein the first compound is the compound as claimed in claim 1, and the second compound is represented by Chemical Formula 2; or a combination of Chemical Formula 3 and Chemical Formula 4,

[Chemical Formula 2]

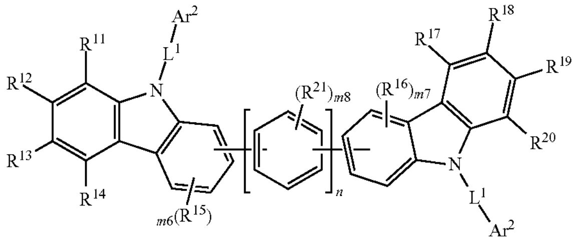

in Chemical Formula 2, $Ar^2$ and $Ar^3$ are each independently a substituted or unsubstituted C6 to C20 aryl group or a substituted or unsubstituted C2 to C30 heterocyclic group, $L^1$ and $L^2$ are each independently a single bond or a substituted or unsubstituted C6 to C20 arylene group, $R^{11}$ to $R^{21}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, m6 and m7 are each independently an integer of 1 to 3, m8 is an integer of 1 to 4, and n is an integer of 0 to 2;

[Chemical Formula 3]

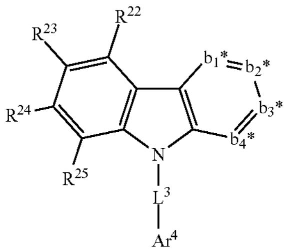

[Chemical Formula 4]

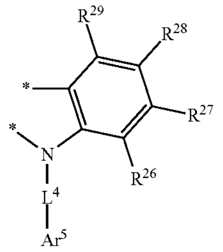

wherein, in Chemical Formulas 3 and 4, $Ar^4$ and $Ar^5$ are each independently a substituted or unsubstituted C6 to C20 aryl group or a substituted or unsubstituted C2 to C30 heterocyclic group, two adjacent ones of $b_1$* to $b_4$* of Chemical Formula 3 are linking carbons linked at * of Chemical Formula 4, the remaining two of of $b_1$* to $b_4$* of Chemical Formula 3, not linked at * of Chemical Formula 4, are each independently C-$L^a$-$R^a$, $L^a$, $L^3$, and $L^4$ are each independently a single bond or a substituted or unsubstituted C6 to C20 arylene group, and $R^a$ and $R^{22}$ to $R^{29}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

The embodiments may be realized by providing an organic optoelectronic device including an anode and a cathode facing each other, and at least one organic layer between the anode and the cathode, wherein the at least one organic layer includes the compound according to an embodiment.

The embodiments may be realized by providing an organic optoelectronic device including an anode and a cathode facing each other, and at least one organic layer between the anode and the cathode, wherein the at least one organic layer includes the composition according to an embodiment.

The embodiments may be realized by providing a display device including the organic optoelectronic device according to an embodiment.

BRIEF DESCRIPTION OF THE DRAWING

Features will be apparent to those of skill in the art by describing in detail exemplary embodiments with reference to the attached drawing in which:

the FIGURE is a cross-sectional view illustrating an organic light emitting diode according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "or" is not an exclusive term, e.g., "A or B" would include A, B, or A and B.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples, "substituted" refers to replacement of at least one hydrogen of a substituent or a compound by deuterium, a C1 to C20 alkyl group, a C6 to C30 aryl group, or a cyano group. In addition, in specific examples, "substituted" refers to replacement of at least one hydrogen of a substituent or a compound by deuterium, a C1 to C5 alkyl group, a C6 to C18 aryl group, or a cyano group. In addition, in specific examples, "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, "unsubstituted" refers to non-replacement of a hydrogen atom by another substituent and remaining of the hydrogen atom.

As used herein, "hydrogen substitution (—H)" may include "deuterium substitution (-D)" or "tritium substitution (-T)."

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example, a fluorenyl group, and the like.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, a substituted or unsubstituted furanyl group, or a combination thereof, but is not limited thereto.

As used herein, the term "non-fused aryl group" refers to a monocyclic aryl group in which all carbon atoms of a hydrocarbon aromatic moiety have p-orbitals, and these p-orbitals form a conjugate, or an aryl group in which the above monocyclic aryl groups are linked through a sigma bond.

More specifically, the substituted or unsubstituted C6 to C30 non-fused aryl group may be a substituted or unsubstituted phenyl group, a substituted or unsubstituted biphenyl group, a substituted or unsubstituted terphenyl group, a substituted or unsubstituted quaterphenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound for an organic optoelectronic device according to an embodiment is described.

The compound for an organic optoelectronic device according to an embodiment may be represented by, e.g., Chemical Formula 1.

[Chemical Formula 1]

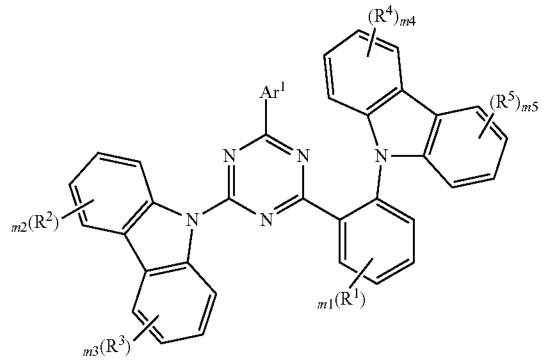

In Chemical Formula 1, $Ar^1$ may be or may include, e.g., a substituted or unsubstituted C6 to C30 non-fused aryl group.

Each $R^1$ may independently be, e.g., hydrogen, deuterium, or an unsubstituted C6 to C12 aryl group.

$R^2$ to $R^5$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof.

m1 to m5 may each independently be, e.g., an integer of 1 to 4.

In the compound represented by Chemical Formula 1, one carbazole group is directly linked (e.g., without a linking group therebetween) to the triazine moiety in the N-direction (e.g., at the N of the carbazole group) centering on the triazine moiety, another carbazole group is linked to the triazine in the N-direction through an ortho-phenylene linking group, and a substituted or unsubstituted C6 to C30 non-fused aryl group is also bonded to the triazine moiety.

One carbazole group is directly linked to the triazine without a linking group in the N-direction, e.g., the 9 position of the carbazole group, so that it has a relatively deep LUMO energy level, which is advantageous for electron injection and movement.

In addition, another carbazole group is linked to the triazine in the N-direction, e.g., the 9 position of the carbazole group, thereby breaking the π-bonding through the C—N bond, so that the electron cloud between HOMO-LUMO may be clearly localized into a hole transport moiety and an electron transport moiety.

In an implementation, the HOMO-LUMO band gap may be widened due to the ortho-phenylene, the efficiency improvement effect may be maximized, and the steric hindrance of molecules may be increased, so that a deposition temperature may not be relatively high, which may be advantageous in the process.

In an implementation, the substituted or unsubstituted C6 to C30 non-fused aryl group is bonded to the triazine core moiety, and a low-driving, high-efficiency, and long life-span organic optoelectronic device may be manufactured by controlling the electron transport capability to the appropriate mobility and charge balance in the light emitting layer.

In an implementation, $Ar^1$ of Chemical Formula 1 may be, e.g., a substituted or unsubstituted phenyl group, a substituted or unsubstituted biphenyl group, a substituted or unsubstituted terphenyl group, a substituted or unsubstituted quaterphenyl group, or a combination thereof.

In an implementation, $Ar^1$ of Chemical Formula 1 may be, e.g., a group of Group I.

[Group 1]

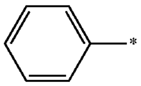

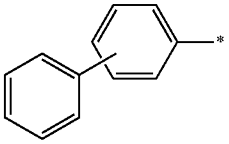

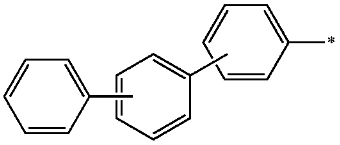

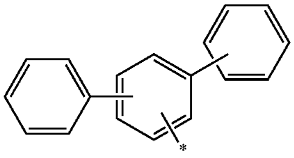

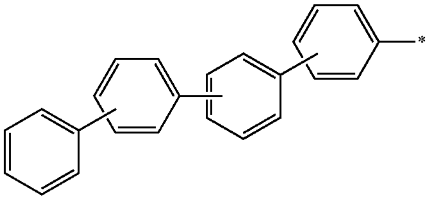

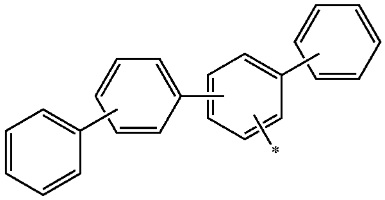

-continued

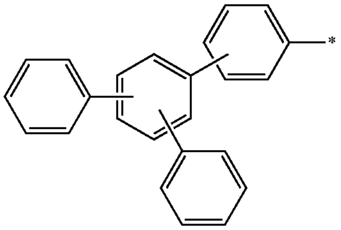

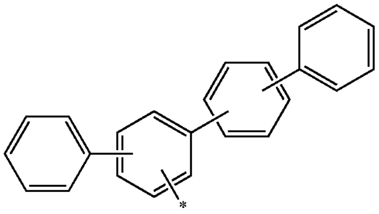

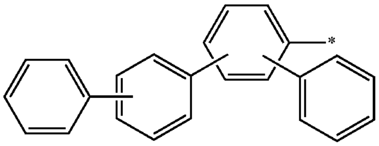

In Group I, * is a linking point

In an implementation, the groups of Group I may be unsubstituted or may be substituted with additional suitable substituents.

In an implementation, the additional suitable substituents may include, e.g., deuterium, a cyano group, a substituted or unsubstituted C1 to C10 alkyl group, or a substituted or unsubstituted C6 to C12 aryl group.

In an implementation, the additional suitable substituents may include, e.g., deuterium, a substituted or unsubstituted C1 to C5 alkyl group, a substituted or unsubstituted phenyl group, a substituted or unsubstituted biphenyl group, or a substituted or unsubstituted naphthyl group.

In an implementation, $R^1$ may be, e.g., hydrogen, deuterium, or an unsubstituted phenyl group.

In an implementation, $R^2$ to $R^5$ may each independently be, e.g., hydrogen, deuterium, a cyano group, or a substituted or unsubstituted C6 to C12 aryl group.

In an implementation, the compound for an organic optoelectronic device represented by Chemical Formula 1 may be, e.g., a compound of Group 1.

[Group 1]

[A-1]

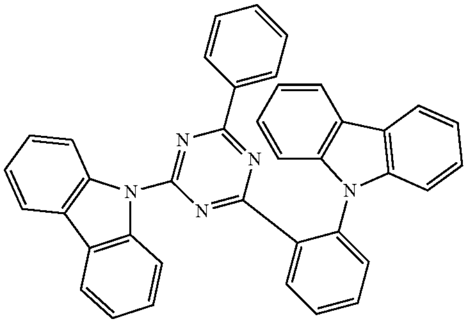

-continued
[A-2]
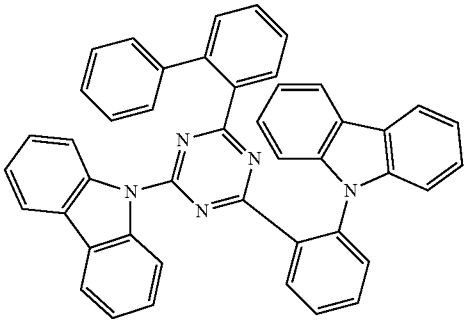
[A-3]
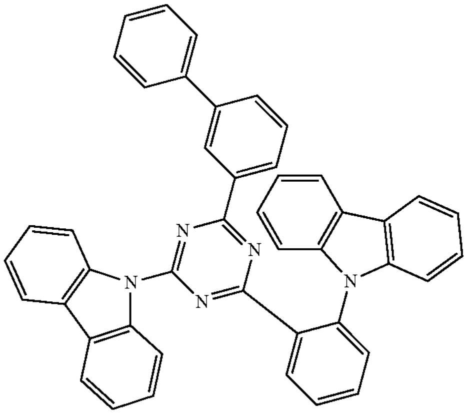
[A-4]
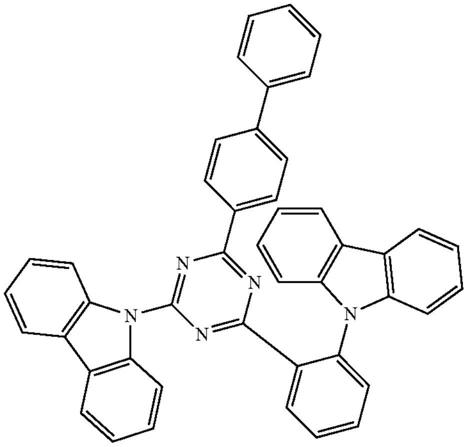
[A-5]
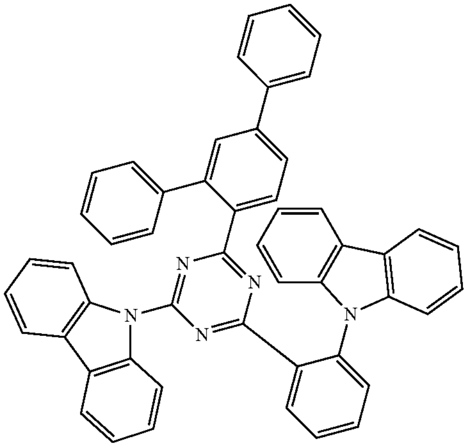
-continued
[A-6]
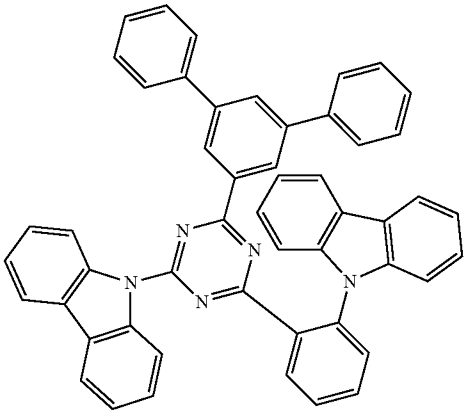
[A-7]
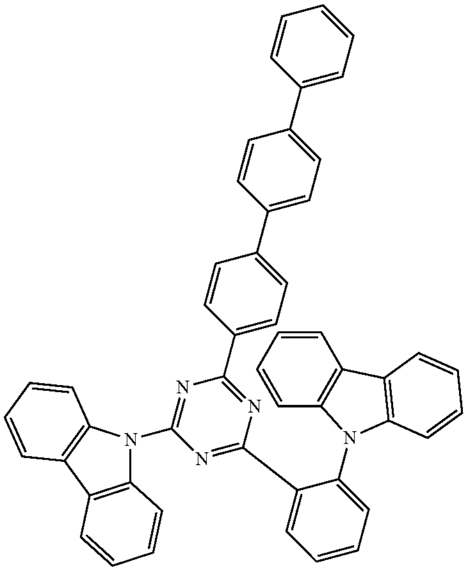
[A-8]
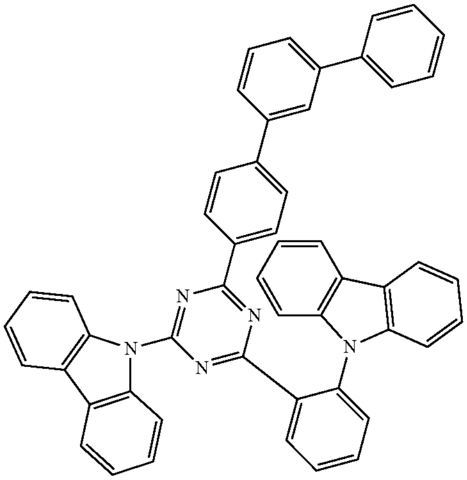

-continued
[A-9]
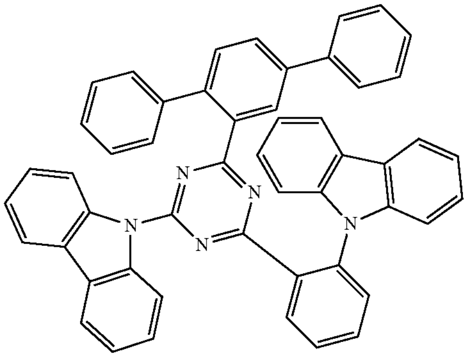
[A-10]
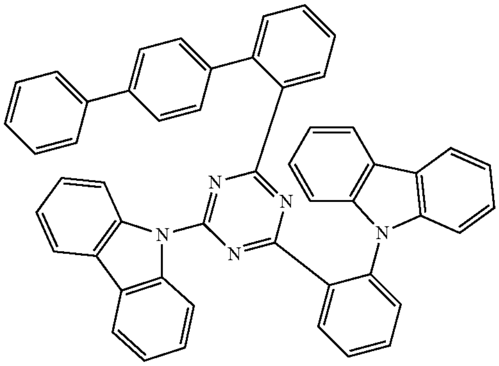
[A-11]
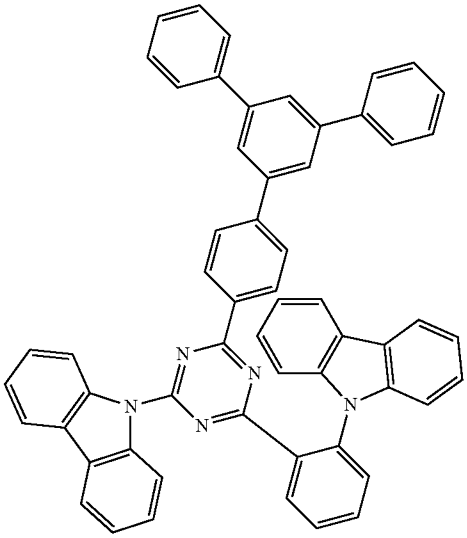
-continued
[A-12]
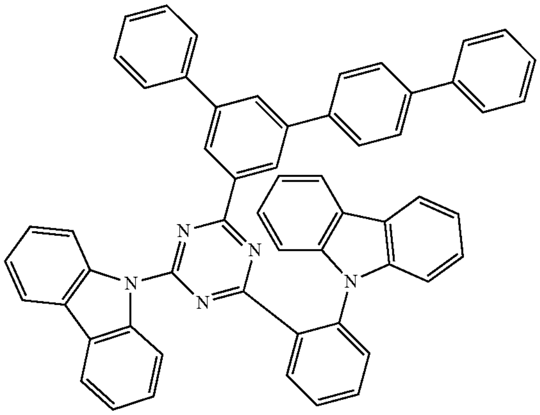
[A-13]
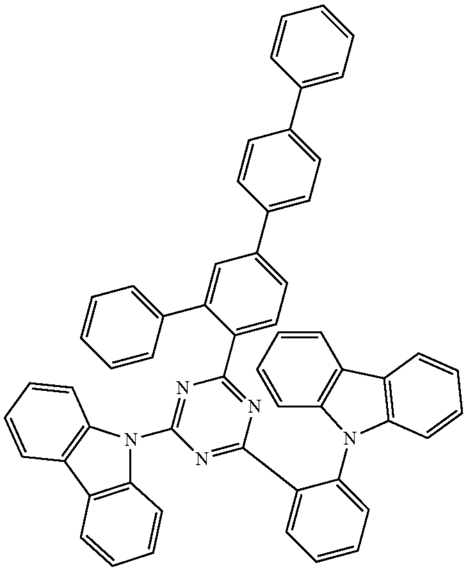
[A-14]
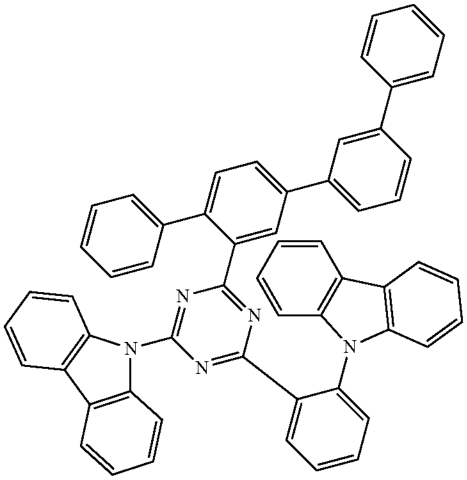

-continued
[A-15]
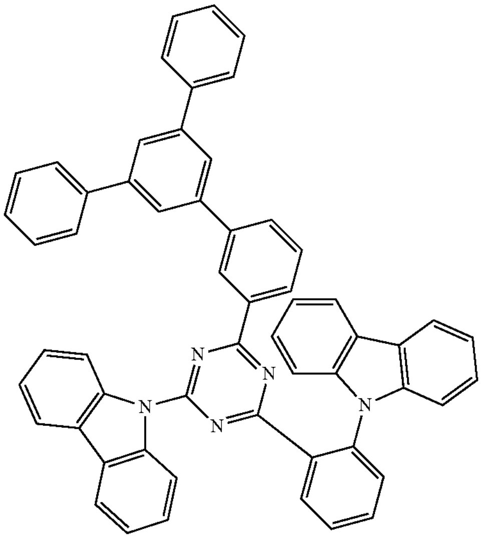
[A-16]
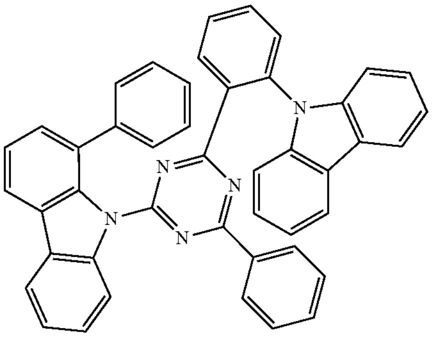
[A-17]
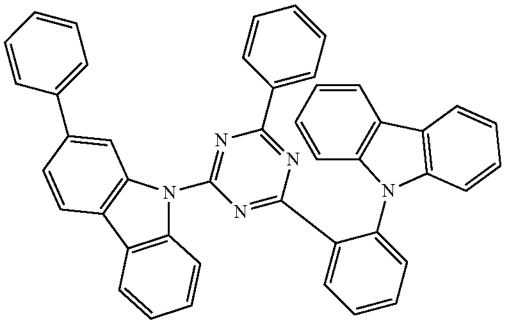
[A-18]
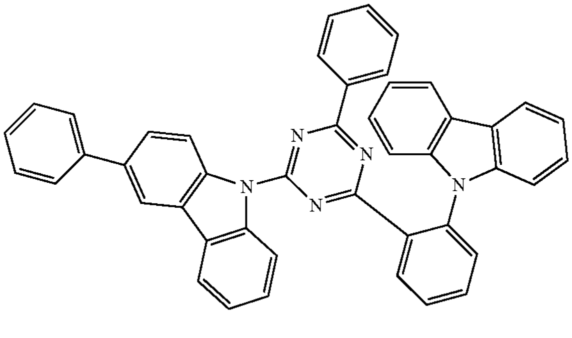
-continued
[A-19]
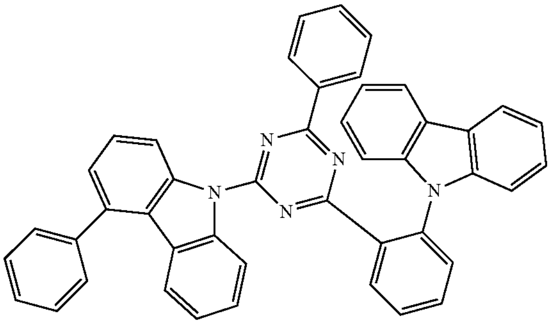
[A-20]
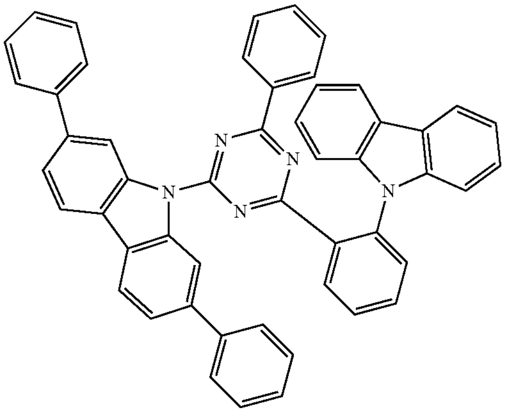
[A-21]
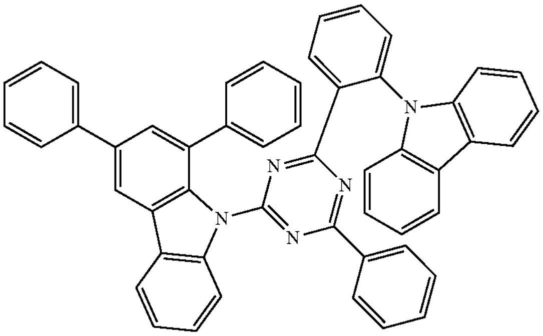
[A-22]
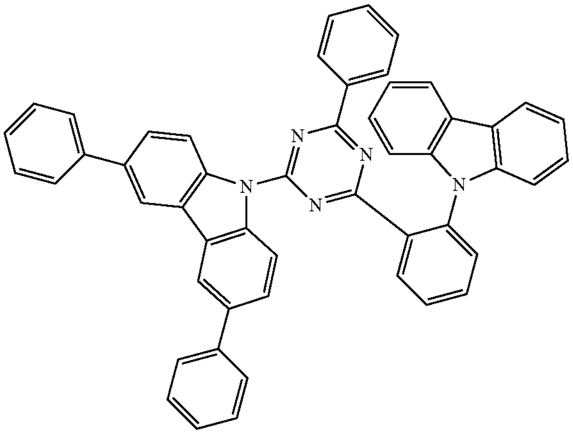

-continued
[A-23]
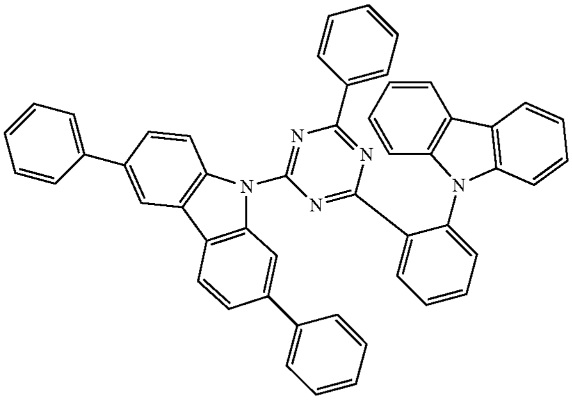
[A-24]
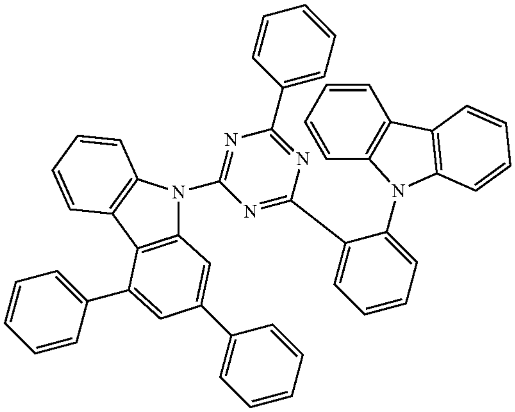
[A-25]
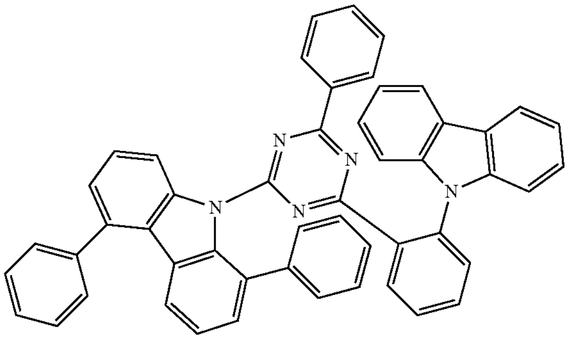
-continued
[A-26]
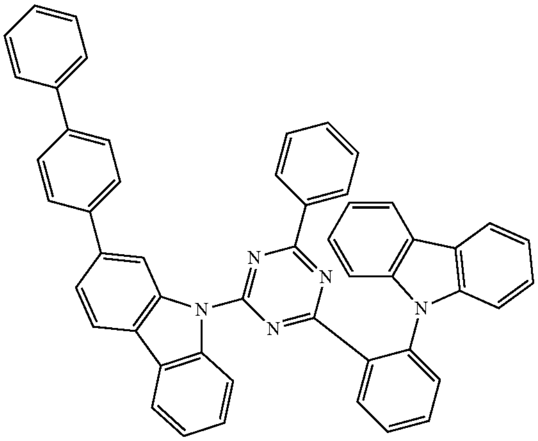
[A-27]
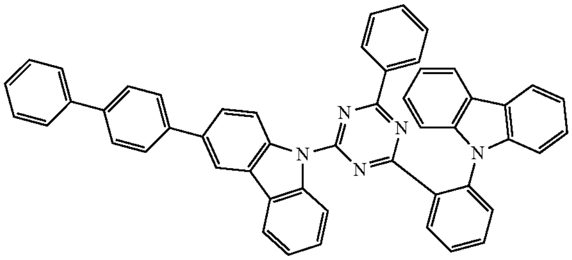
[A-28]
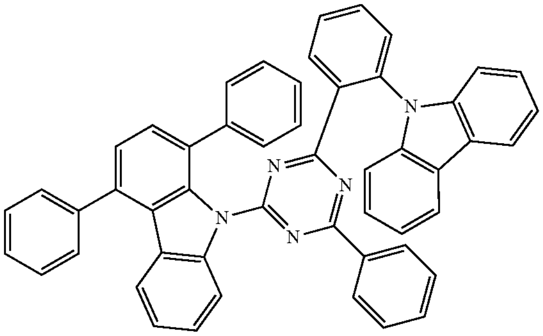
[A-29]
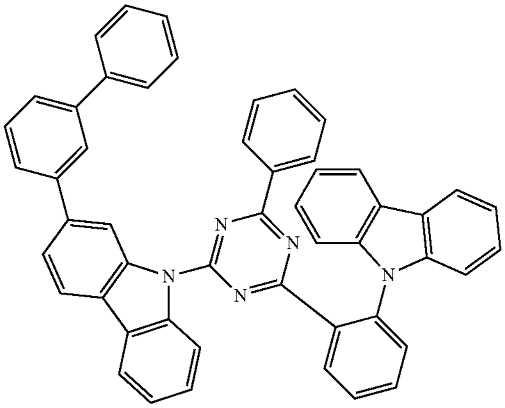

-continued
[A-30]
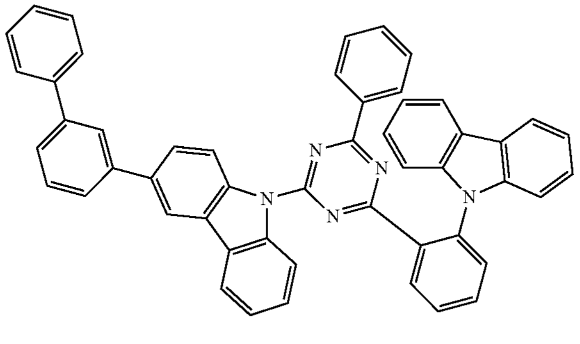
[A-31]
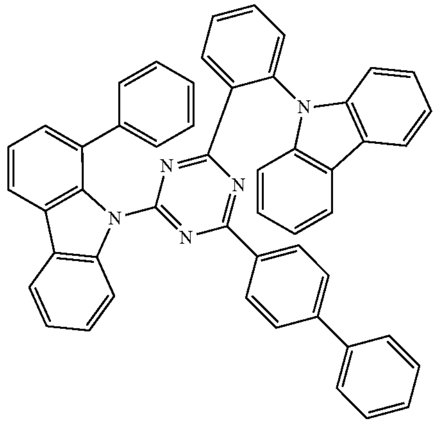
[A-32]
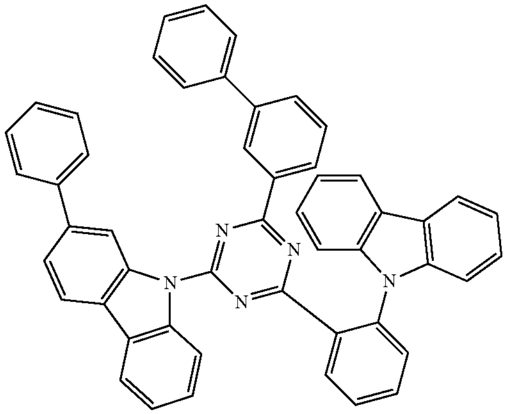
-continued
[A-33]
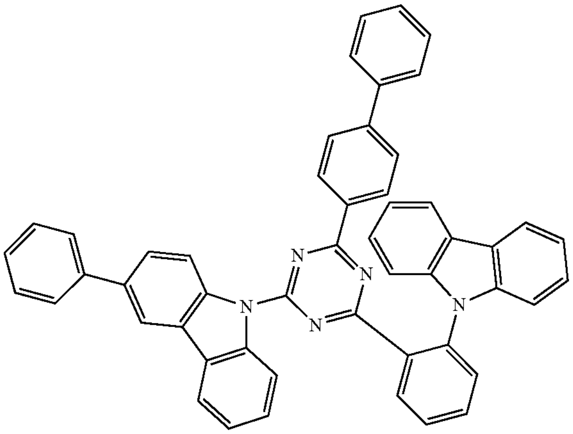
[A-34]
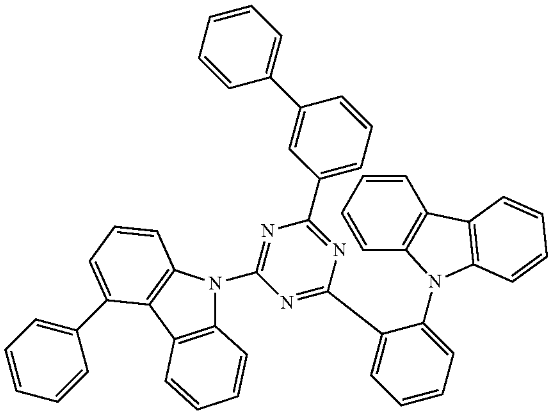
[A-35]
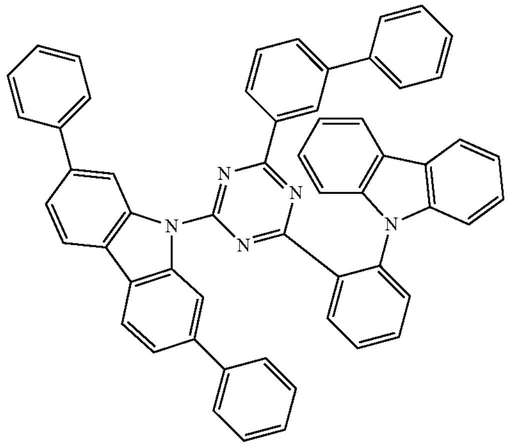

-continued
[A-36]
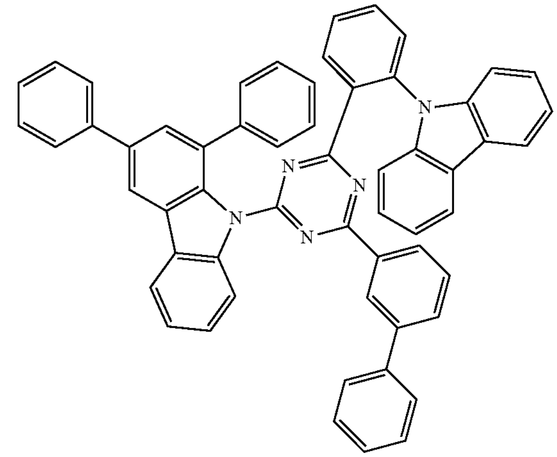
[A-37]
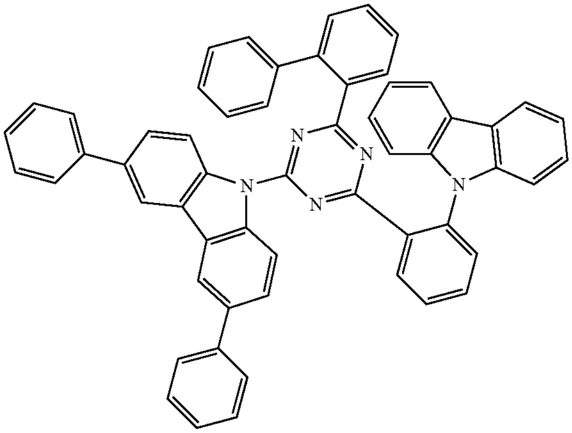
[A-38]
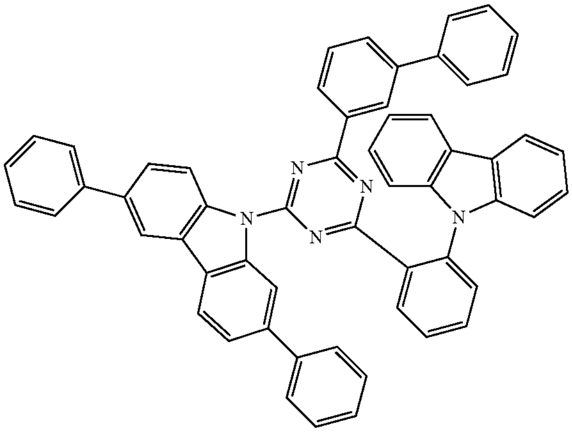
-continued
[A-39]
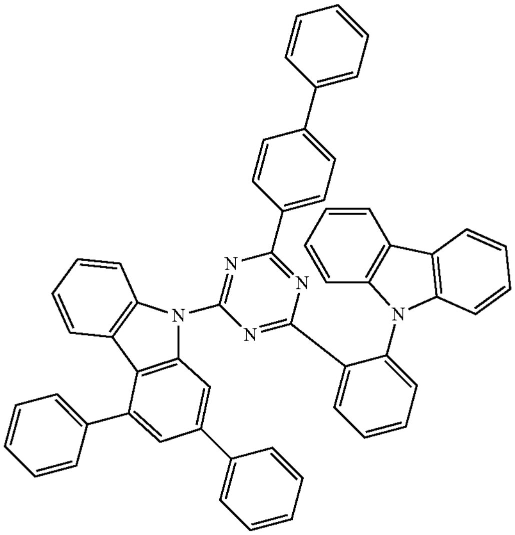
[A-40]
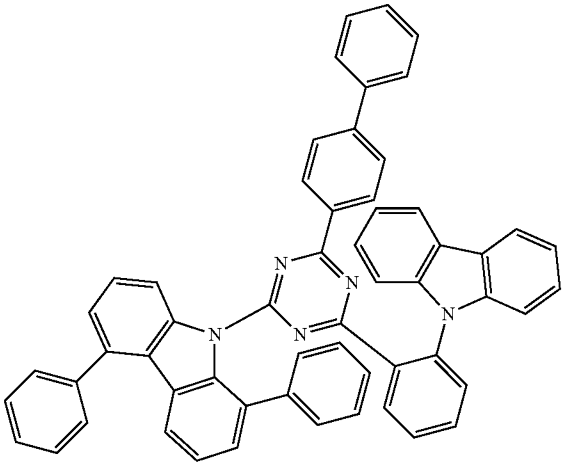
[A-41]
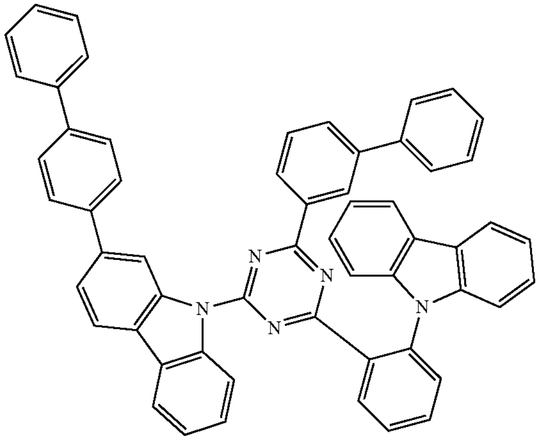

-continued
[A-42]
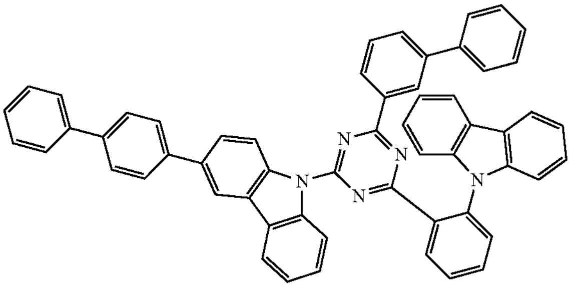
[A-43]
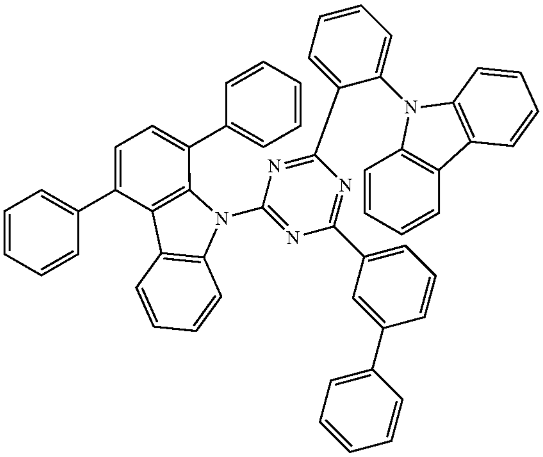
[A-44]
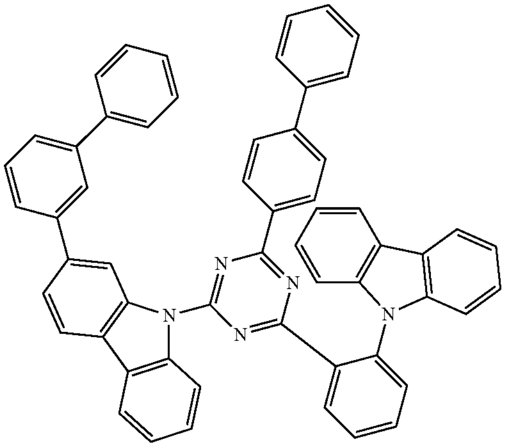
[A-45]
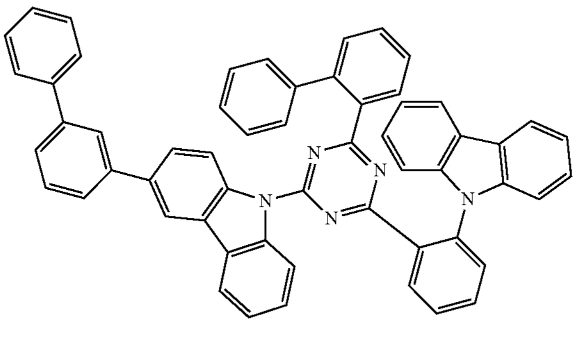
-continued
[A-46]
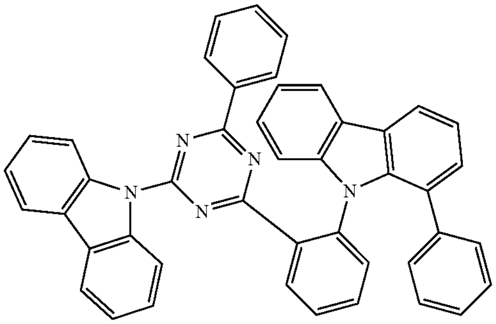
[A-47]
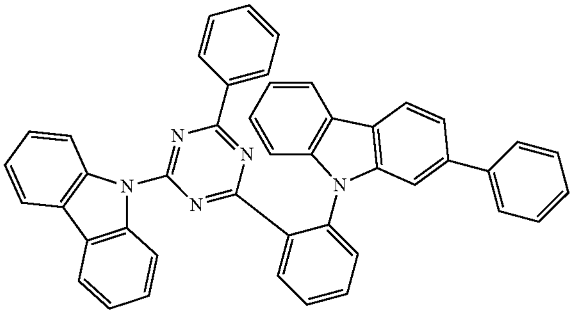
[A-48]
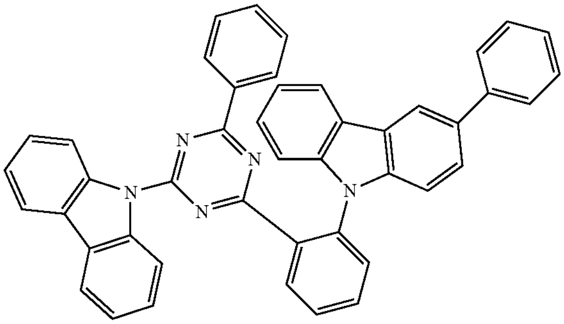
[A-49]
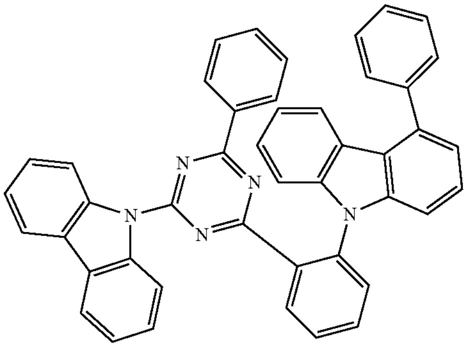

-continued
[A-50]
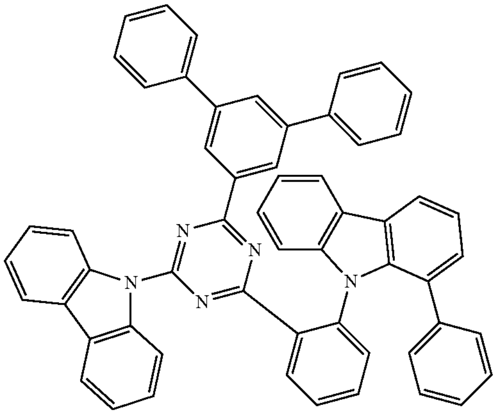
[A-51]
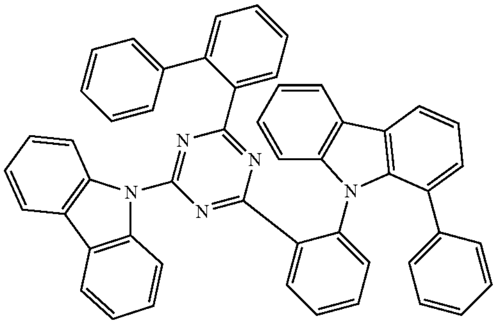
[A-52]
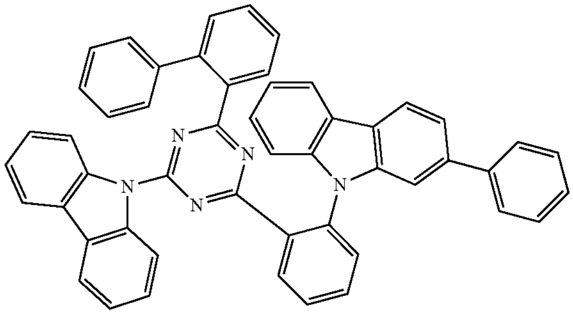
[A-53]
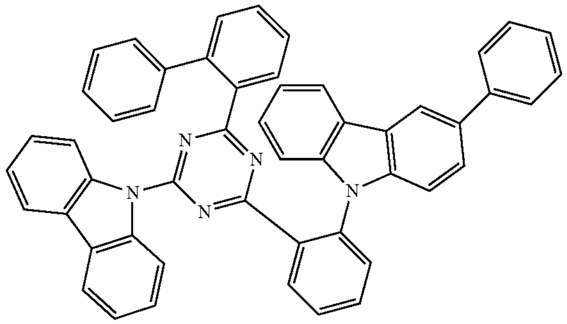
-continued
[A-54]
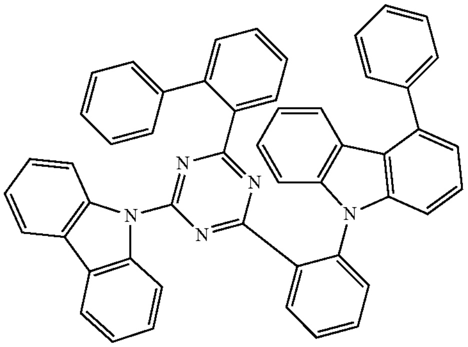
[A-55]
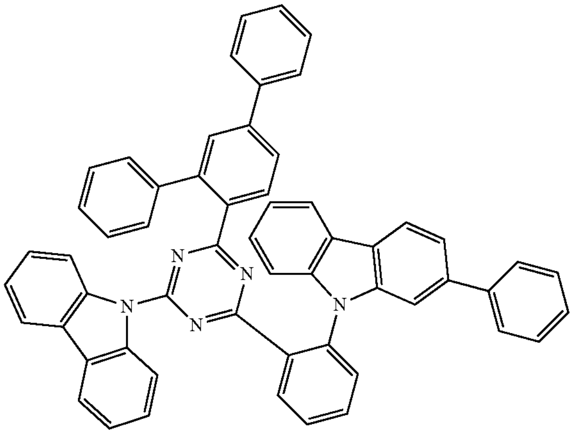
[A-56]
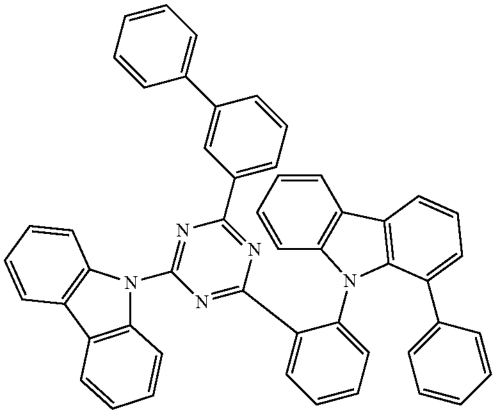

-continued
[A-57]
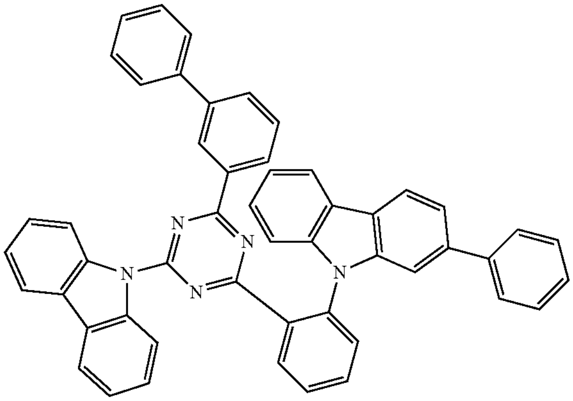
[A-58]
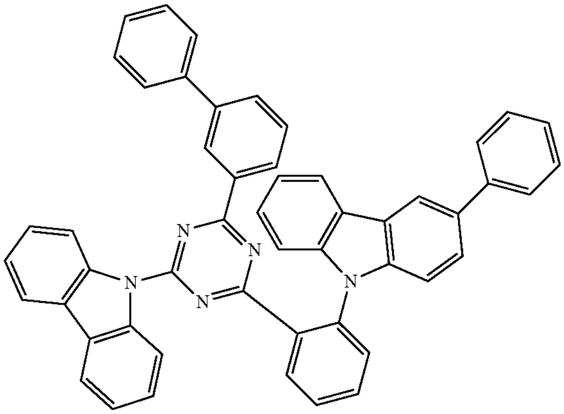
[A-59]
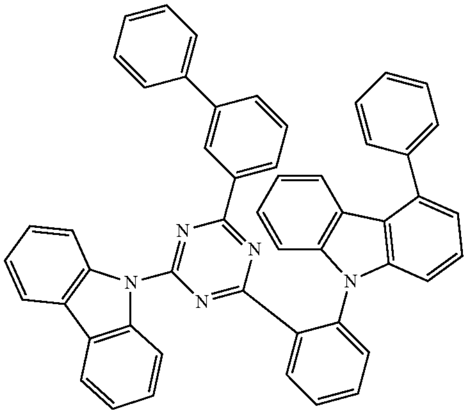
-continued
[A-60]
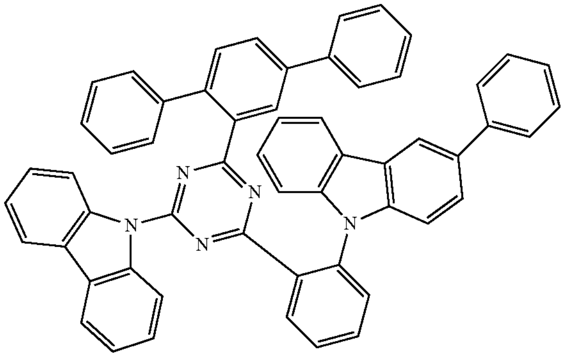
[A-61]
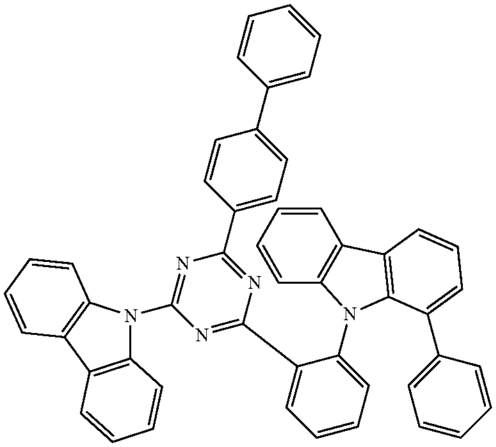
[A-62]
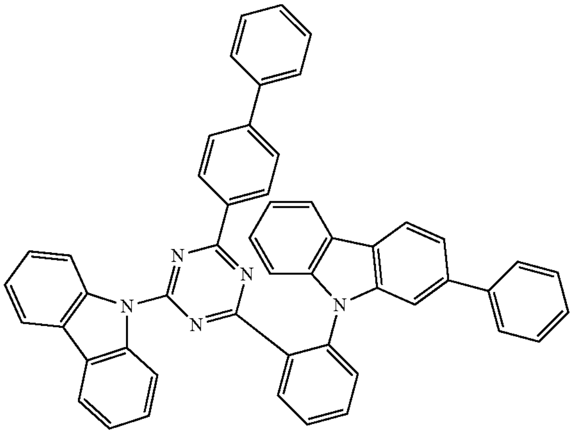

-continued
[A-63]
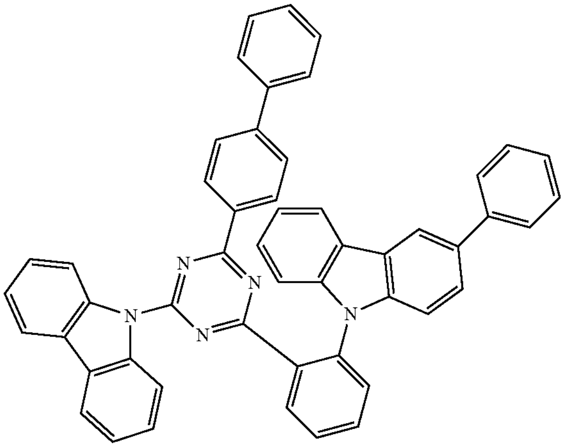
[A-64]
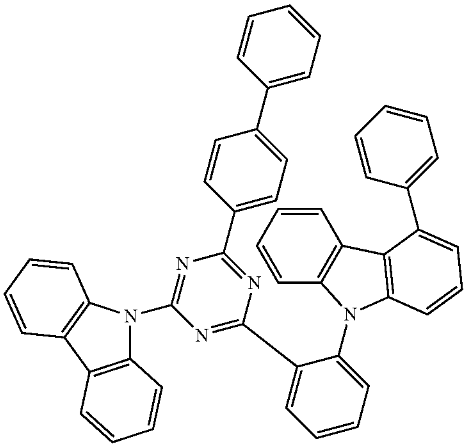
[A-65]
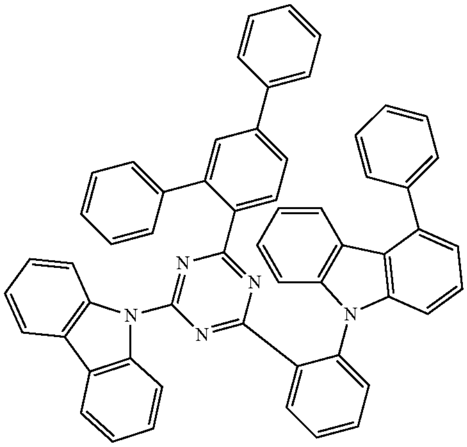
-continued
[A-66]
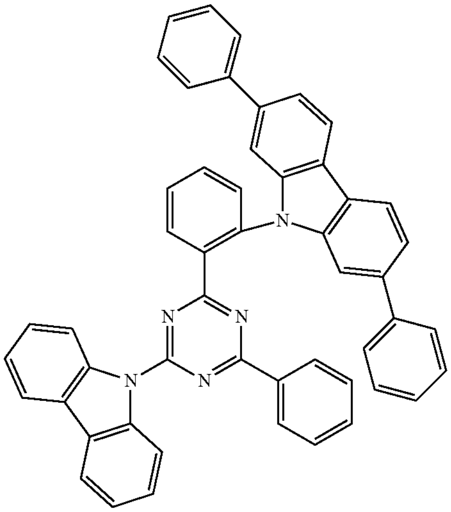
[A-67]
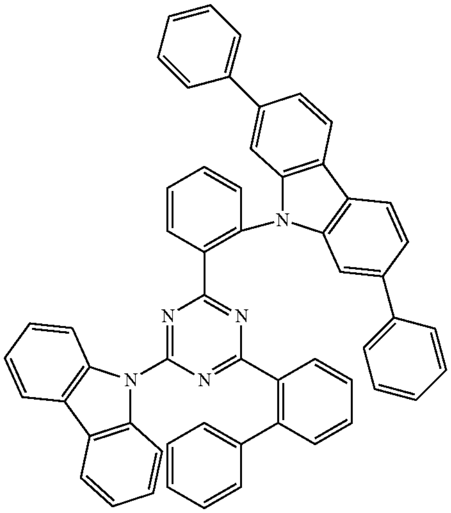
[A-68]
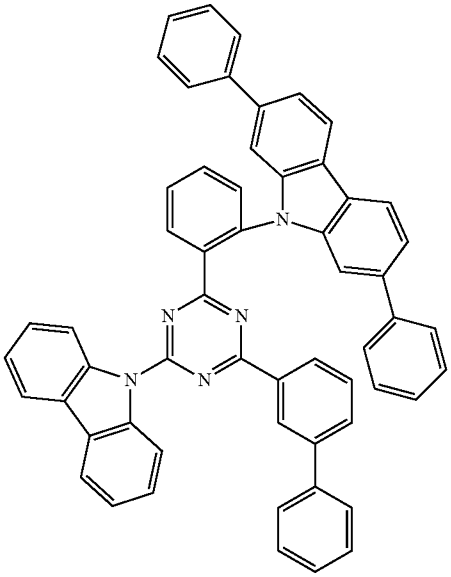

-continued
[A-69]
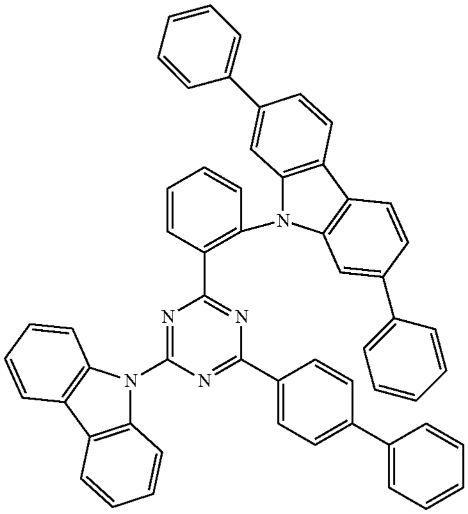
[A-70]
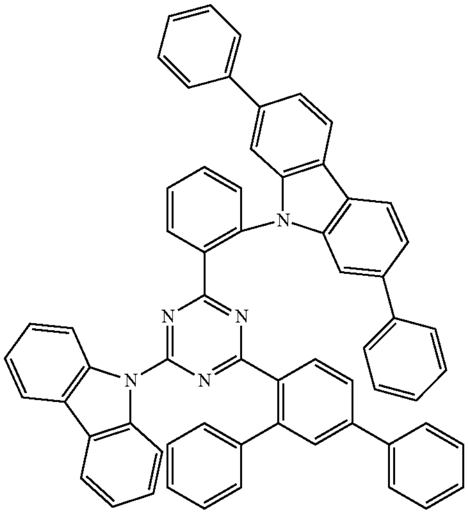
[A-71]
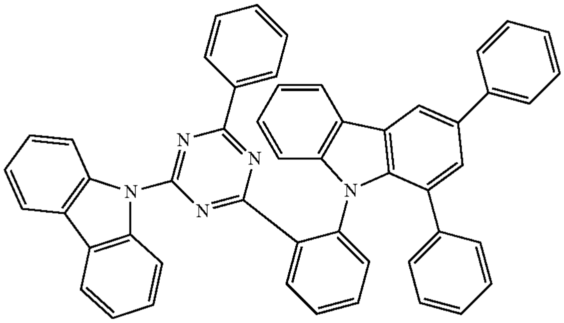
-continued
[A-72]
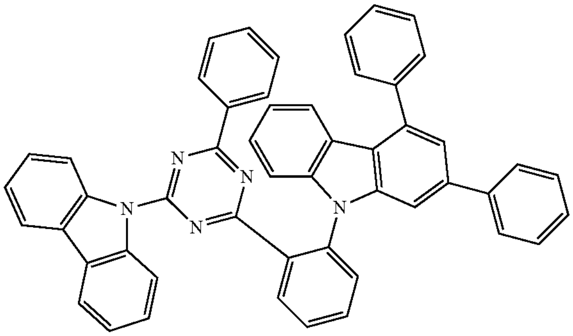
[A-73]
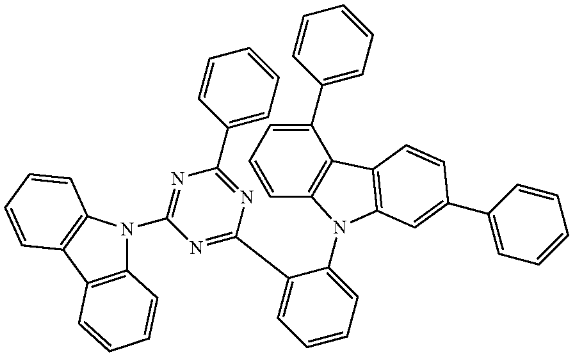
[A-74]
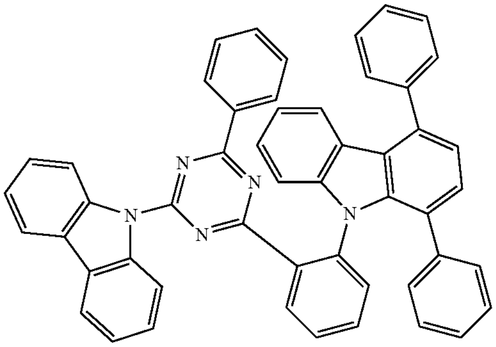
[A-75]
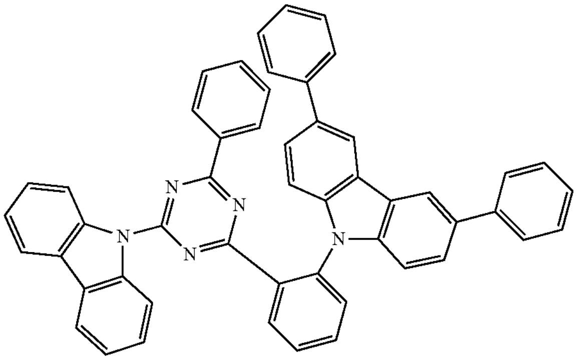

-continued
[A-76]
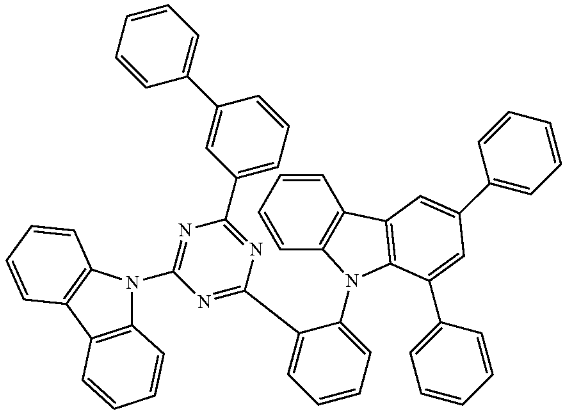
[A-77]
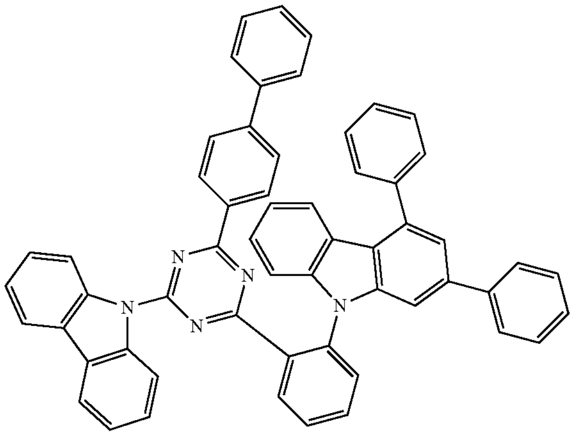
[A-78]
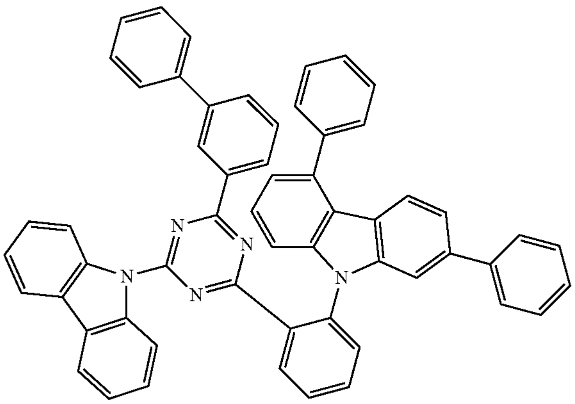
-continued
[A-79]
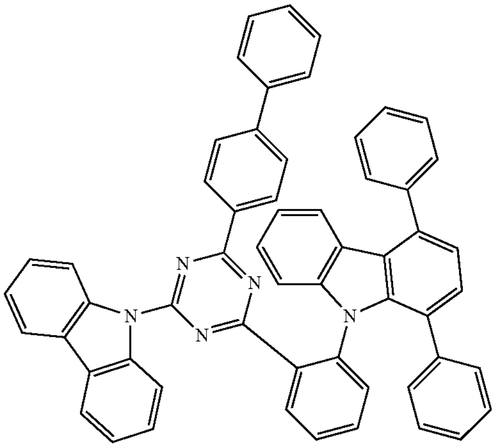
[A-80]
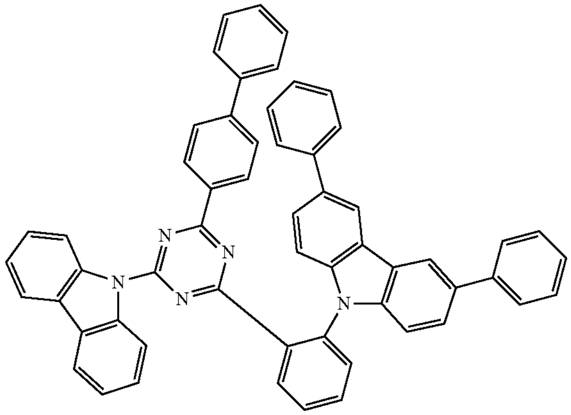
[A-81]
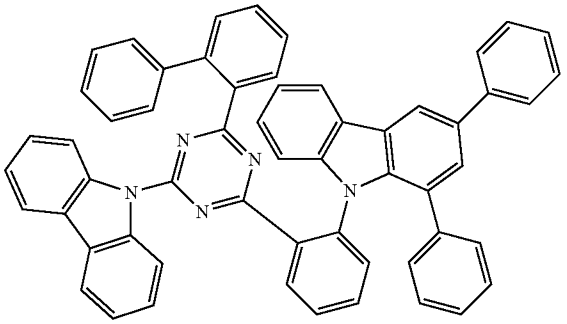

-continued
[A-82]
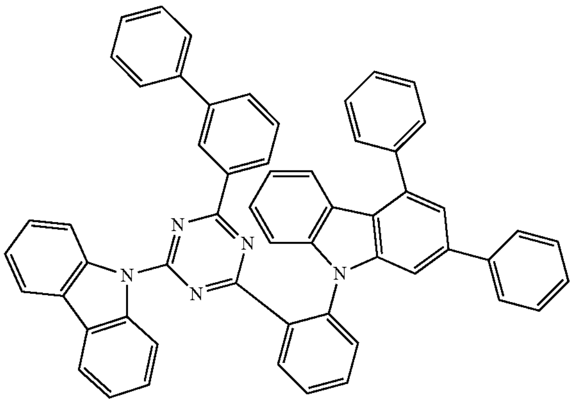
[A-83]
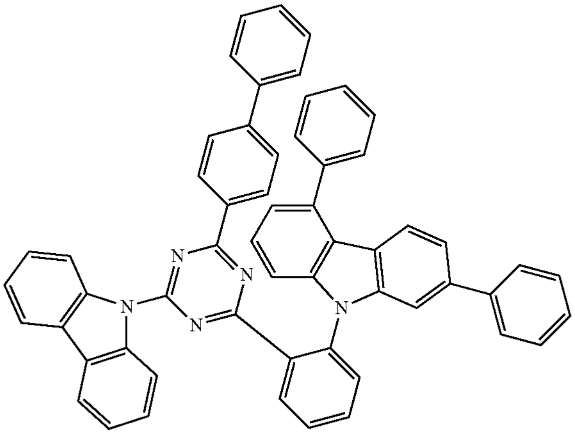
[A-84]
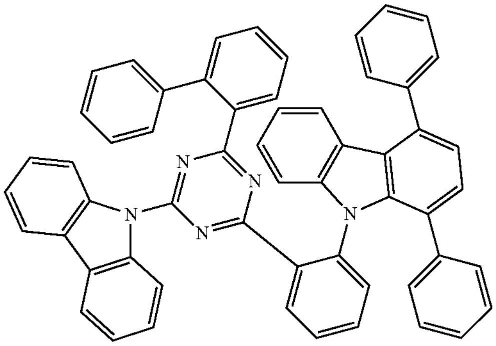
[A-85]
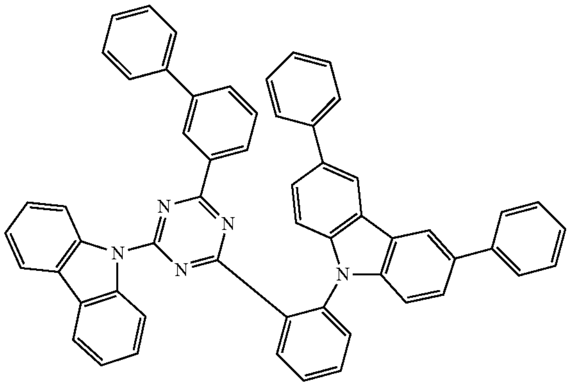
-continued
[A-86]
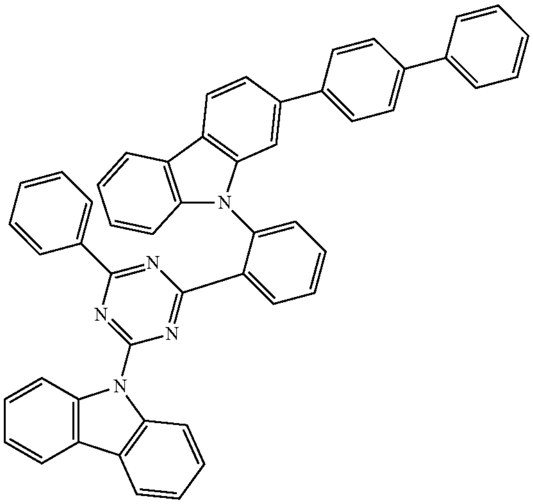
[A-87]
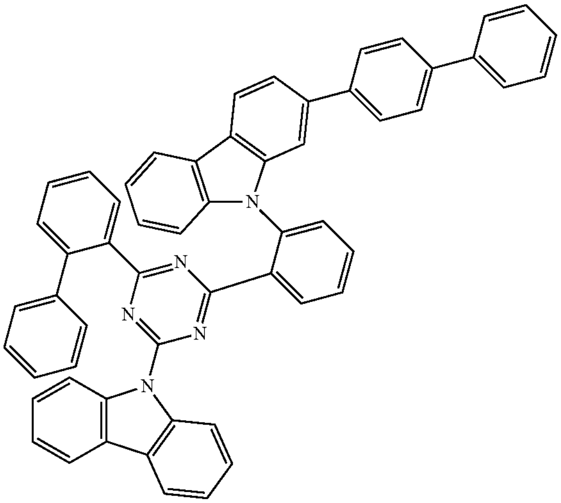
[A-88]
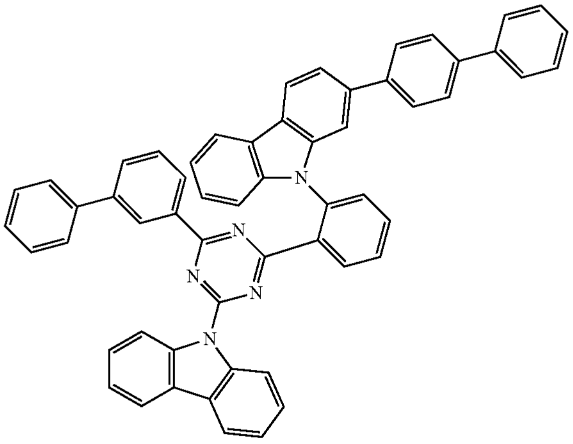

-continued
[A-89]
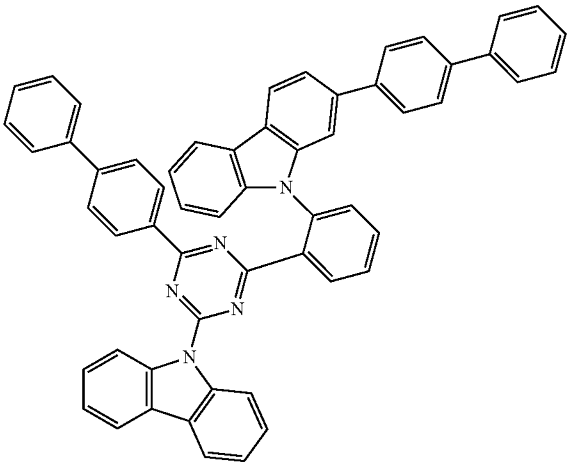
[A-90]
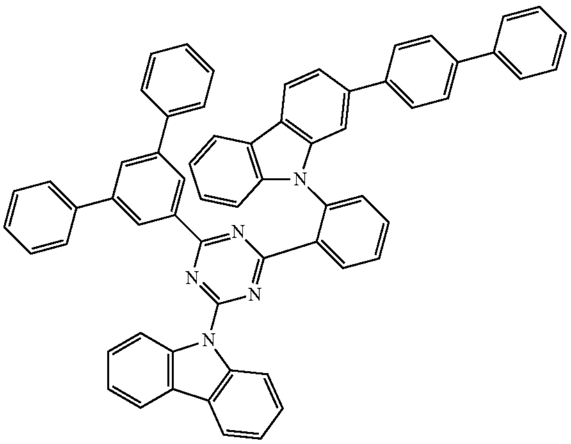
[A-91]
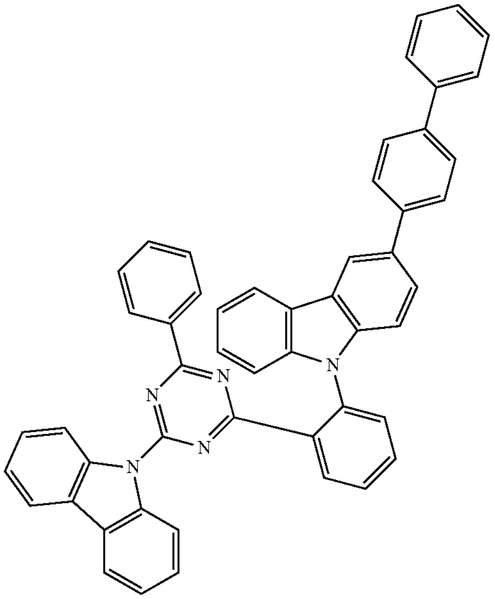
-continued
[A-92]
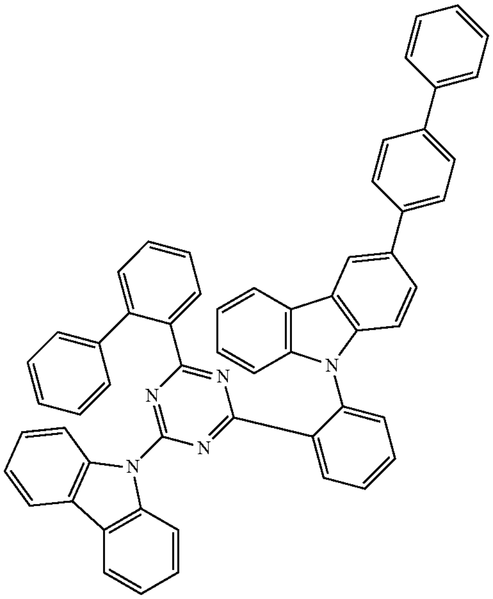
[A-93]
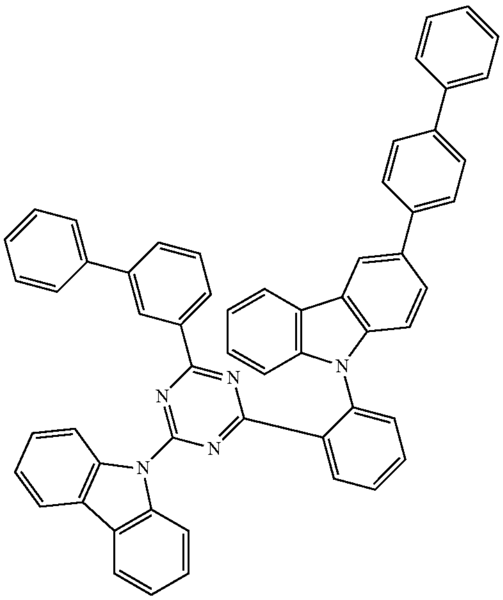

-continued
[A-94]
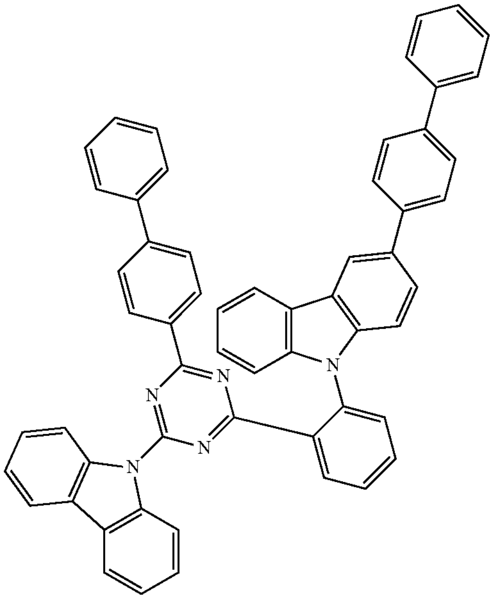
[A-95]
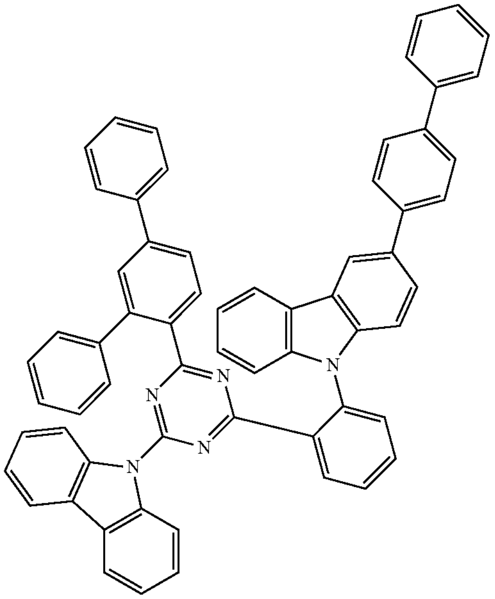
[A-96]
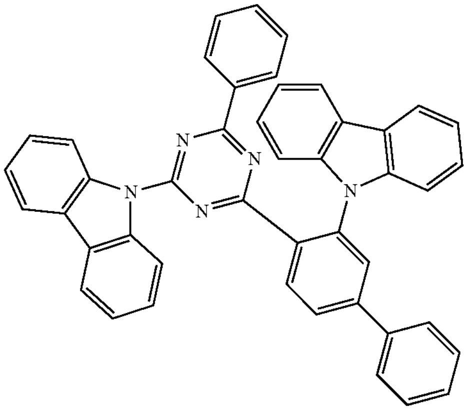
-continued
[A-97]
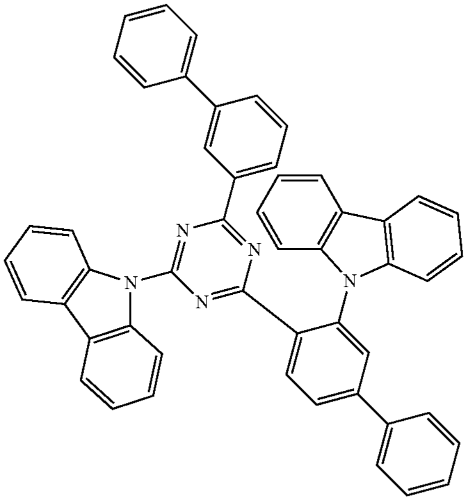
[A-98]
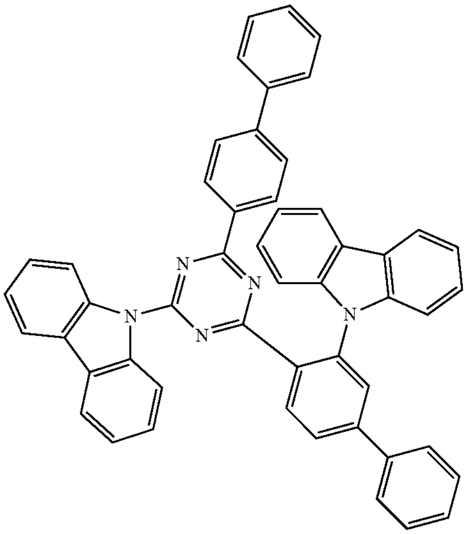
[A-99]
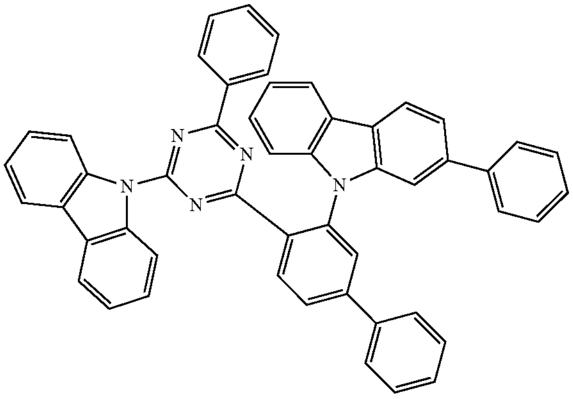

-continued
[A-100]
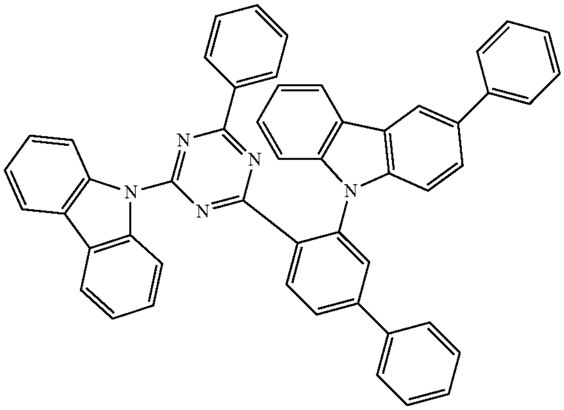
[A-101]
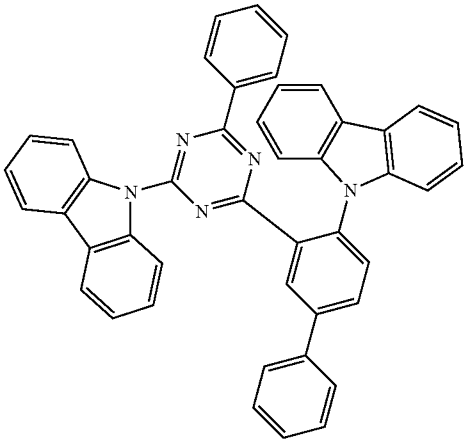
[A-102]
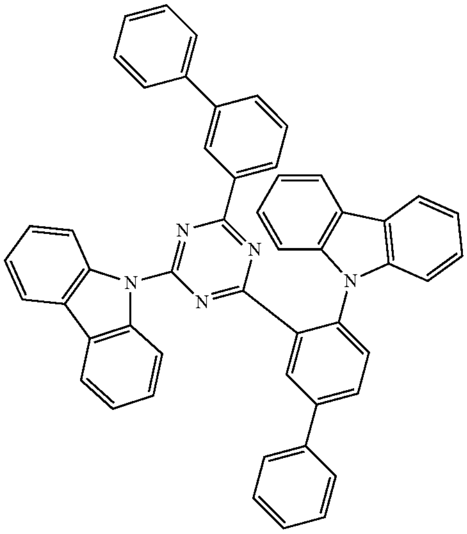
-continued
[A-103]
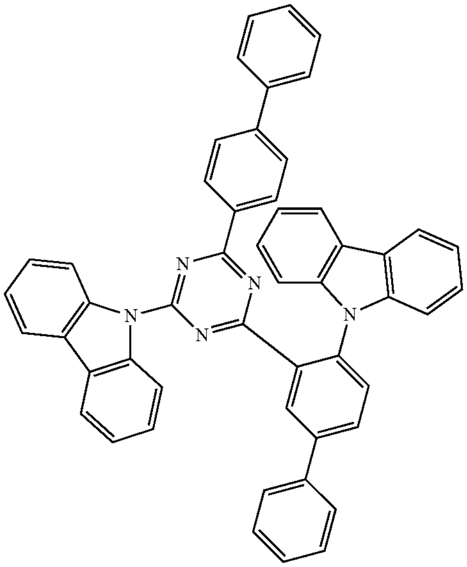
[A-104]
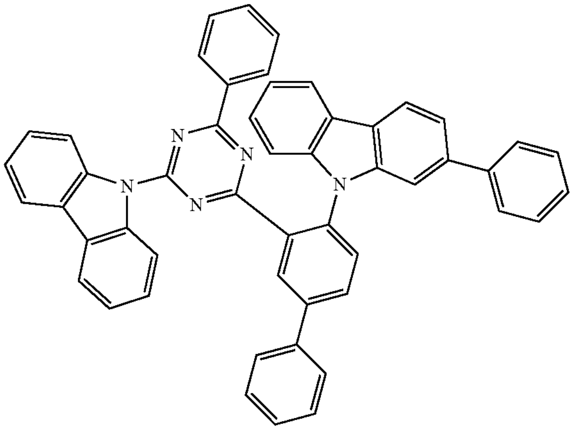
[A-105]
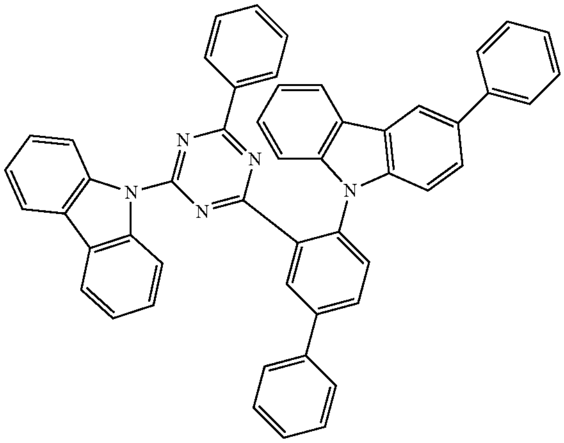

-continued
[A-106]
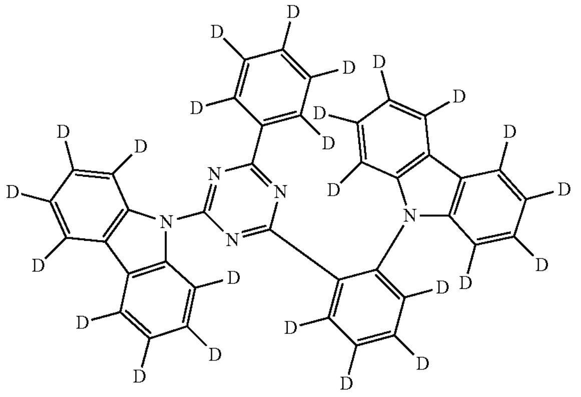
[A-107]
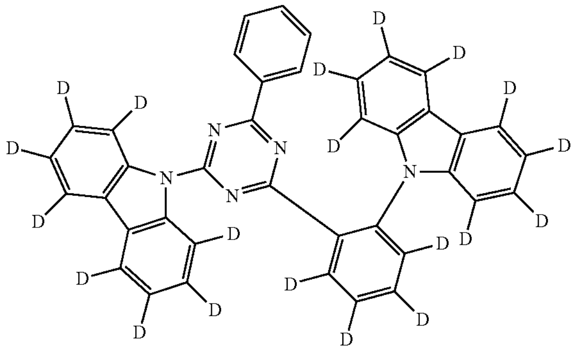
[A-108]
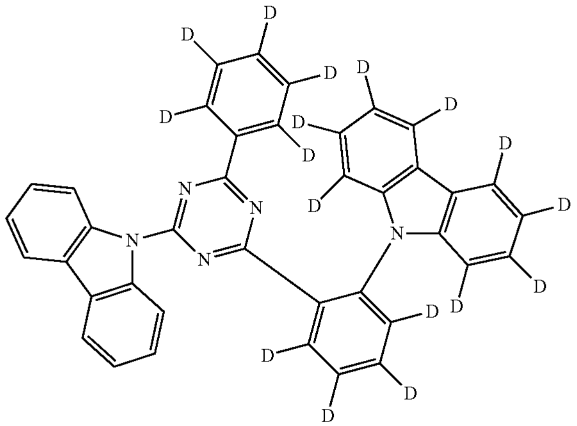
[A-109]
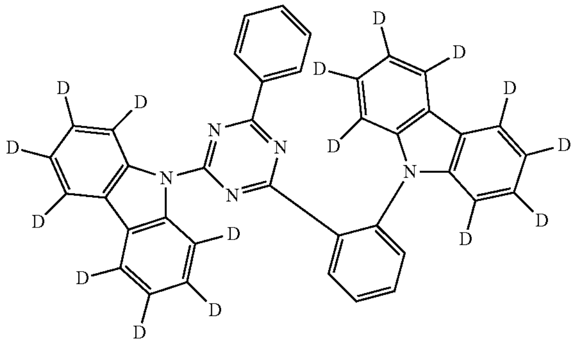
-continued
[A-110]
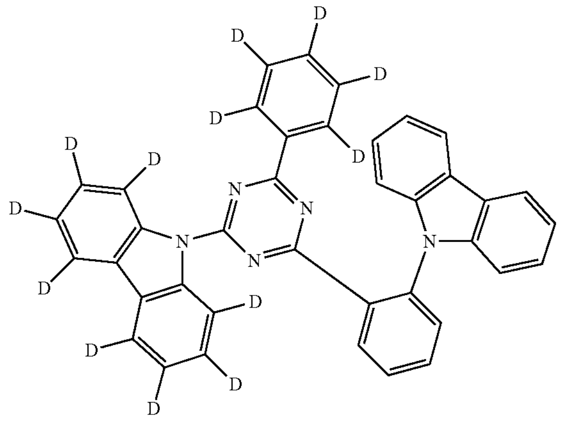
[A-111]
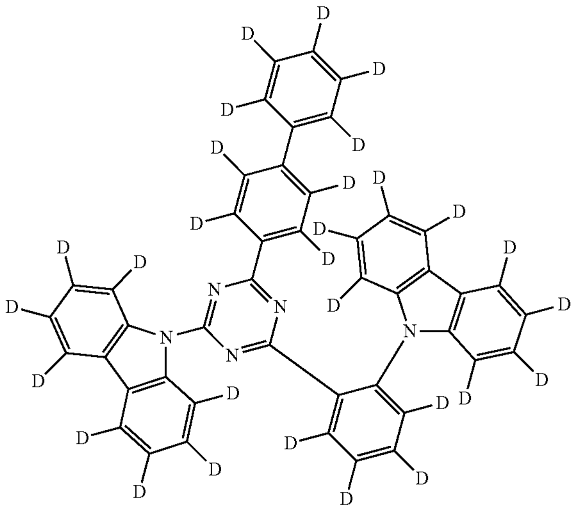
[A-112]
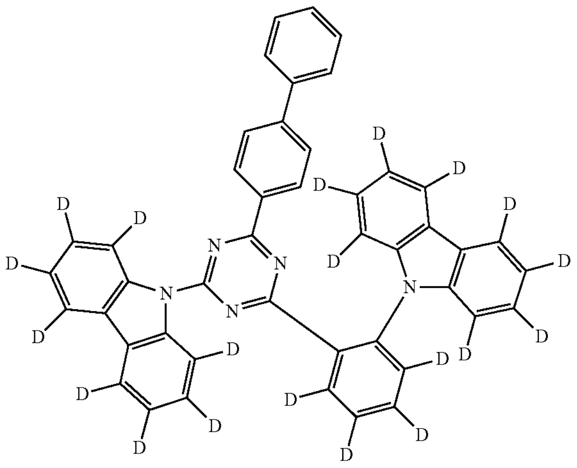

-continued
[A-113]
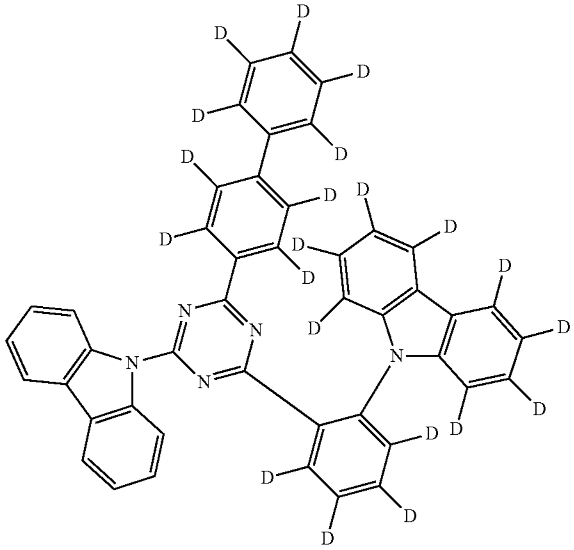
[A-114]
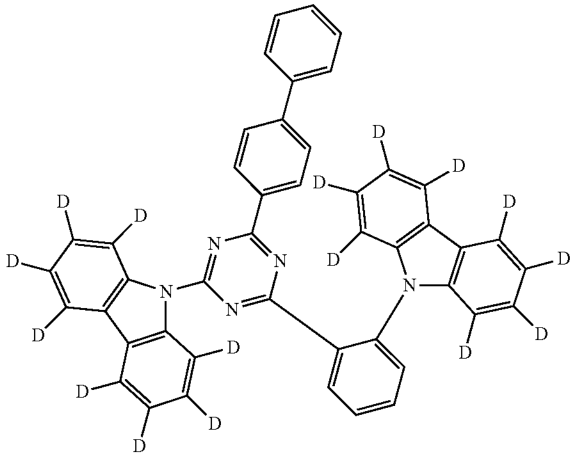
[A-115]
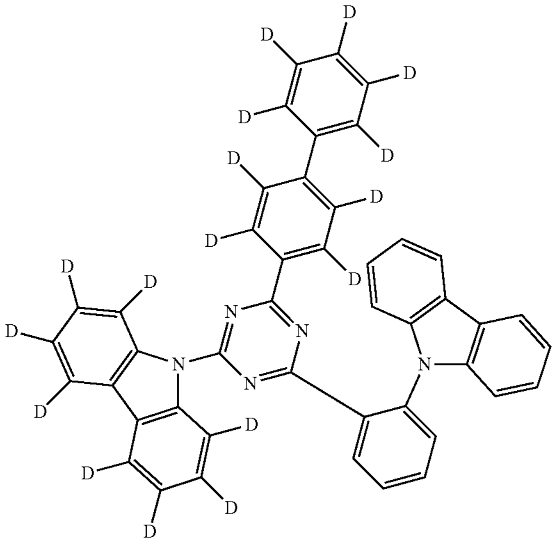
-continued
[A-116]
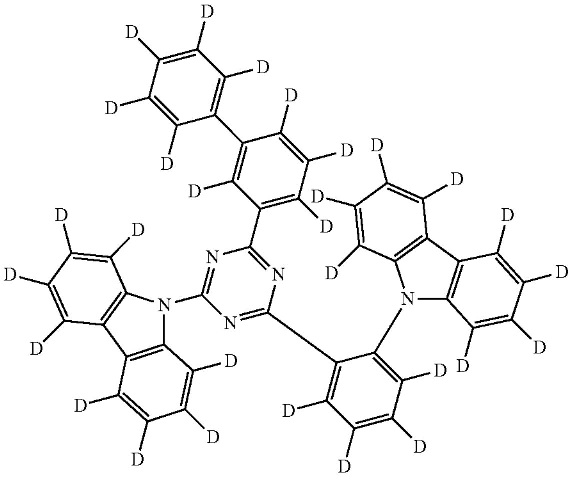
[A-117]
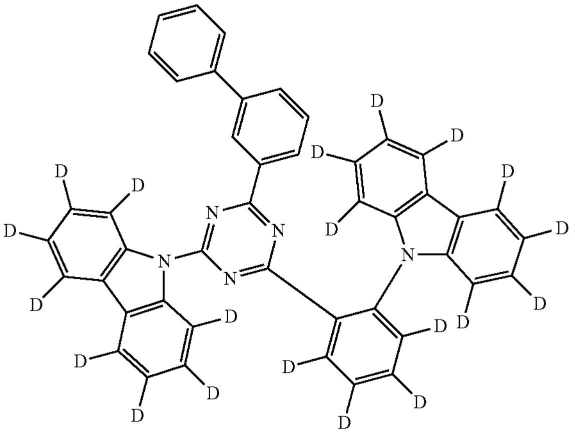
[A-118]
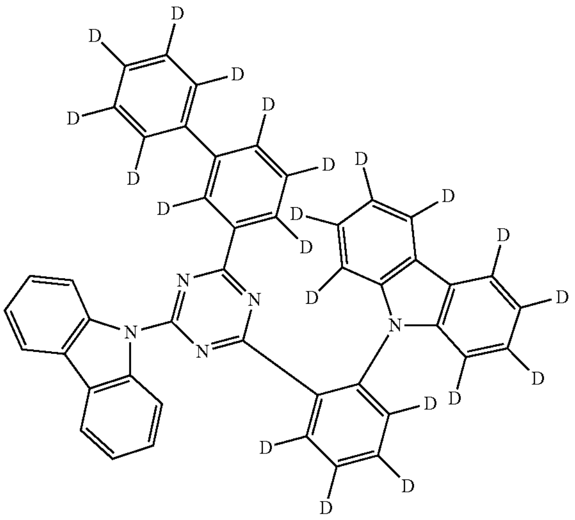

-continued
[A-119]
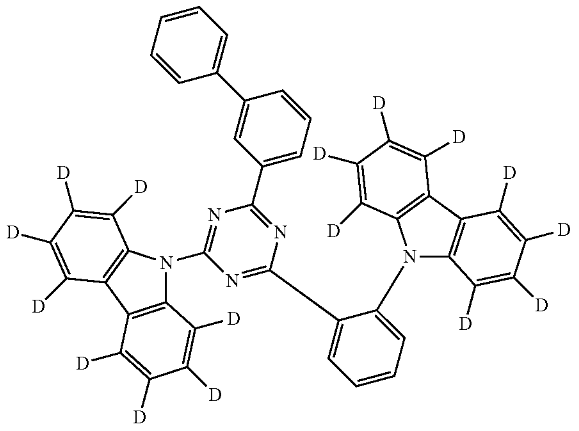
[A-120]
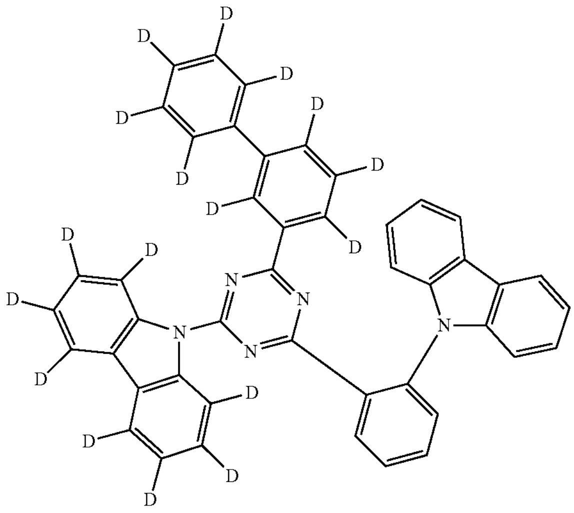
[A-121]
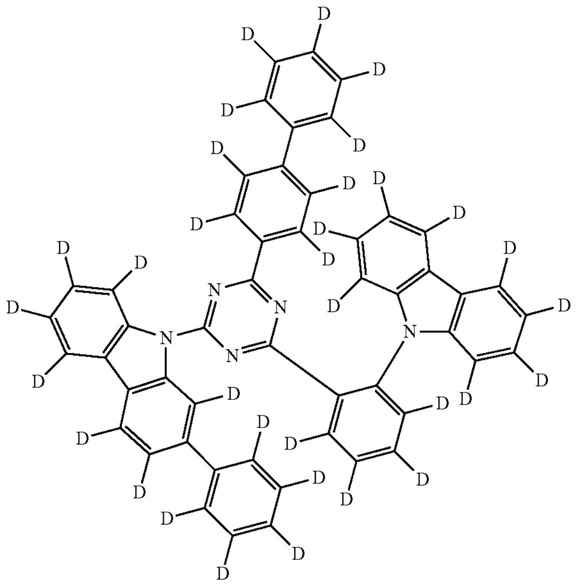
-continued
[A-122]
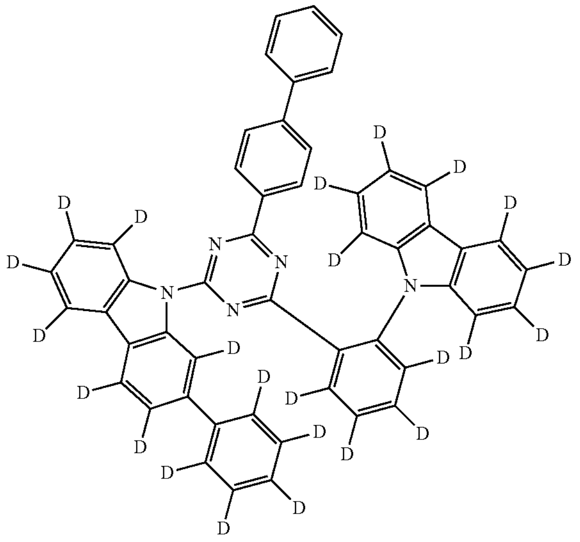
[A-123]
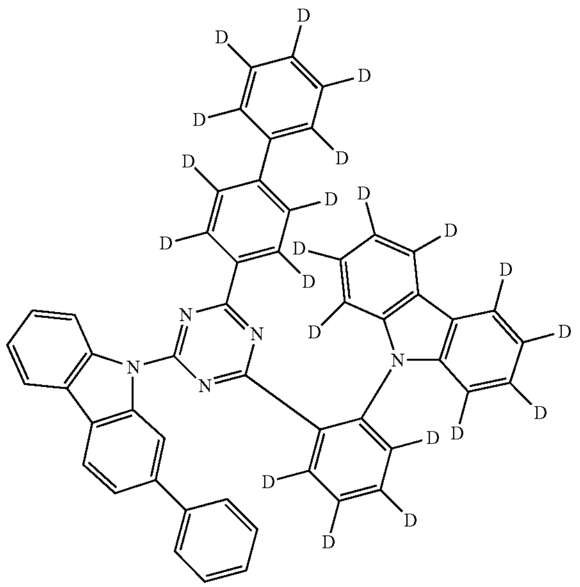

-continued
[A-124]
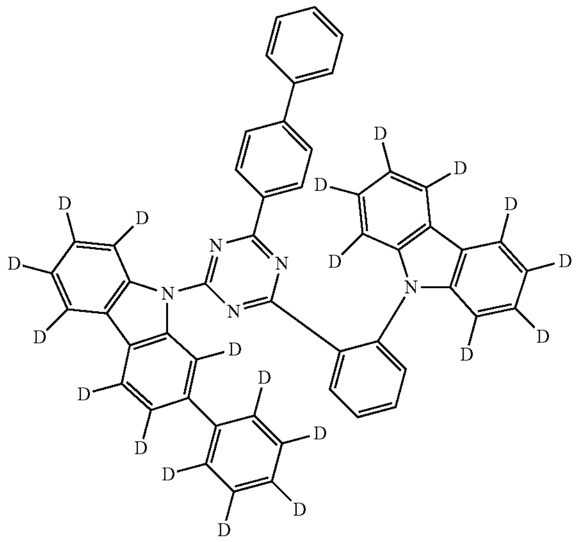
[A-125]
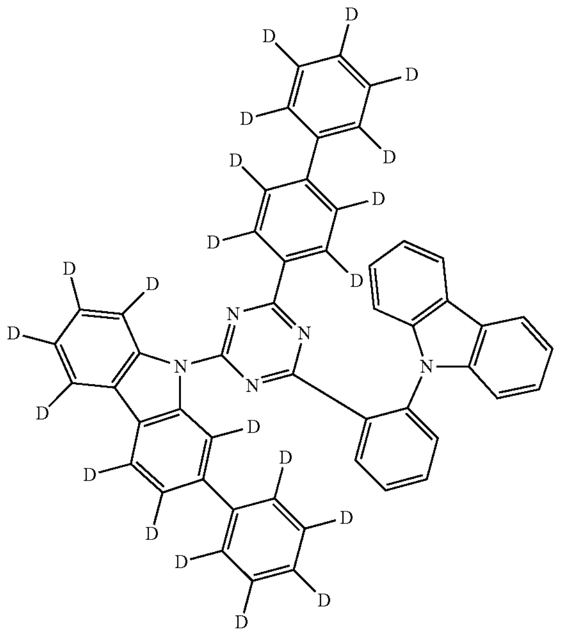
[A-126]
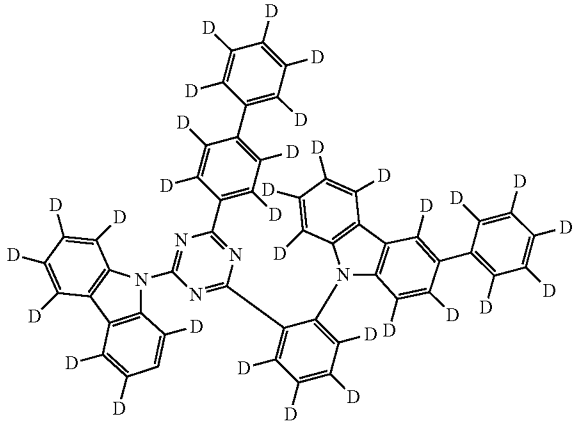
-continued
[A-127]
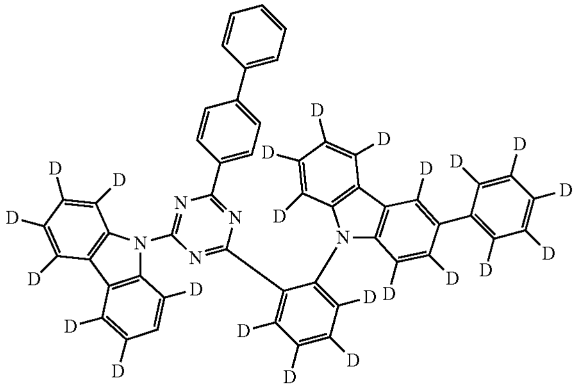
[A-128]
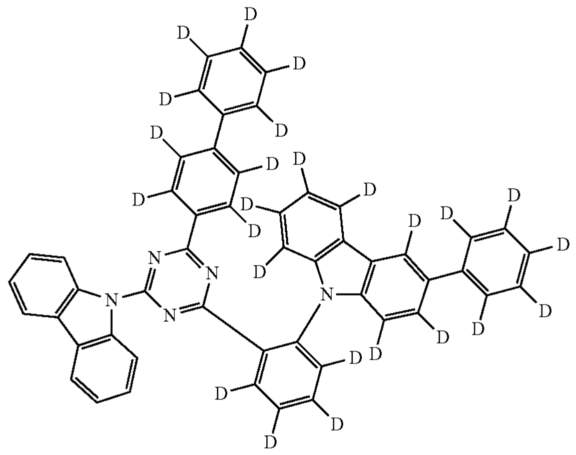
[A-129]
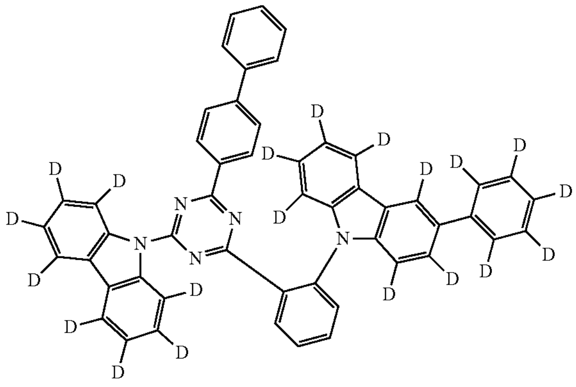

-continued
[A-130]
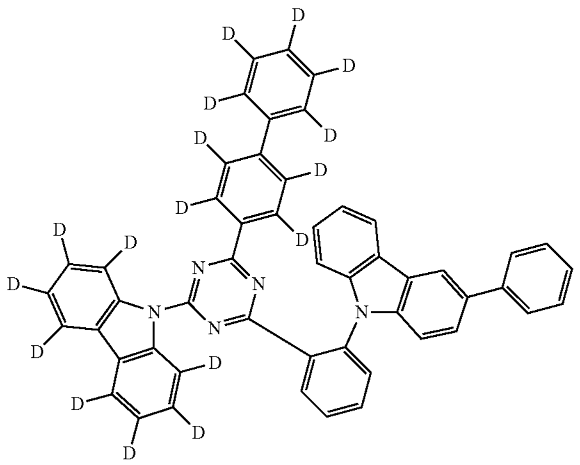
[A-131]
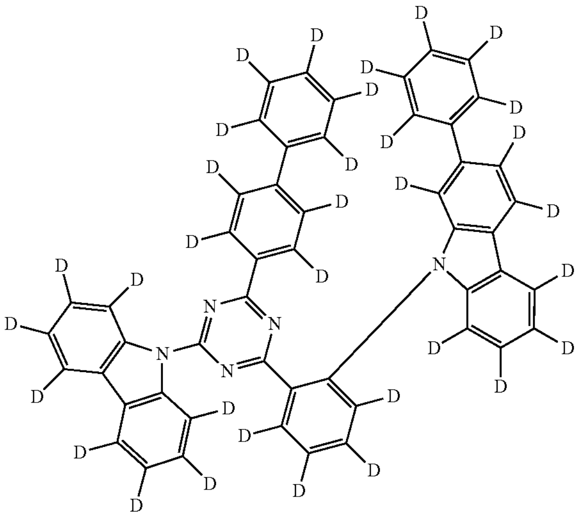
[A-132]
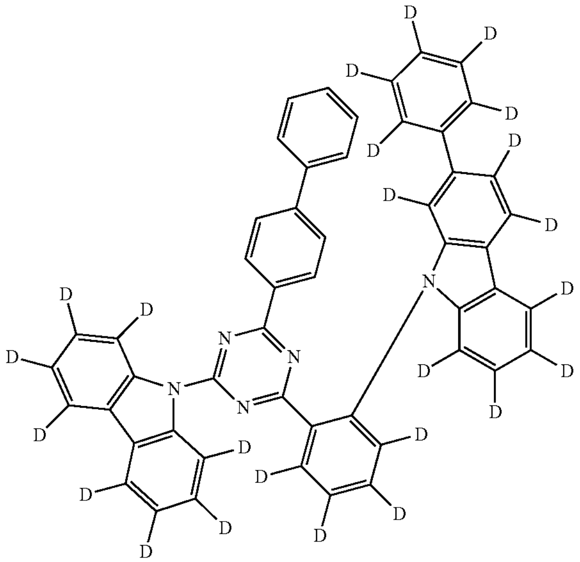
-continued
[A-133]
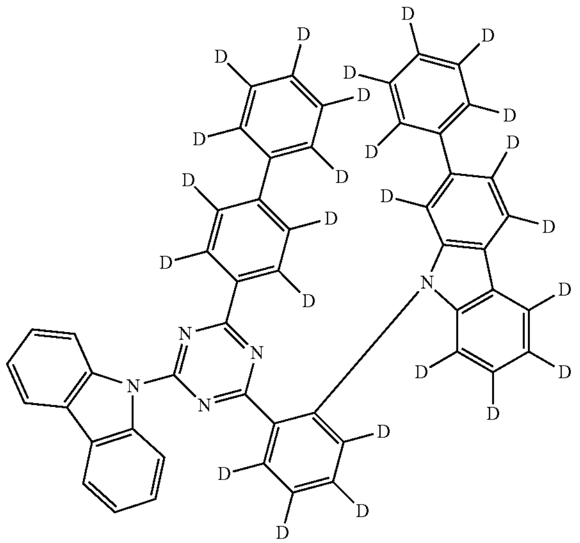
[A-134]
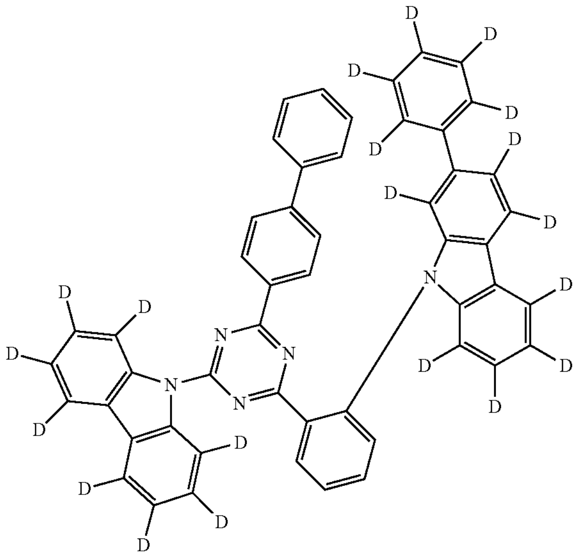

-continued
[A-135]
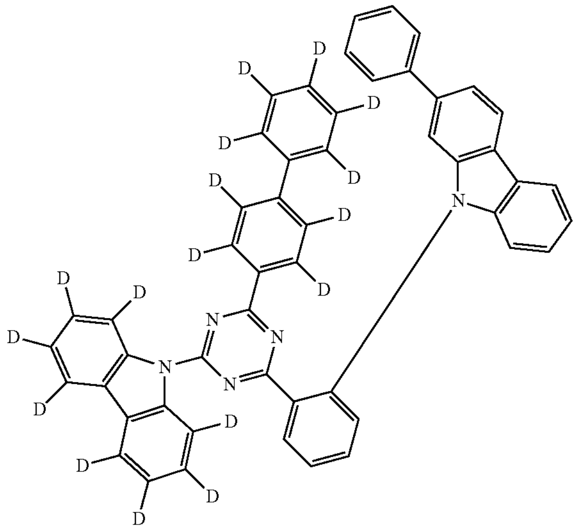
[A-136]
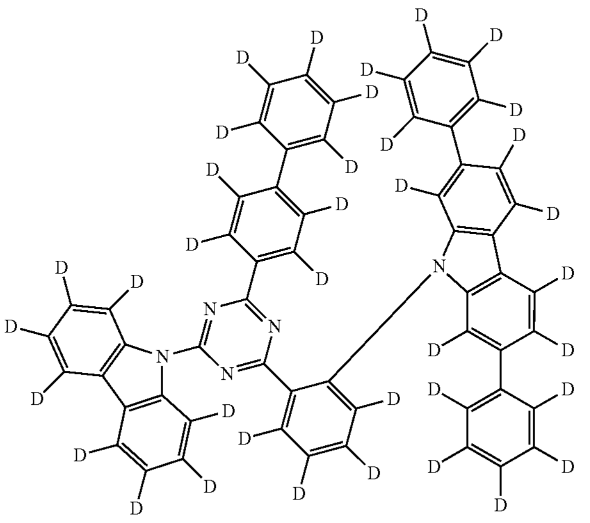
-continued
[A-137]
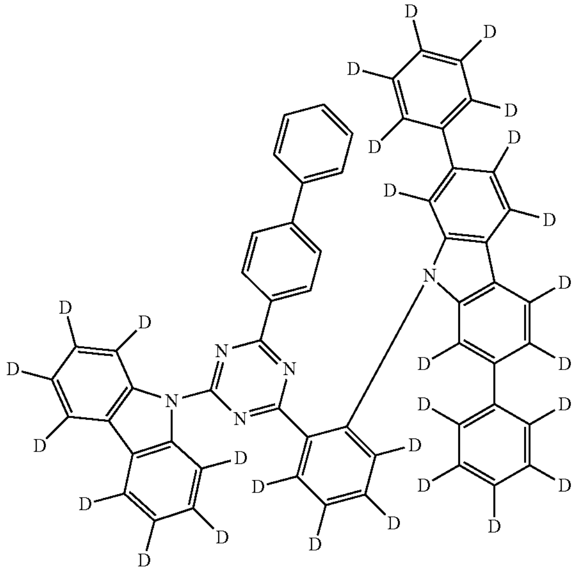
[A-138]
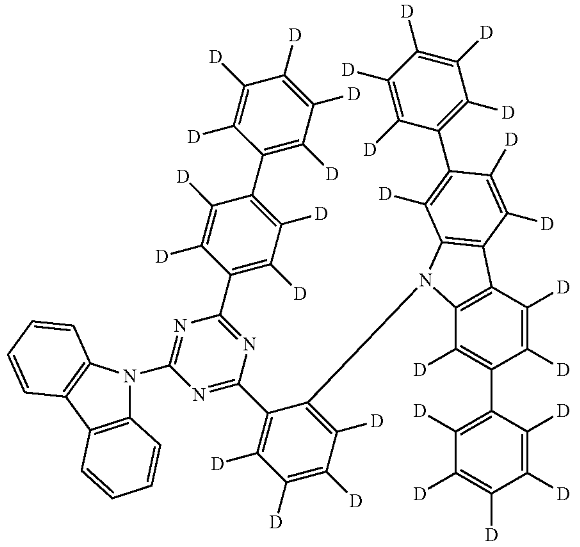

-continued
[A-139]
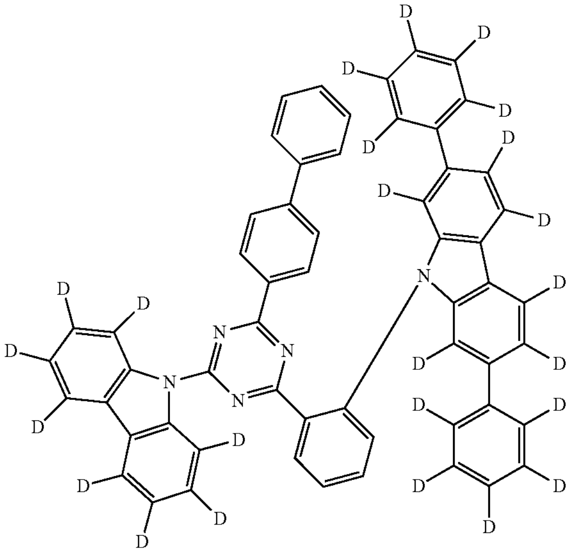
[A-140]
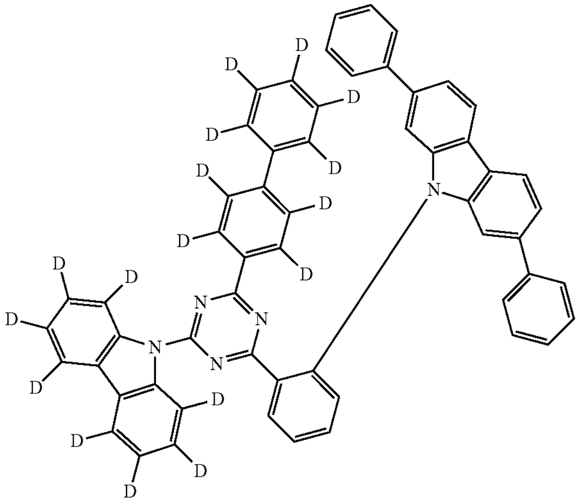
-continued
[A-141]
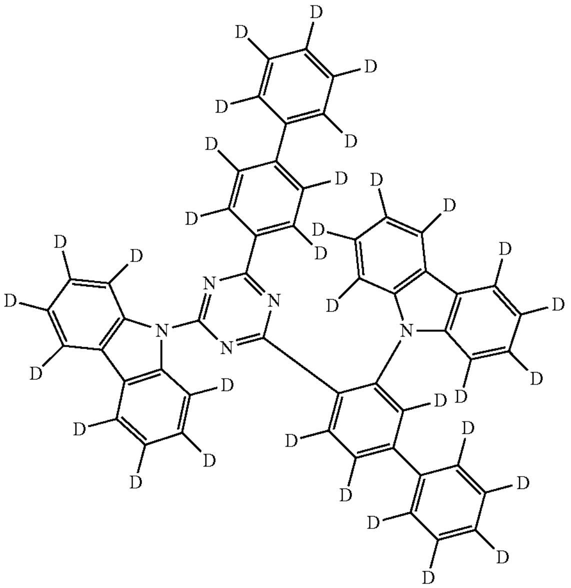
[A-142]
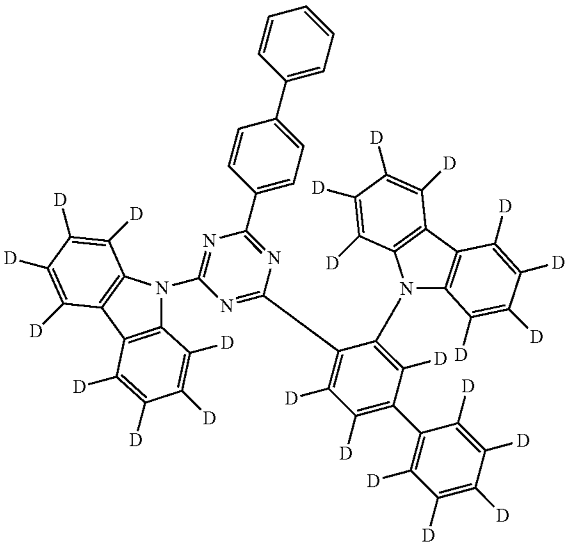

-continued

[A-143]

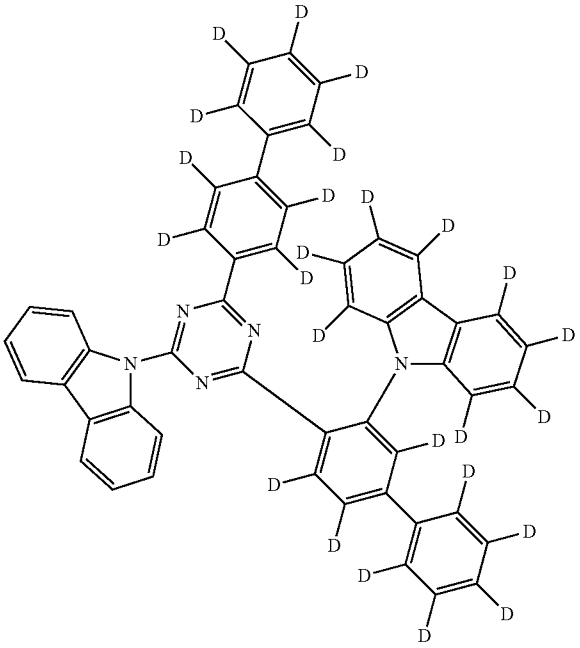

[A-144]

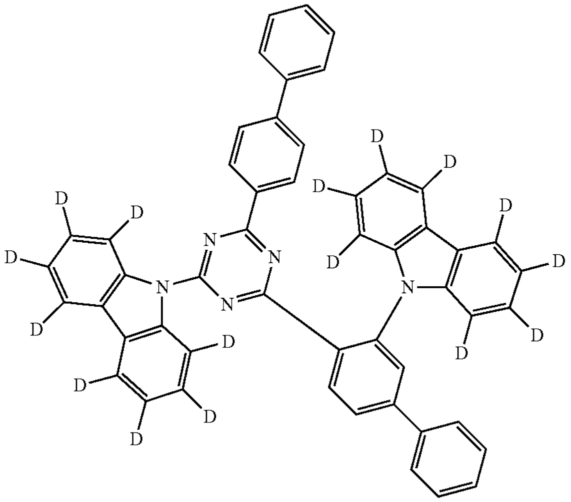

-continued

[A-145]

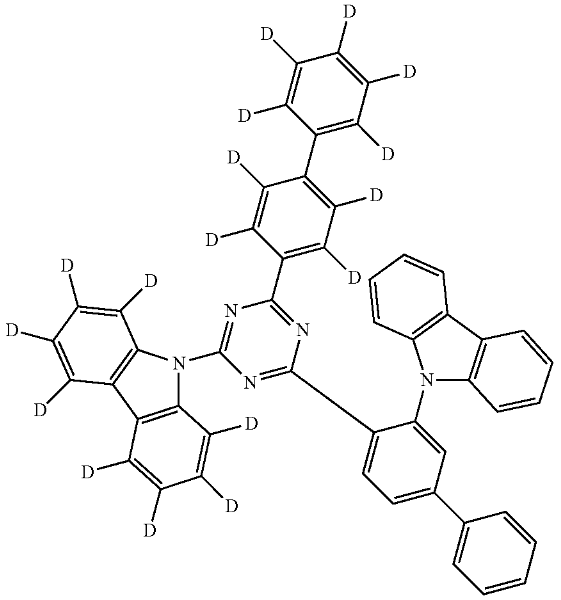

A composition for an organic optoelectronic device according to another embodiment may include, e.g., a first compound and a second compound. The first compound may be, e.g., the aforementioned compound for the organic optoelectronic device, and the second compound may be, e.g., a compound represented by Chemical Formula 2; or a compound represented by a combination of Chemical Formula 3 and Chemical Formula 4.

[Chemical Formula 2]

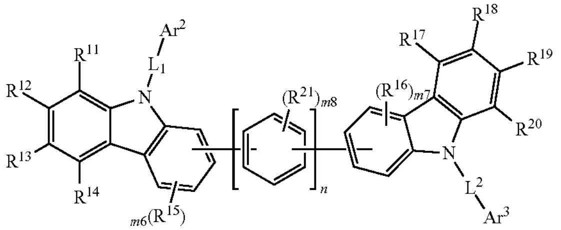

In Chemical Formula 2, $Ar^2$ and $Ar^3$ may each independently be or include, e.g., a substituted or unsubstituted C6 to C20 aryl group or a substituted or unsubstituted C2 to C30 heterocyclic group.

$L^1$ and $L^2$ may each independently be or include, e.g., a single bond or a substituted or unsubstituted C6 to C20 arylene group.

$R^{11}$ to $R^{21}$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

m6 and m7 may each independently be, e.g., an integer of 1 to 3.

m8 may be, e.g., an integer of 1 to 4.

n may be, e.g., an integer of 0 to 2.

[Chemical Formula 3]

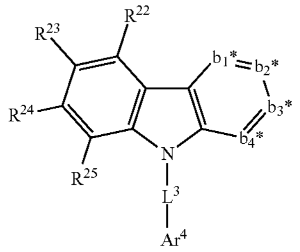

[Chemical Formula 4]

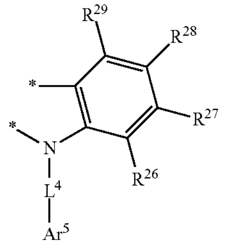

In Chemical Formulae 3 and 4, $Ar^4$ and $Ar^5$ may each independently be or include, e.g., a substituted or unsubstituted C6 to C20 aryl group or a substituted or unsubstituted C2 to C30 heterocyclic group.

Two adjacent ones of $b_1$* to $b_4$* of Chemical Formula 3 may be linking carbons linked at * of Chemical Formula 4, and the remaining two of $b_1$* to $b_4$* of Chemical Formula 3, not linked at * of Chemical Formula 4, may each independently be, e.g., C-$L^a$-$R^a$. As used herein, the term "linking carbon" refers to a shared carbon at which fused rings are linked.

$L^a$, $L^3$, and $L^4$ may each independently be or include, e.g., a single bond or a substituted or unsubstituted C6 to C20 arylene group.

$R^a$ and $R^{22}$ to $R^{29}$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

The second compound may be used in the light emitting layer together with the first compound to help improve luminous efficiency and life-span characteristics by increasing charge mobility and increasing stability.

In an implementation, $Ar^2$ and $Ar^3$ in Chemical Formula 2 may each independently be, e.g., a substituted or unsubstituted C6 to C20 aryl group or a substituted or unsubstituted C2 to C30 heterocyclic group.

In an implementation, at least one of $Ar^2$ and $Ar^3$ may be, e.g., a C6 to C20 aryl group substituted with deuterium or a C2 to C30 heterocyclic group substituted with deuterium.

In an implementation, $R^{11}$ to $R^{21}$ in Chemical Formula 2 may each independently be, e.g., hydrogen, deuterium, a cyano group, a halogen group, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

In an implementation, at least one of $R^{11}$ to $R^{21}$ may be, e.g., deuterium, a C1 to C30 alkyl group substituted with deuterium, a C6 to C30 aryl group substituted with deuterium, or a C2 to C30 heterocyclic group substituted with deuterium.

In an implementation, at least one of $Ar^2$ and $Ar^3$ in Chemical Formula 2 may be, e.g., a C6 to C20 aryl group substituted with deuterium or a C2 to C30 heterocyclic group substituted with deuterium, and at least one of $R^{11}$ to $R^{21}$ in Chemical Formula 2 may be, e.g., deuterium, a C1 to C30 alkyl group substituted with deuterium, a C6 to C30 aryl group substituted with deuterium, or a C2 to C30 heterocyclic group substituted with deuterium.

In an implementation, $Ar^4$ and $Ar^5$ of Chemical Formulas 3 and 4 may each independently be, e.g., a substituted or unsubstituted C6 to C20 aryl group or a substituted or unsubstituted C2 to C30 heterocyclic group.

In an implementation, at least one of $Ar^4$ and $Ar^5$ may be, e.g., a C6 to C20 aryl group substituted with deuterium or a C2 to C30 heterocyclic group substituted with deuterium.

In an implementation, in Chemical Formulae 3 and 4, $R^a$ and $R^{22}$ to $R^{29}$ may each independently be, e.g., hydrogen, deuterium, a cyano group, a halogen group, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

In an implementation, at least one of $R^a$ and $R^{22}$ to $R^{29}$ may be, e.g., deuterium, a C1 to C30 alkyl group substituted with deuterium, a C6 to C30 aryl group substituted with deuterium, or a C2 to C30 heterocyclic group substituted with deuterium.

In an implementation, at least one of $Ar^4$ and $Ar^5$ in Chemical Formulas 3 and 4 may be, e.g., a C6 to C20 aryl group substituted with deuterium or a C2 to C30 heterocyclic group substituted with deuterium, and at least one of $R^a$ and $R^{22}$ to $R^{29}$ may be, e.g., deuterium, a C1 to C30 alkyl group substituted with deuterium, a C6 to C30 aryl group substituted with deuterium, or a C2 to C30 heterocyclic group substituted with deuterium.

In an implementation, $Ar^2$ and $Ar^3$ of Chemical Formula 2 may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, or a substituted or unsubstituted fluorenyl group.

In an implementation, $L^1$ and $L^2$ of Chemical Formula 2 may each independently be, e.g., a single bond, a substituted or unsubstituted phenylene group, or a substituted or unsubstituted biphenylene group.

In an implementation, $R^{11}$ to $R^{21}$ of Chemical Formula 2 may each independently be, e.g., hydrogen, deuterium, or a substituted or unsubstituted C6 to C12 aryl group.

In an implementation, n may be, e.g., 0 or 1.

In an implementation, $Ar^2$ and $Ar^3$ of Chemical Formula 2 may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, or a substituted or unsubstituted fluorenyl group.

In an implementation, at least one of $Ar^2$ and $Ar^3$ may be, e.g., a phenyl group substituted with deuterium, a biphenyl group substituted with deuterium, a terphenyl group substituted with deuterium, a naphthyl group substituted with deuterium, an anthracenyl group substituted with deuterium, a triphenylenyl group substituted with deuterium, a carbazolyl group substituted with deuterium, a dibenzothiophenyl group substituted with deuterium, a dibenzofuranyl group substituted with deuterium, or a fluorenyl group substituted with deuterium.

In an implementation, $R^{11}$ to $R^{21}$ in Chemical Formula 2 may each independently be, e.g., hydrogen, deuterium, or a substituted or unsubstituted C6 to C12 aryl group.

In an implementation, at least one of $R^{11}$ to $R^{21}$ may be, e.g., deuterium or a C6 to C12 aryl group substituted with deuterium.

In an implementation, at least one of $Ar^2$ and $Ar^3$ in Chemical Formula 2 may be, e.g., a phenyl group substituted with deuterium, a biphenyl group substituted with deuterium, a terphenyl group substituted with deuterium, a naphthyl group substituted with deuterium, an anthracenyl group substituted with deuterium, a triphenylenyl group substituted with deuterium, a carbazolyl group substituted with deuterium, a dibenzothiophenyl group substituted with deuterium, a dibenzofuranyl group substituted with deuterium, or a fluorenyl group substituted with deuterium, and at least one of $R^{11}$ to $R^{21}$ in Chemical Formula 2 may be, e.g., deuterium or a C6 to C12 aryl group substituted with deuterium.

In an implementation, "substituted" in Chemical Formula 2 means that at least one hydrogen is replaced by deuterium, a C1 to C4 alkyl group, a C6 to C18 aryl group, or a C2 to C30 heteroaryl group.

In an implementation, the compound represented by Chemical Formula 2 may be represented by, e.g., one of Chemical Formula 2-1 to Chemical Formula 2-15.

[Chemical Formula 2-1]

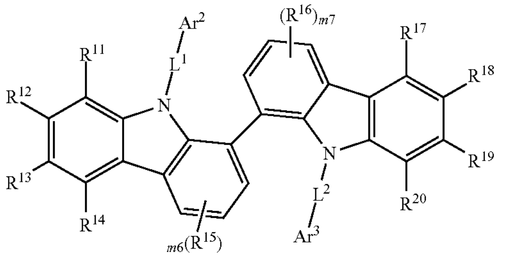

[Chemical Formula 2-2]

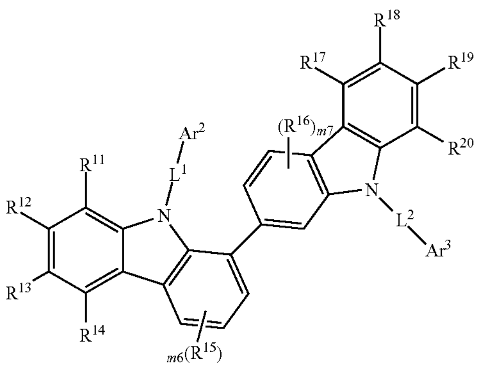

-continued

[Chemical Formula 2-3]

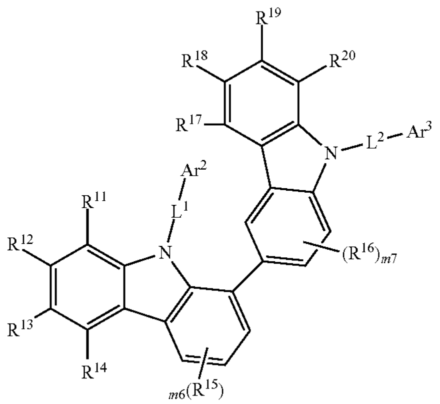

[Chemical Formula 2-4]

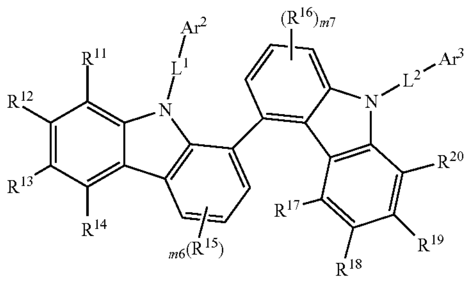

[Chemical Formula 2-5]

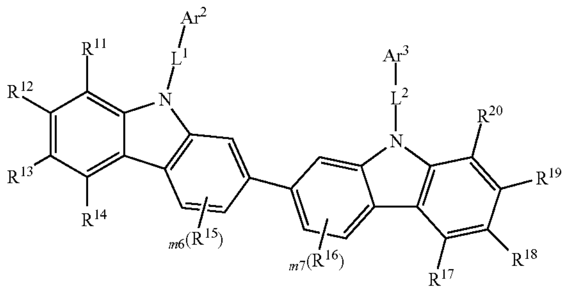

[Chemical Formula 2-6]

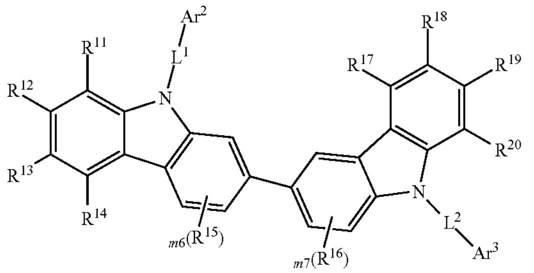

[Chemical Formula 2-7]

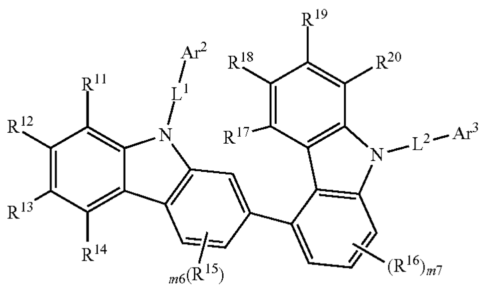

-continued
[Chemical Formula 2-8]
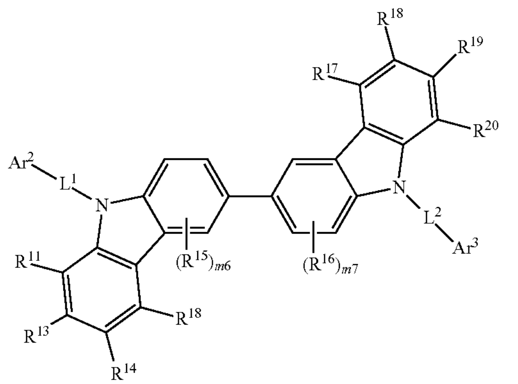
[Chemical Formula 2-9]
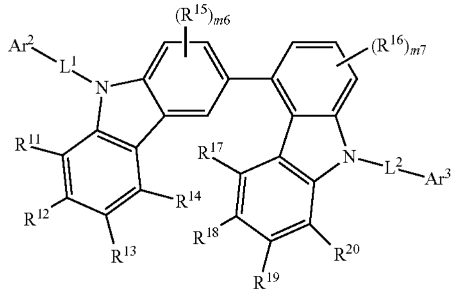
[Chemical Formula 2-10]
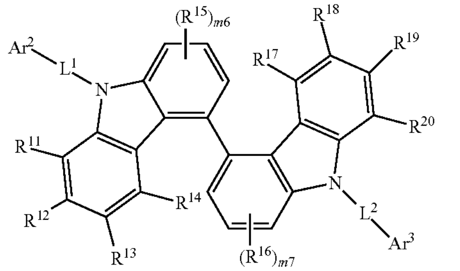
[Chemical Formula 2-11]
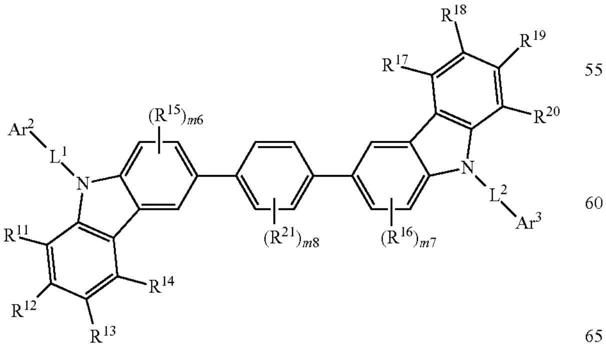
-continued
[Chemical Formula 2-12]
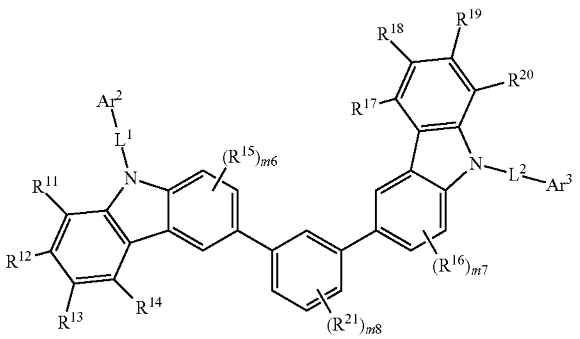
[Chemical Formula 2-13]
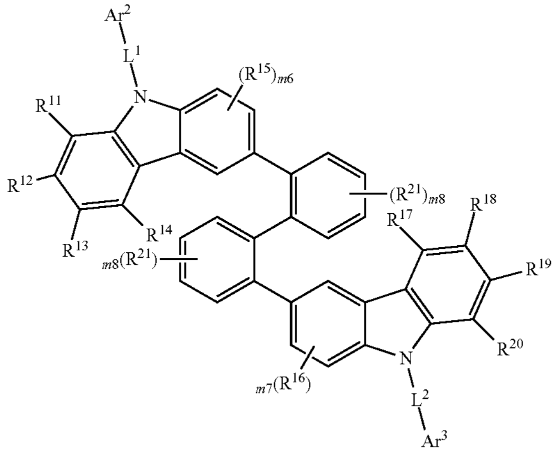
[Chemical Formula 2-14]
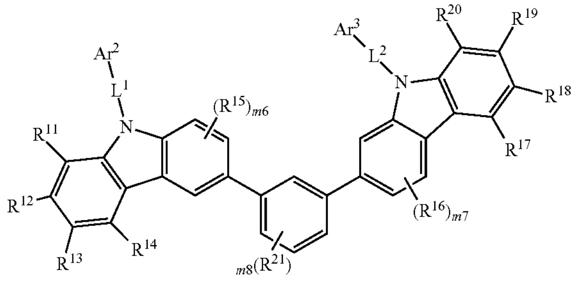
[Chemical Formula 2-15]
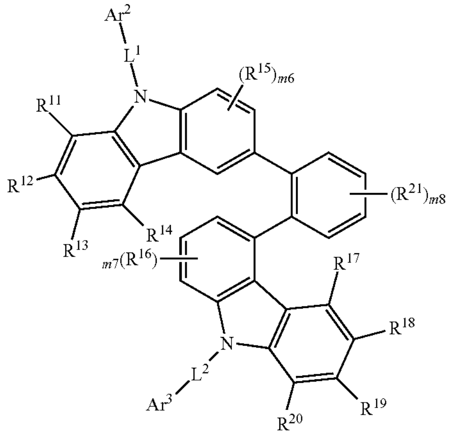
In Chemical Formula 2-1 to Chemical Formula 2-15, $R^{11}$ to $R^{21}$ may each independently be, e.g., hydrogen, deuterium, or a substituted or unsubstituted C6 to C12 aryl group, m6 and m7 may each independently be, e.g., an integer of 1 to 3, m8 may be, e.g., an integer of, and moieties *-L-$Ar^2$ and *-$L^2Ar^3$ may each independently be, e.g., a moiety of Group II.
[Group II]
C-1
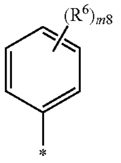
C-2
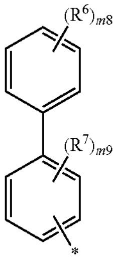
C-3
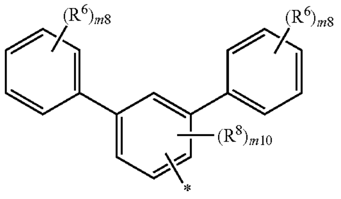
C-4
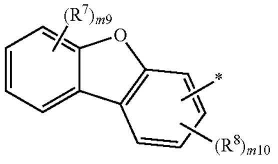
C-5
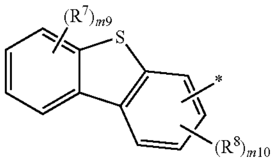
C-6
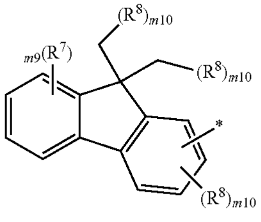
-continued
C-7
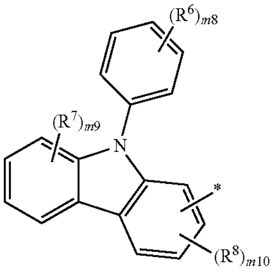
C-8
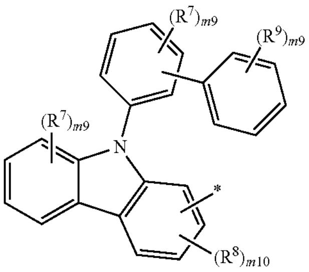
C-9
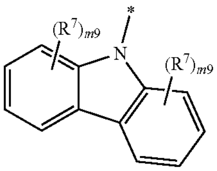
C-10
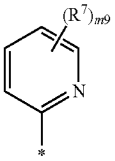
C-11
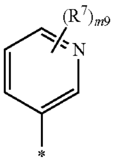
C-12
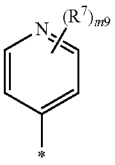
C-13
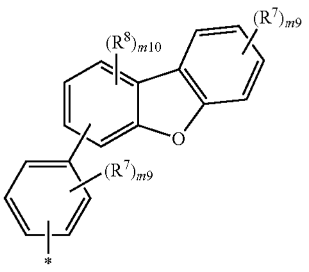

-continued
C-14
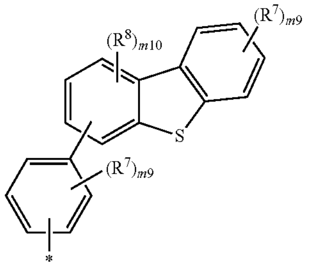
C-15
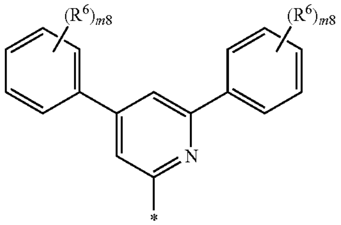
C-16
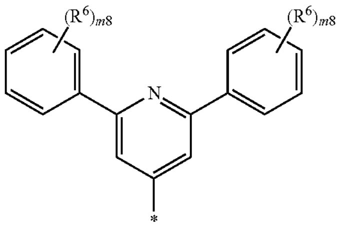
C-17
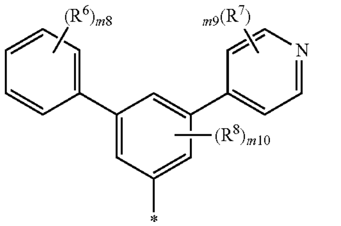
C-18
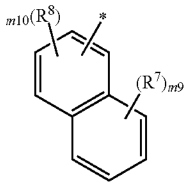
C-19
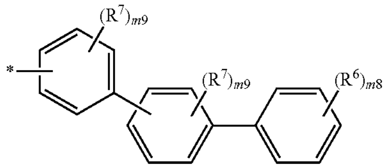
C-20
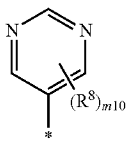
-continued
C-21
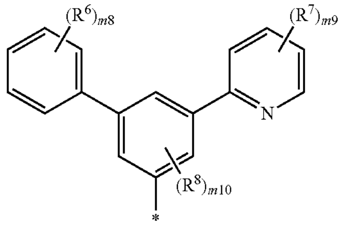
C-22
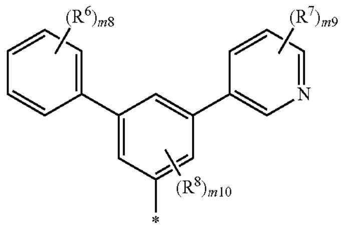
C-23
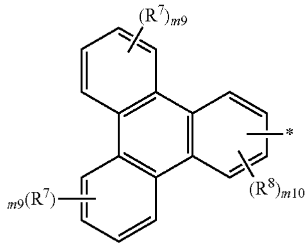
C-24
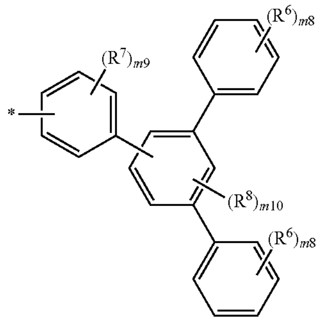
C-25
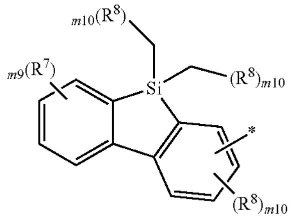
C-26
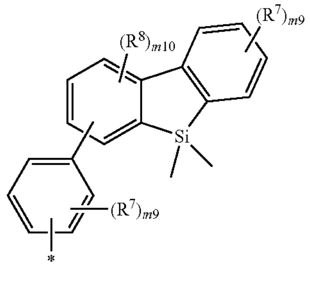
In Group II, $R^6$ to $R^8$ may each independently be, e.g., hydrogen, deuterium, a substituted or unsubstituted C1 to C4 alkyl group, a substituted or unsubstituted C6 to C18 aryl group, or a substituted or unsubstituted C2 to C30 heteroaryl group.

m8 may be, e.g., an integer of 1 to 5.

m9 may be, e.g., an integer of 1 to 4.

m10 may be, e.g., an integer of 1 to 3.

* is a linking point.

In an implementation, the compound represented by Chemical Formula 2 may be represented by, e.g., Chemical Formula 2-8.

In an implementation, moieties $*\text{-}L^1\text{-}Ar^2$ and $*\text{-}L^2\text{-}Ar^3$ of Chemical Formula 2-8 may each independently be a moiety of Group II, e.g., moiety C-1, C-2, C-3, C-4, C-7, C-8, or C-9.

In an implementation, the second compound represented by the combination of Chemical Formula 3 and Chemical Formula 4 may be represented by, e.g., Chemical Formula 3A, Chemical Formula 3B, Chemical Formula 3C, Chemical Formula 3D, or Chemical Formula 3E.

[Chemical Formula 3A]

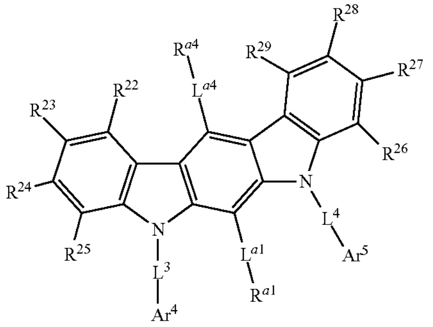

[Chemical Formula 3B]

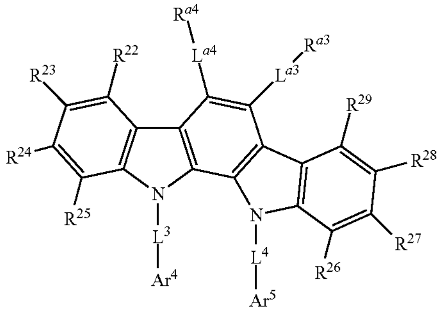

[Chemical Formula 3C]

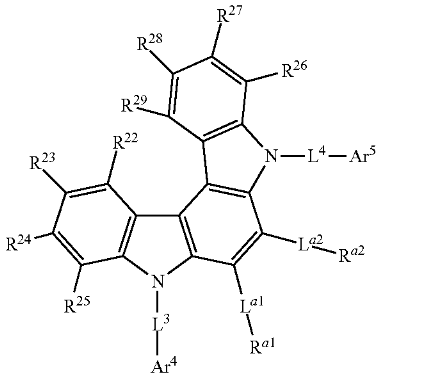

-continued

[Chemical Formula 3D]

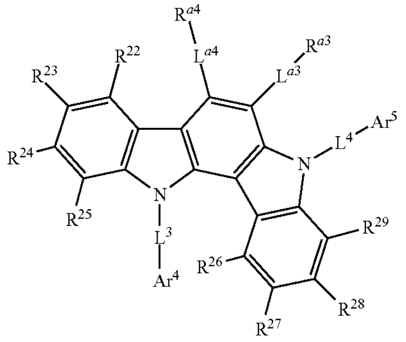

[Chemical Formula 3E]

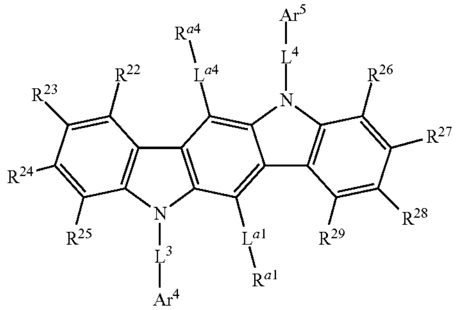

In Chemical Formula 3A to Chemical Formula 3E, $Ar^4$, $Ar^5$, $L^3$, $L^4$, and $R^{22}$ to $R^{29}$ may be defined the same as those described above.

$L^{a1}$ to $L^{a4}$ may be defined the same as $L^3$ and $L^4$.

$R^{a1}$ to $R^{a4}$ may be defined the same as $R^{22}$ to $R^{29}$.

In an implementation, $Ar^4$ and $Ar^5$ of Chemical Formulas 3 and 4 may each independently be, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{a1}$ to $R^{a4}$ and $R^{22}$ to $R^{29}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $Ar^4$ and $Ar^5$ in Chemical Formulas 3 and 4 may each independently be, e.g., a group of Group II.

In an implementation, $R^{a1}$ to $R^{a4}$ and $R^{22}$ to $R^{29}$ may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, $R^{a1}$ to $R^{a4}$ and $R^{22}$ to $R^{29}$ may each independently be, e.g., hydrogen, deuterium, a cyano group, or a substituted or unsubstituted phenyl group.

In an implementation, $R^{a1}$ to $R^{a4}$, and $R^{22}$ to $R^{29}$ may each independently be hydrogen, deuterium, or an unsubstituted phenyl group.

In an implementation, $Ar^4$ and $Ar^5$ of Chemical Formulas 3 and 4 may each independently be, e.g., a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, at least one of $Ar^4$ and $Ar^5$ may be, e.g., a phenyl group substituted with deuterium, a biphenyl group substituted with deuterium, a pyridinyl group substituted with deuterium, a carbazolyl group substituted with deuterium, a dibenzofuranyl group substituted with deuterium, a dibenzofuranyl group substituted with deuterium, or a dibenzothiophenyl group substituted with deuterium.

In an implementation, $R^{a1}$ to $R^{a4}$, and $R^{22}$ to $R^{29}$ of Chemical Formulas 3 and 4 may each independently be, e.g., hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, at least one of $R^{a1}$ to $R^{a4}$, and $R^{22}$ to $R^{29}$ may be a phenyl group substituted with deuterium, a biphenyl group substituted with deuterium, a pyridinyl group substituted with deuterium, a carbazolyl group substituted with deuterium, a dibenzofuranyl group substituted with deuterium, a dibenzofuranyl group substituted with deuterium, or a dibenzothiophenyl group substituted with deuterium.

In an implementation, at least one of $Ar^4$ and $Ar^5$ of Chemical Formulas 3 and 4 may be, e.g., a phenyl group substituted with deuterium, a biphenyl group substituted with deuterium, a pyridinyl group substituted with deuterium, a carbazolyl group substituted with deuterium, a dibenzofuranyl group substituted with deuterium, a dibenzofuranyl group substituted with deuterium, or a dibenzothiophenyl group substituted with deuterium, and at least one of $R^{a1}$ to $R^{a4}$, and $R^{22}$ to $R^{29}$ may be, e.g., a phenyl group substituted with deuterium, a biphenyl group substituted with deuterium, a pyridinyl group substituted with deuterium, a carbazolyl group substituted with deuterium, a dibenzofuranyl group substituted with deuterium, a dibenzofuranyl group substituted with deuterium, or a dibenzothiophenyl group substituted with deuterium.

In an implementation, the second compound may be, e.g., represented by Chemical Formula 2-8, and in Chemical Formula 2-8, $Ar^2$ and $Ar^3$ may each independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, $L^1$ and $L^2$ may each independently be a single bond, or a substituted or unsubstituted C6 to C20 arylene group, and $R^{11}$ to $R^{20}$ may each independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

In an implementation, the second compound may be represented by Chemical Formula 3C, and in Chemical Formula 3C, $L^{a1}$ and $L^{a2}$ may be a single bond, $L^3$ and $L^4$ may each independently be a single bond or a substituted or unsubstituted a C6 to C12 arylene group, $R^{22}$ to $R^{29}$, $R^{a1}$, and $R^{a2}$ may each be hydrogen, deuterium, or a phenyl group, and $Ar^4$ and $Ar^5$ may each independently be a substituted or unsubstituted phenyl group, a substituted or unsubstituted biphenyl group, or a substituted or unsubstituted terphenyl group.

In an implementation, the second compound may be, e.g., a compound of Group 2.

[Group 2]

[B-1]

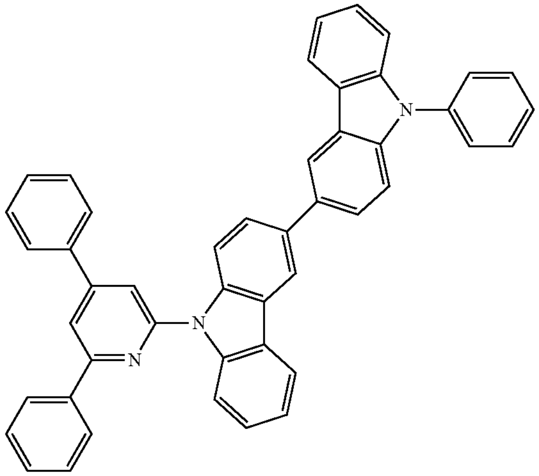

[B-2]

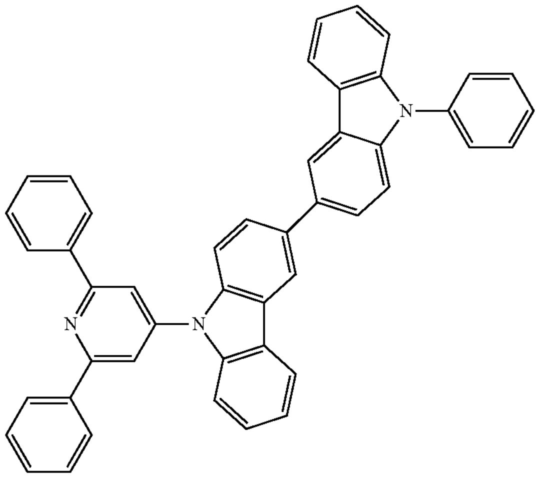

[B-3]

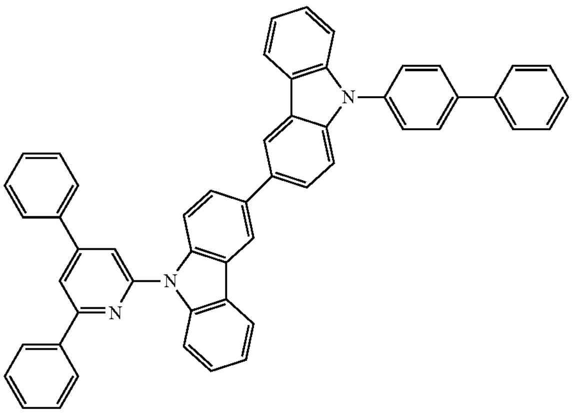

-continued
[B-4]
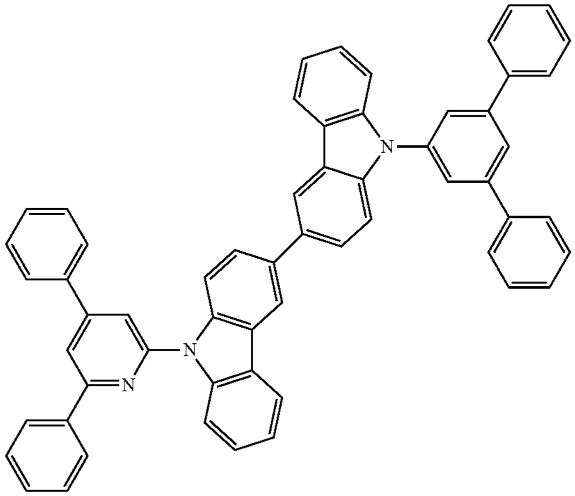
[B-5]
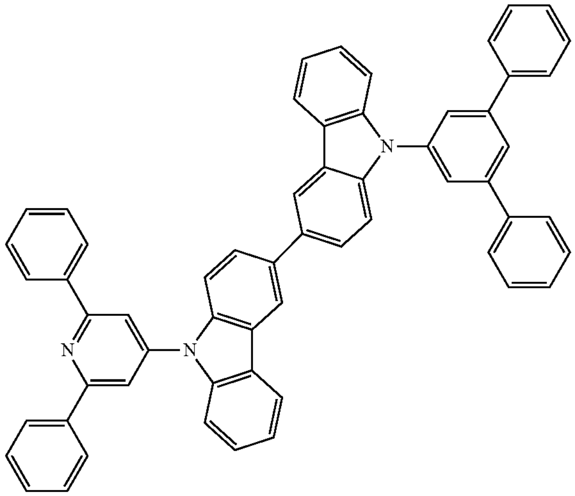
[B-6]
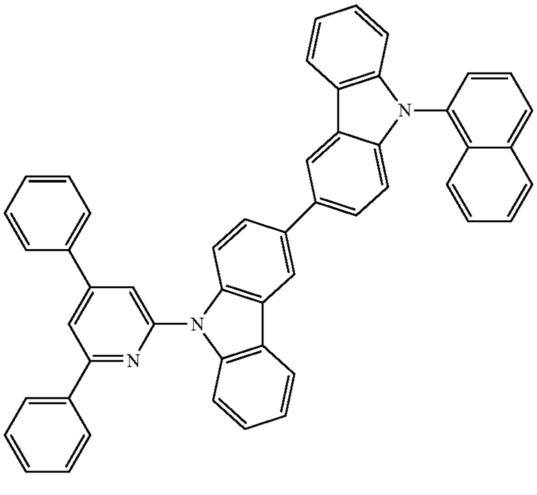
-continued
[B-7]
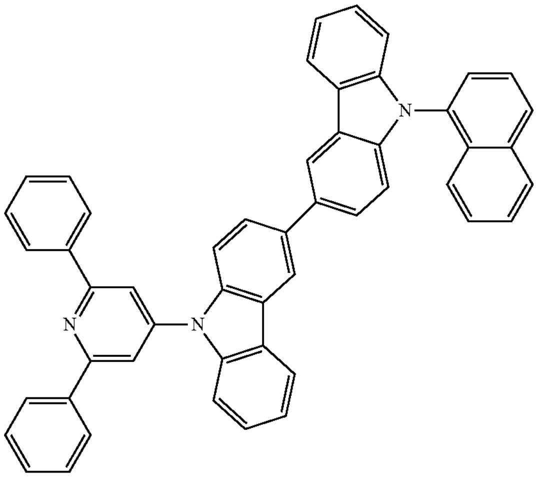
[B-8]
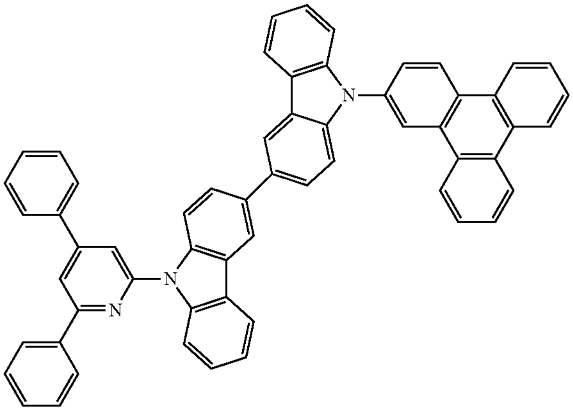
[B-9]
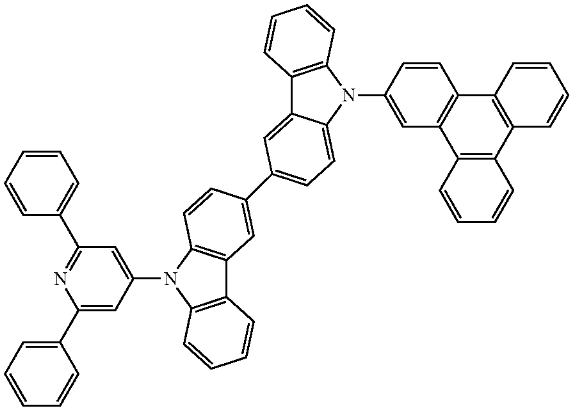

-continued
[B-10]
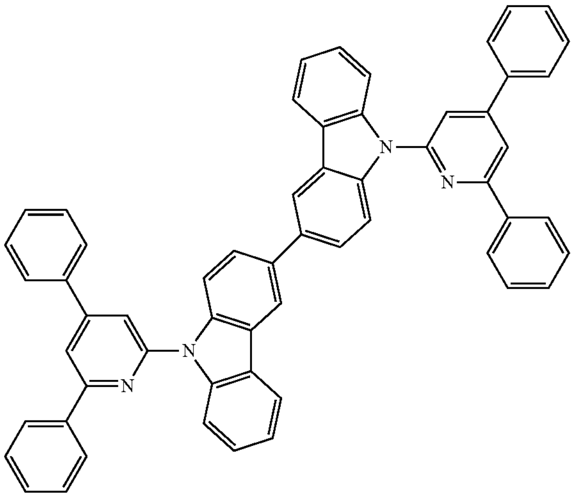
[B-11]
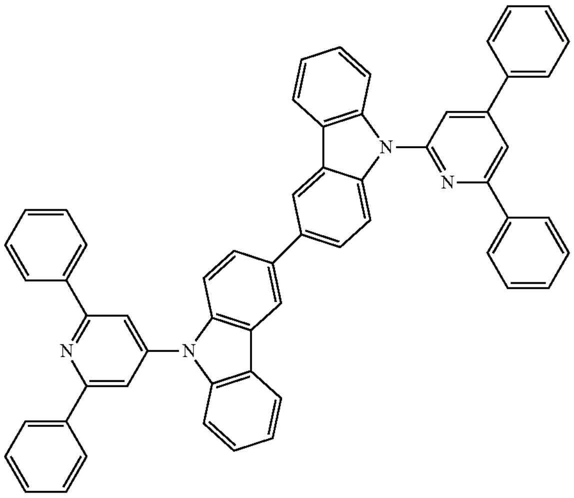
[B-12]
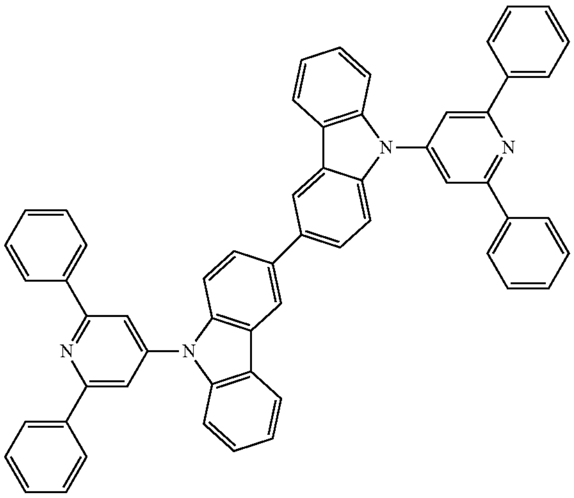
-continued
[B-13]
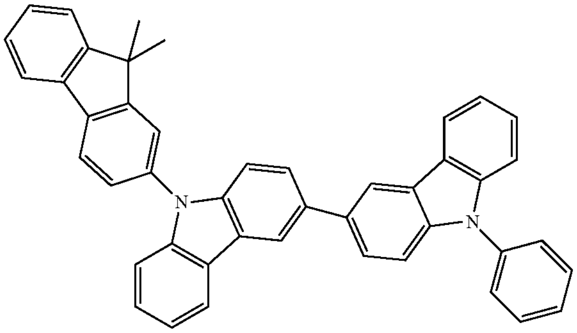
[B-14]
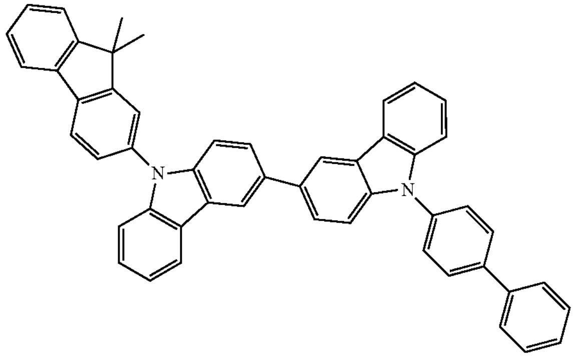
[B-15]
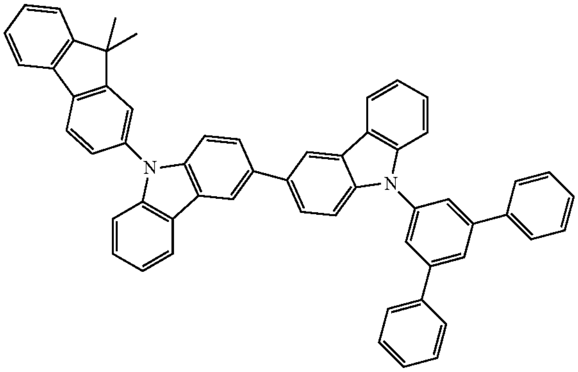
[B-16]
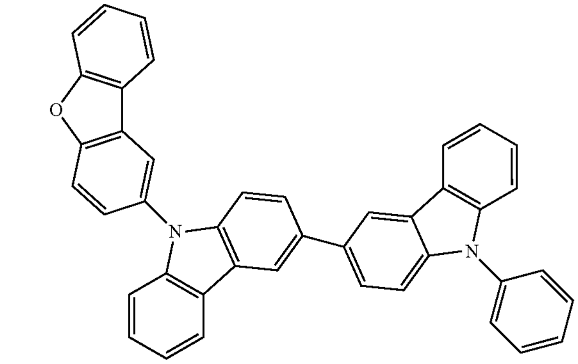

-continued
[B-17]
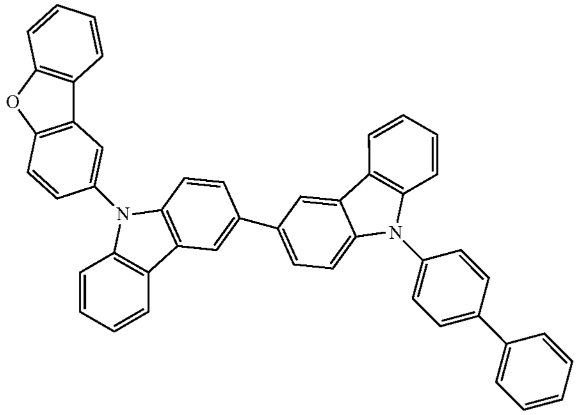
[B-18]
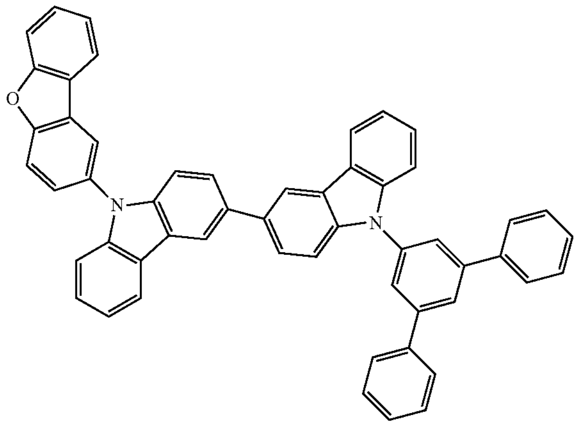
[B-19]
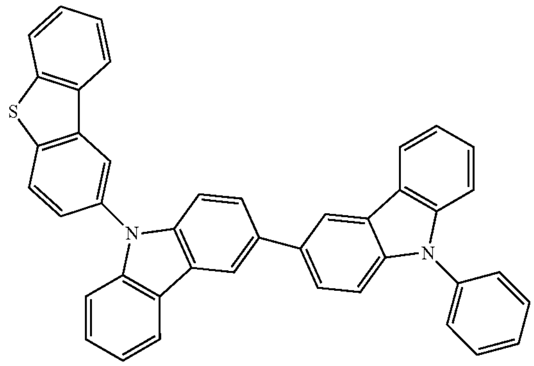
-continued
[B-20]
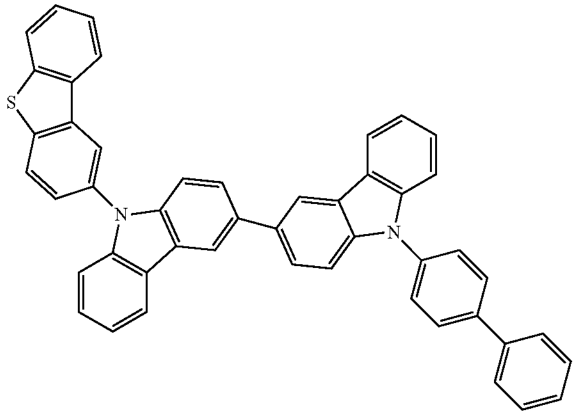
[B-21]
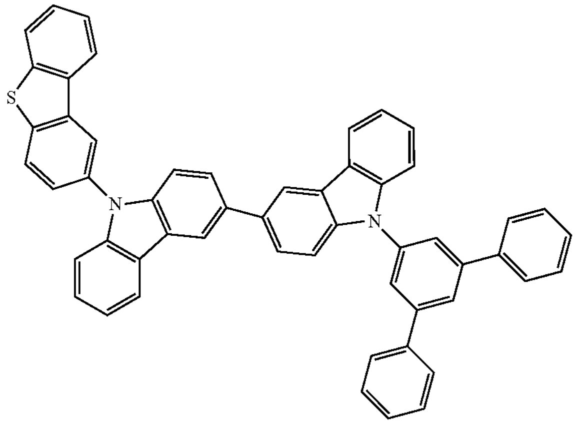
[B-22]
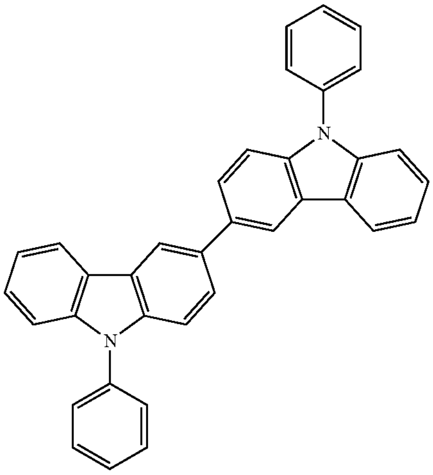

-continued
[B-23]
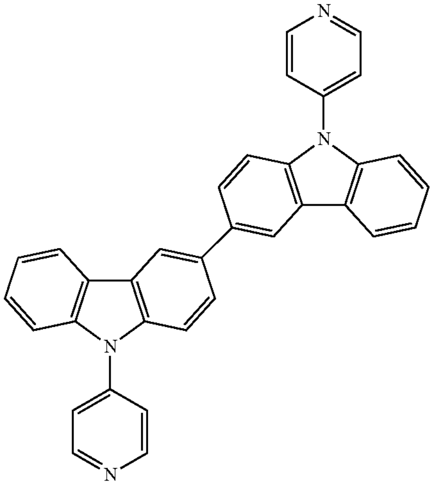
[B-24]
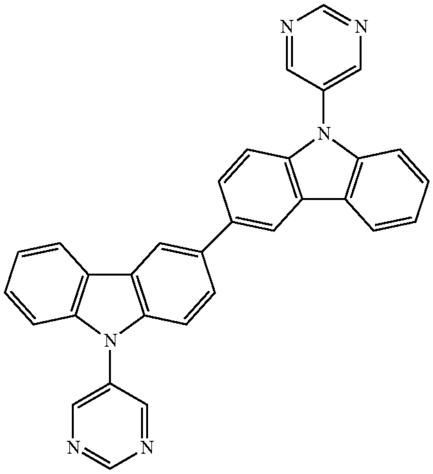
[B-25]
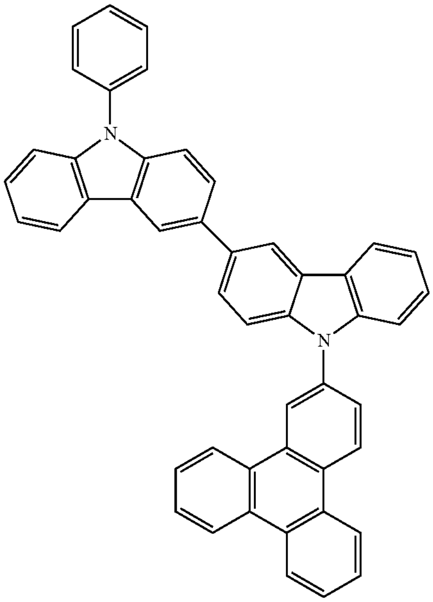
-continued
[B-26]
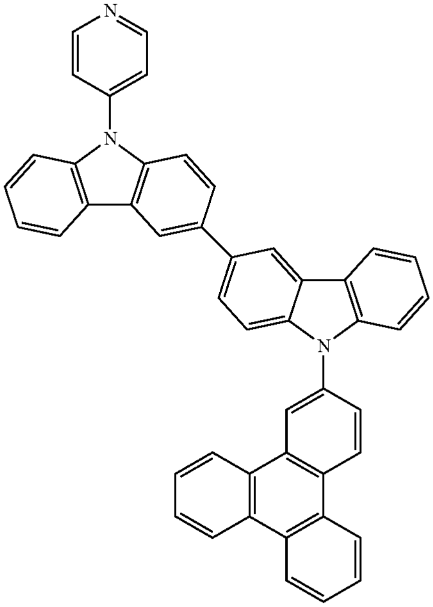
[B-27]
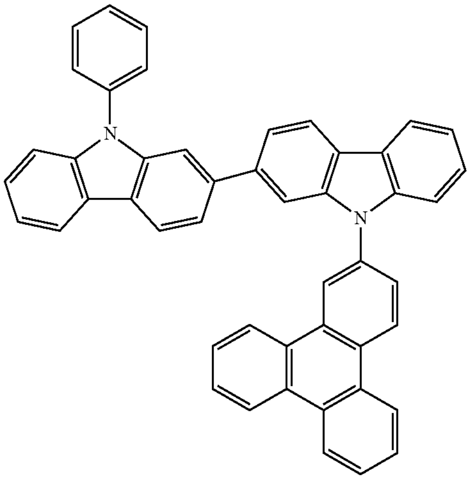
[B-28]
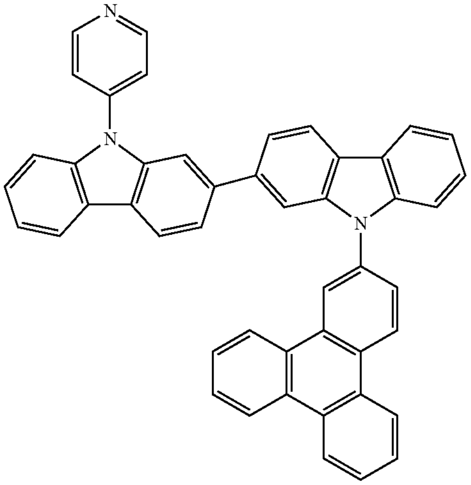

-continued
[B-29]
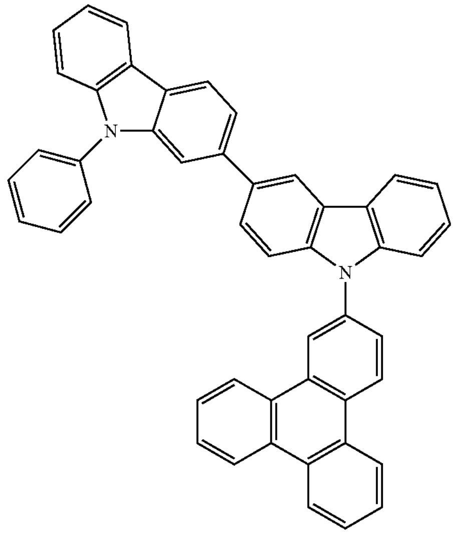
[B-30]
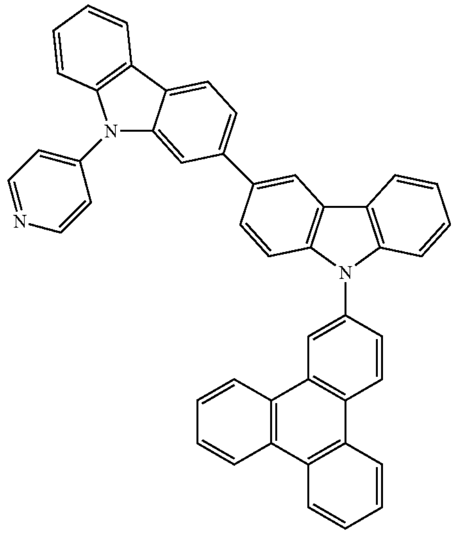
-continued
[B-31]
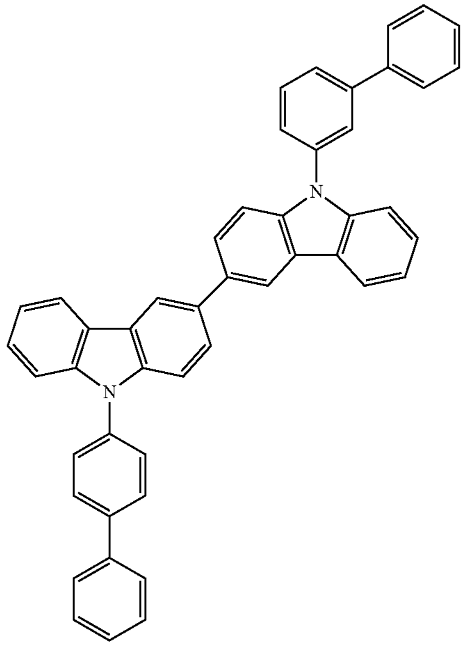
[B-32]
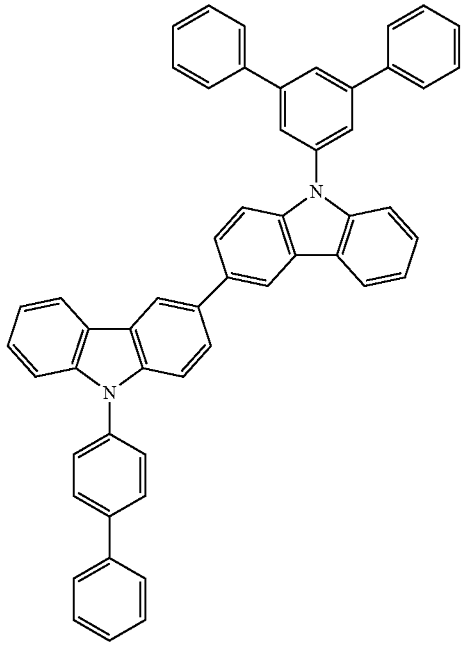

-continued
[B-33]
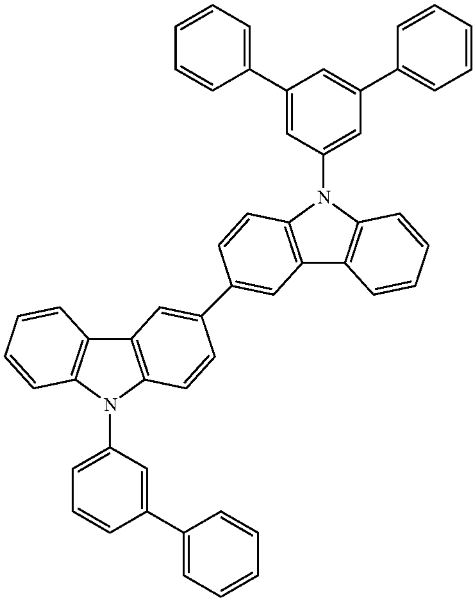
[B-34]
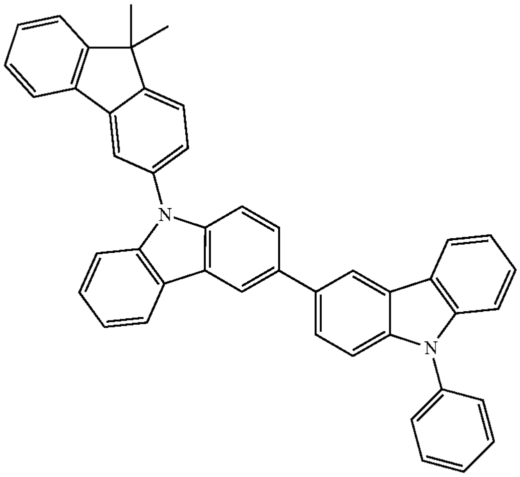
-continued
[B-35]
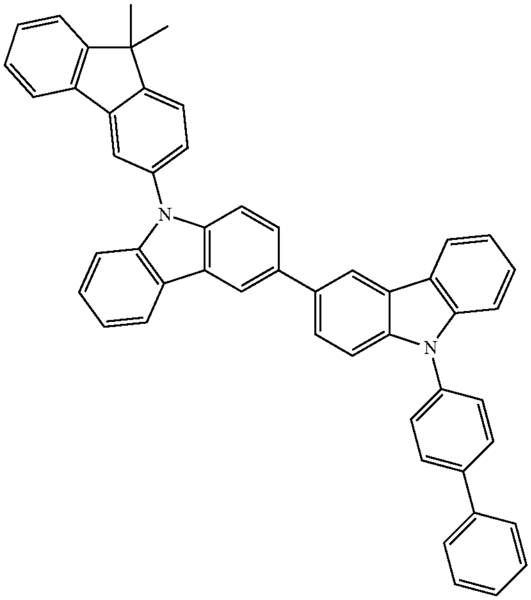
[B-36]
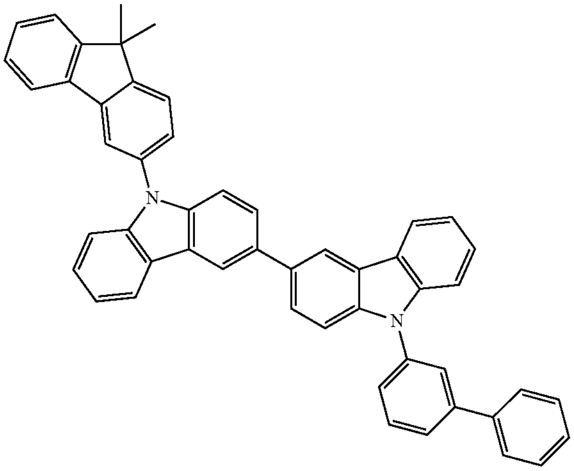
[B-37]
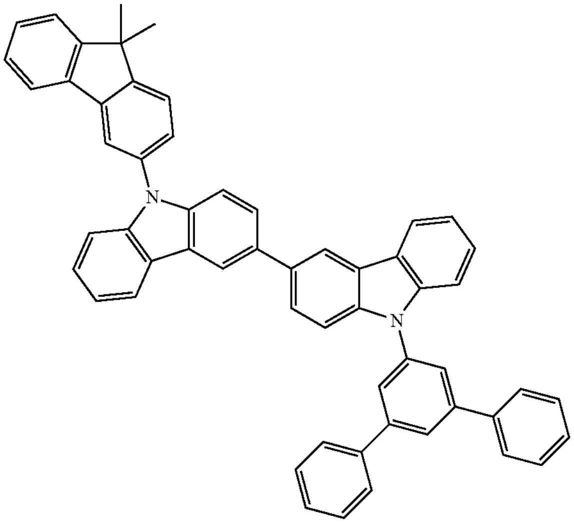

-continued
[B-38]
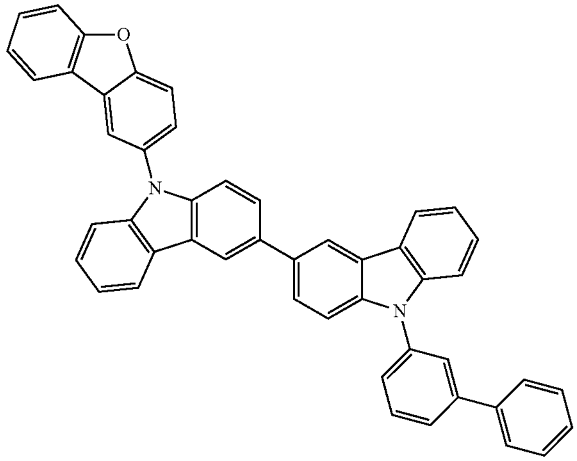
[B-39]
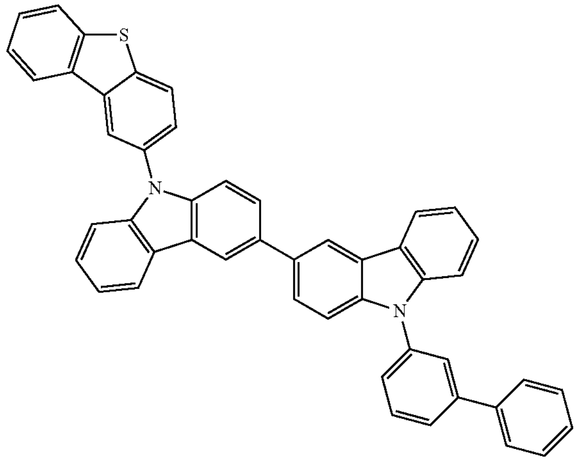
[B-40]
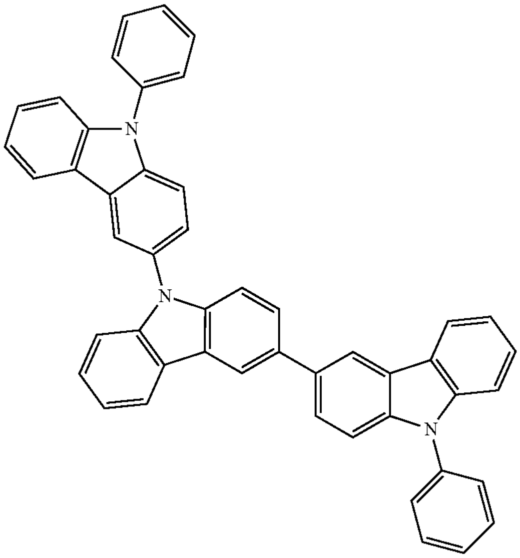
-continued
[B-41]
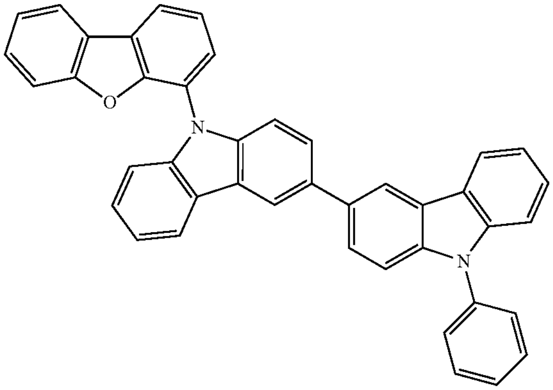
[B-42]
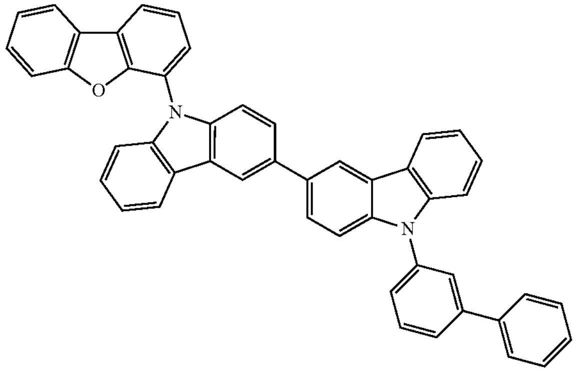
[B-43]
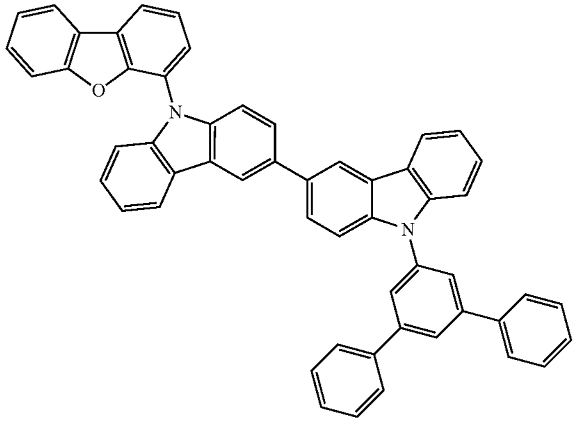

-continued
[B-44]
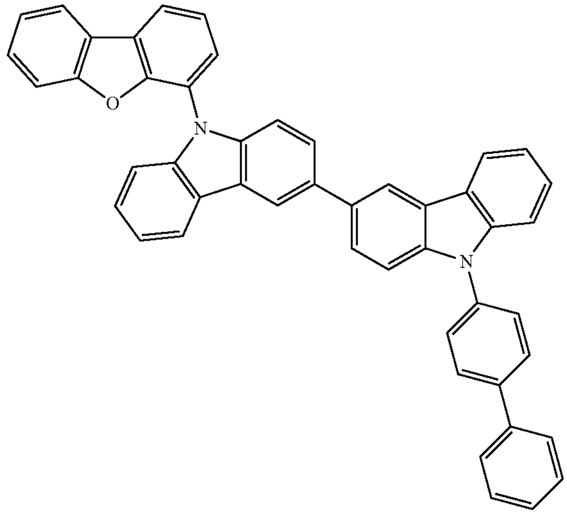
[B-45]
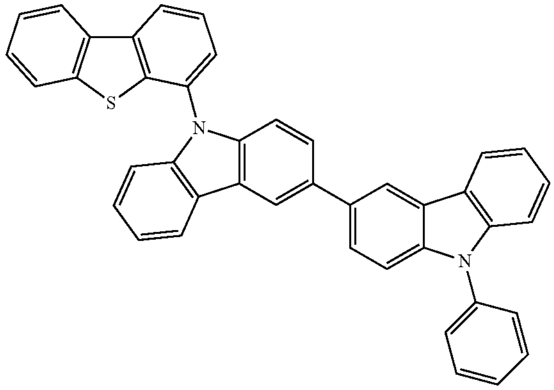
[B-46]
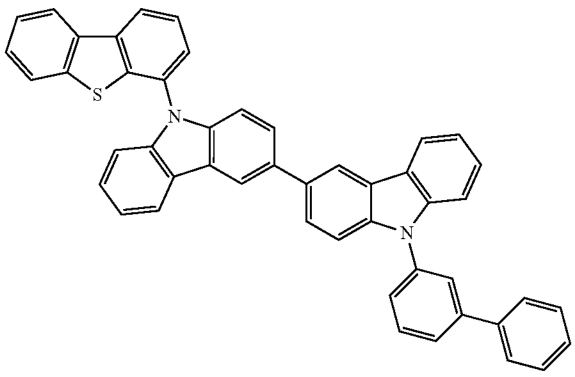
-continued
[B-47]
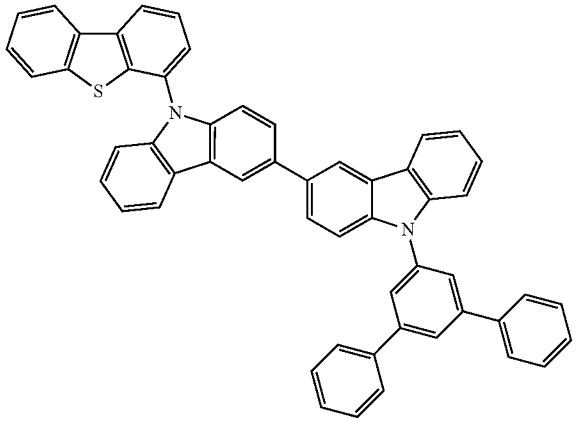
[B-48]
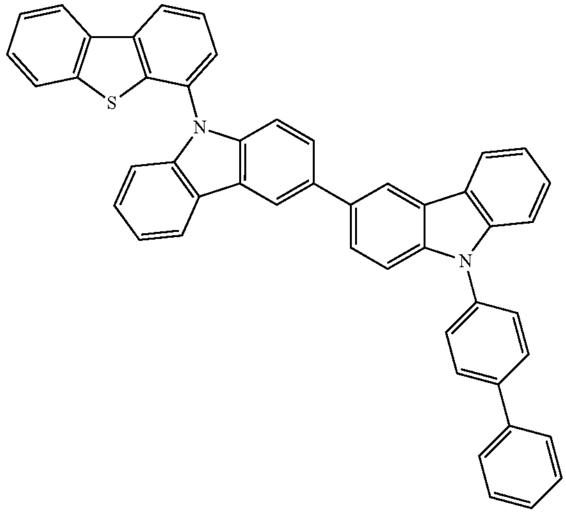
[B-49]
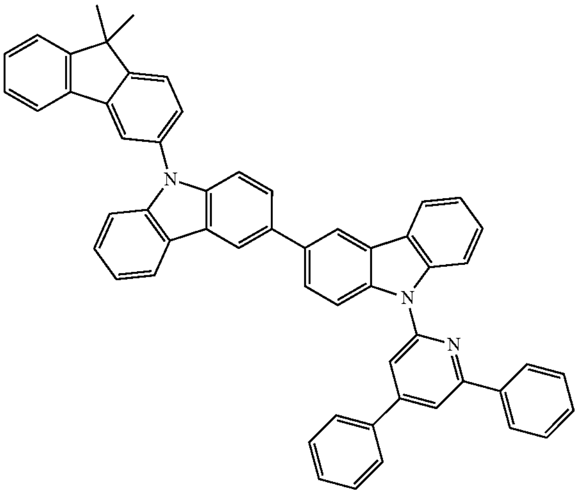

-continued
[B-50]
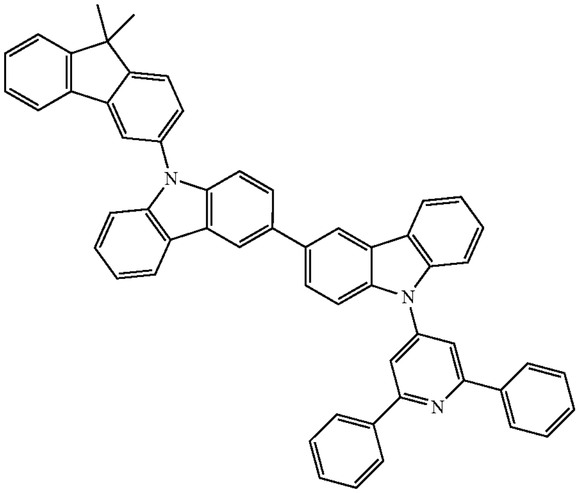
[B-51]
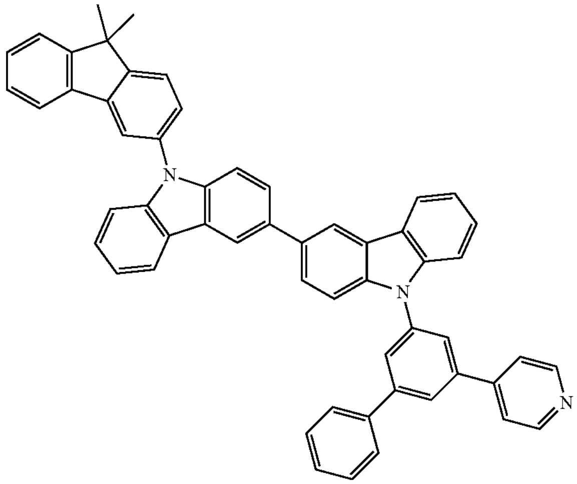
[B-52]
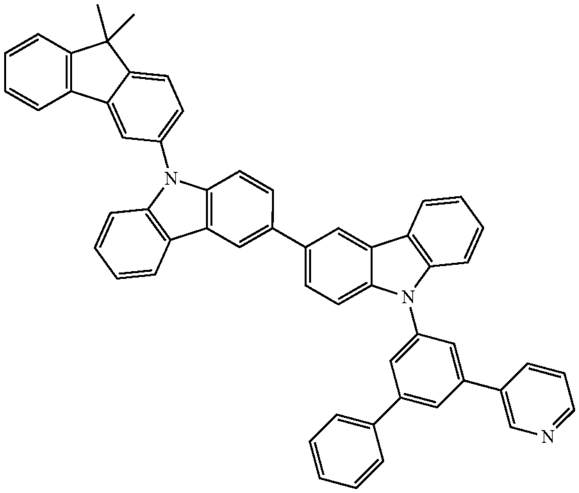
-continued
[B-53]
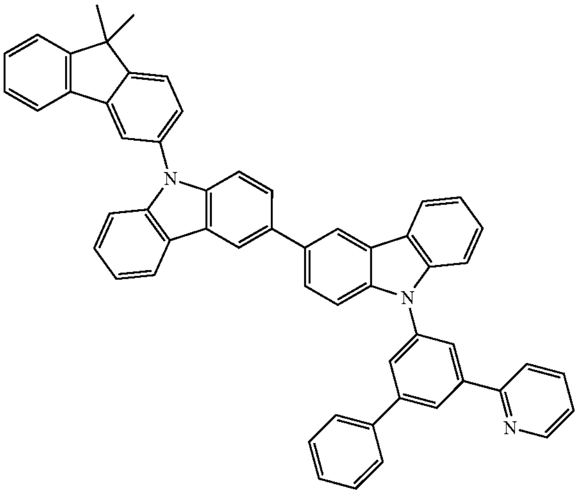
[B-54]
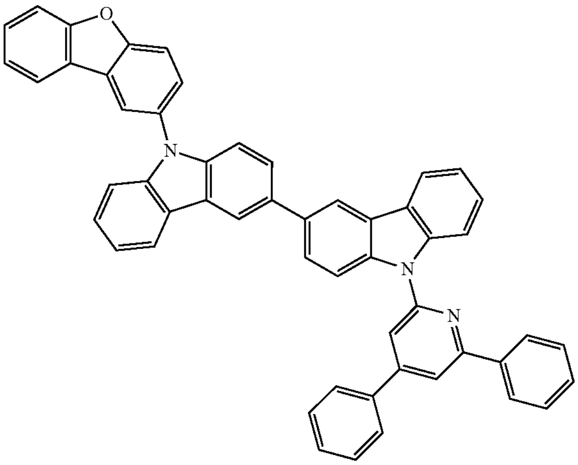
[B-55]
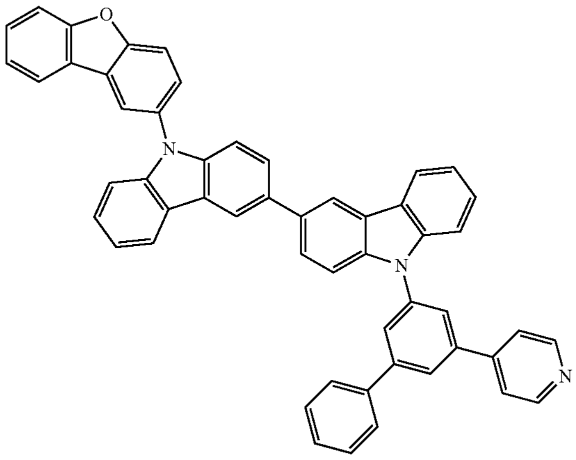

-continued
[B-56]
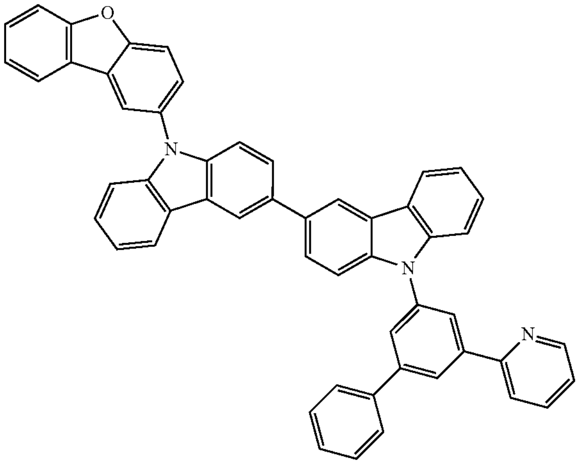
[B-57]
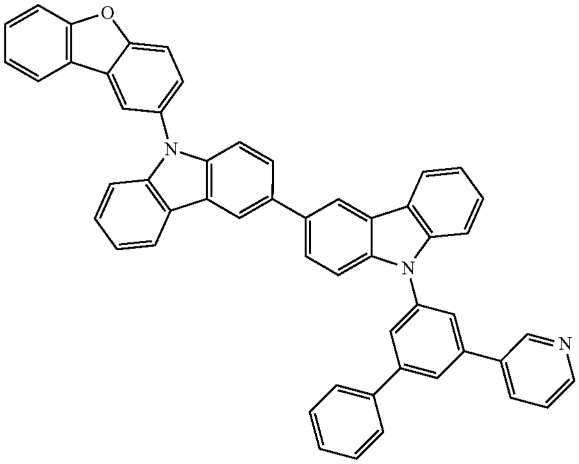
[B-58]
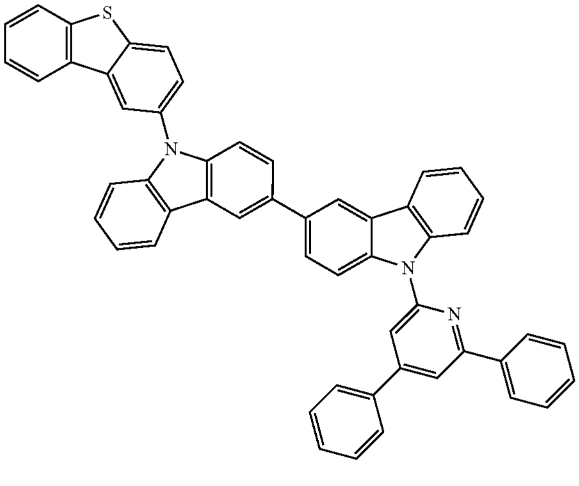
-continued
[B-59]
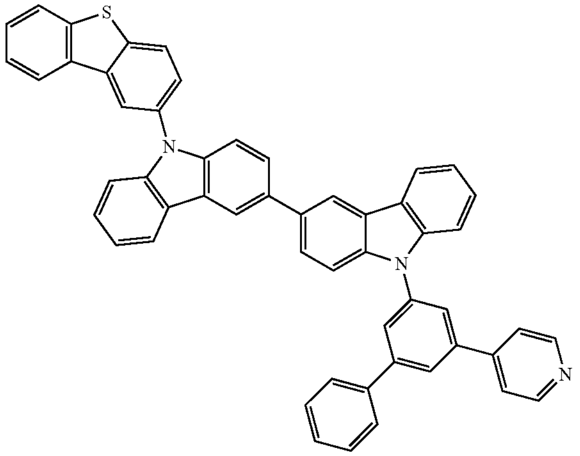
[B-60]
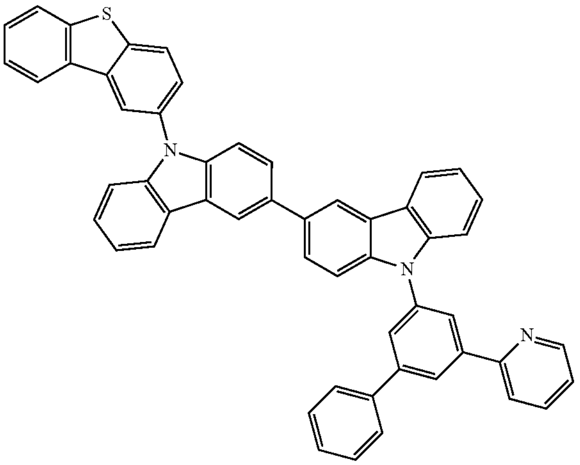
[B-61]
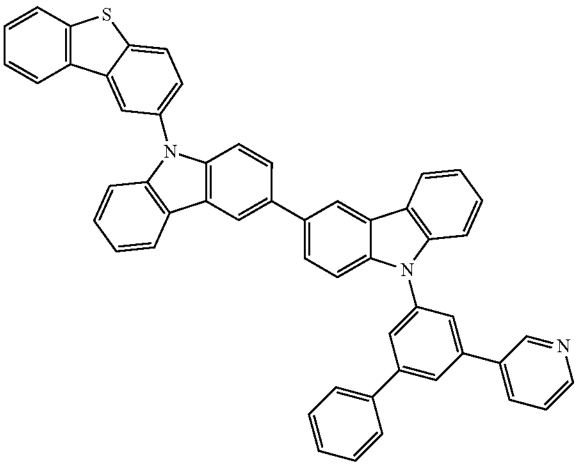

-continued
[B-62]
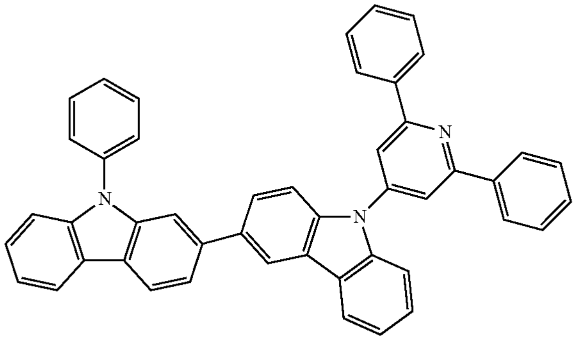
[B-63]
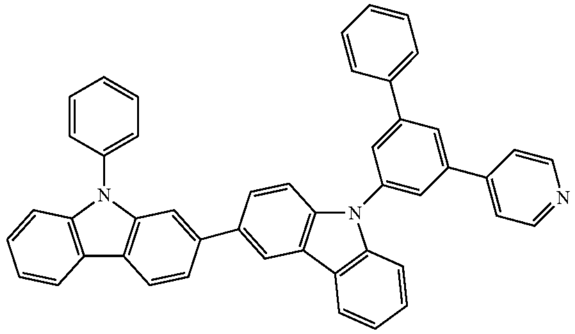
[B-64]
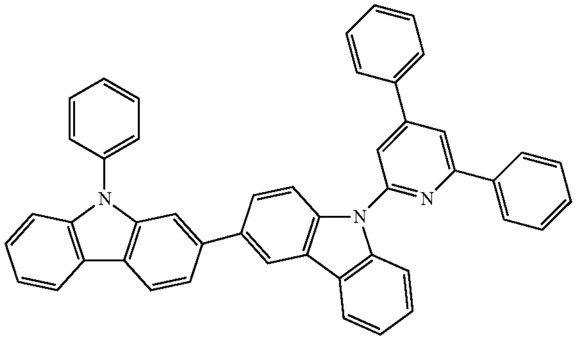
[B-65]
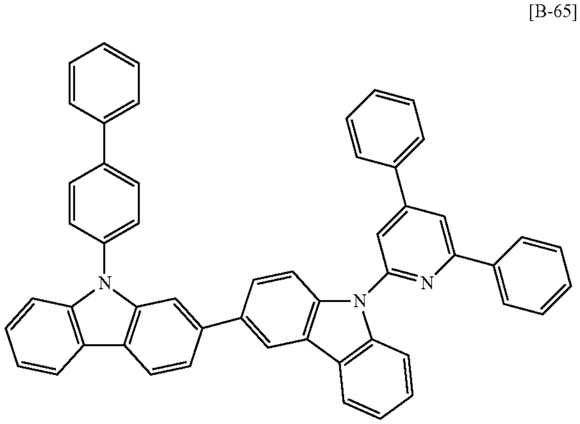
-continued
[B-66]
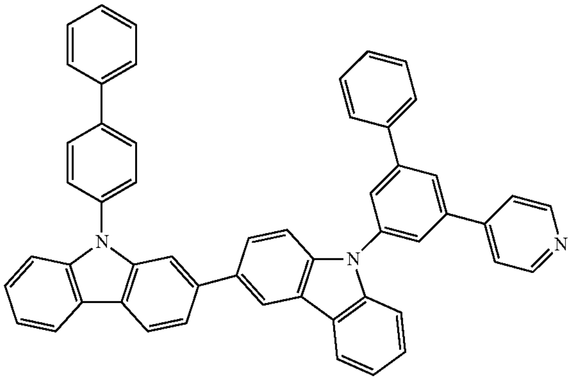
[B-67]
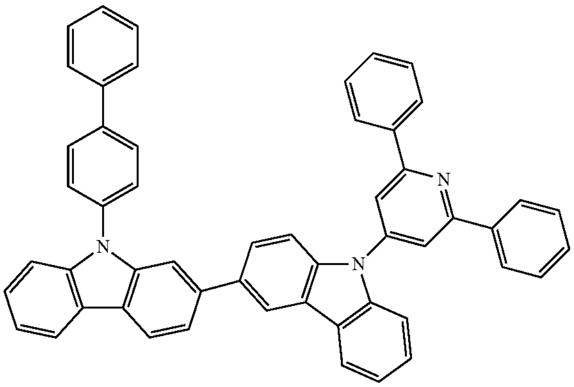
[B-68]
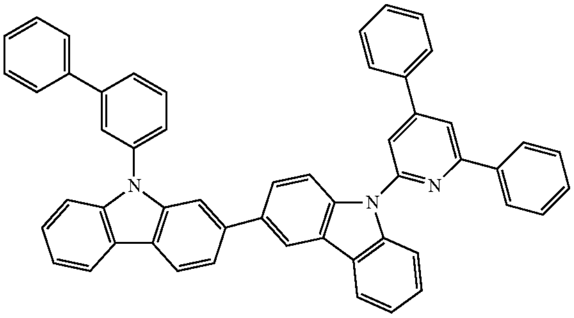
[B-69]
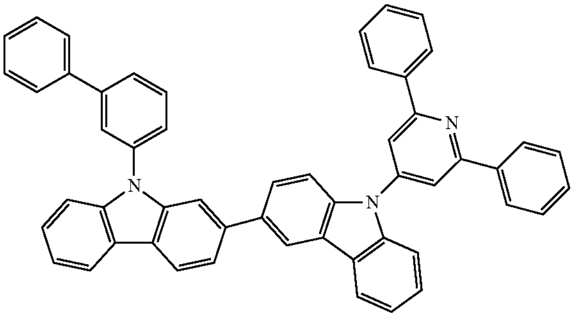

-continued
[B-70]
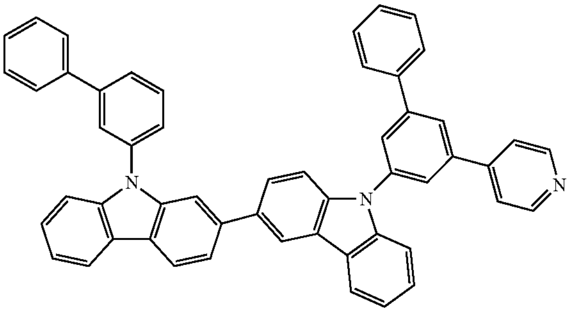
[B-71]
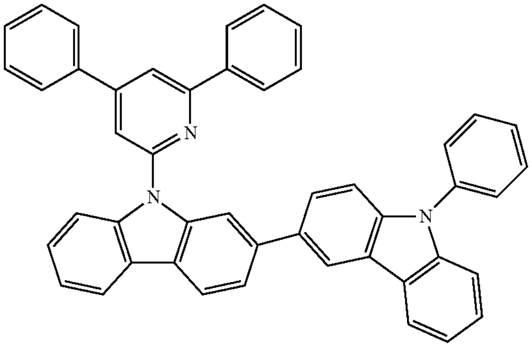
[B-72]
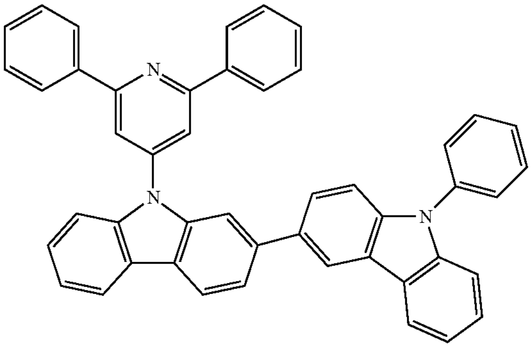
[B-73]
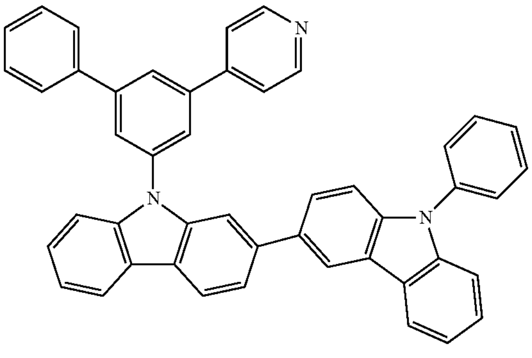
-continued
[B-74]
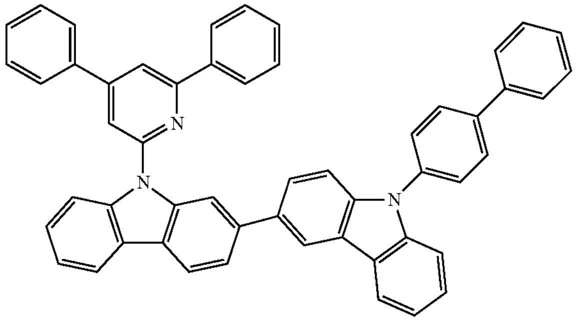
[B-75]
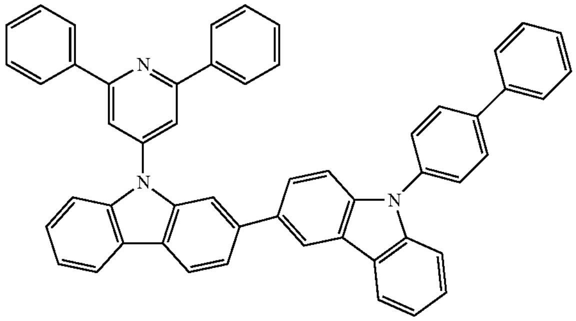
[B-76]
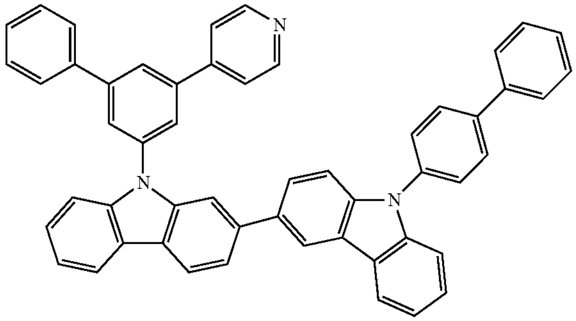
[B-77]
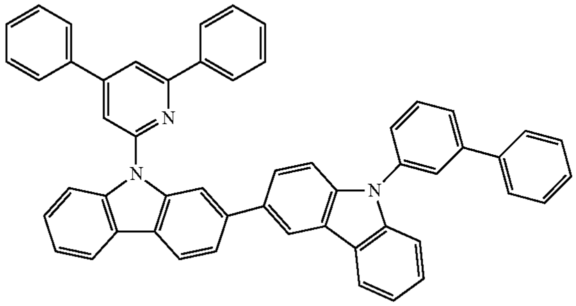

-continued
[B-78]
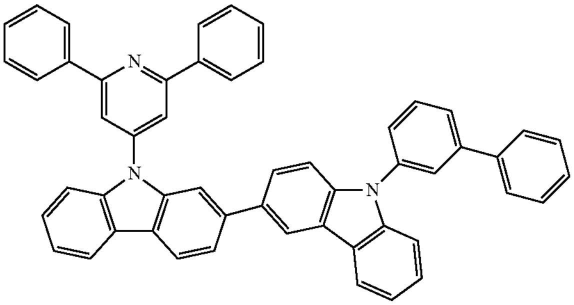
[B-79]
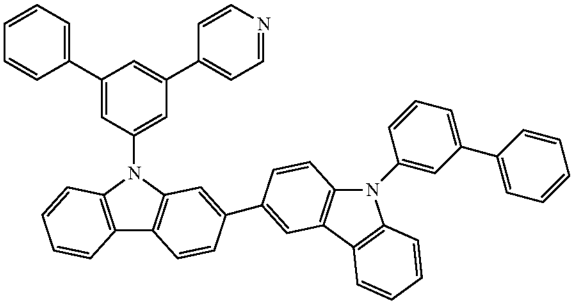
[B-80]
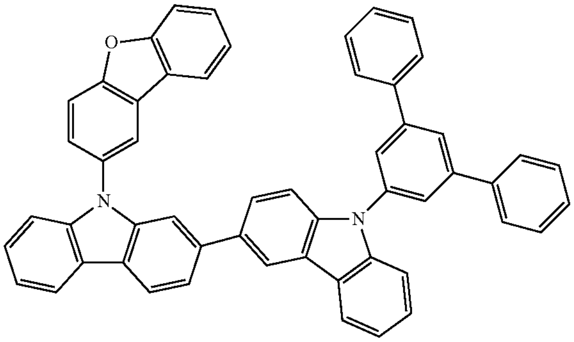
[B-81]
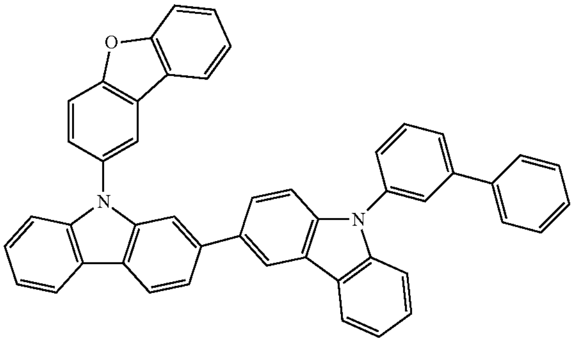
-continued
[B-82]
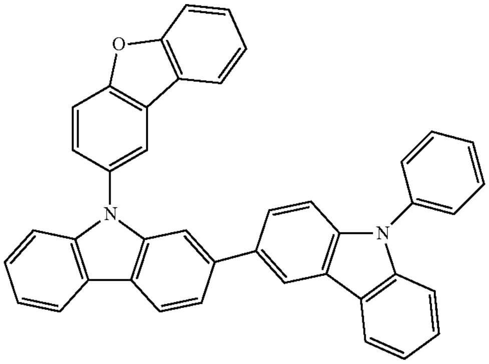
[B-83]
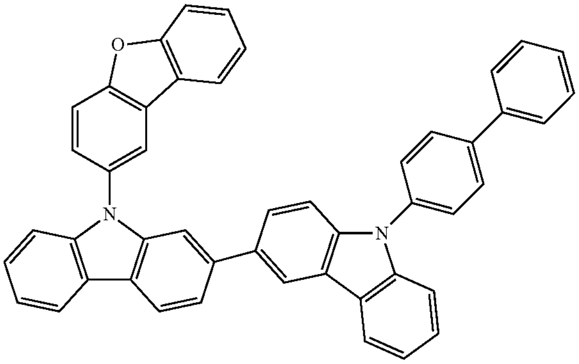
[B-84]
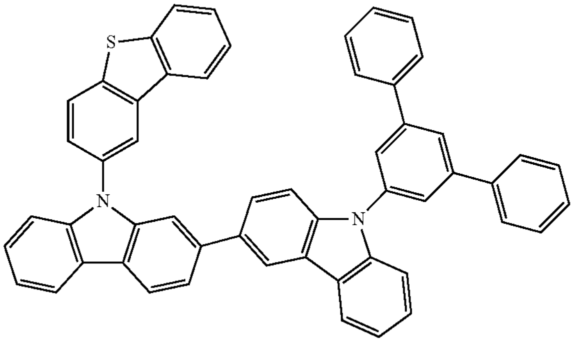
[B-85]
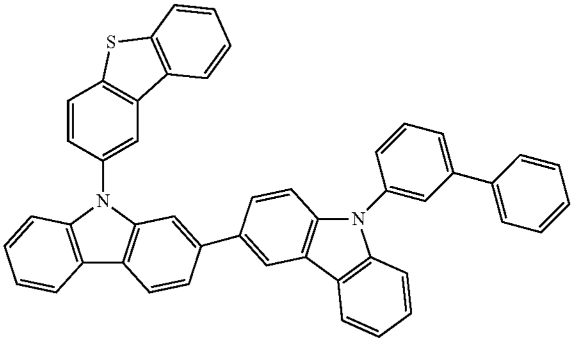

-continued
[B-86]
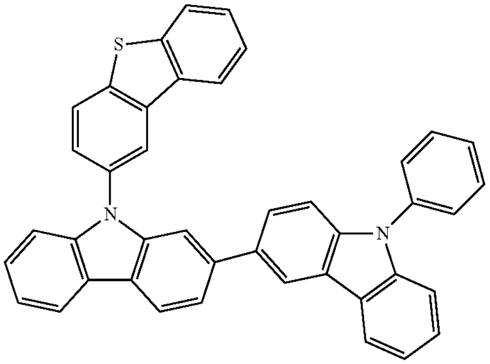
[B-87]
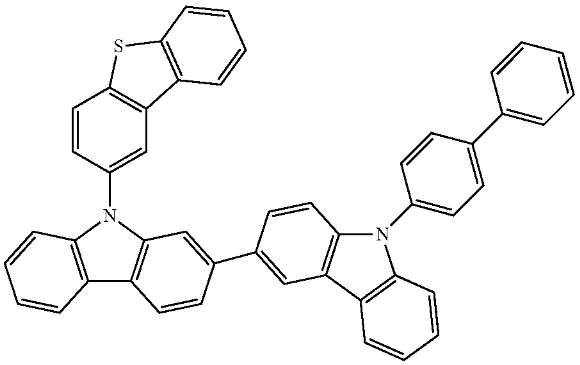
[B-88]
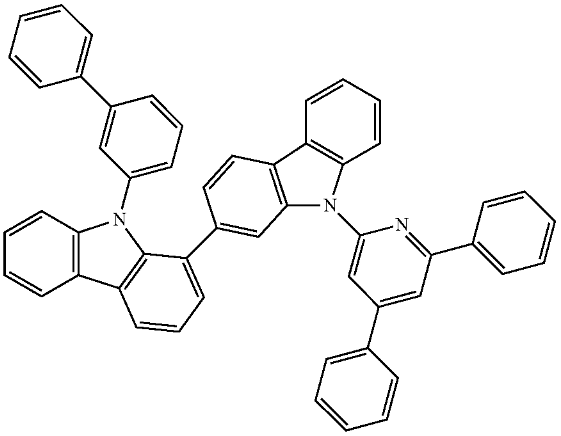
[B-89]
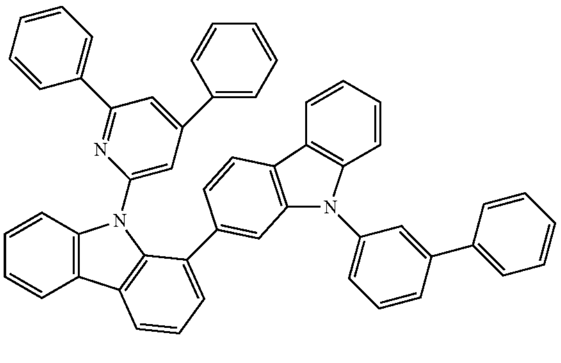
-continued
[B-90]
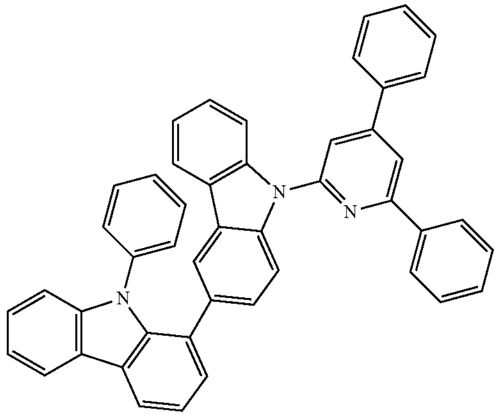
[B-91]
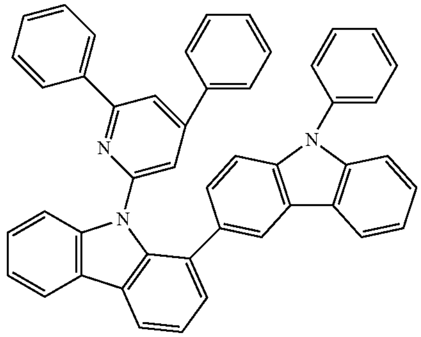
[B-92]
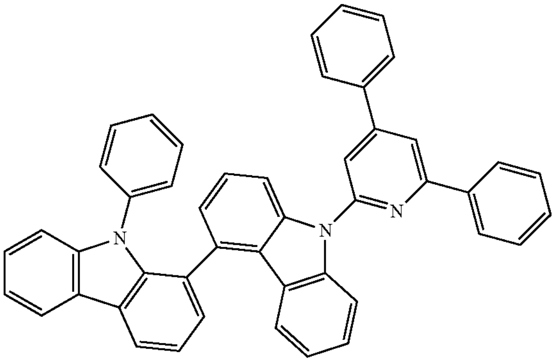
[B-93]
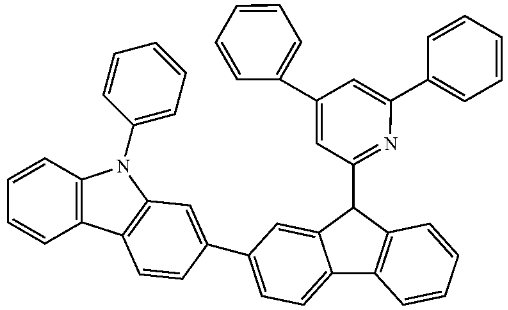

-continued
[B-94]
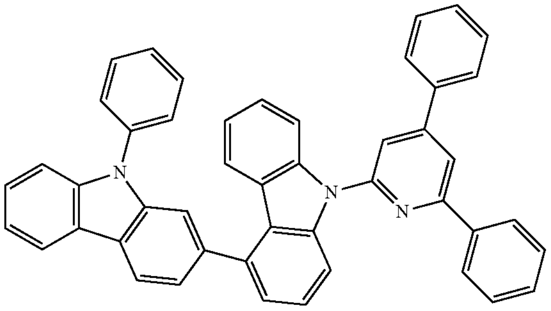
[B-95]
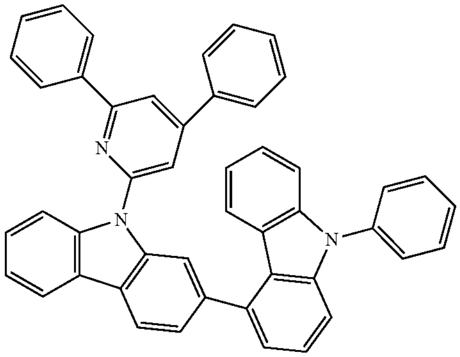
[B-95]
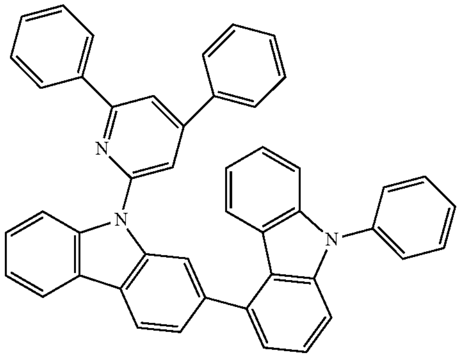
[B-96]
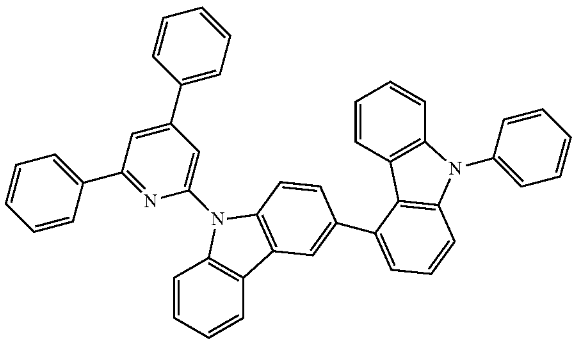
-continued
[B-97]
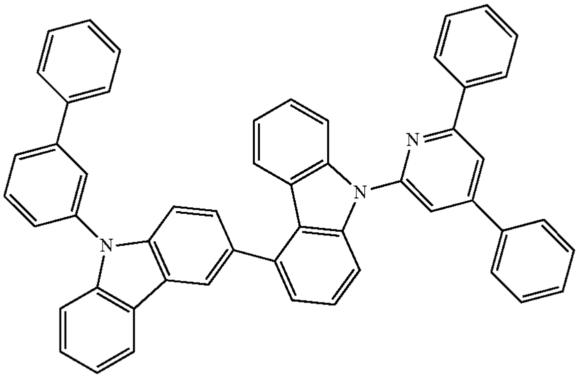
[B-98]
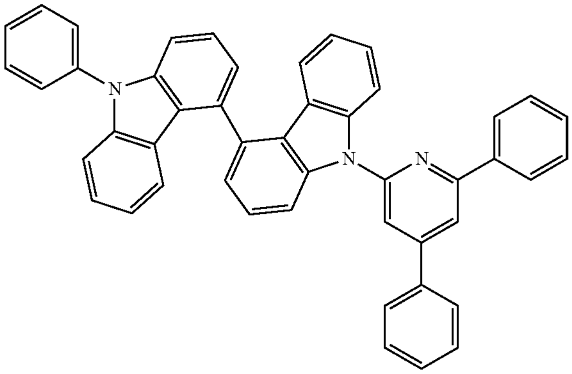
[B-99]
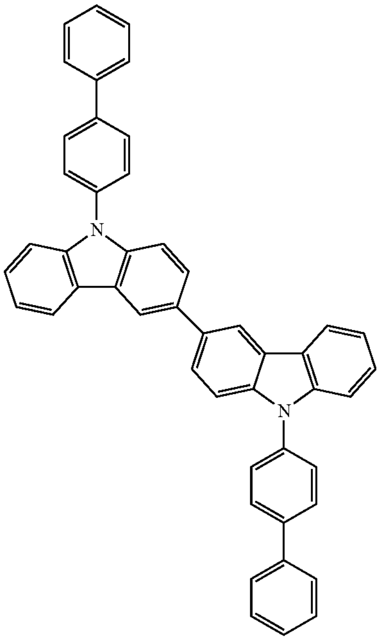

-continued
[B-100]
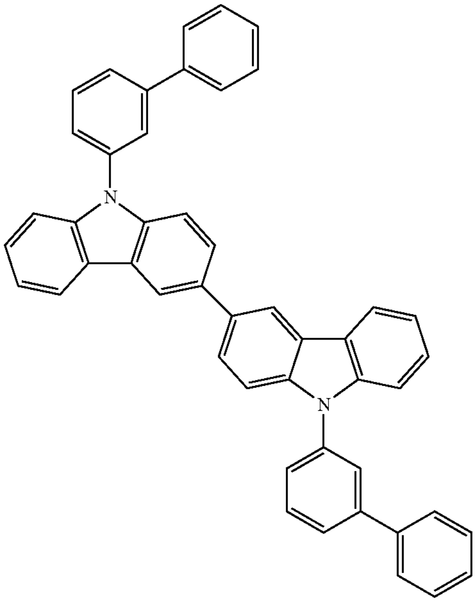
[B-101]
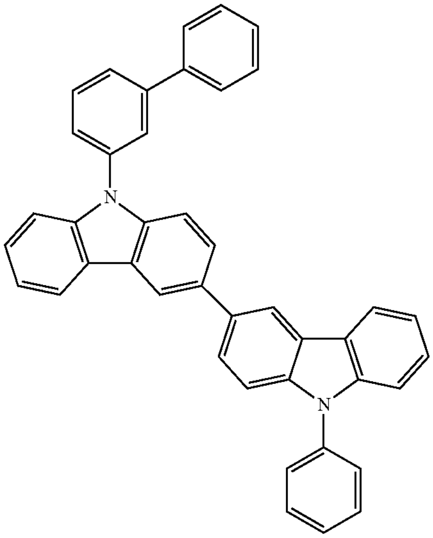
[B-102]
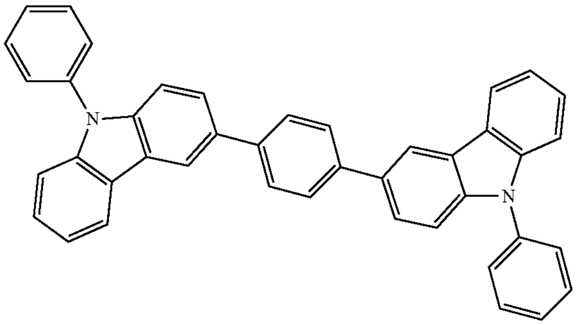
-continued
[B-103]
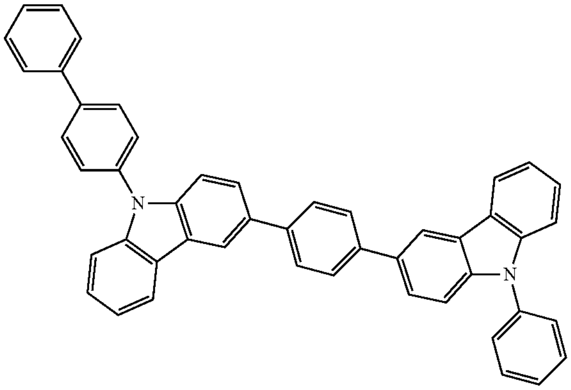
[B-104]
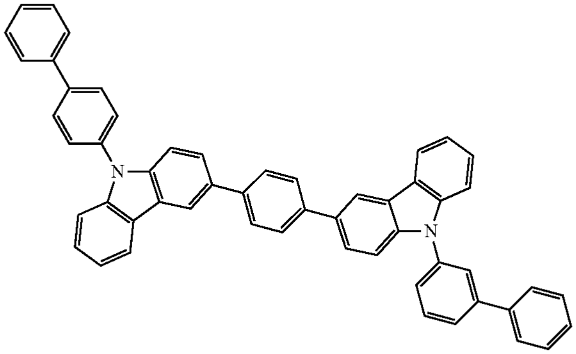
[B-105]
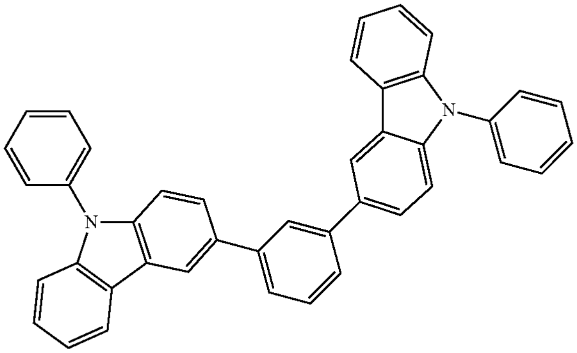
[B-106]
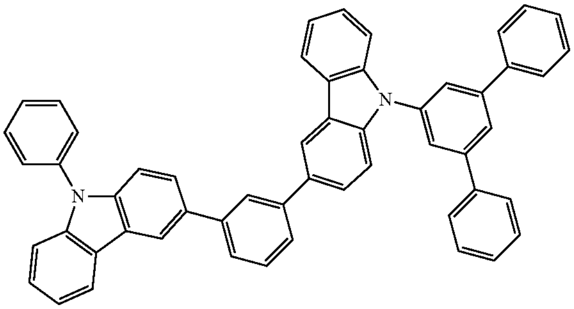

[B-107]
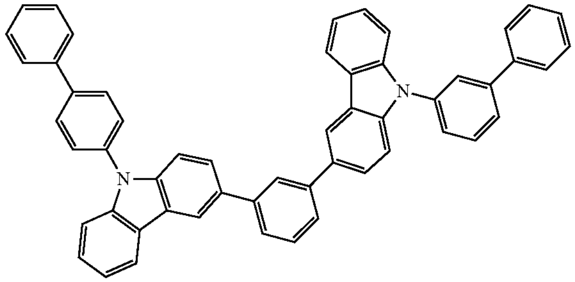
[B-108]
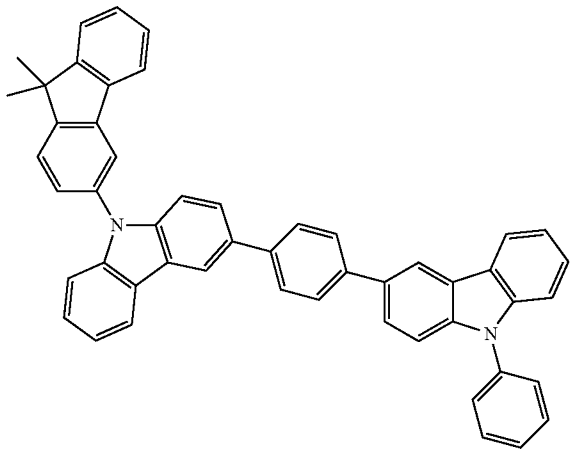
[B-109]
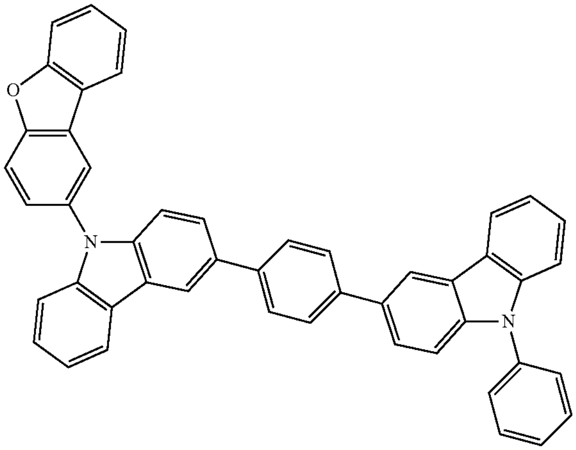
[B-110]
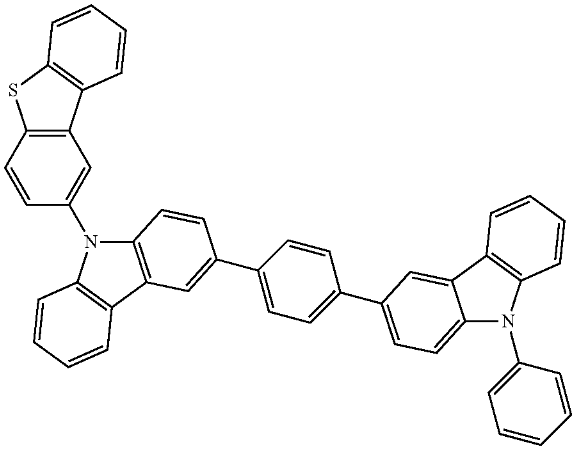
[B-111]
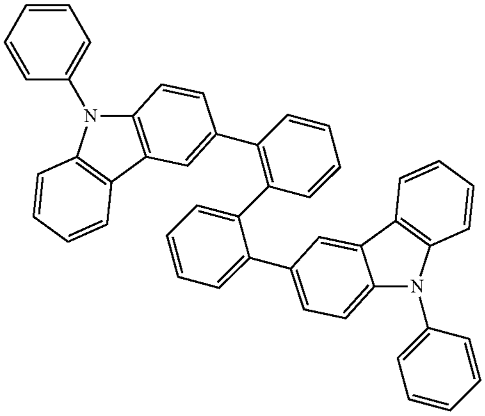
[B-112]
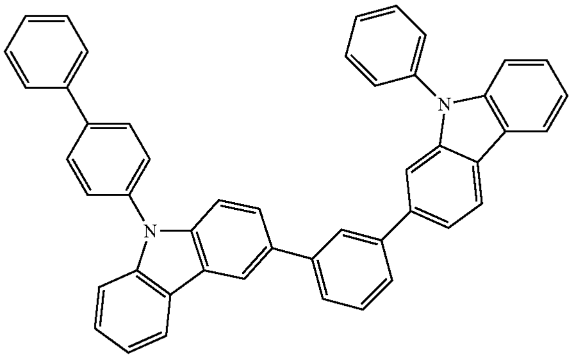

[B-113]
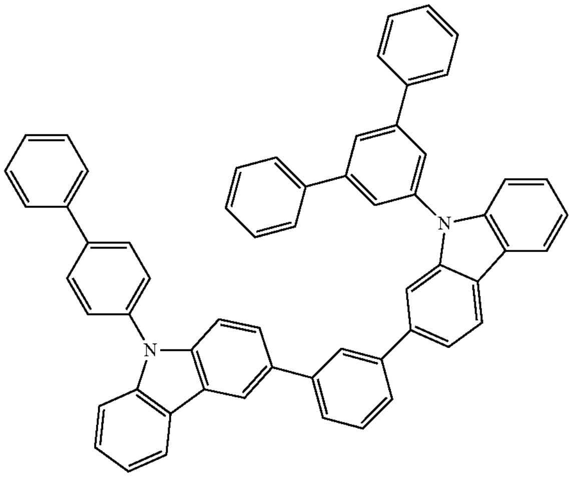
[B-114]
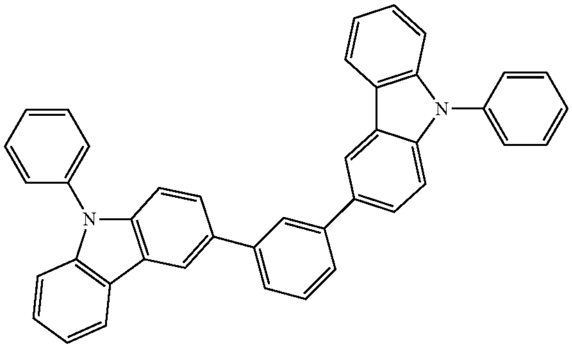
[B-115]
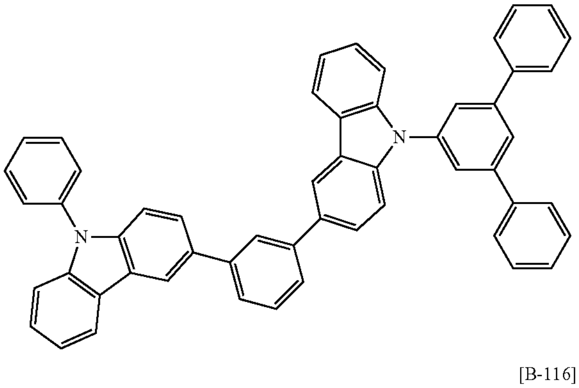
[B-116]
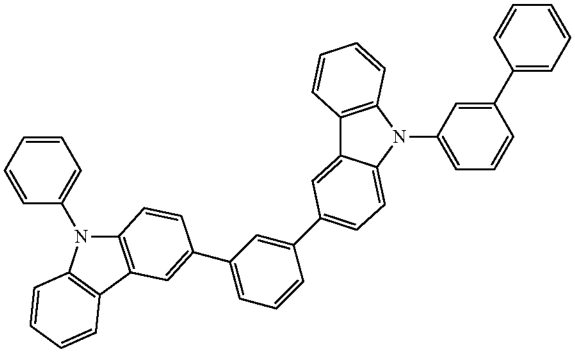
[B-117]
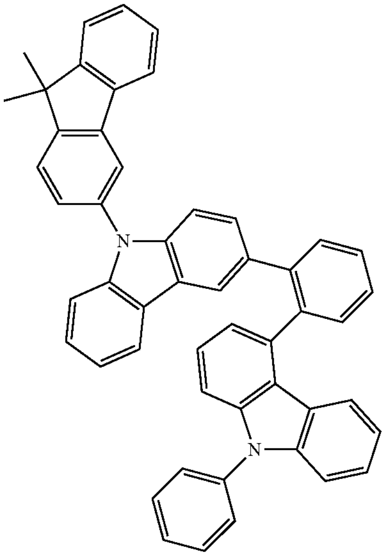
[B-118]
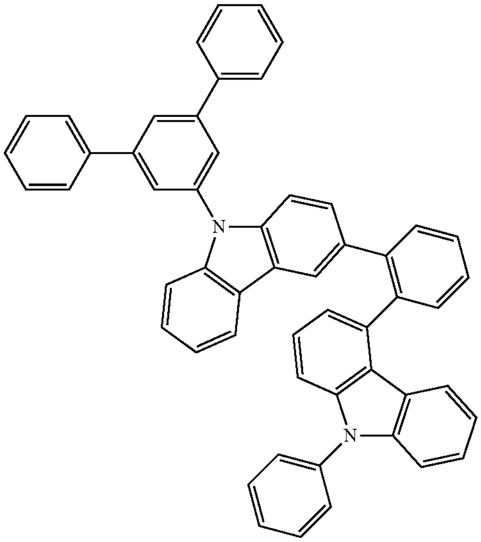

-continued
[B-119]
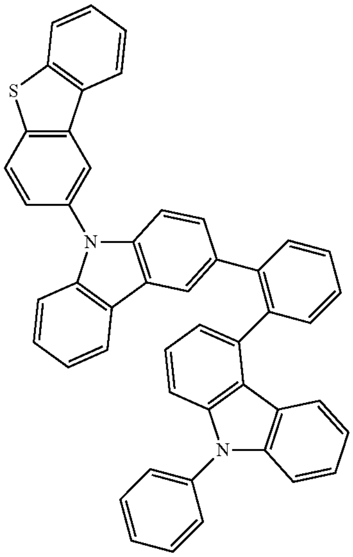
[B-120]
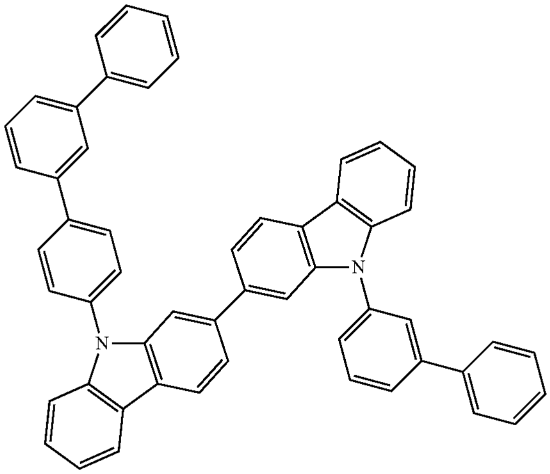
[B-121]
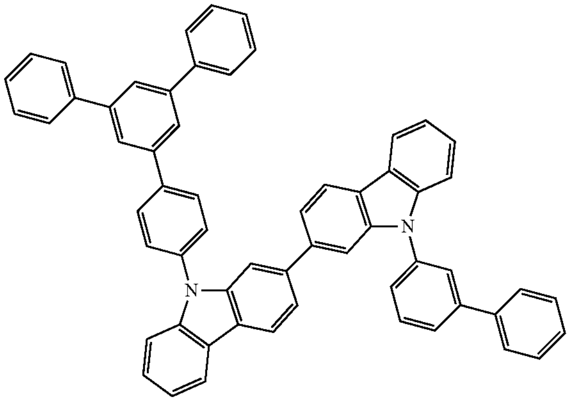
-continued
[B-122]
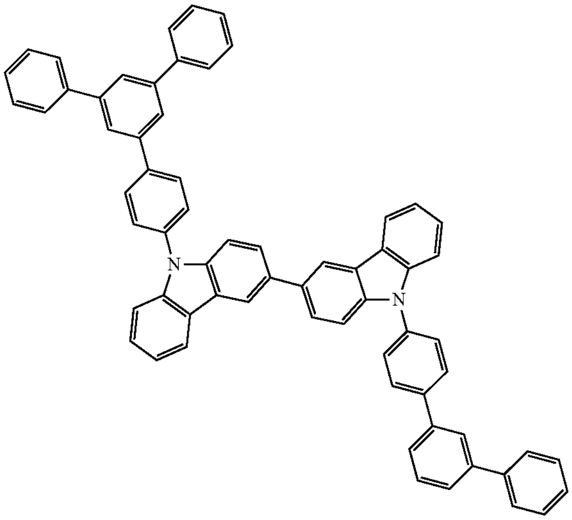
[B-123]
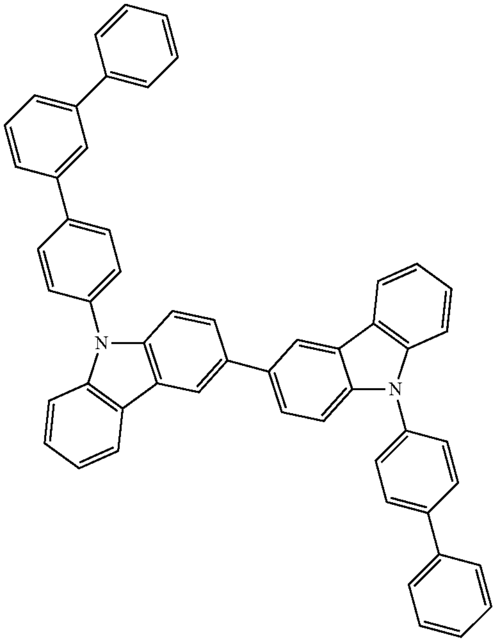

-continued
[B-124]
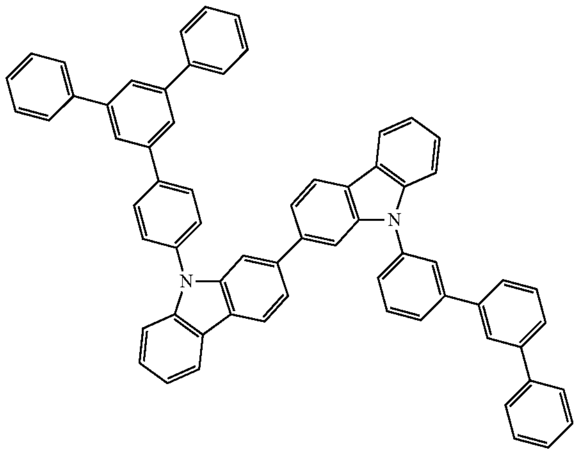
[B-125]
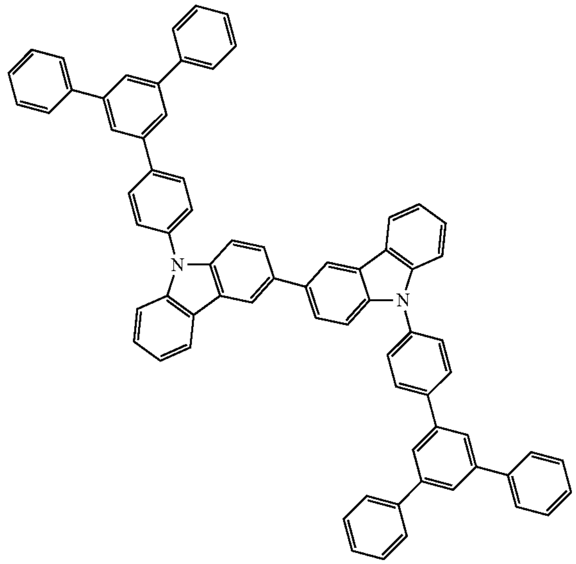
[B-126]
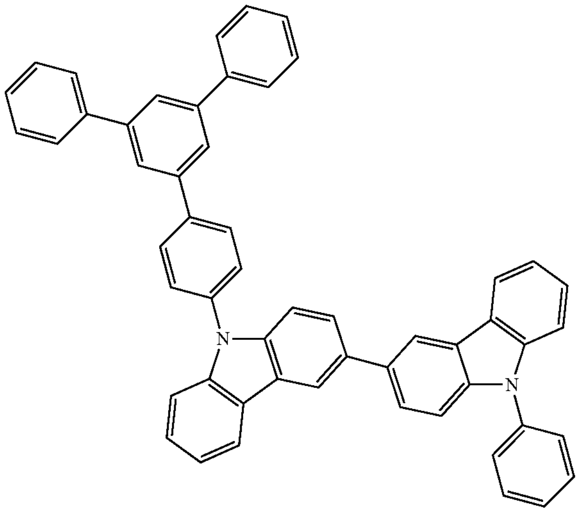
-continued
[B-127]
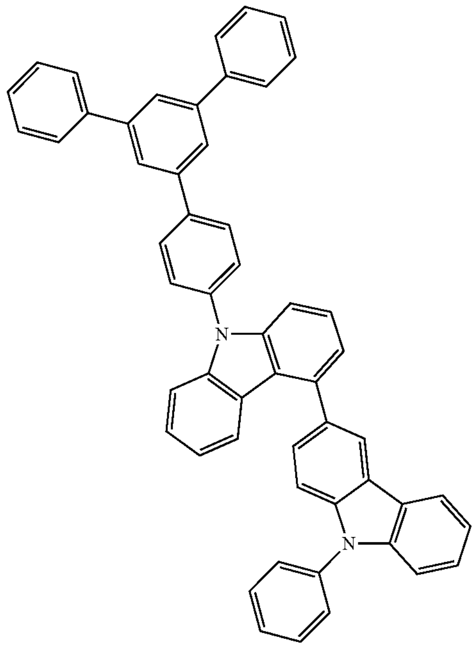
[B-128]
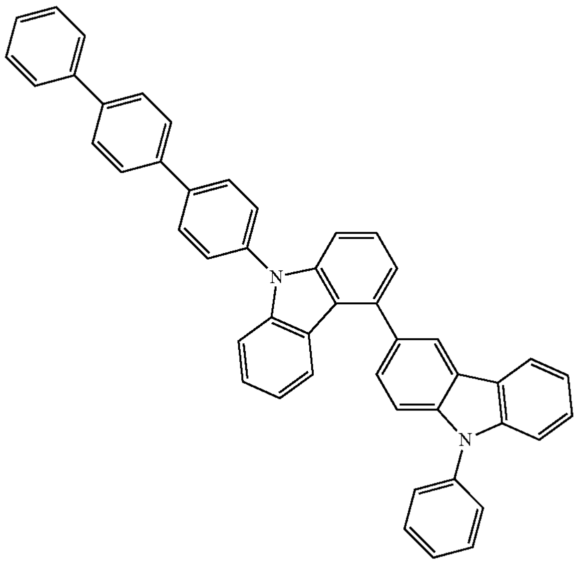

-continued
[B-129]
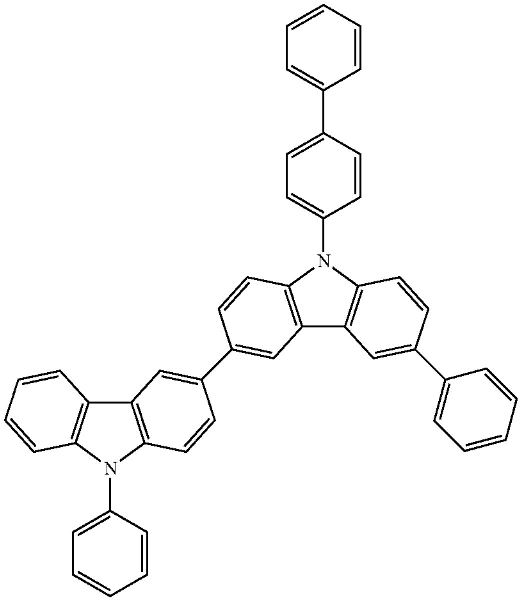
[B-130]
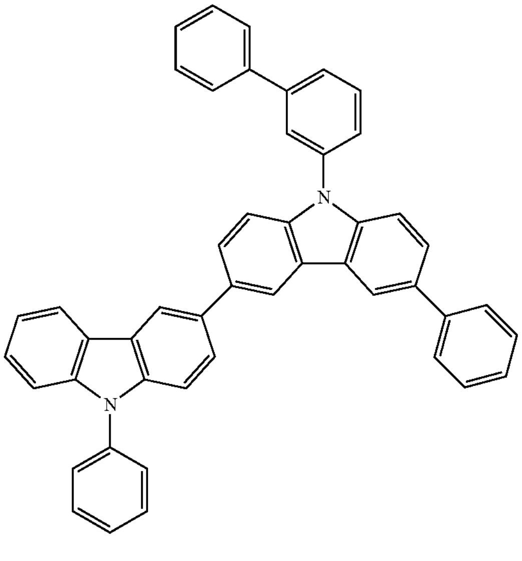
-continued
[B-131]
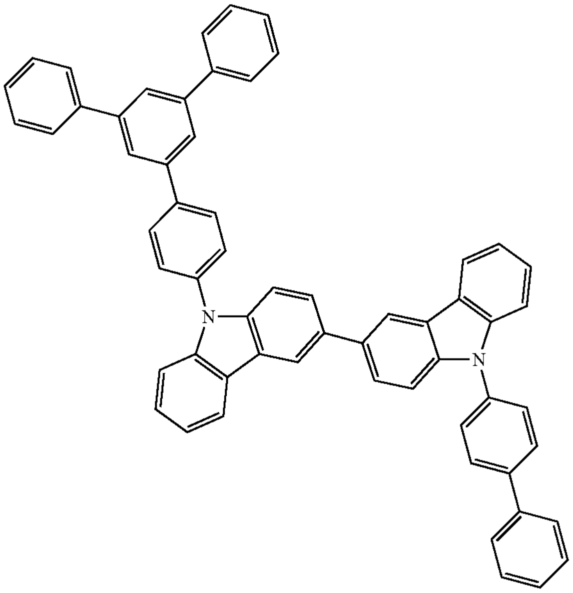
[B-132]
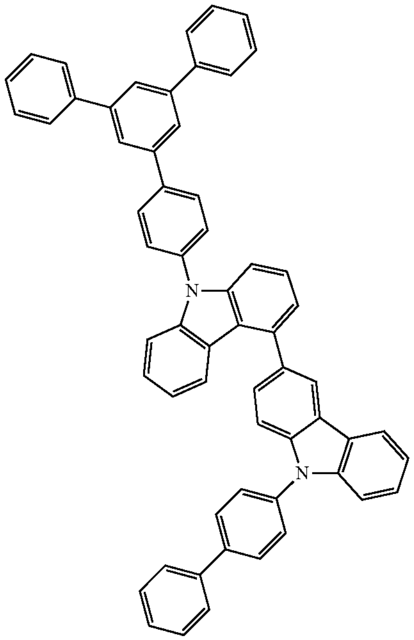

-continued
[B-133]
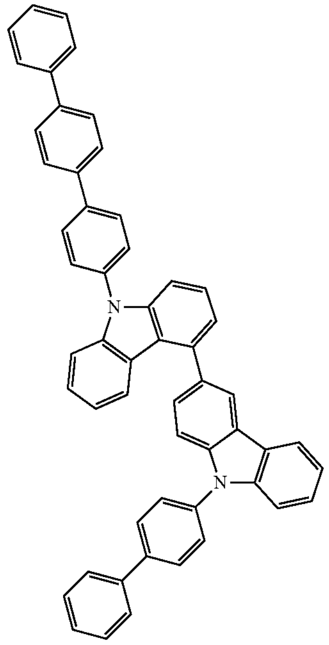
[B-134]
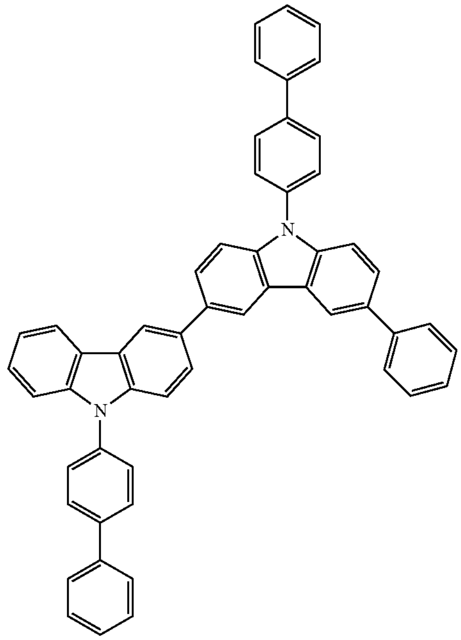
-continued
[B-135]
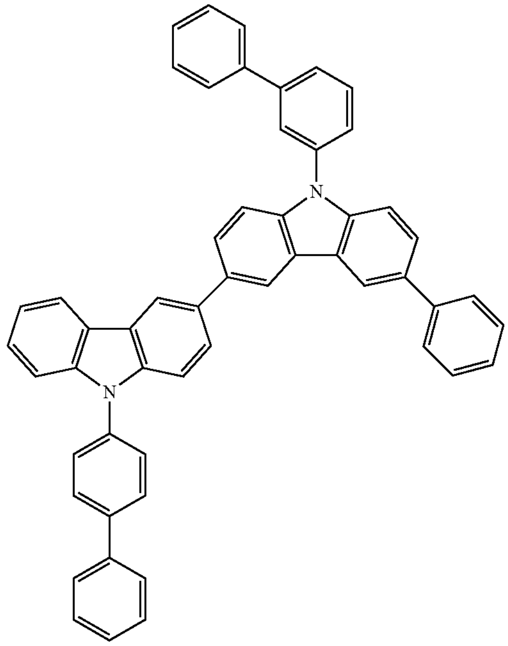
[B-136]
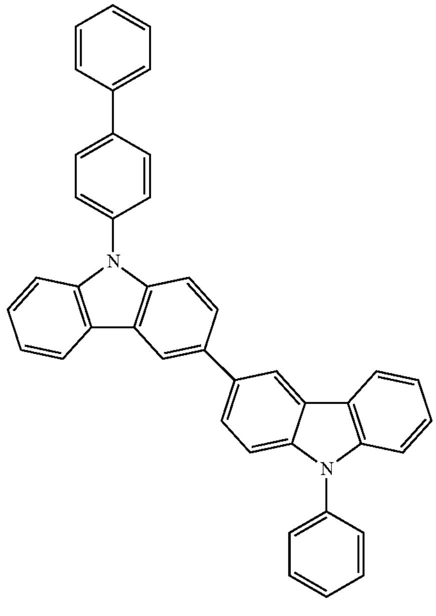

-continued
[B-137]
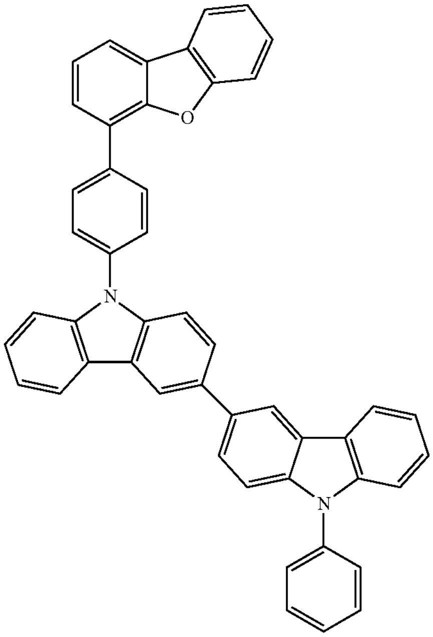
[B-138]
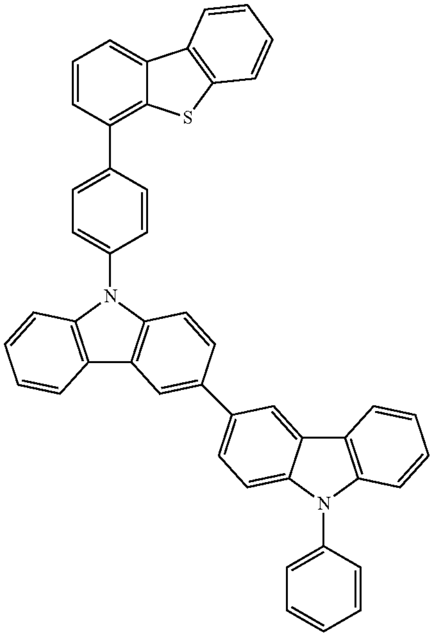
-continued
[B-139]
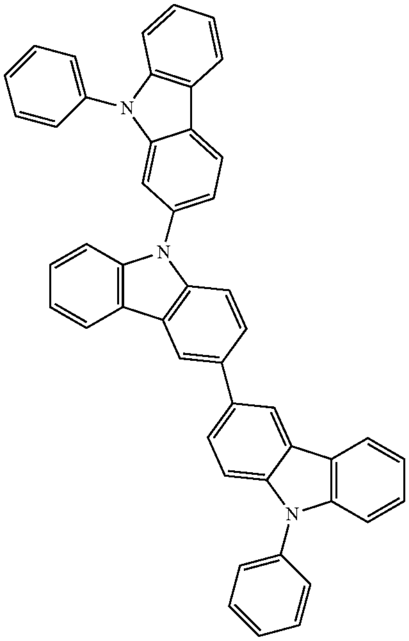
[B-140]
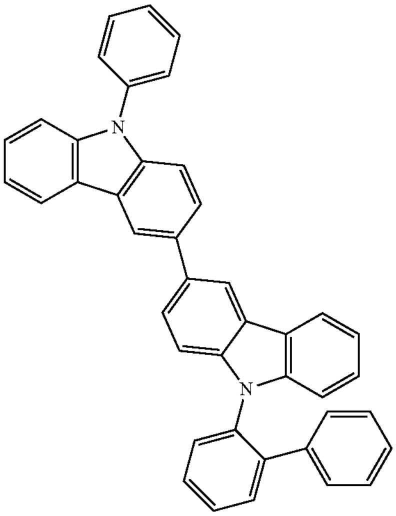
[B-141]
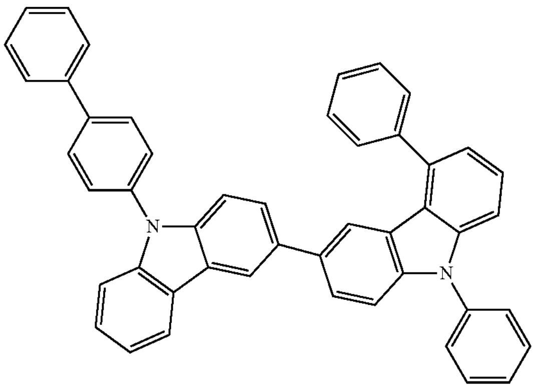

-continued
[B-142]
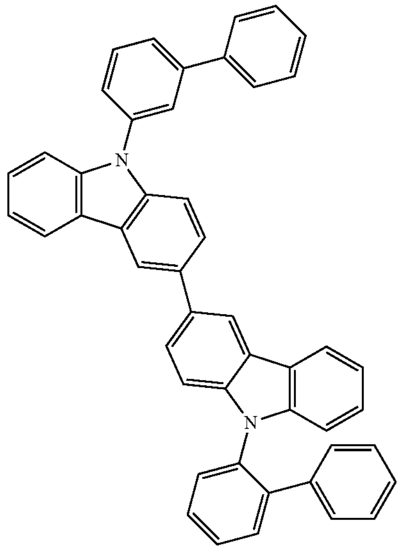
[B-143]
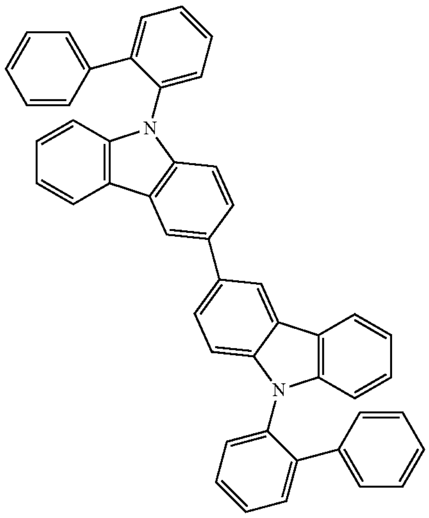
-continued
[B-144]
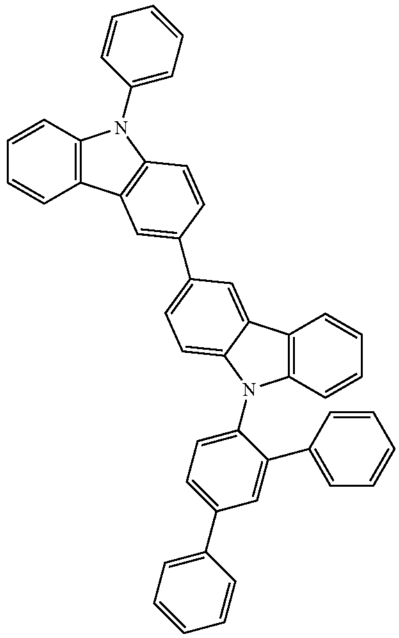
[B-145]
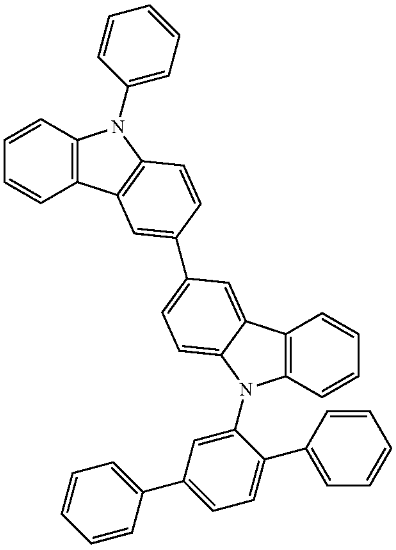

-continued
[B-146]
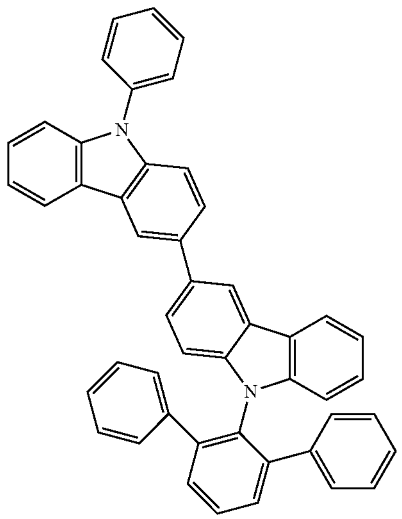
[B-147]
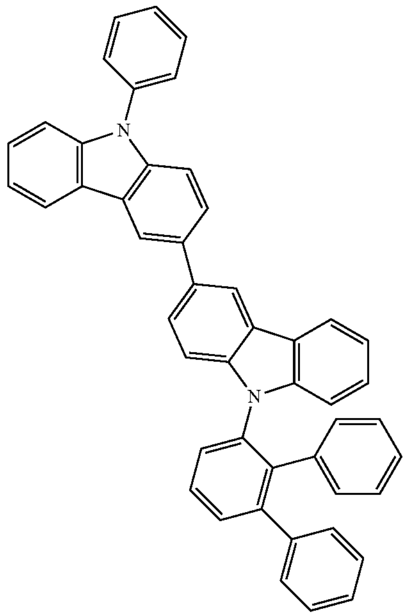
-continued
[B-148]
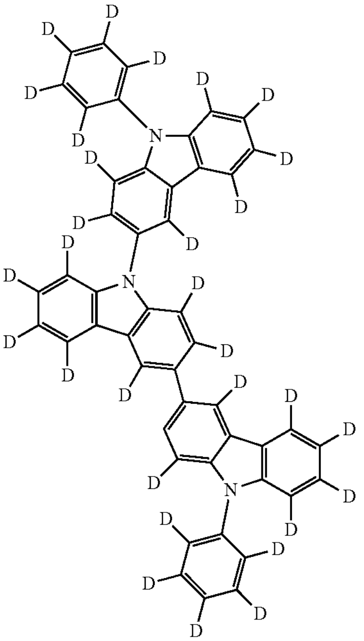
[B-149]
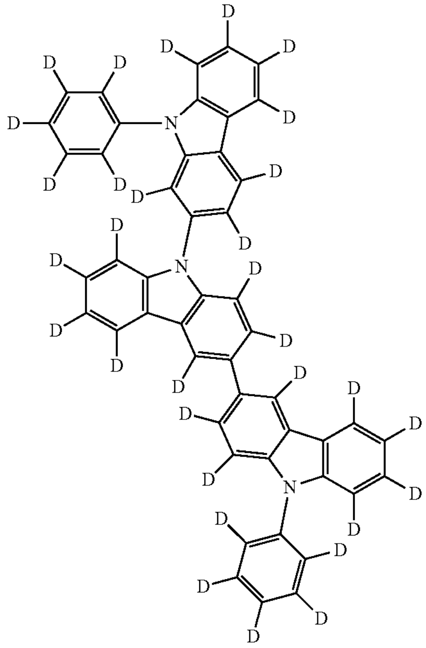

-continued
[B-150]
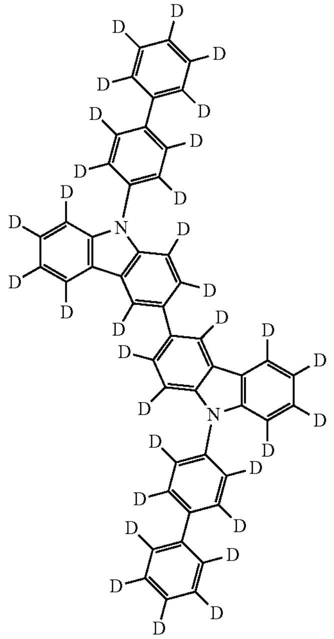
[B-151]
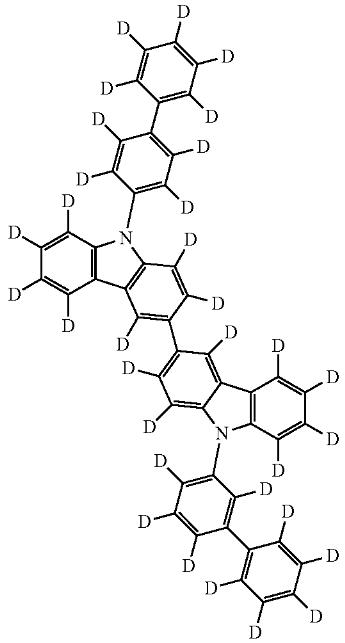
-continued
[B-152]
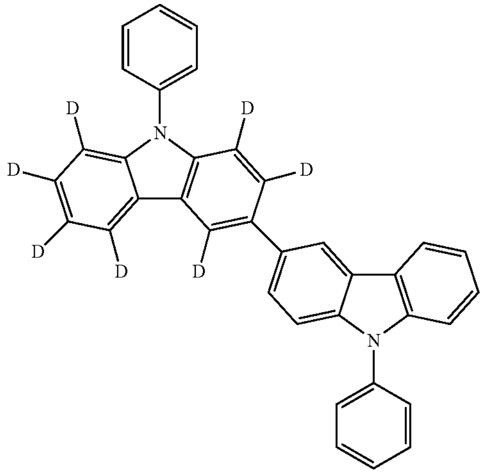
[B-153]
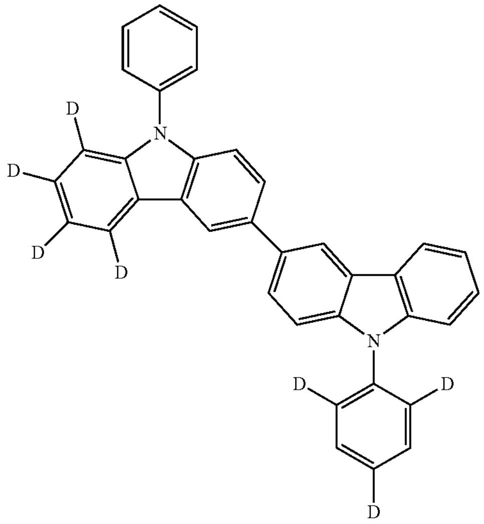
[B-154]
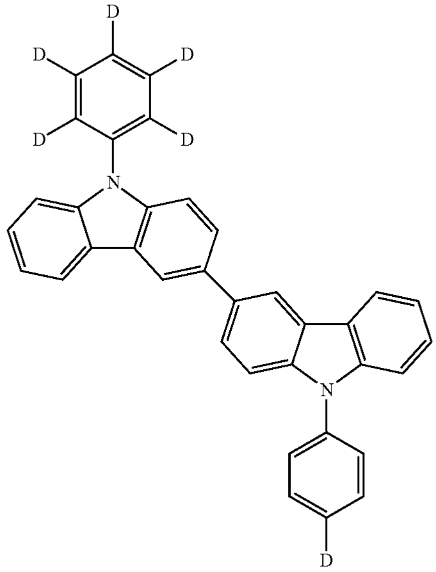

-continued
[B-155]
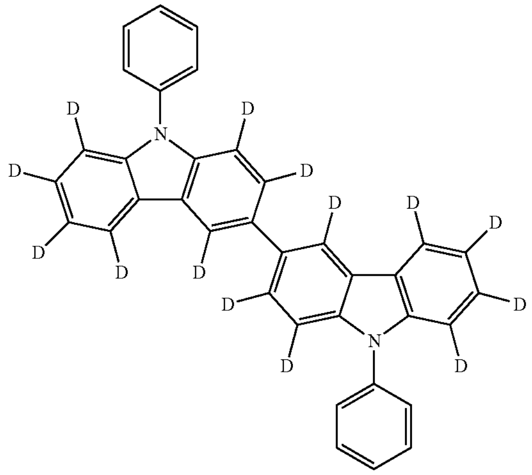
[B-156]
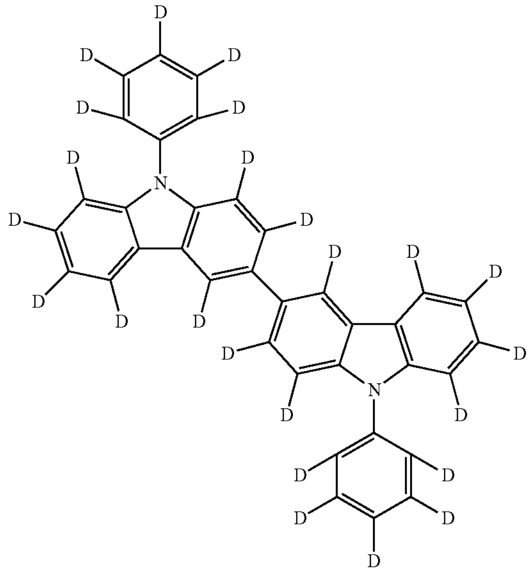
-continued
[B-157]
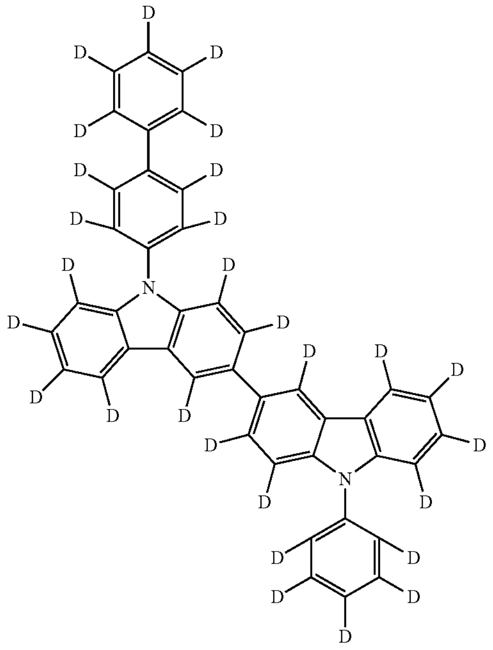
[B-158]
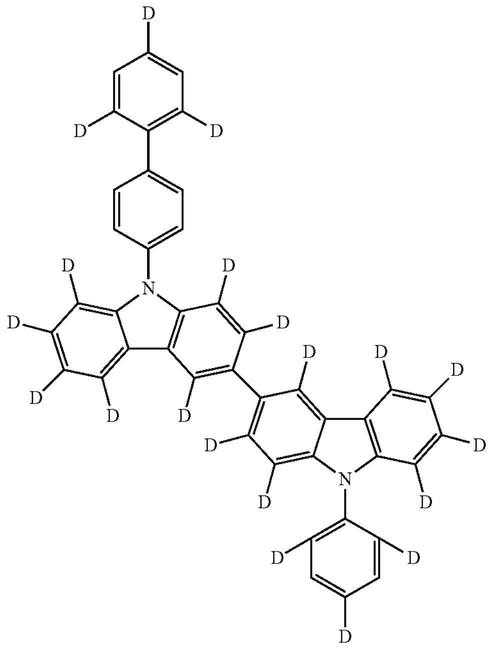

-continued
[B-159]
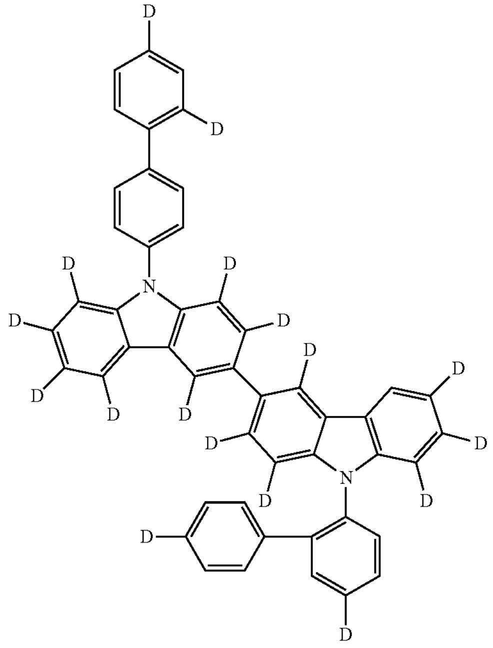
[B-160]
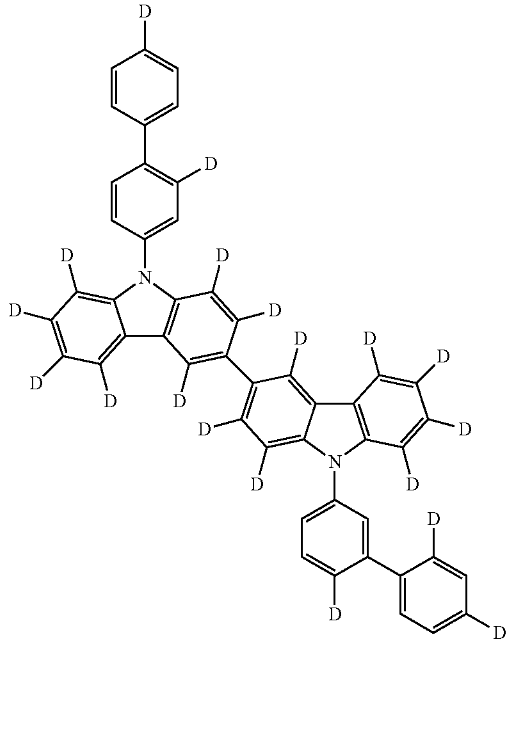
-continued
[B-161]
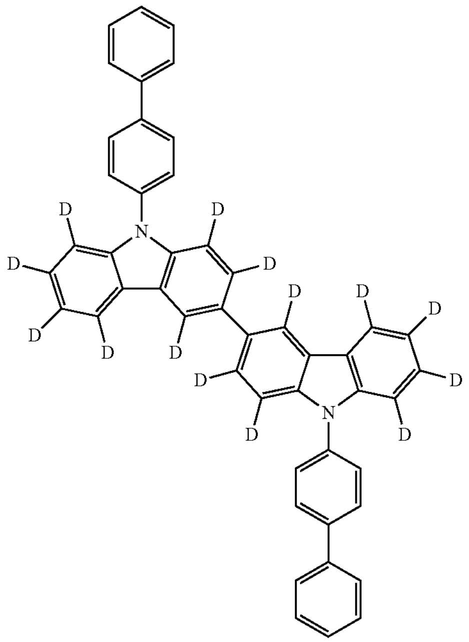
[B-162]
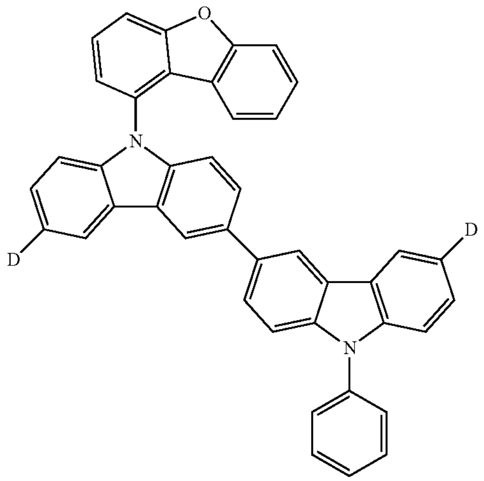

-continued
[B-163]
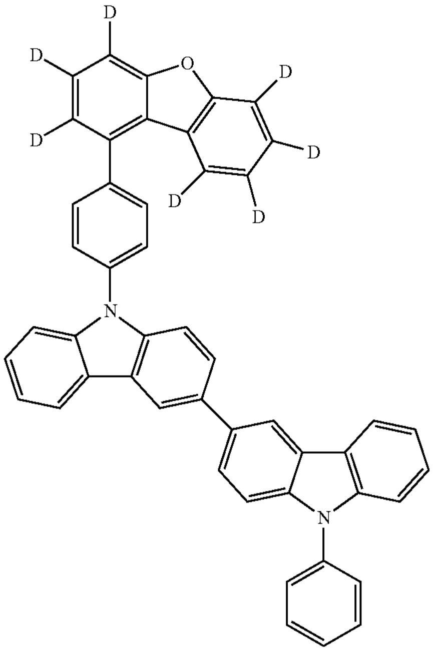
[B-164]
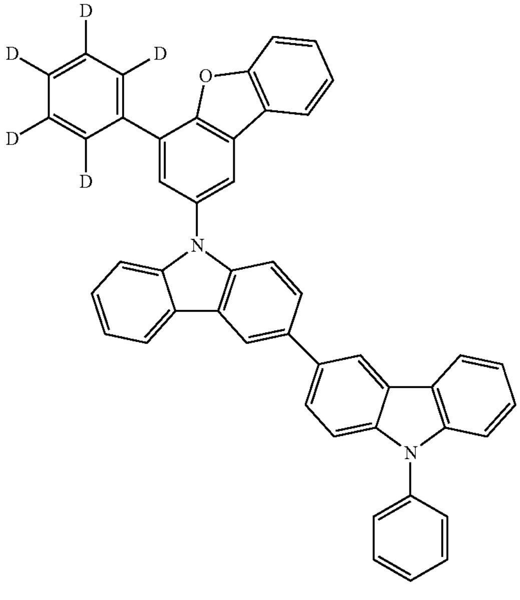
-continued
[B-165]
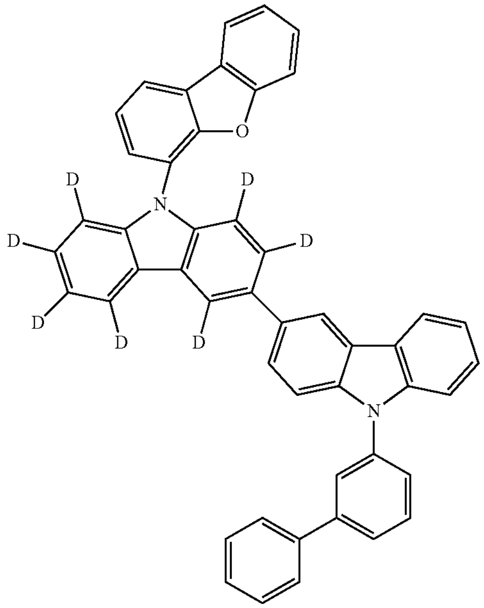
[B-166]
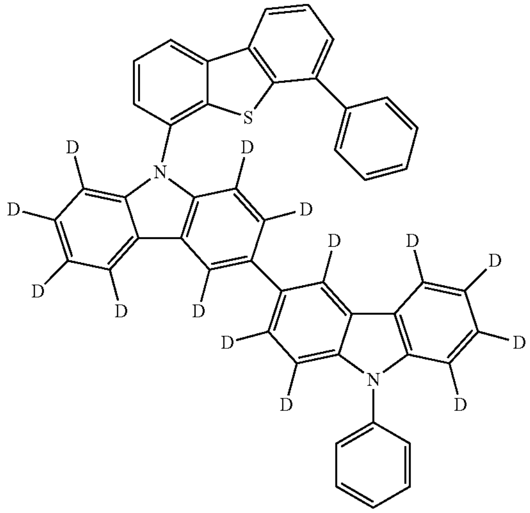
[B-167]
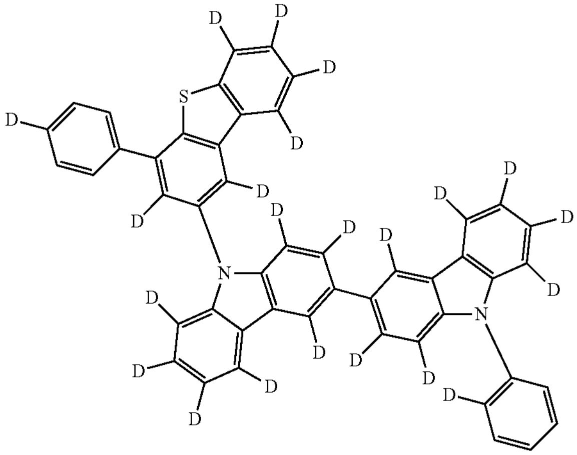

-continued
[B-168]
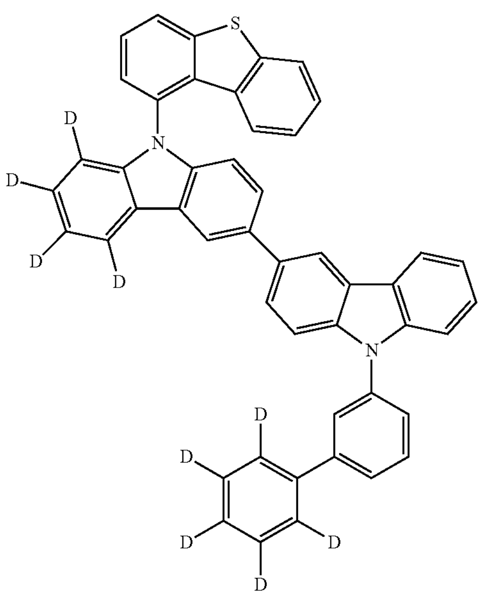
[B-169]
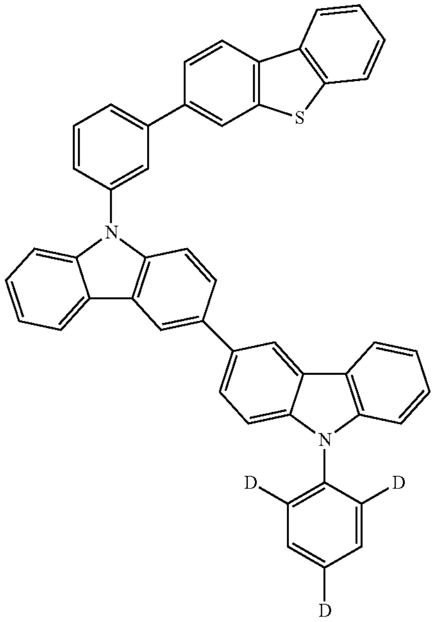
-continued
[B-170]
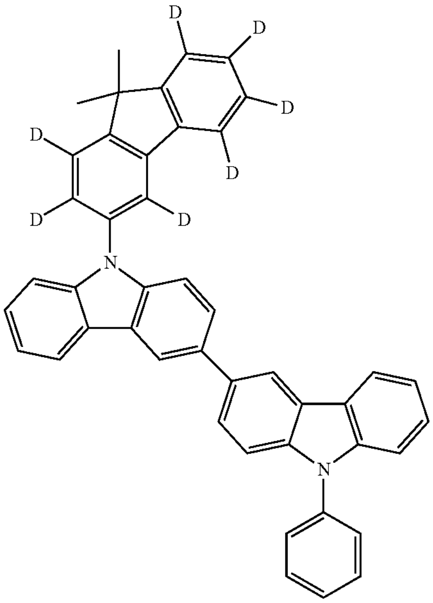
[B-171]
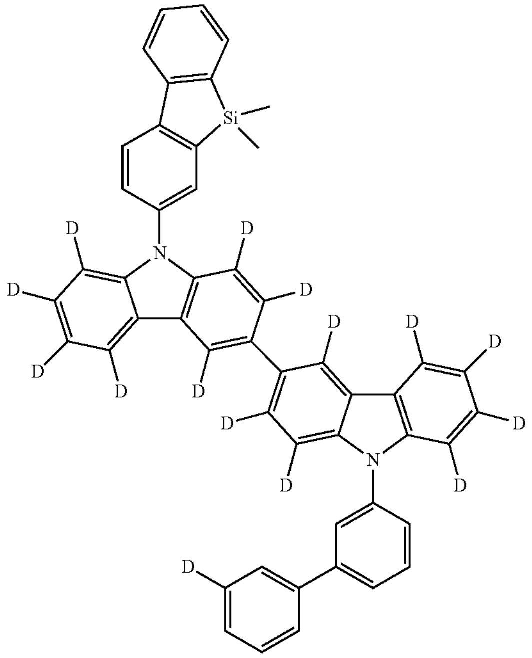

-continued
[B-172]
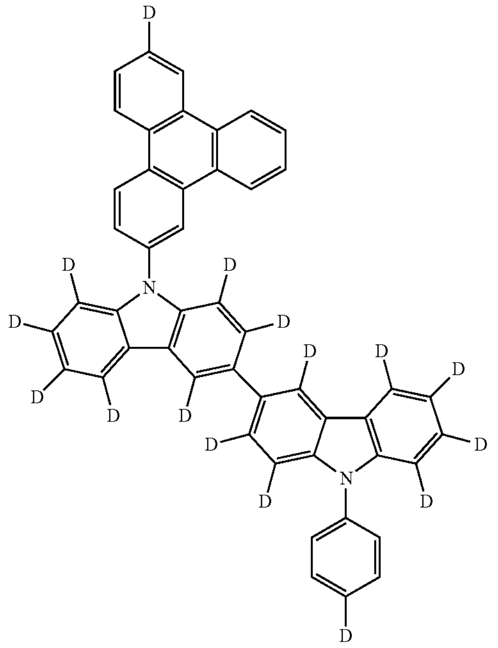
[B-173]
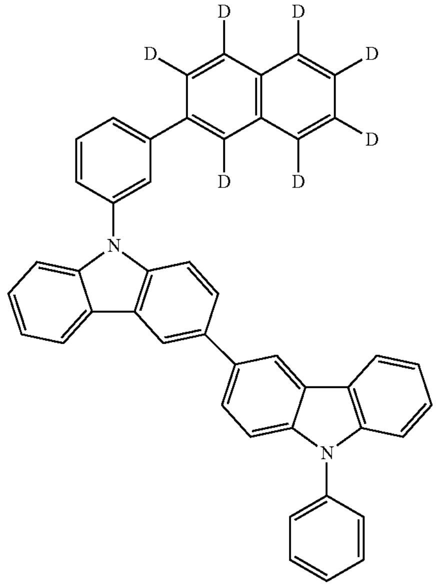
-continued
[B-174]
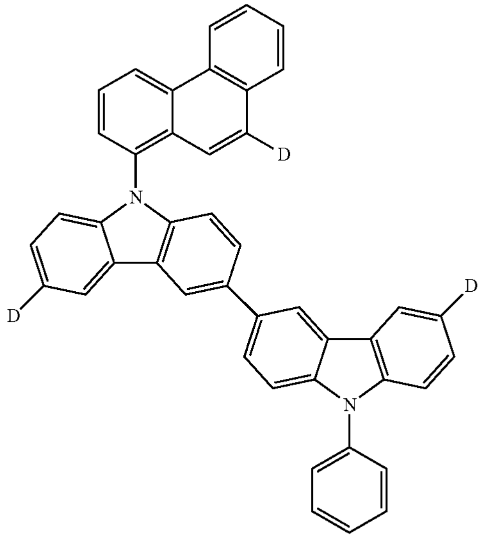
[B-175]
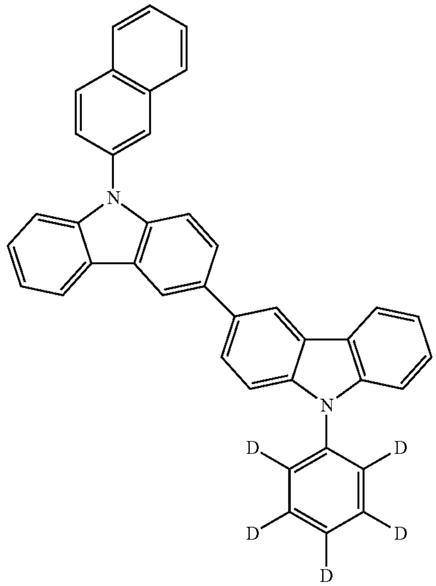

-continued
[B-176]
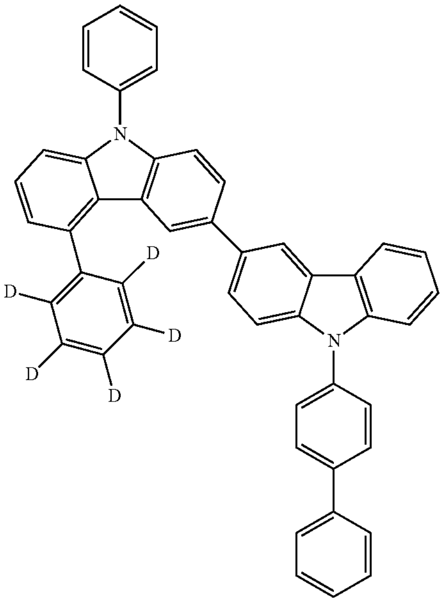
[B-177]
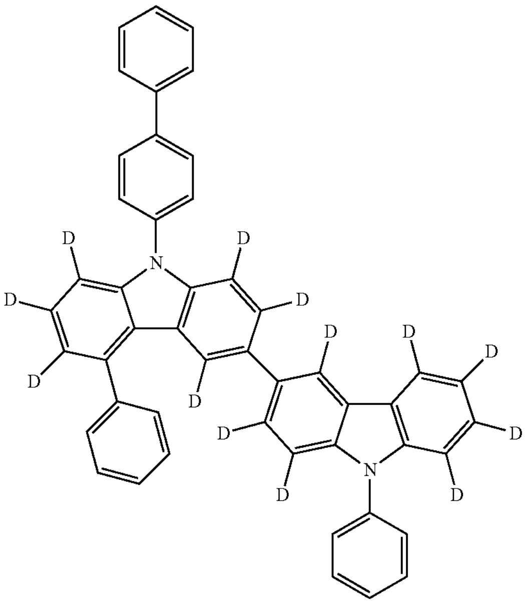
-continued
[B-178]
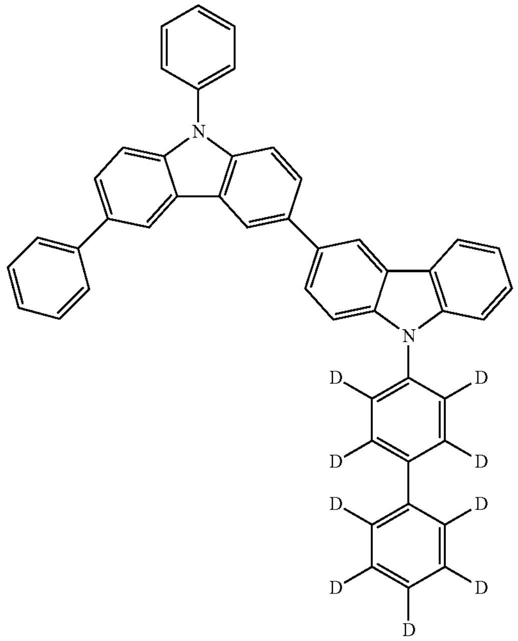
[B-179]
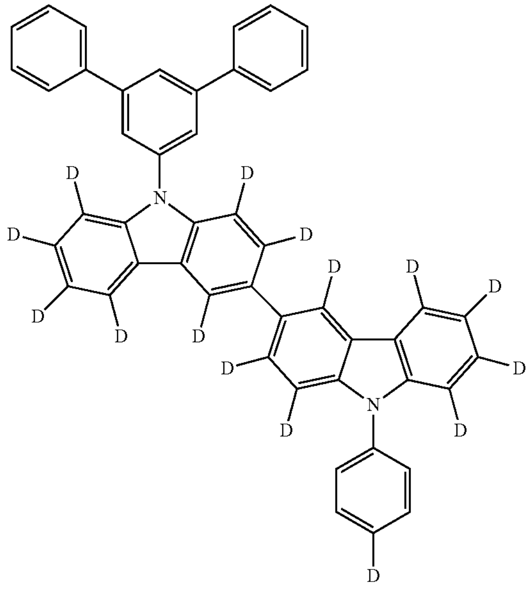

-continued
[B-180]
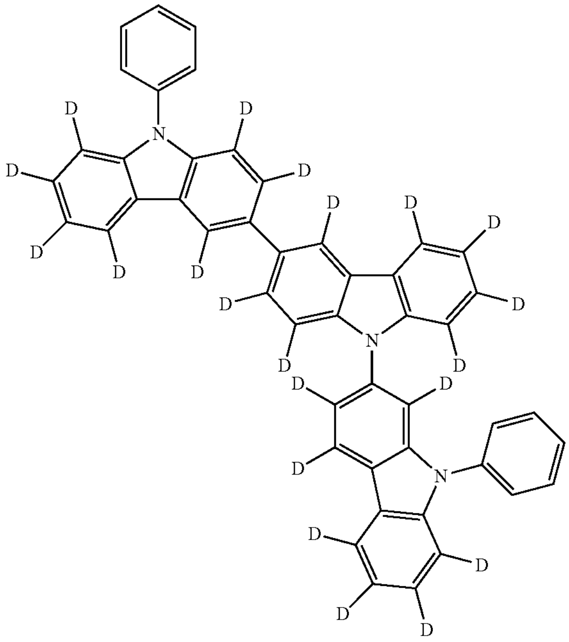
[B-181]
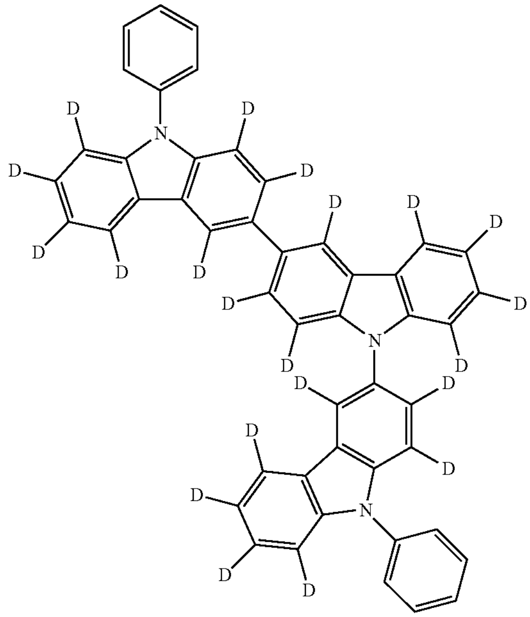
-continued
[B-182]
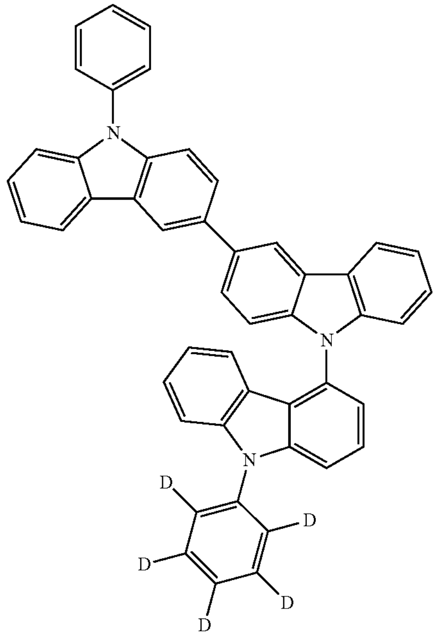
[B-183]
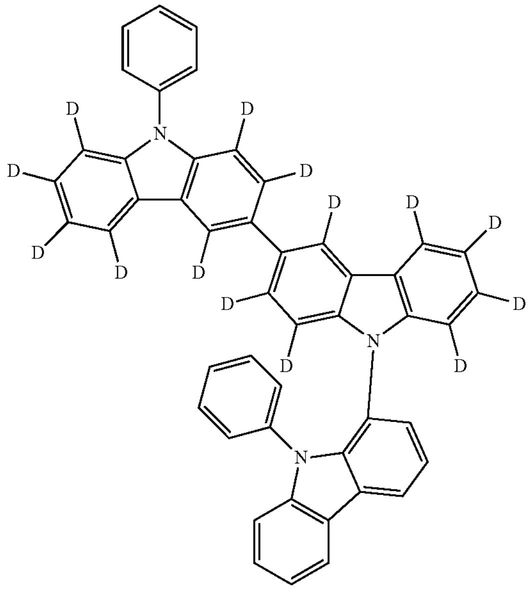

[B-184]
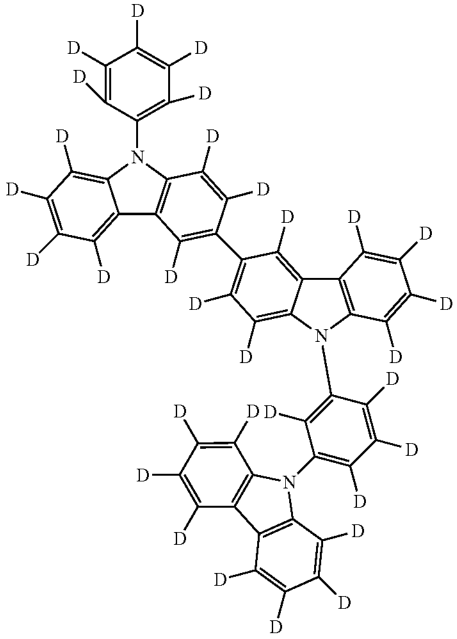
[B-185]
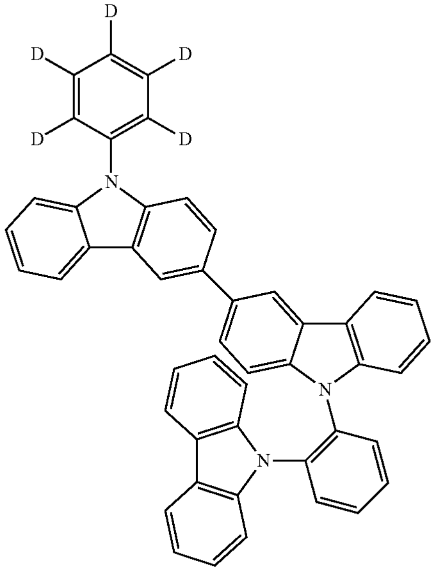
[C-1]
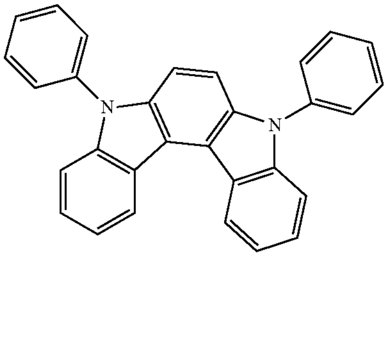
[C-2]
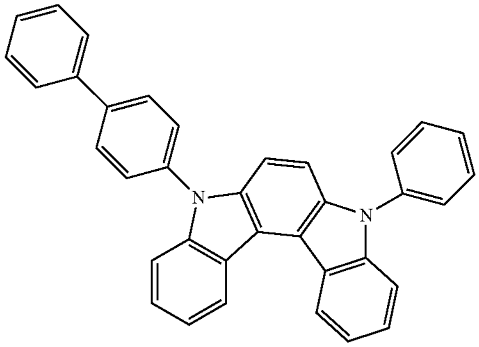
[C-3]
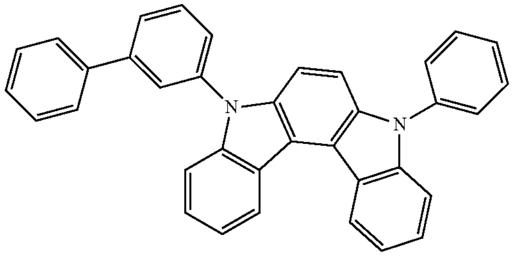
[C-4]
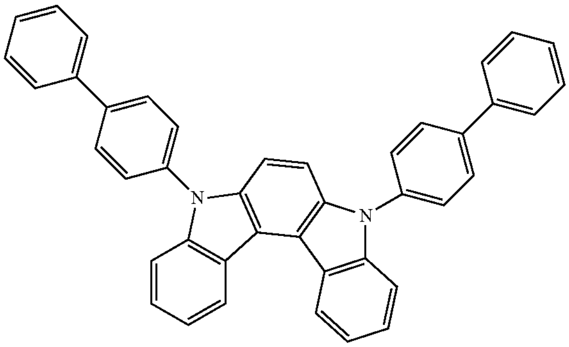
[C-5]
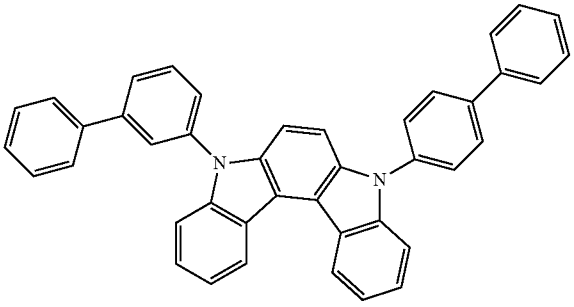

-continued
[C-6]
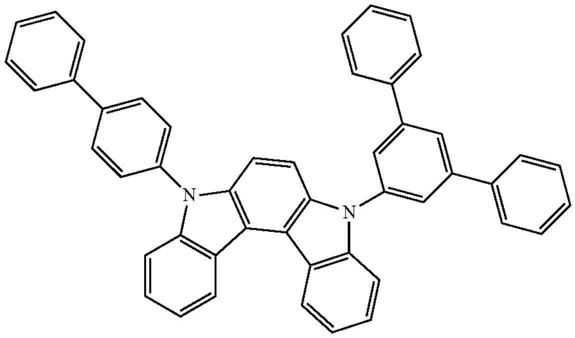
[C-7]
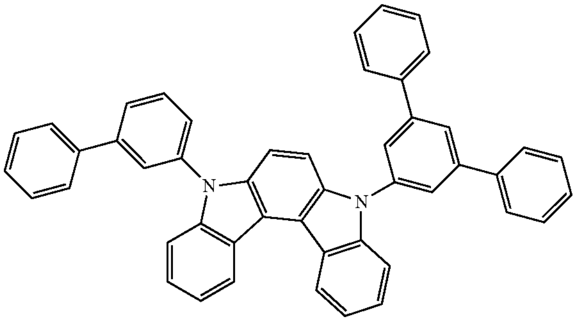
[C-8]
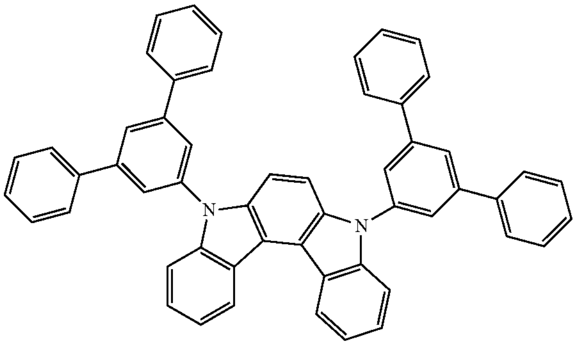
[C-9]
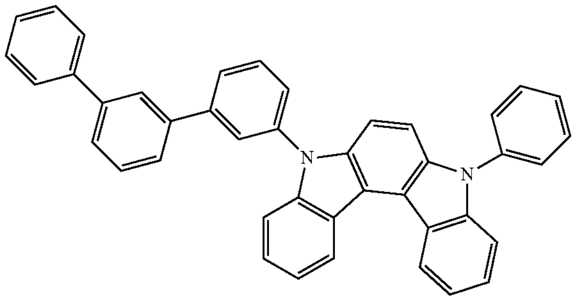
-continued
[C-10]
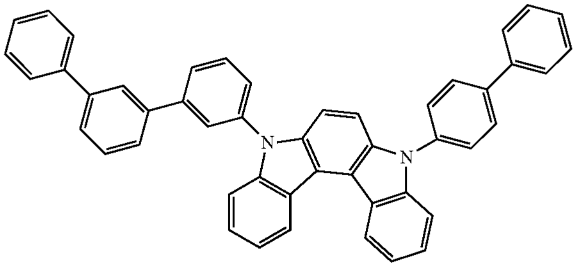
[C-11]
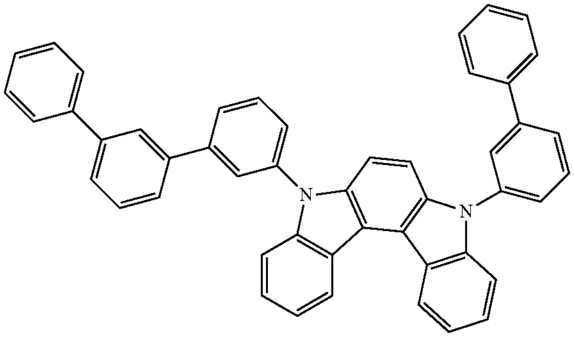
[C-12]
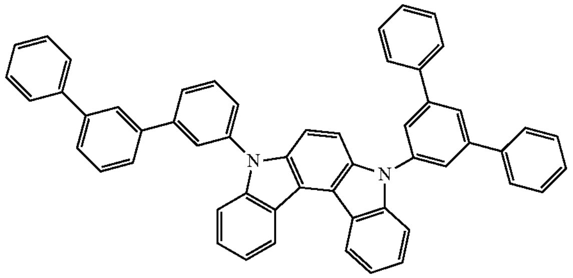
[C-13]
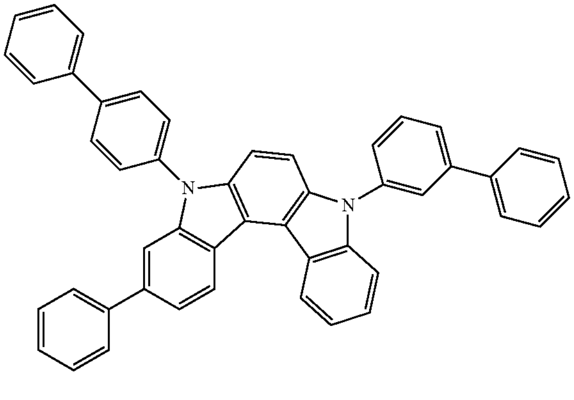

-continued
[C-14]
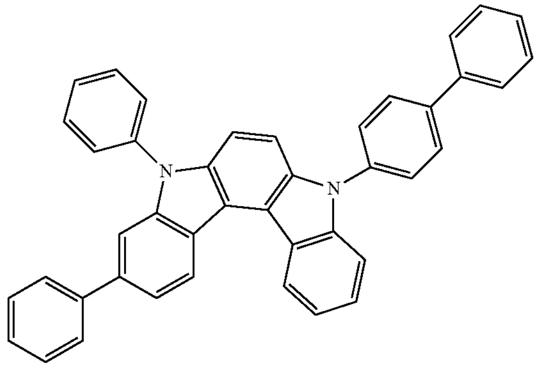
[C-15]
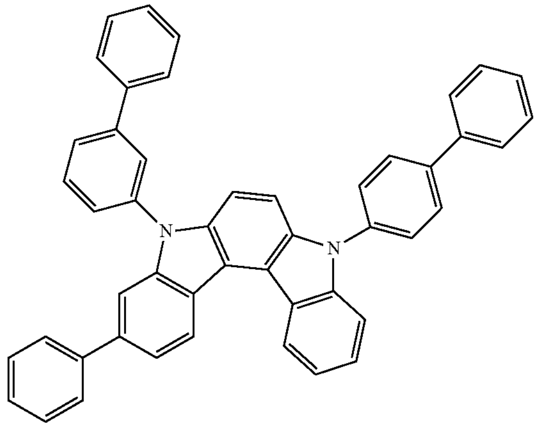
[C-16]
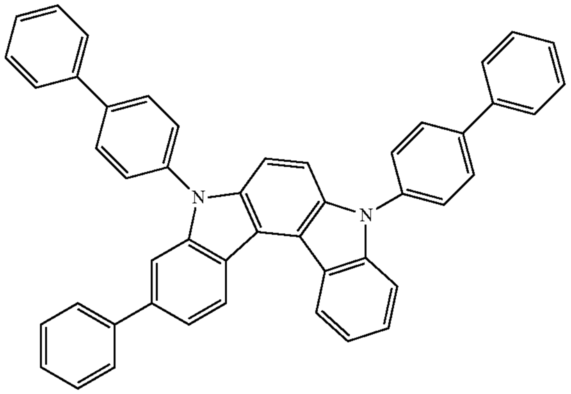
-continued
[C-17]
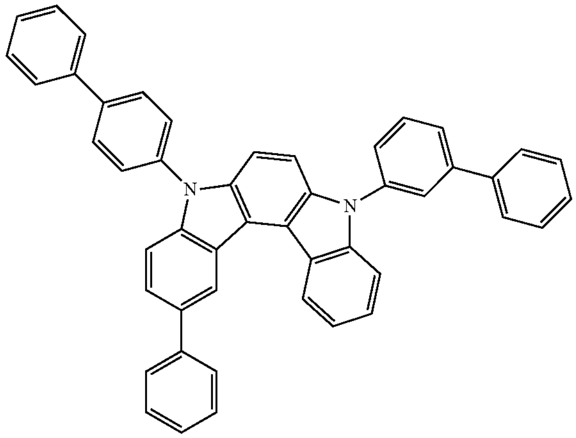
[C-18]
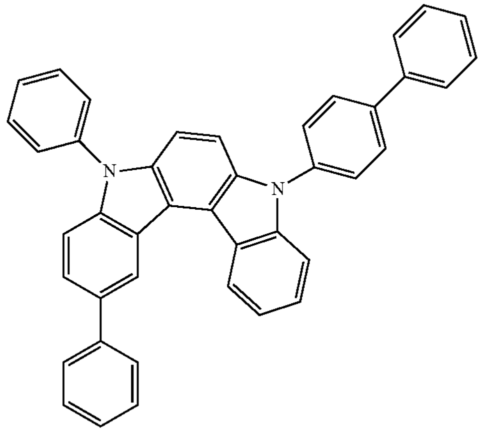
[C-19]
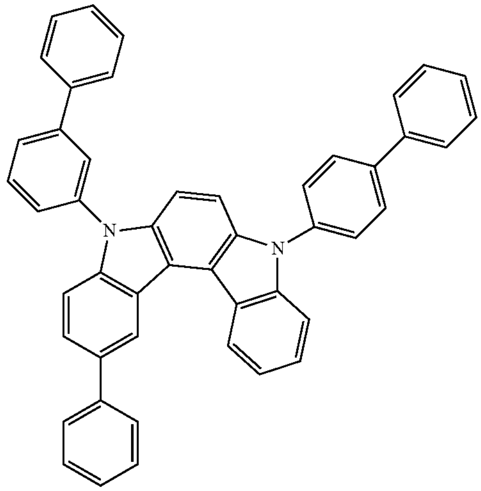

-continued
[C-20]
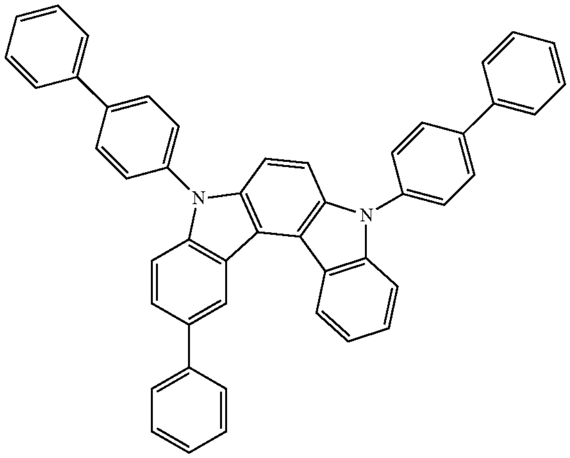
[C-21]
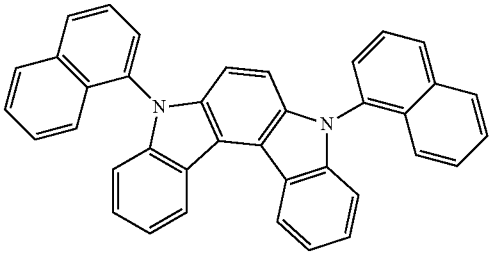
[C-22]
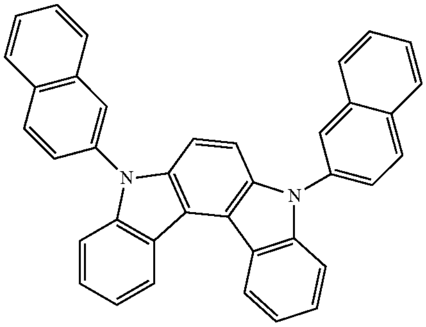
[C-23]
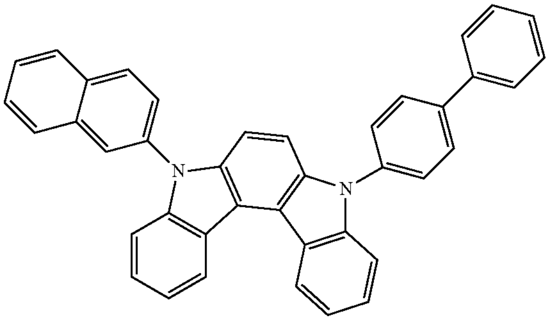
-continued
[C-24]
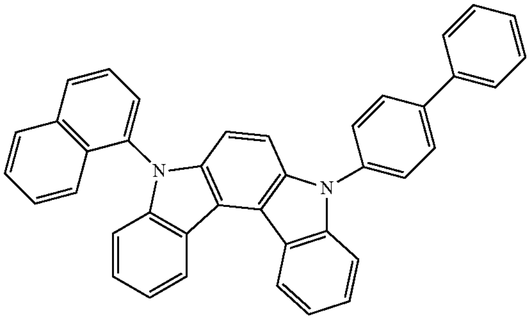
[C-25]
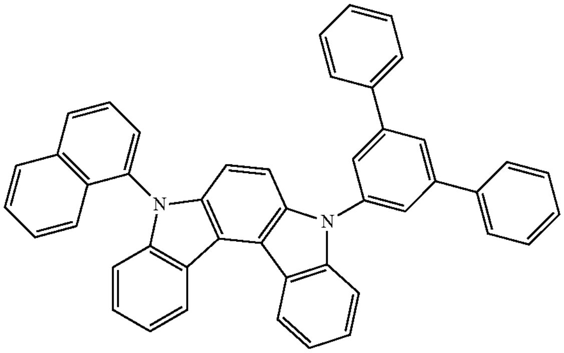
[C-26]
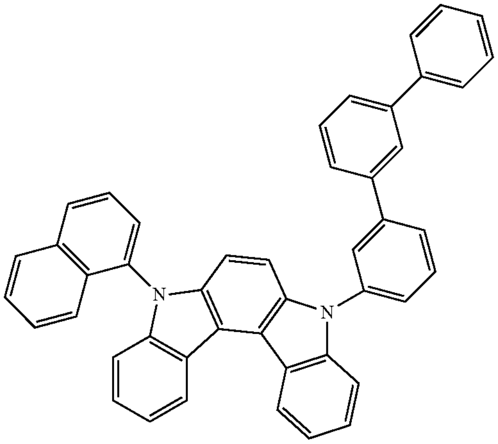
[C-27]
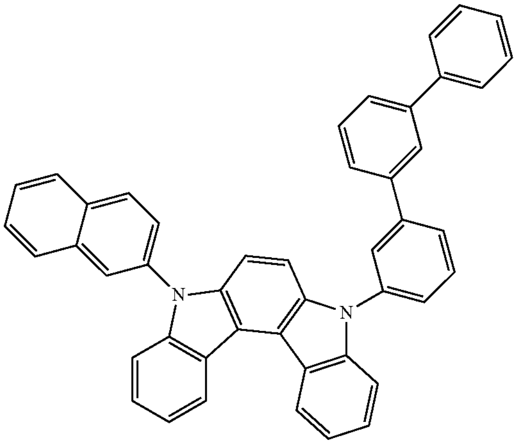

-continued
[C-28]
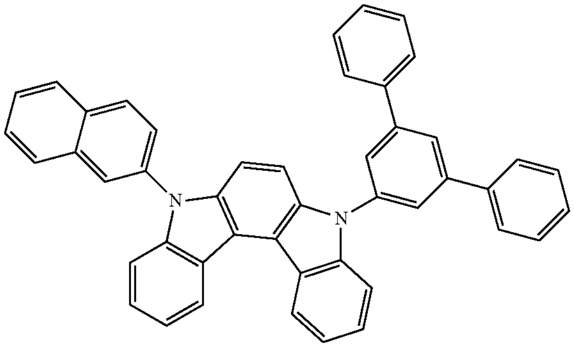
[C-29]
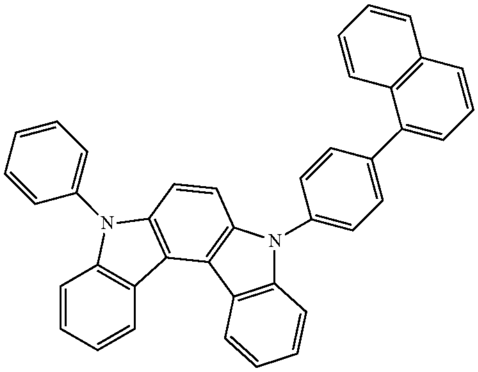
[C-30]
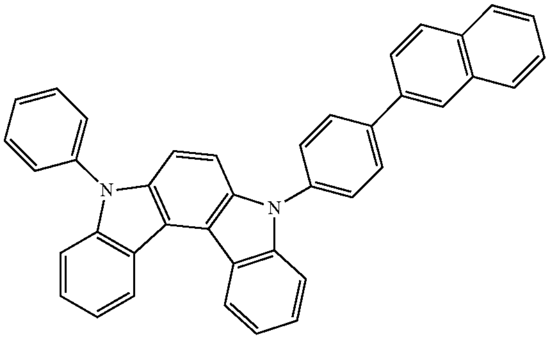
[C-31]
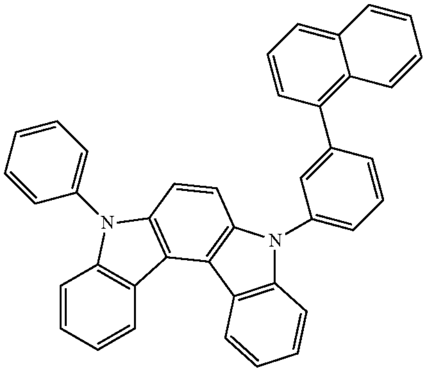
-continued
[C-32]
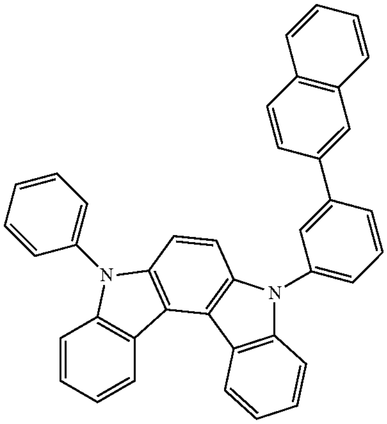
[C-33]
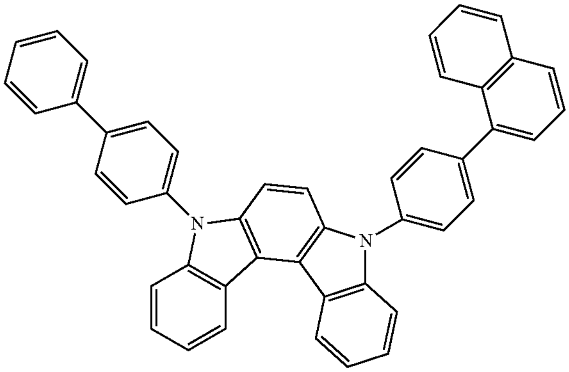
[C-34]
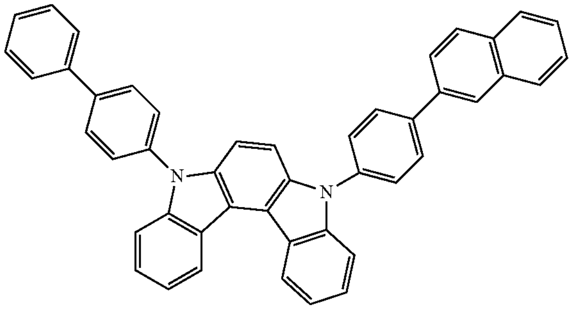
[C-35]
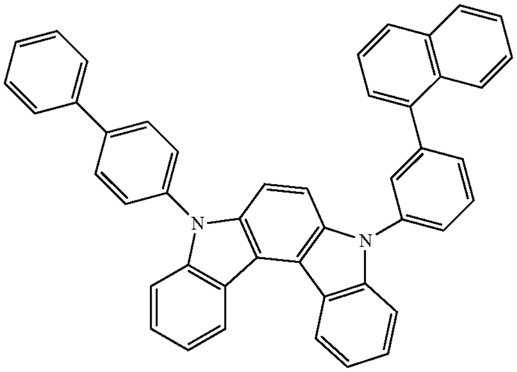

-continued
[C-36]
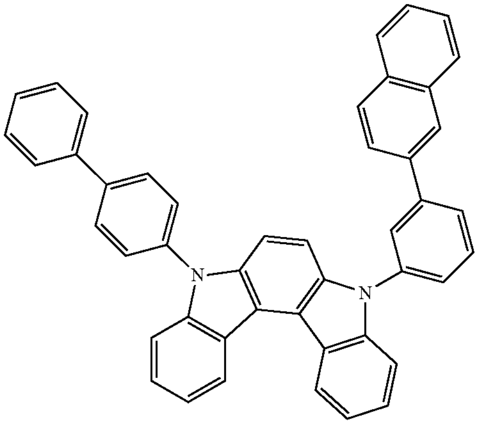
[C-37]
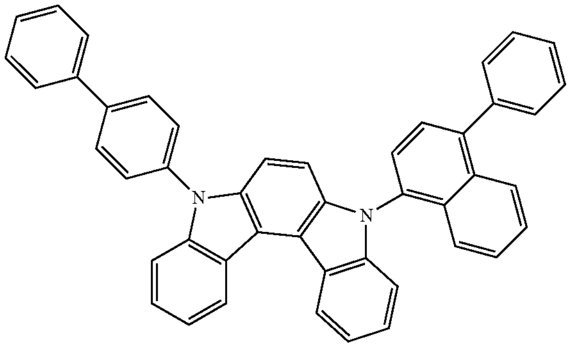
[C-38]
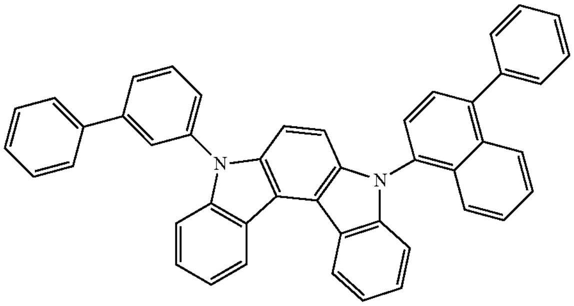
[C-39]
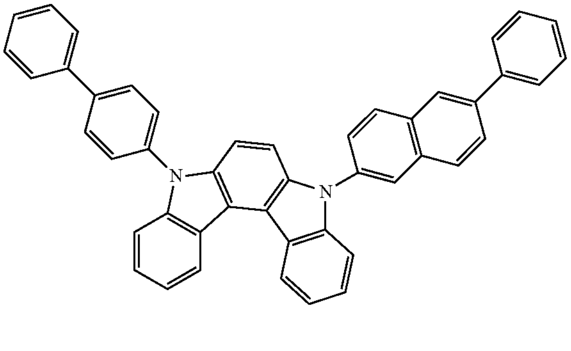
-continued
[C-40]
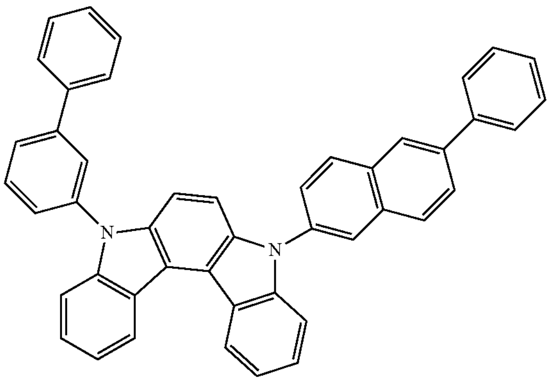
[C-41]
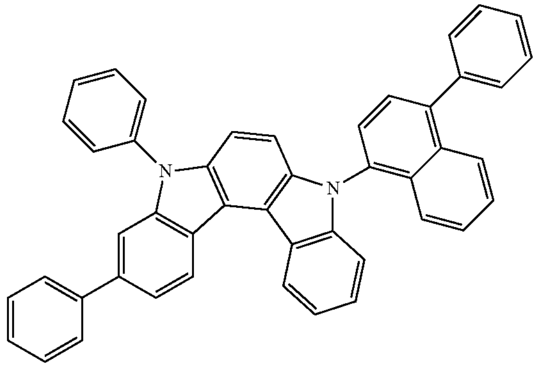
[C-42]
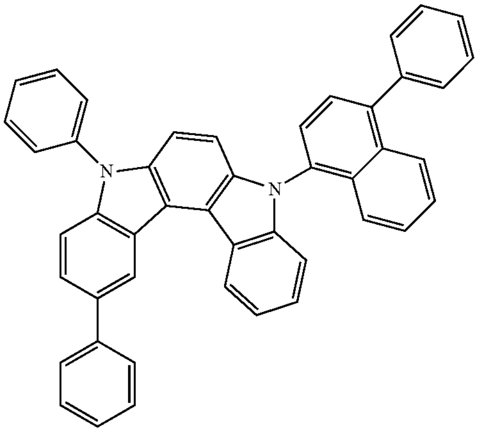
[C-43]
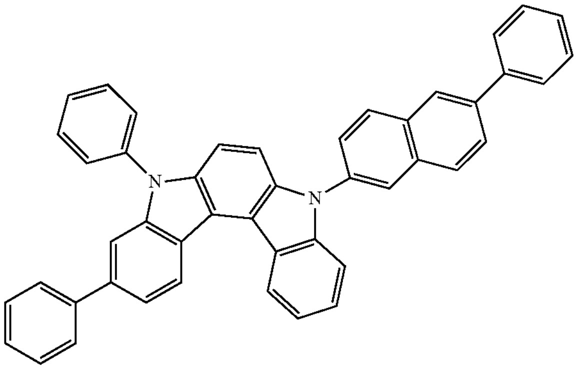

-continued
[C-44]
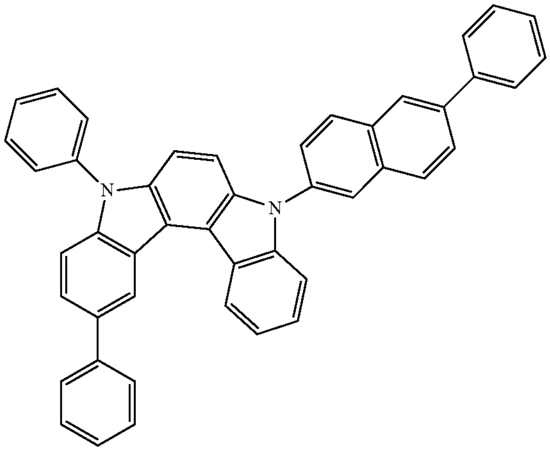
[C-45]
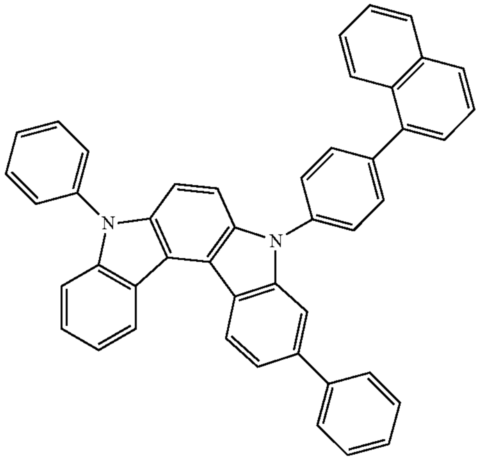
[C-46]
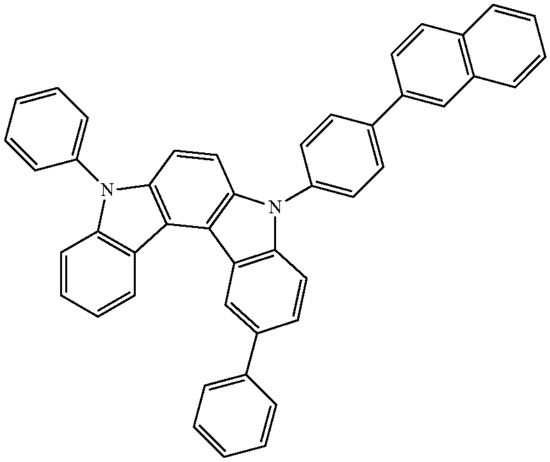
-continued
[C-47]
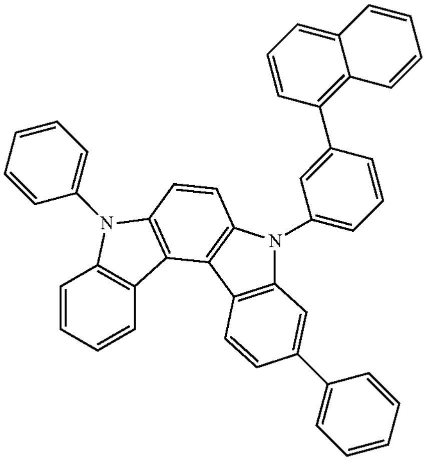
[C-48]
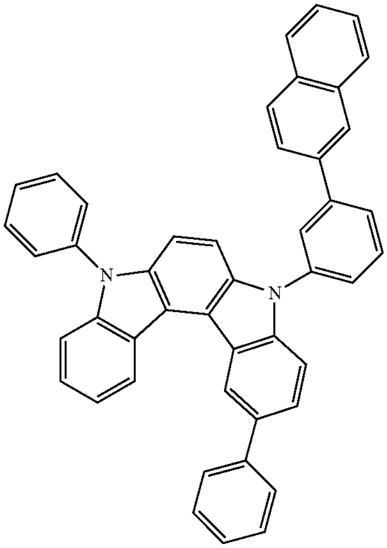
[C-49]
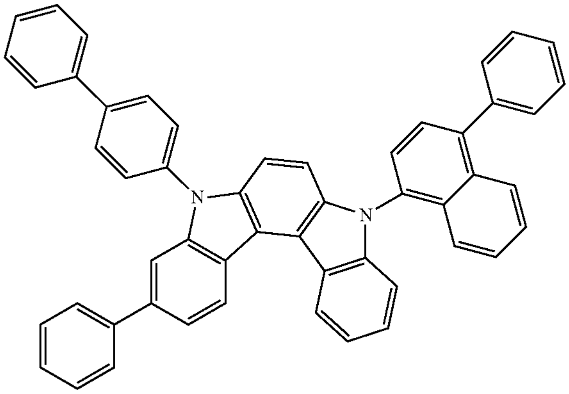

-continued
[C-50]
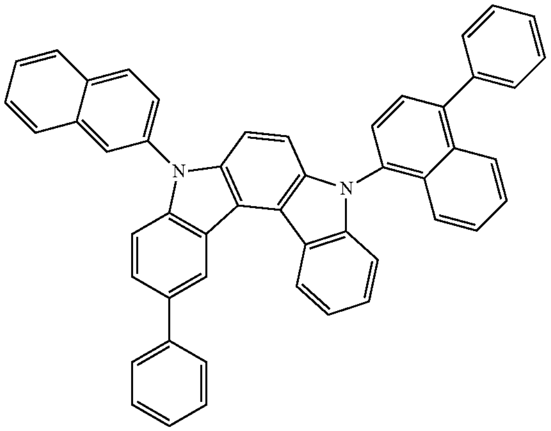
[C-51]
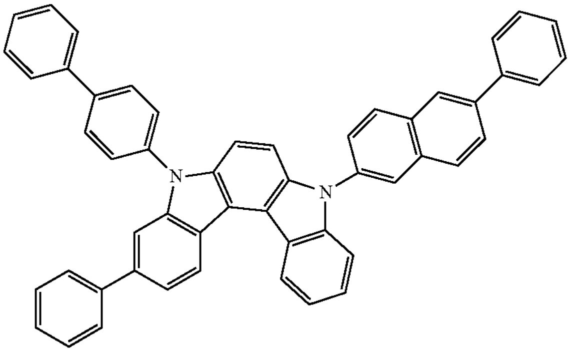
[C-52]
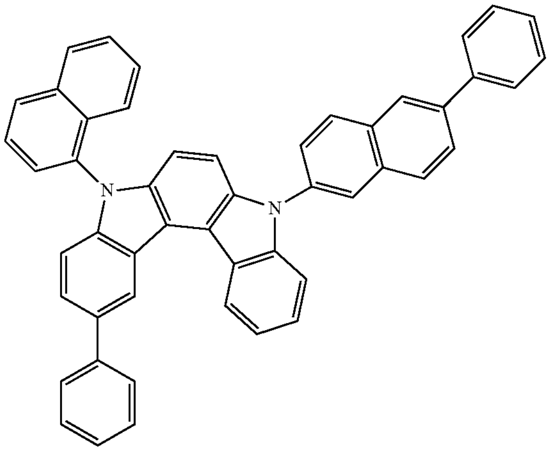
-continued
[C-53]
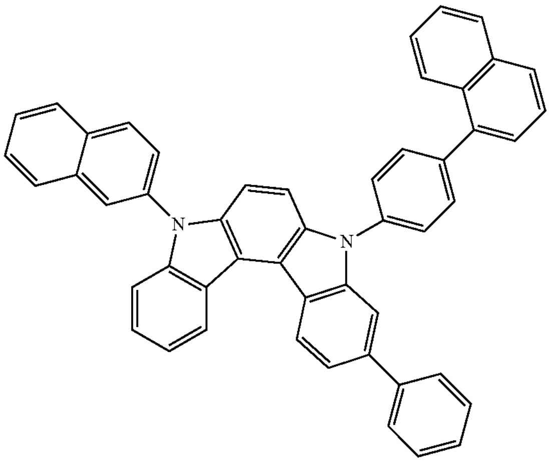
[C-54]
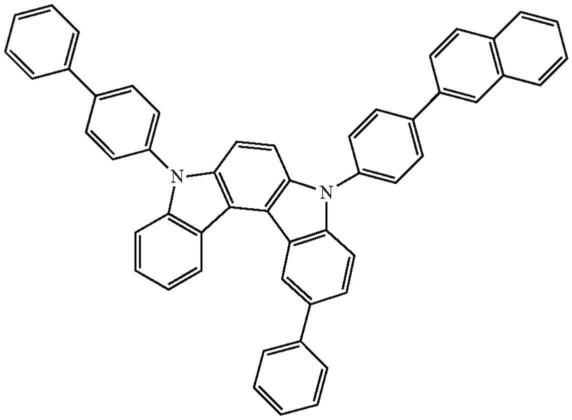
[C-55]
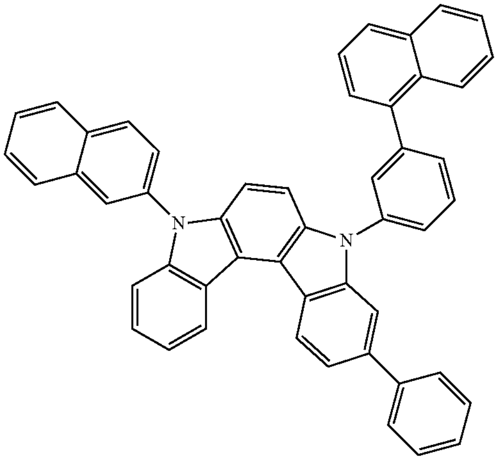

-continued
[C-56]
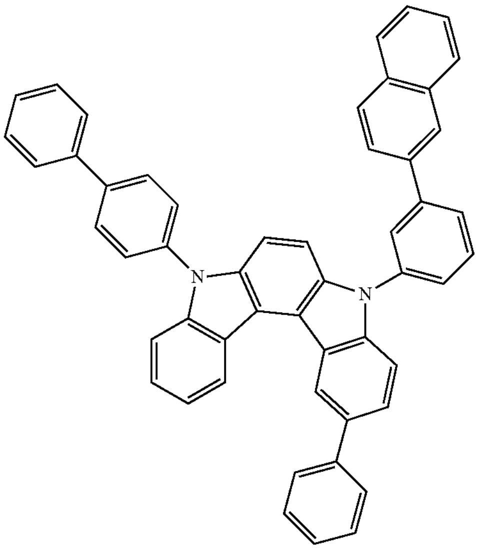
[C-57]
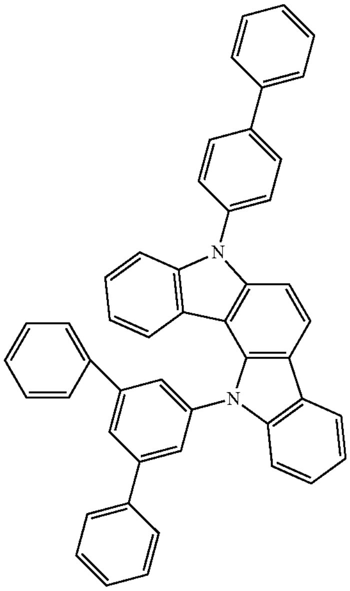
-continued
[C-58]
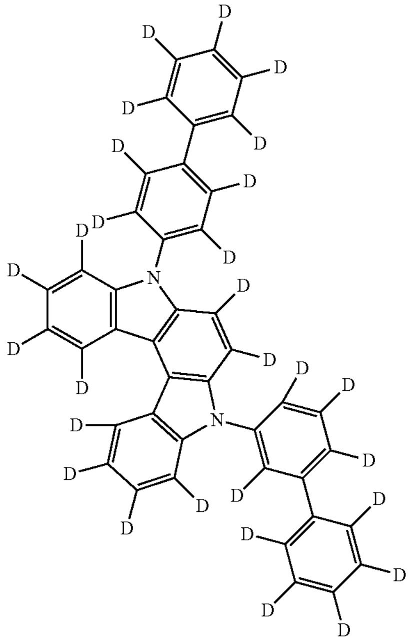
[C-59]
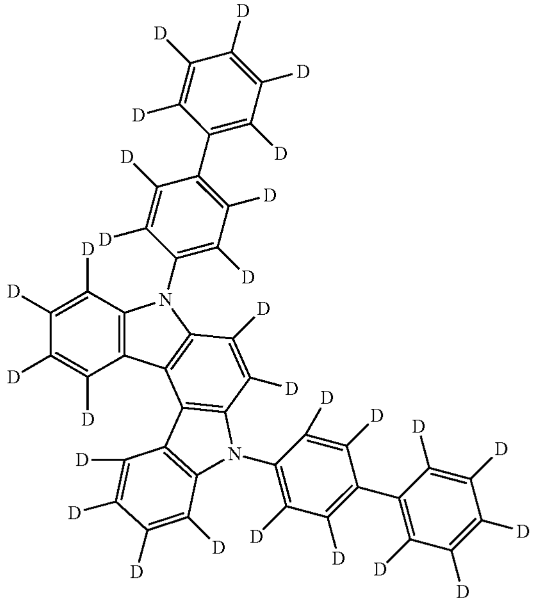
[C-60]
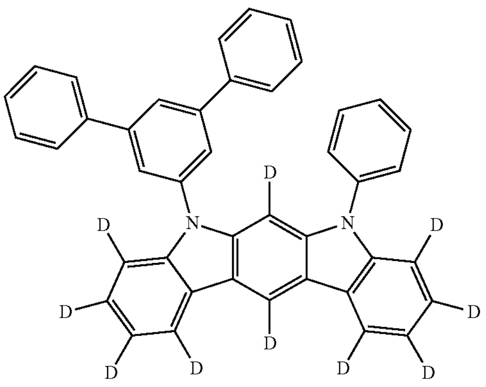

-continued
[C-61]
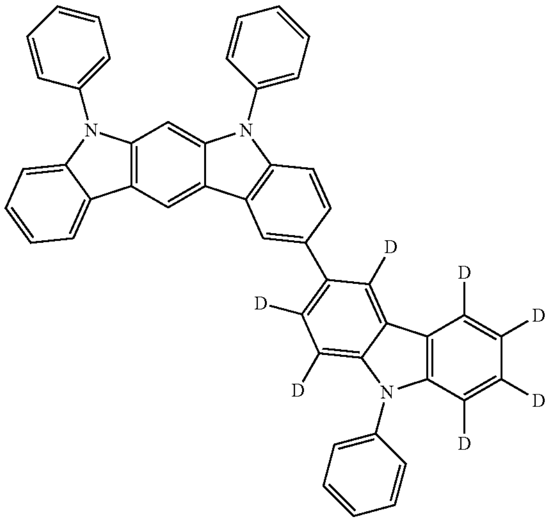
[C-62]
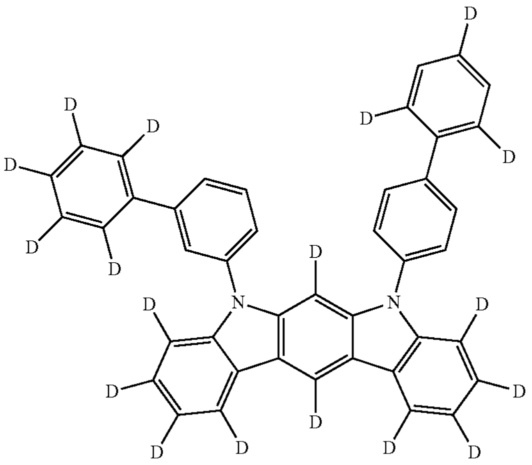
[C-63]
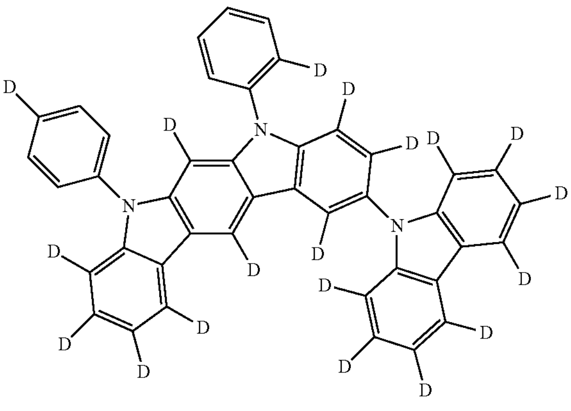
-continued
[C-64]
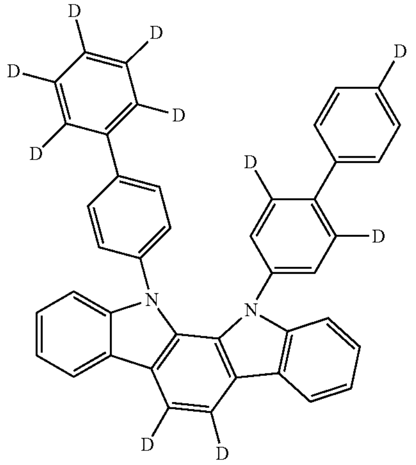
[C-65]
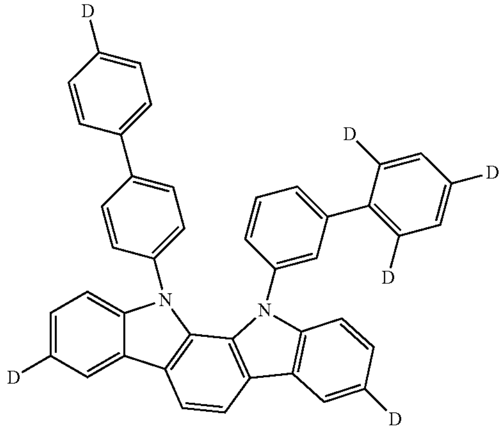
[C-66]
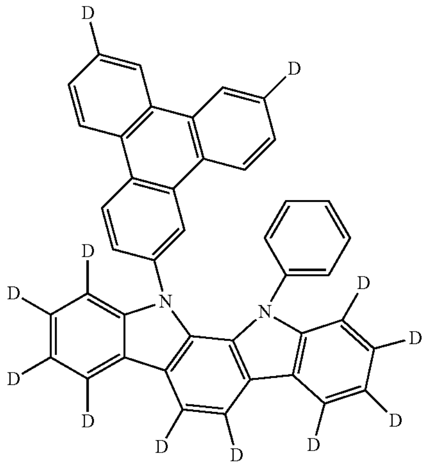

-continued
[C-67]
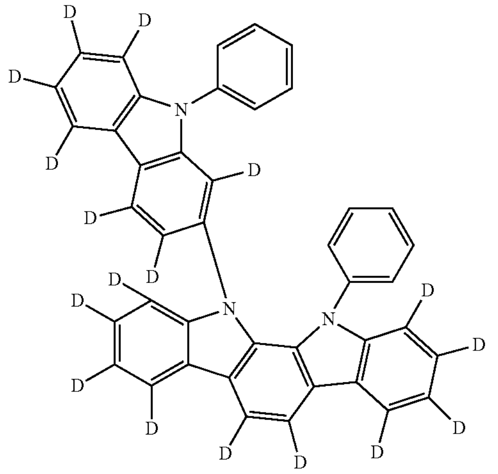
[C-68]
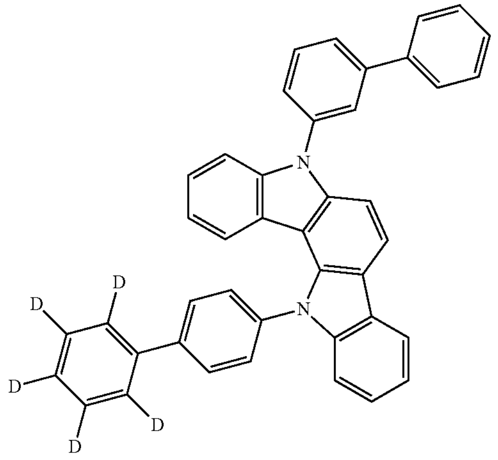
[C-69]
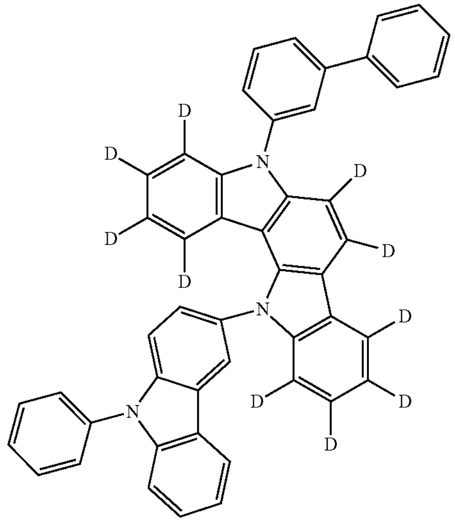
-continued
[C-70]
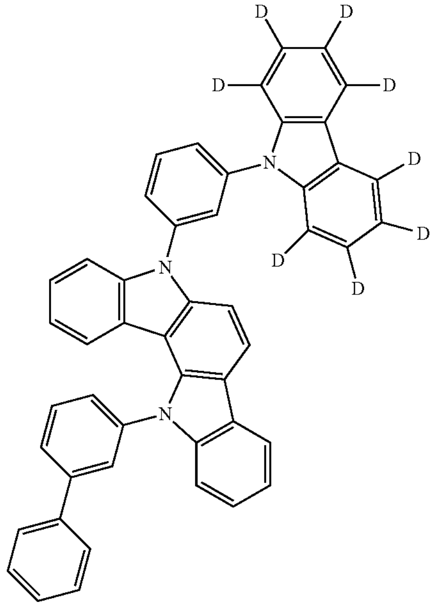
[C-71]
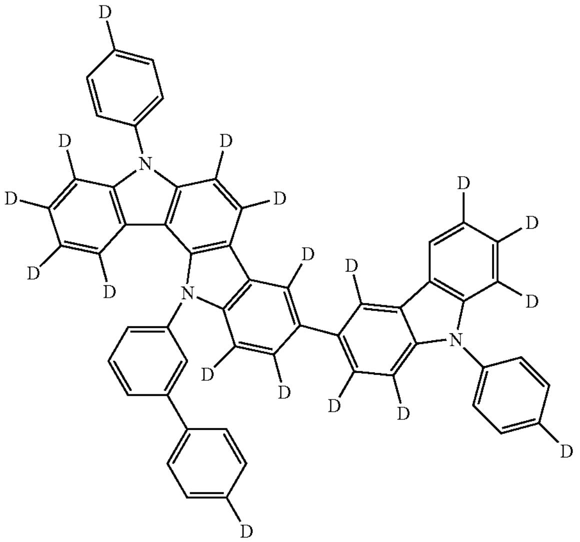
[C-72]
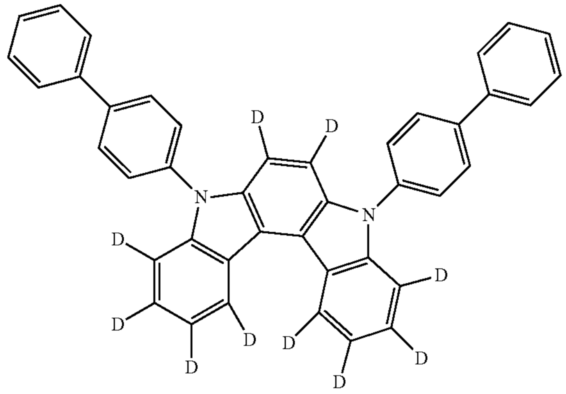

-continued
[C-73]
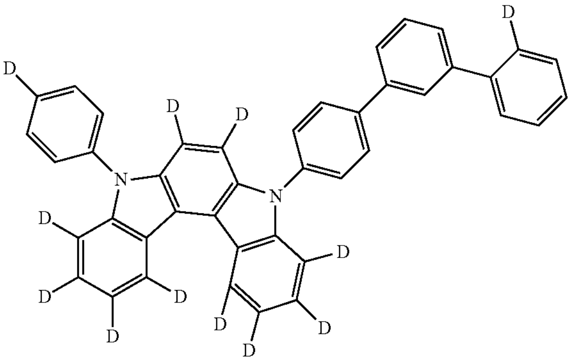
[C-74]
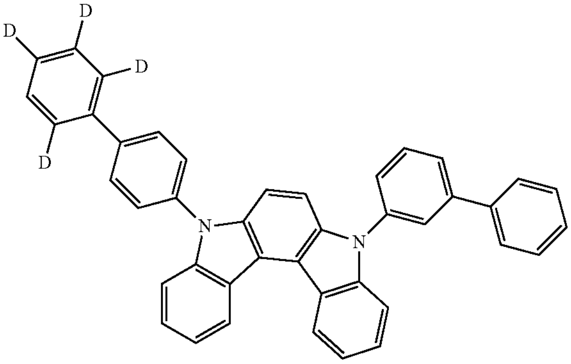
[C-75]
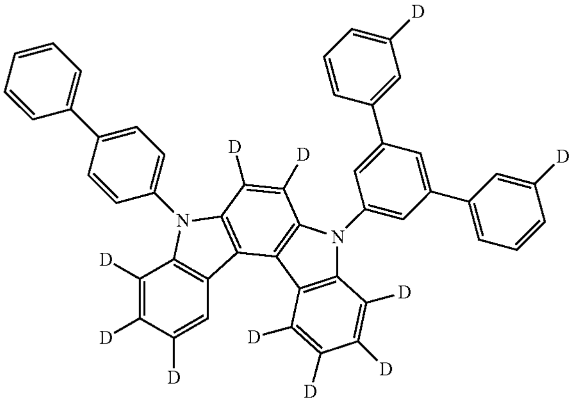
[C-76]
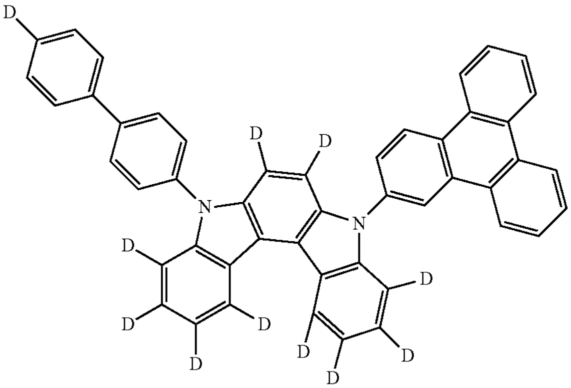
-continued
[C-77]
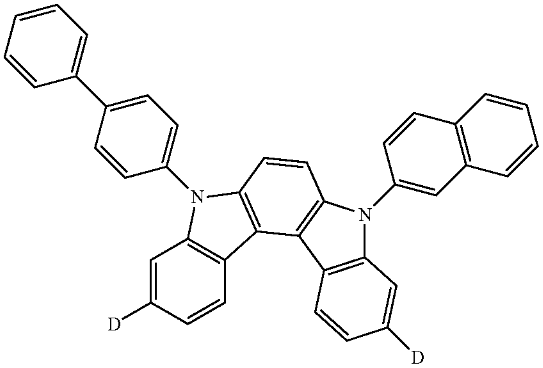
[C-78]
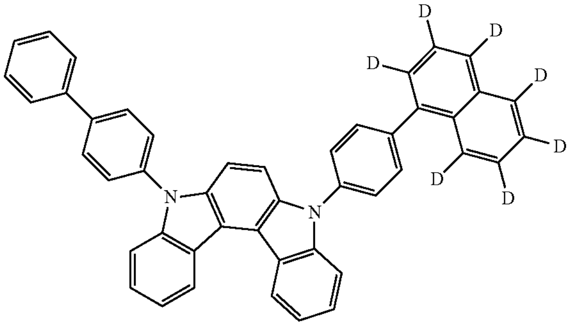
[C-79]
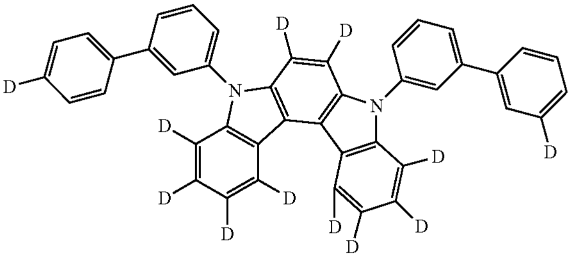
[C-80]
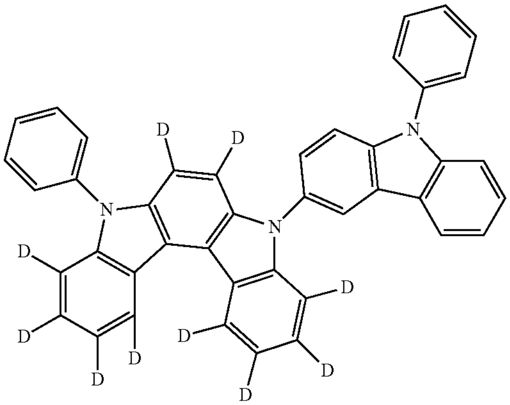

-continued

[C-81]

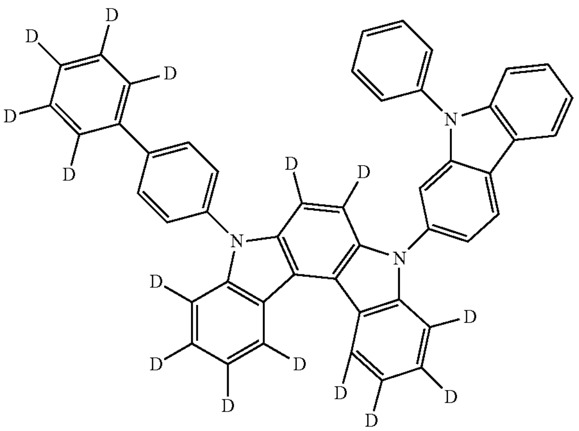

[C-82]

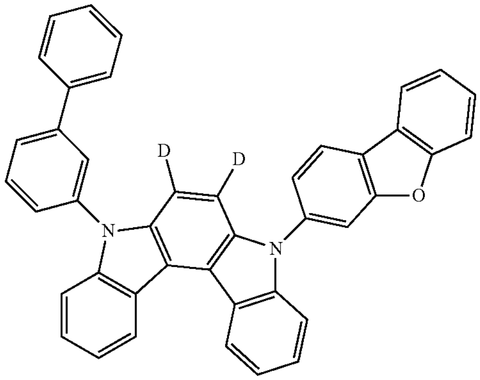

[C-83]

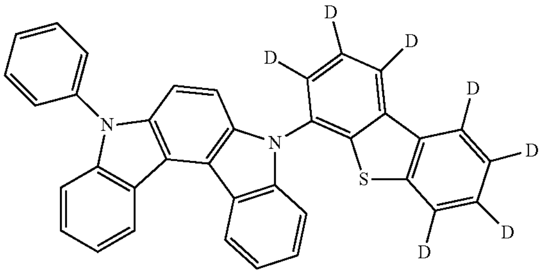

[C-84]

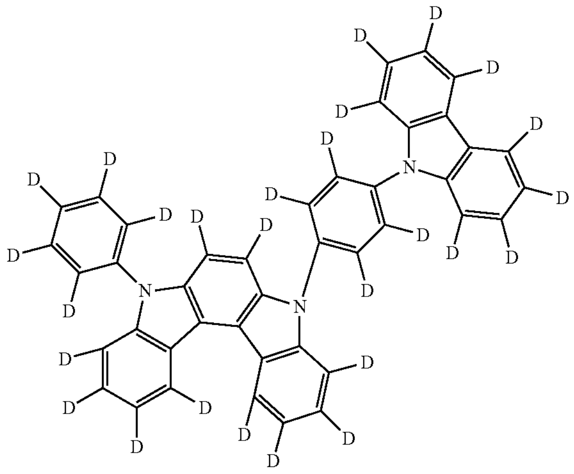

-continued

[C-85]

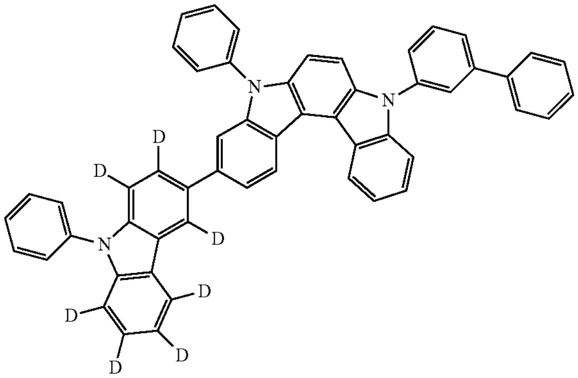

[C-86]

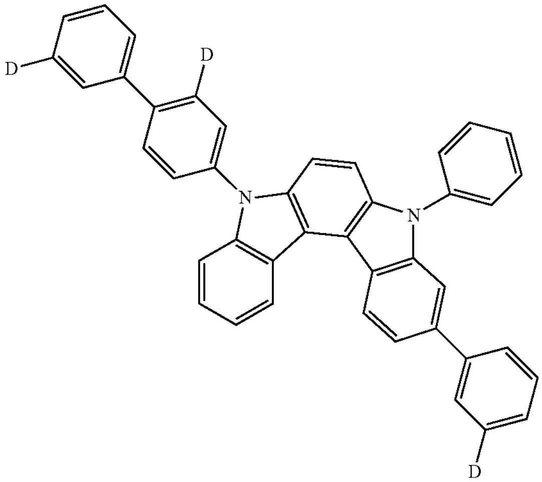

[C-87]

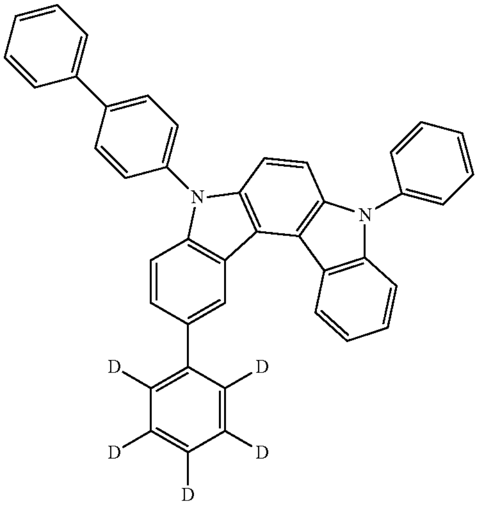

The first compound and the second compound may be, e.g., included (or mixed) in a weight ratio of about 1:99 to about 99:1. Within the range, a desirable weight ratio may be adjusted using an electron transport capability of the first compound and a hole transport capability of the second compound to realize bipolar characteristics and thus to improve efficiency and life-span. Within the range, they may be, e.g., included in a weight ratio of about 10:90 to about 90:10, or about 20:80 to about 80:20, for example a weight ratio of about 20:80 to about 70:30, about 20:80 to about 60:40, and about 20:80 to about 50:50. In an implementation, they may be included in a weight ratio of about 20:80, about 30:70, or about 40:60.

One or more compounds may be further included in addition to the aforementioned first and second compounds.

In an implementation, the aforementioned compound for the organic optoelectronic device or composition for the organic optoelectronic device may further include a dopant.

The dopant may be, e.g., a phosphorescent dopant, such as a red, green, or blue phosphorescent dopant. The dopant may be, e.g., a red or green phosphorescent dopant.

The dopant is a material mixed with the compound for the organic optoelectronic device in a small amount to cause light emission and may be a material such as a metal complex that emits light by multiple excitation into a triplet or more. The dopant may be, e.g., an inorganic, organic, or organic-inorganic compound, and one or more types thereof may be used.

Examples of the dopant may include a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

[Chemical Formula Z]

LMX

In Chemical Formula Z, M may be a metal, and L and X are the same as or different from each other, and may be ligands forming a complex compound with M.

The M may be, e.g., Ir, Pt, Os, Ti, Zr, Hf, Eu, Tb, Tm, Fe, Co, Ni, Ru, Rh, Pd, or a combination thereof, and L and X may be, e.g., a bidentate ligand.

Examples of the ligands represented by L and X may be selected from the chemical formulas of Group A.

[Group A]

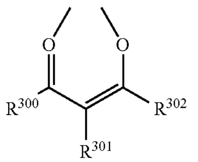

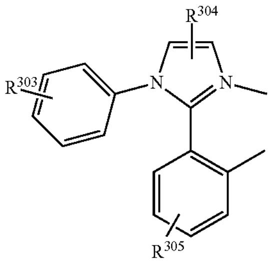

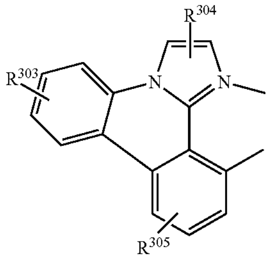

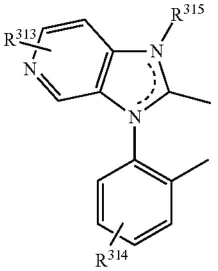

-continued

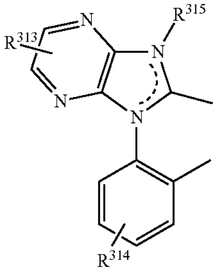

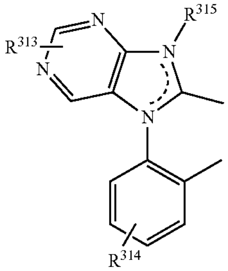

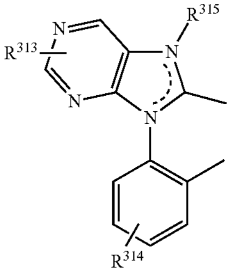

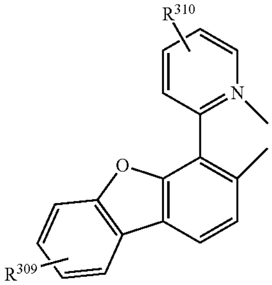

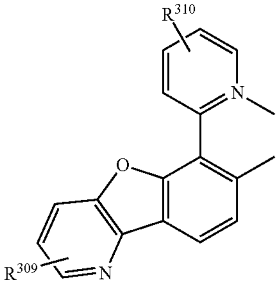

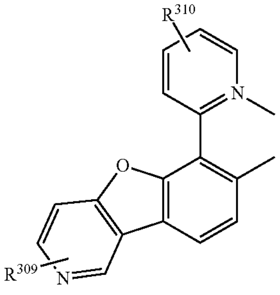

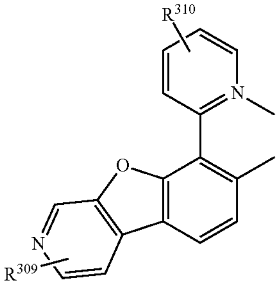

-continued

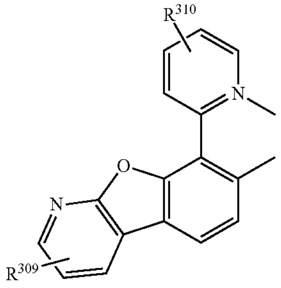

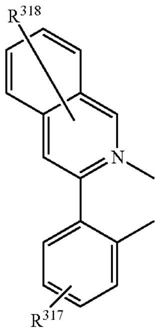

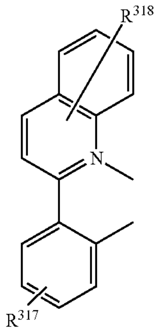

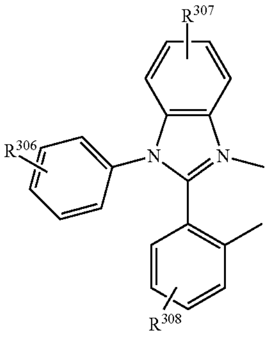

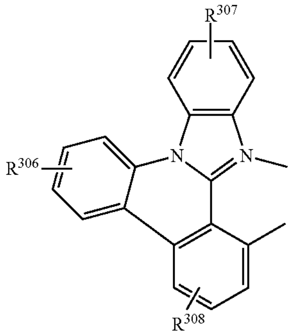

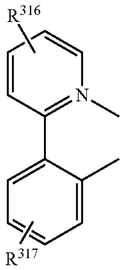

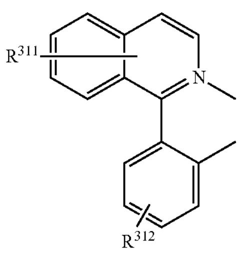

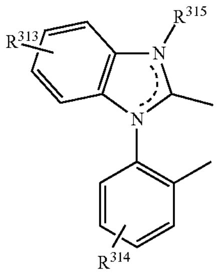

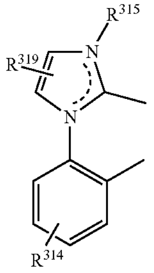

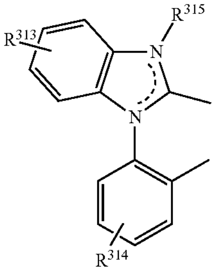

-continued

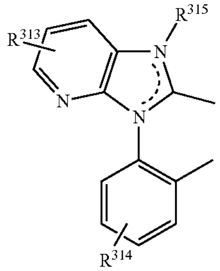

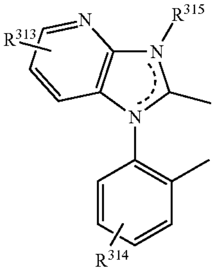

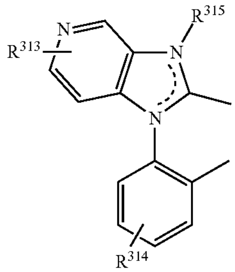

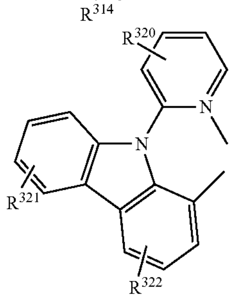

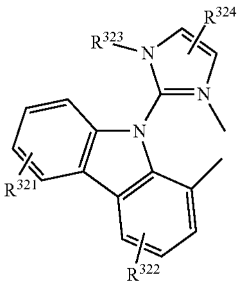

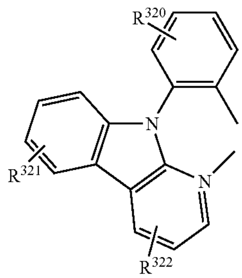

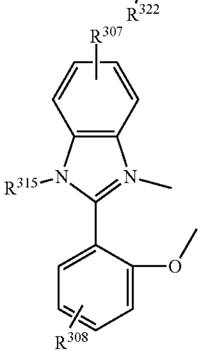

In Group A, $R^{300}$ to $R^{302}$ may each independently be, e.g., hydrogen, deuterium, a C1 to C30 alkyl group that is substituted or unsubstituted with a halogen, a C6 to C30 aryl group that is substituted or unsubstituted with a C1 to C30 alkyl, or a halogen, and $R^{303}$ to $R^{324}$ may each independently be, e.g., hydrogen, deuterium, halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group.

In an implementation, it may include a dopant represented by Chemical Formula V.

[Chemical Formula V]

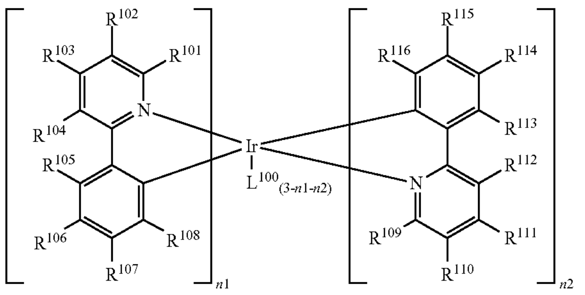

In Chemical Formula V, $R^{101}$ to $R^{116}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$, $R^{132}$ to $R^{134}$ may each independently be, e.g., a C1 to C6 alkyl group, at least one of $R^{101}$ to $R^{116}$ may be a functional group represented by Chemical Formula V-1, $L^{100}$ may be a bidentate ligand of a monovalent anion, and is a ligand that coordinates to iridium through a lone pair of electrons of carbon or heteroatom, n1 and n2 may be each independently any one of integers of 0 to 3, and n1+n2 is any one of integers of 1 to 3.

[Chemical Formula V-1]

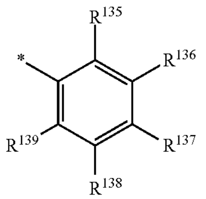

In Chemical Formula V-1, $R^{135}$ to $R^{139}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$, and

* means a portion linked to a carbon atom.

In an implementation, a dopant represented by Chemical Formula Z-1 may be included.

[Chemical Formula Z-1]

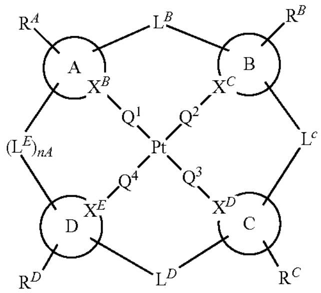

In Chemical Formula Z-1, rings A, B, C, and D each independently represent a 5-membered or 6-membered carbocyclic or heterocyclic ring;

$R^A$, $R^B$, $R^C$, and $R^D$ may each independently be, e.g., mono-, di-, tri-, or tetra-substitution, or unsubstitution;

$L^B$, $L^C$, and $L^D$ may each independently be, e.g., a direct bond, BR, NR, PR, O, S, Se, C═O, S═O, $SO_2$, CRR', SiRR', GeRR', or a combination thereof, when nA is 1, $L^E$ is selected from a direct bond, BR, NR, PR, O, S, Se, C═O, S═O, $SO_2$, CRR', SiRR', GeRR', and a combination thereof, when nA is 0, $L^E$ does not exist; and $R^A$, $R^B$, $R^C$, $R^D$, R, and R' may each independently be, e.g., hydrogen, deuterium, a halogen, an alkyl group, a cycloalkyl group, a heteroalkyl group, an arylalkyl group, an alkoxy group, an aryloxy group, an amino group, a silyl group, an alkenyl group, a cycloalkenyl group, a heteroalkenyl group, an alkynyl group, an aryl group, a heteroaryl group, an acyl group, a carbonyl group, a carboxylic acid group, an ester group, a nitrile group, an isonitrile group, a sulfanyl group, a sulfinyl group, a sulfonyl group, a phosphino group, or a combination thereof, any adjacent $R^A$, $R^B$, $R^C$, $R^D$, R, and R' are optionally linked to each other to provide a ring; $X^B$, $X^C$, $X^D$, and $X^E$ are each independently selected from carbon and nitrogen; and $Q^1$, $Q^2$, $Q^3$, and $Q^4$ each represent oxygen or a direct bond.

The dopant according to an embodiment may be a platinum complex, and may be, e.g., represented by Chemical Formula VI.

[Chemical Formula VI]

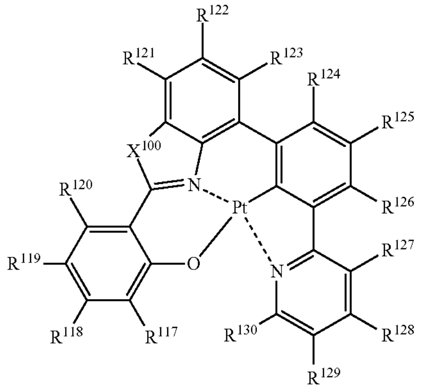

In Chemical Formula VI, $X^{100}$ may be O, S, or $NR^{131}$, $R^{117}$ to $R^{131}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$, $R^{132}$ to $R^{134}$ may each independently be, e.g., a C1 to C6 alkyl group, and at least one of $R^{117}$ to $R^{131}$ may be —$SiR^{132}R^{133}R^{134}$ or a tert-butyl group.

Hereinafter, an organic optoelectronic device including the aforementioned compound for the organic optoelectronic device or composition for the organic optoelectronic device is described.

The organic optoelectronic device may be a suitable device to convert electrical energy into photoenergy and vice versa, and may be, e.g., an organic photoelectric device, an organic light emitting diode, an organic solar cell, or an organic photo-conductor drum.

Herein, an organic light emitting diode as one example of an organic optoelectronic device is described referring to the drawing.

The FIGURE is a cross-sectional view illustrating an organic light emitting diode according to an embodiment.

Referring to the FIGURE, an organic light emitting diode 100 according to an embodiment includes an anode 120 and a cathode 110 facing each other and an organic layer 105 between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; or a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum, silver, tin, lead, cesium, barium, or the like, or an alloy thereof; or a multi-layer structure material such as LiF/Al, $LiO_2$/Al, LiF/Ca, or $BaF_2$/Ca.

The organic layer 105 may include the aforementioned compound for the organic optoelectronic device or composition for the organic optoelectronic device.

The organic layer 105 may include a light emitting layer 130 and the light emitting layer 130 may include the aforementioned compound for the organic optoelectronic device or composition for the organic optoelectronic device.

The composition for the organic optoelectronic device further including the dopant may be, e.g., a red or green light emitting composition.

The light emitting layer 130 may include, e.g., the aforementioned compound for the organic optoelectronic device or composition for the organic optoelectronic device as a phosphorescent host.

The organic layer may further include a charge transport region in addition to the light emitting layer.

The charge transport region may be, e.g., a hole transport region 140.

The hole transport region 140 may further increase hole injection and/or hole mobility between the anode 120 and the light emitting layer 130 and block electrons.

In an implementation, the hole transport region 140 may include a hole transport layer between the anode 120 and the light emitting layer 130, and a hole transport auxiliary layer between the light emitting layer 130 and the hole transport layer and at least one of the compounds of Group B may be included in at least one of the hole transport layer and the hole transport auxiliary layer.

[Group B]

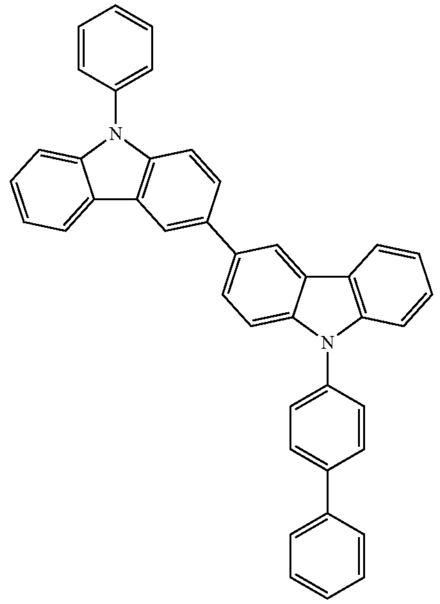

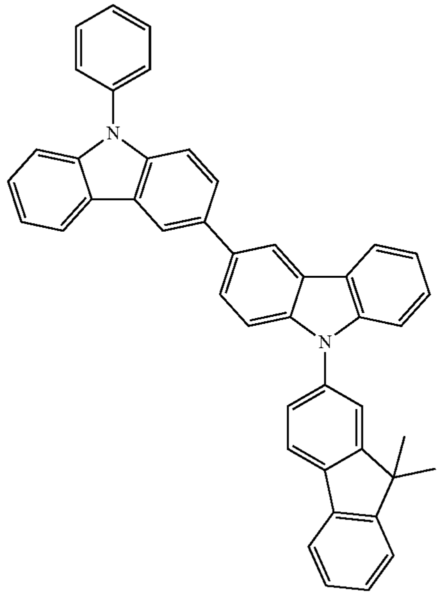

-continued
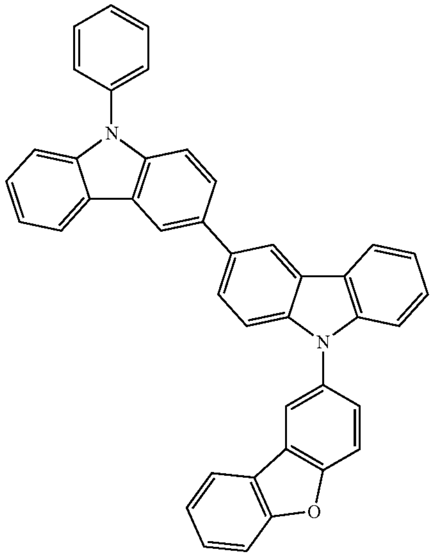
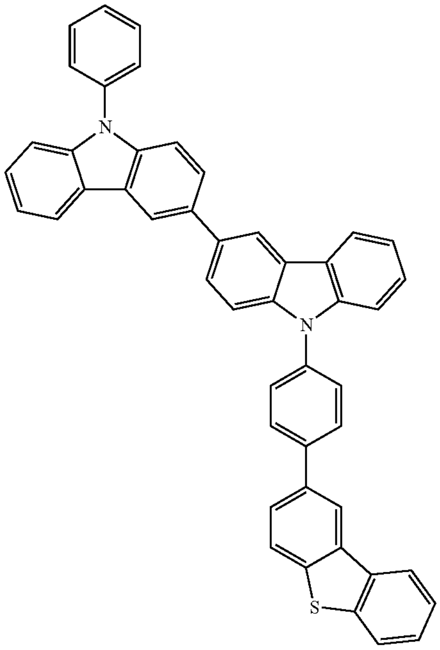
-continued
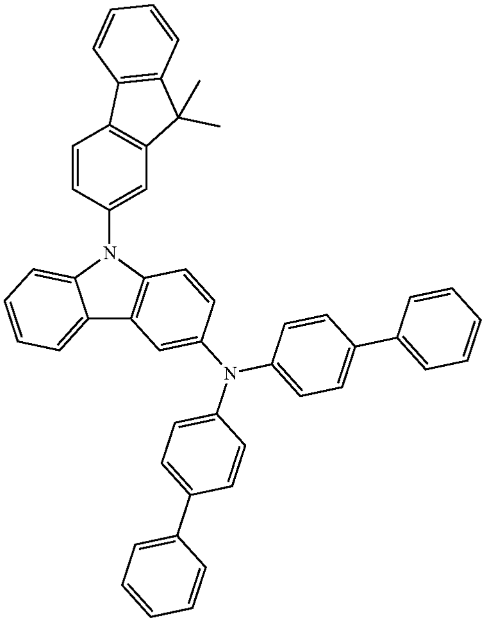
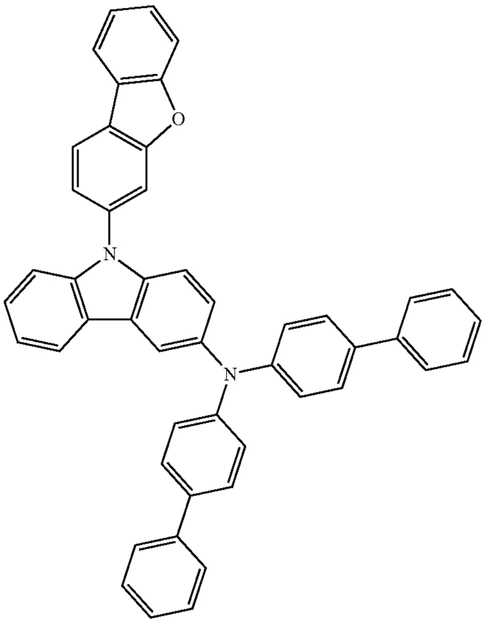

-continued
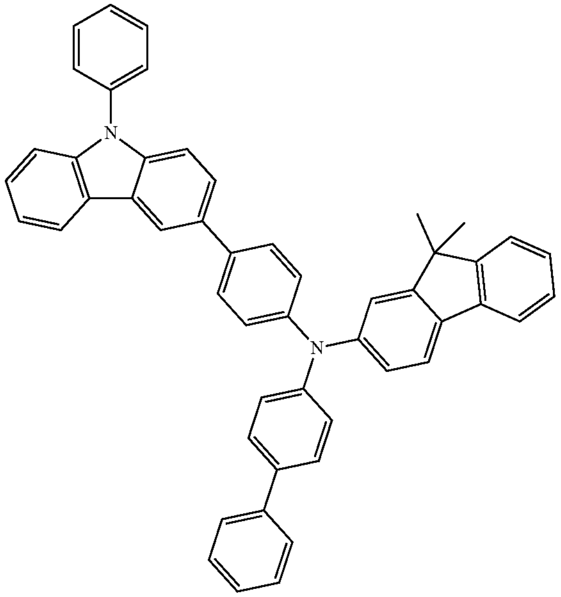
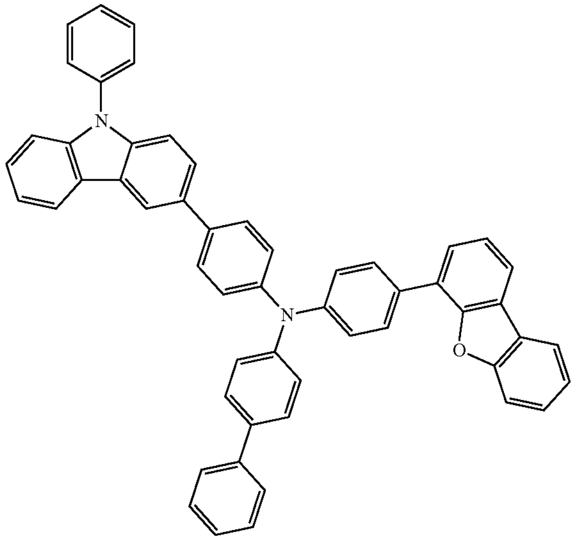
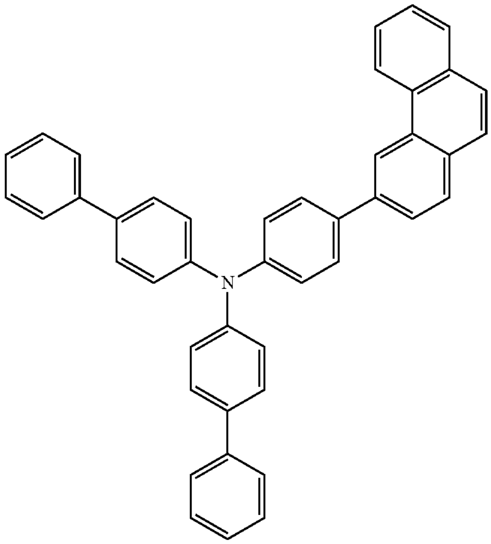
-continued
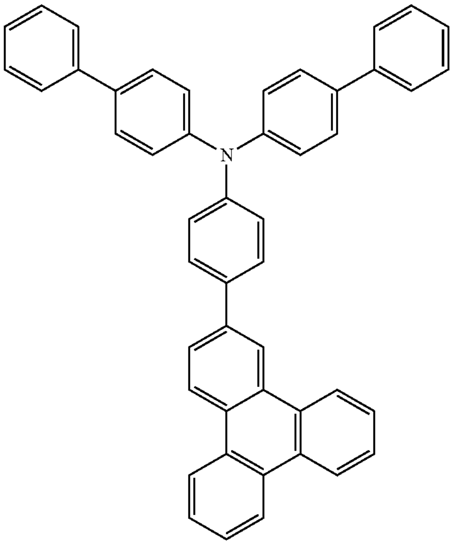
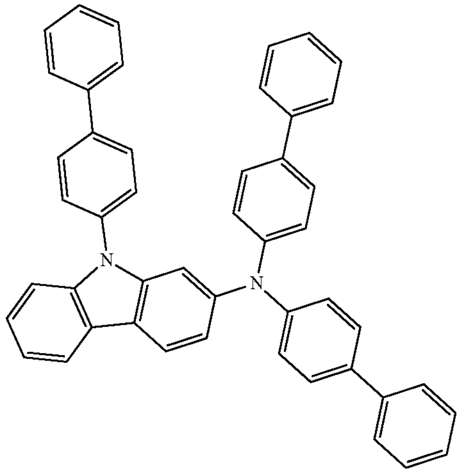
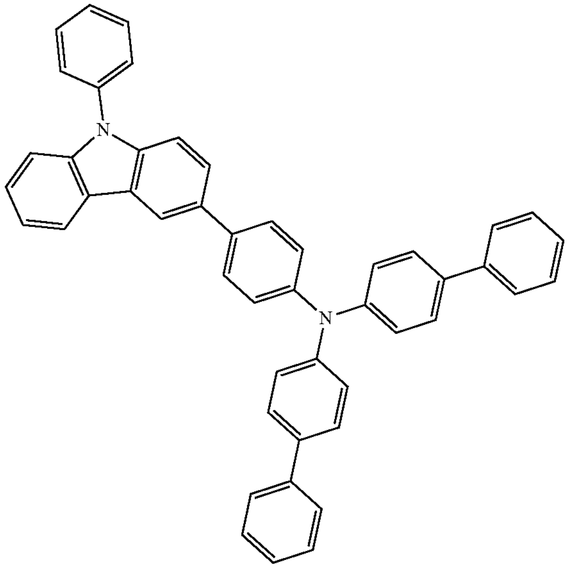

-continued
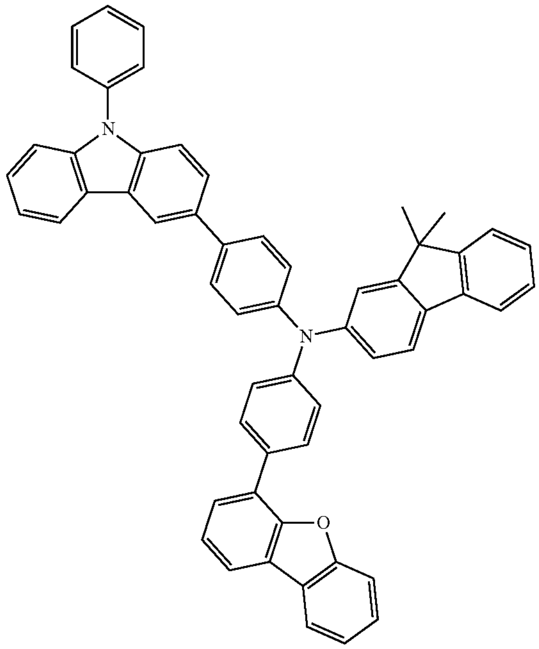
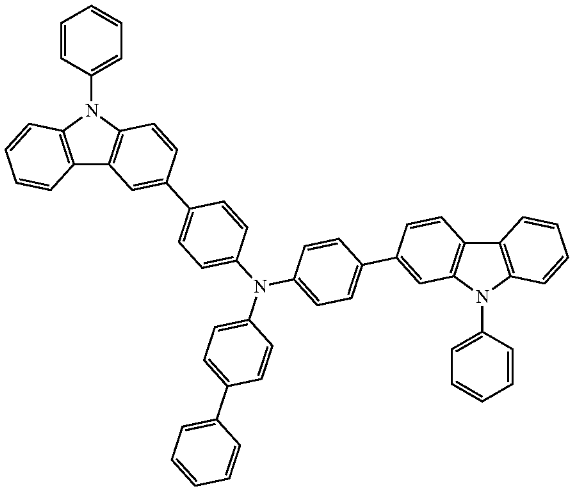
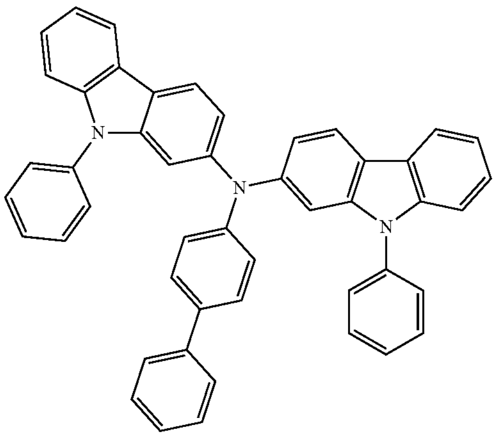
-continued
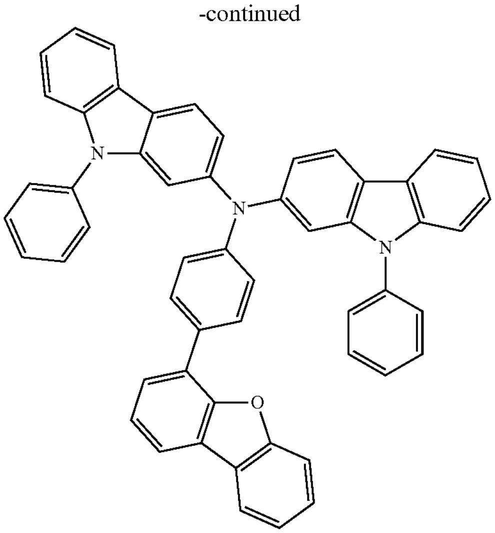
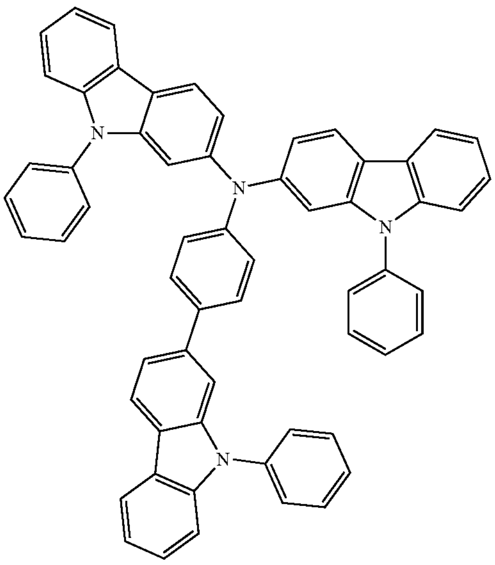
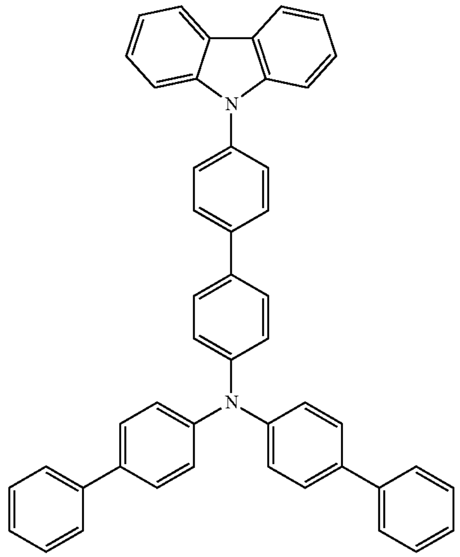

-continued
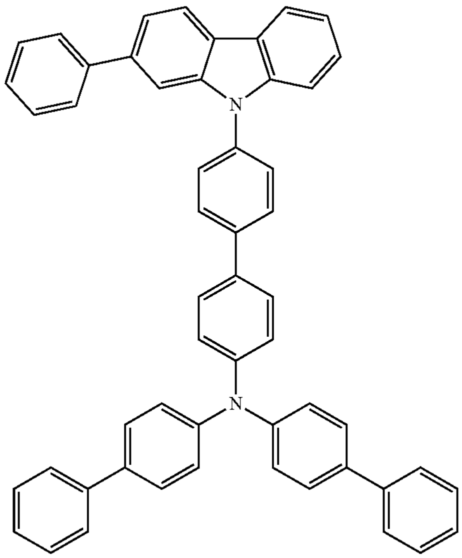
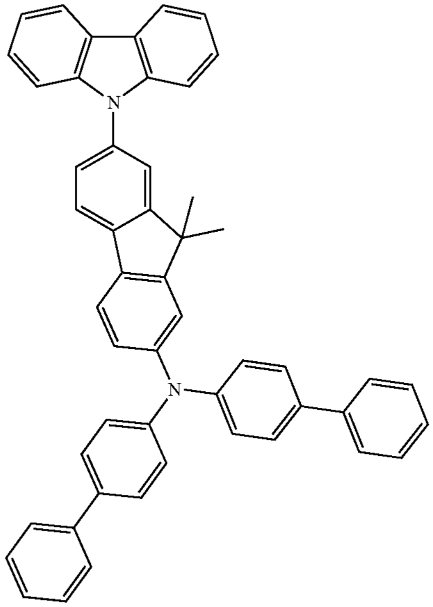
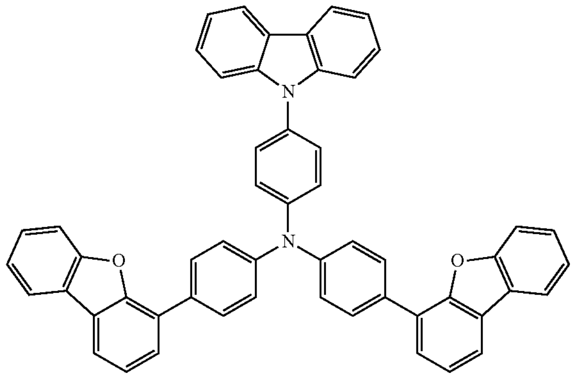
-continued
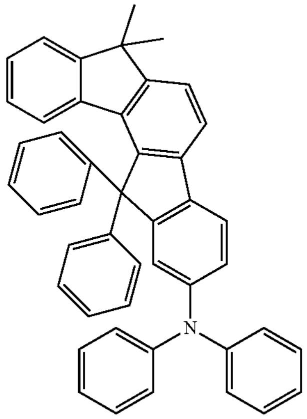
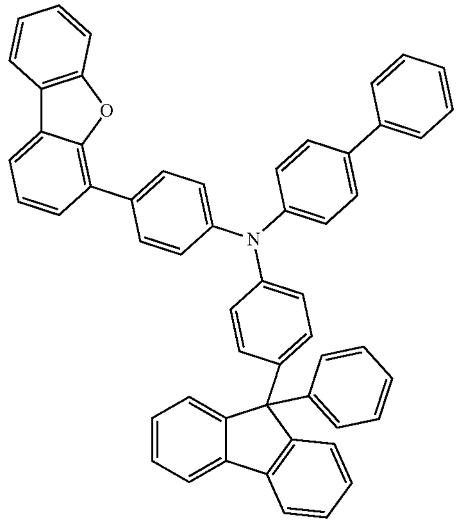
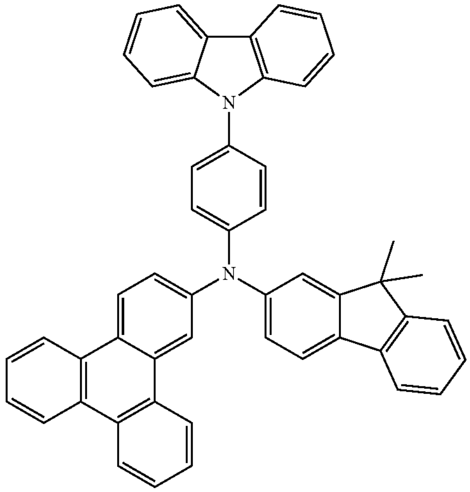

-continued
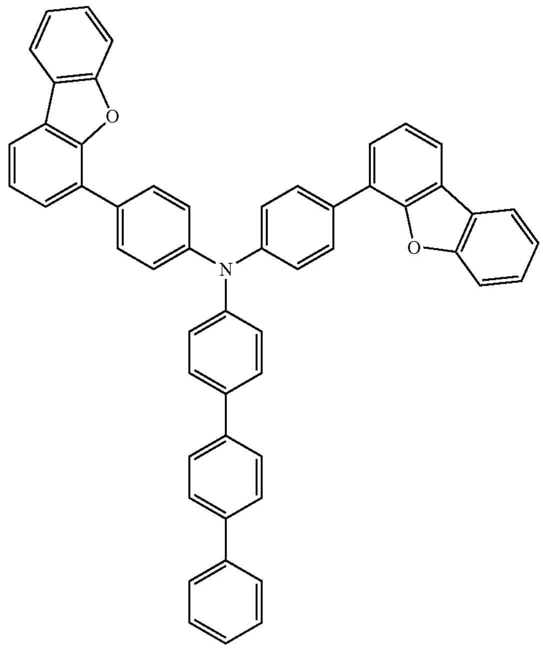
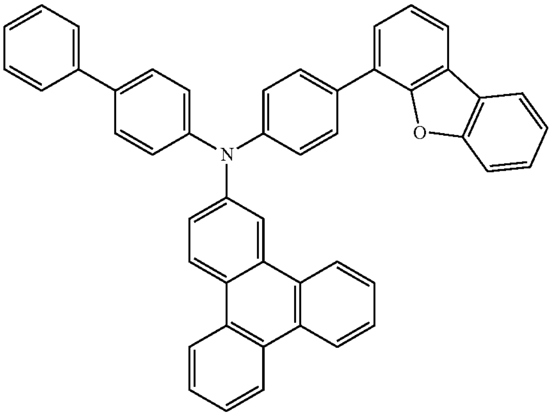
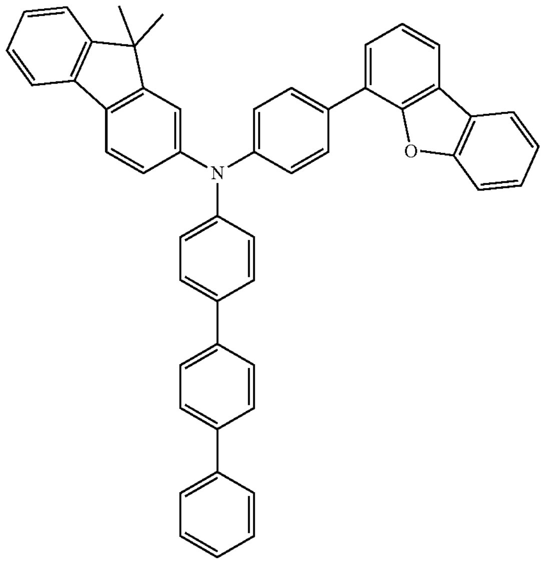
-continued
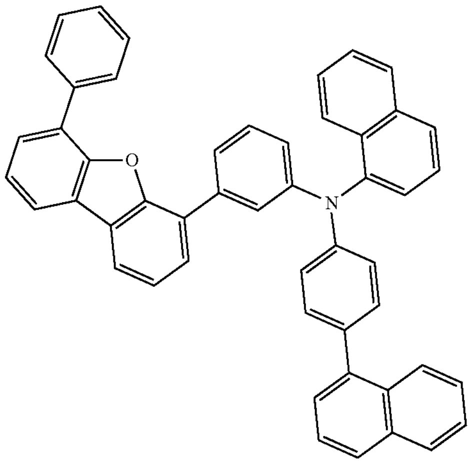
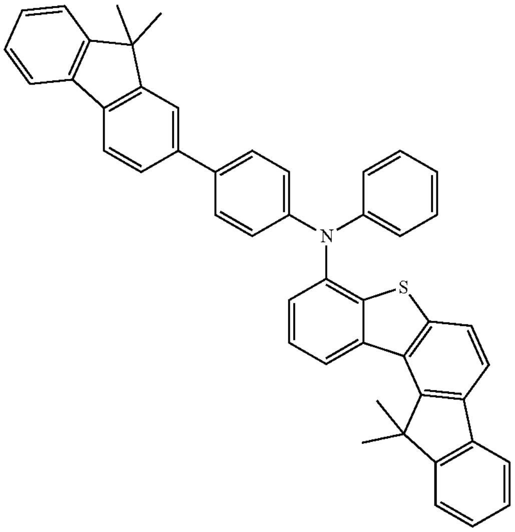
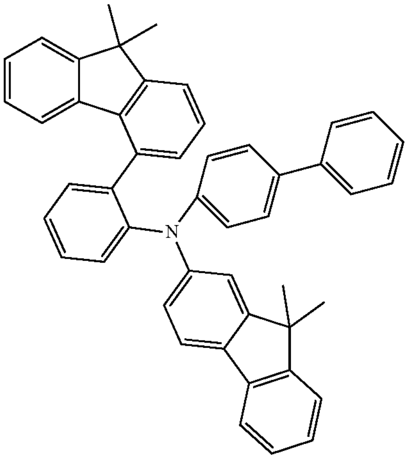

-continued
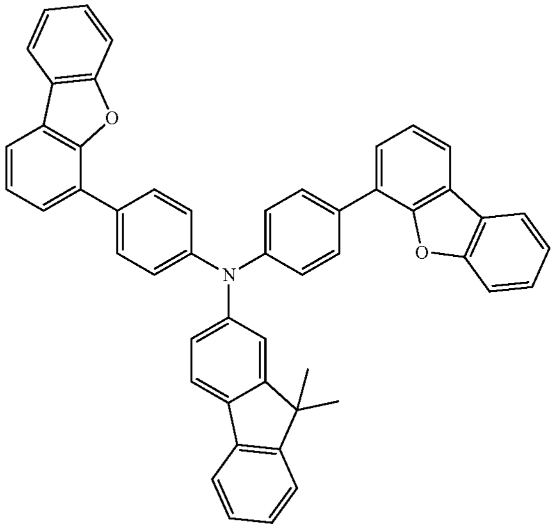
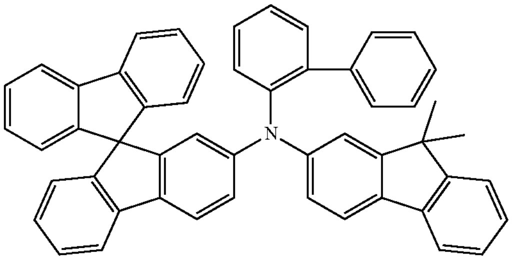
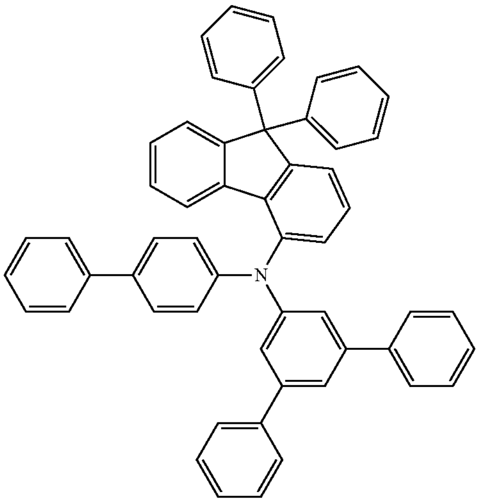
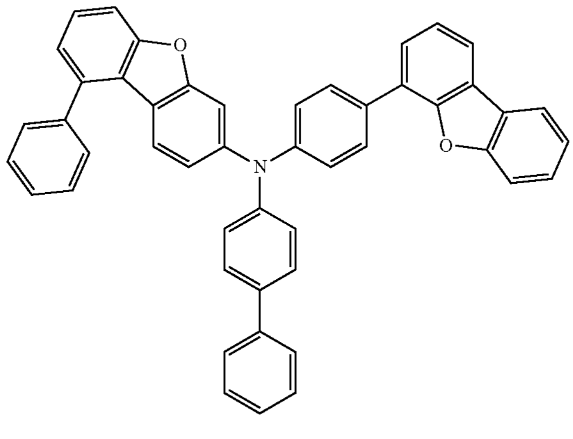
-continued
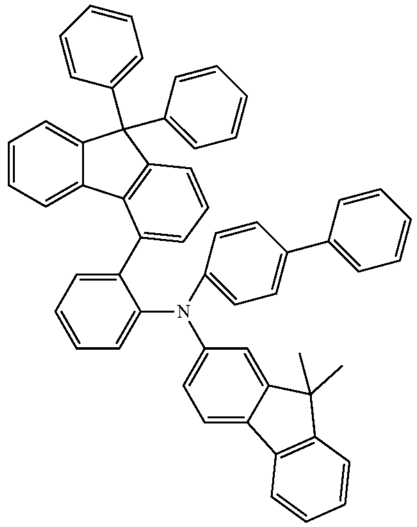
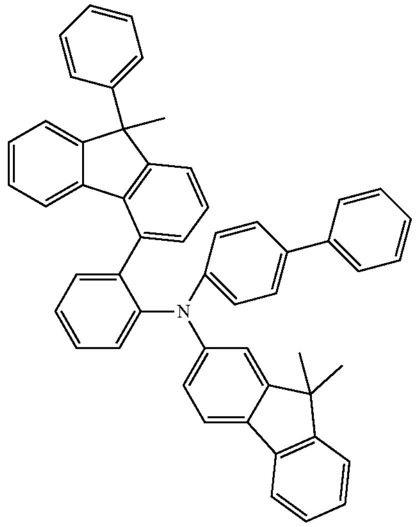
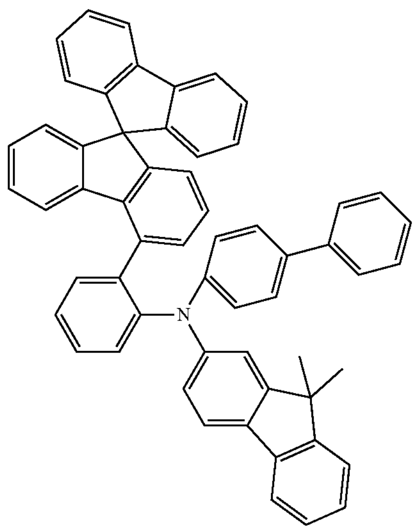

-continued
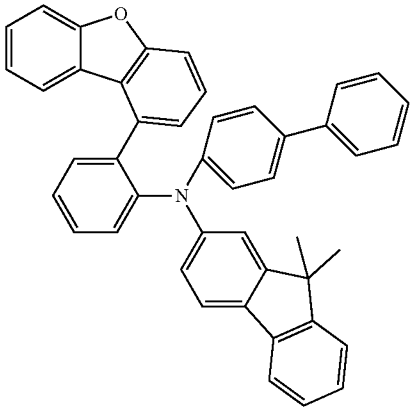
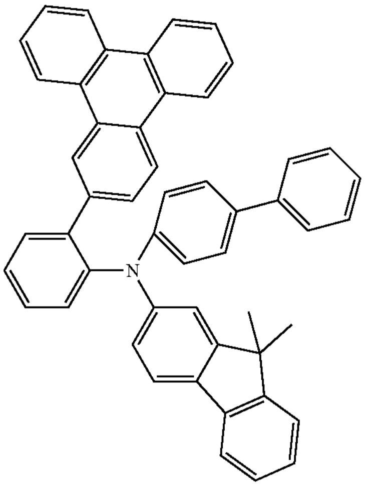
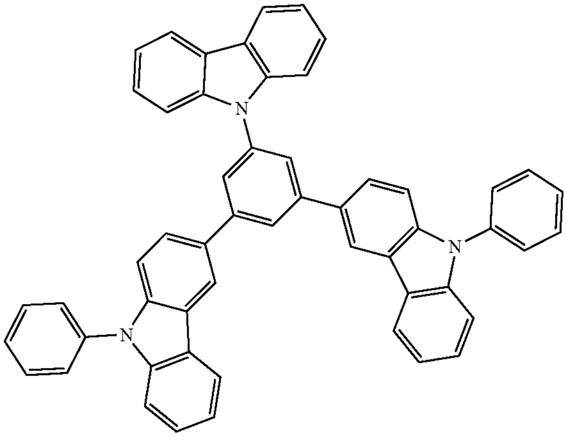
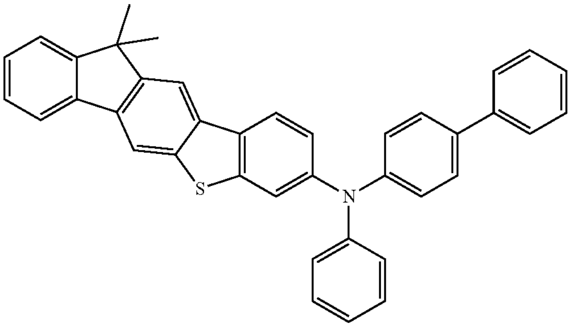
-continued
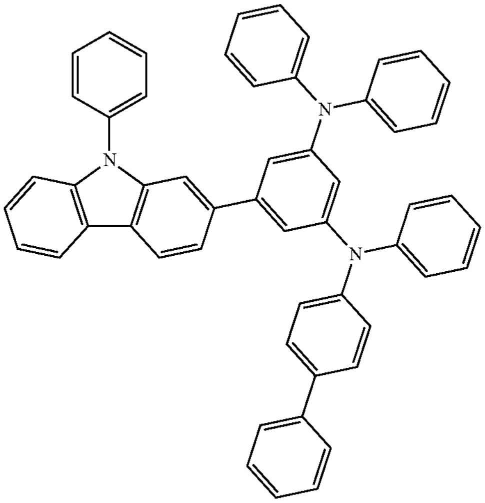
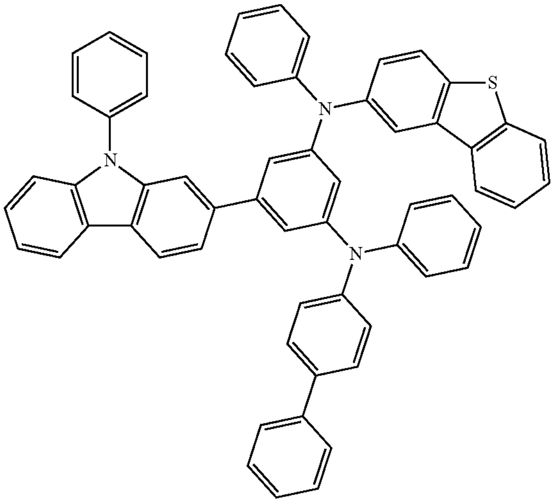
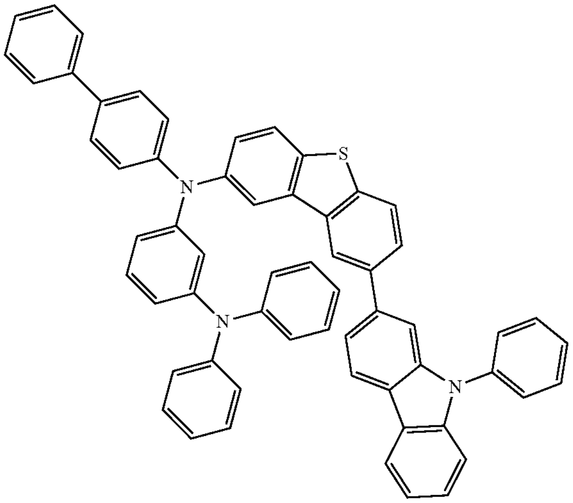

-continued
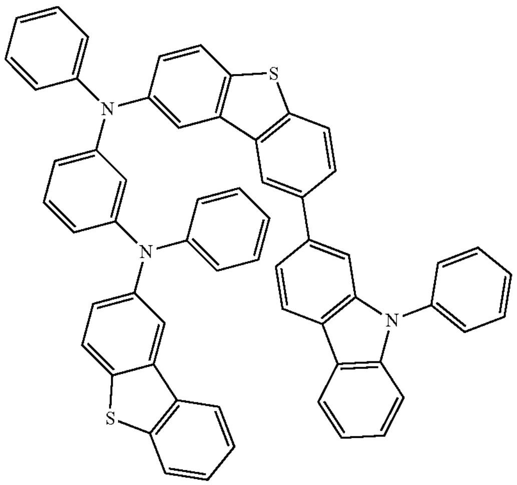
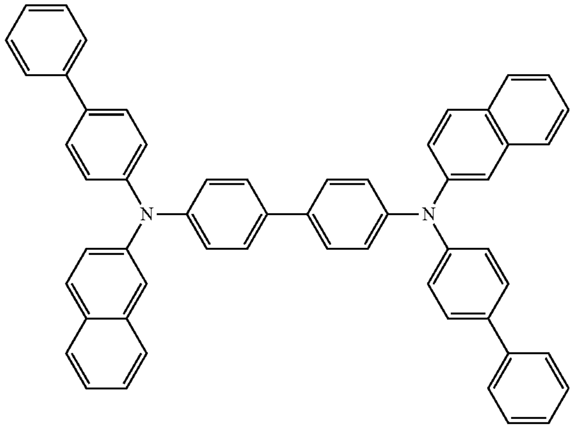
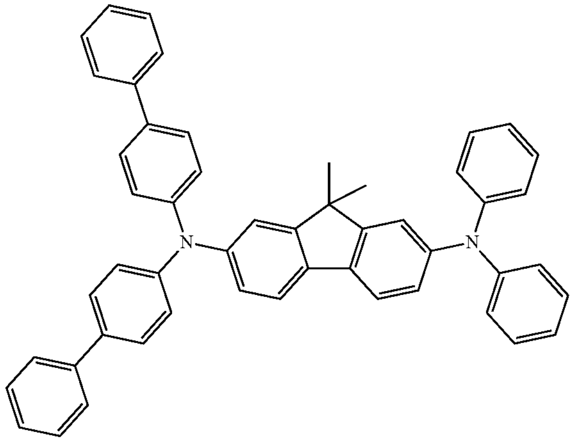
-continued
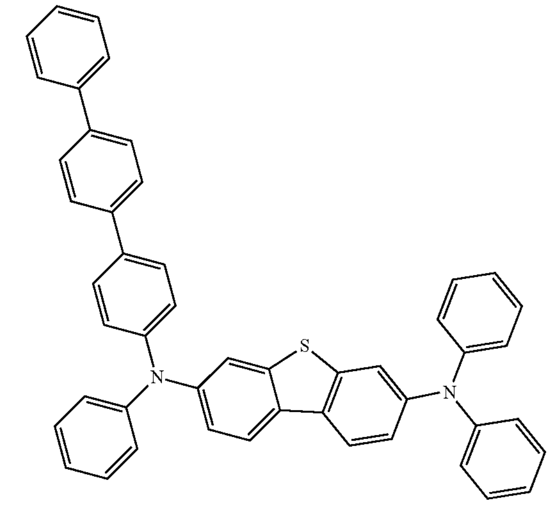
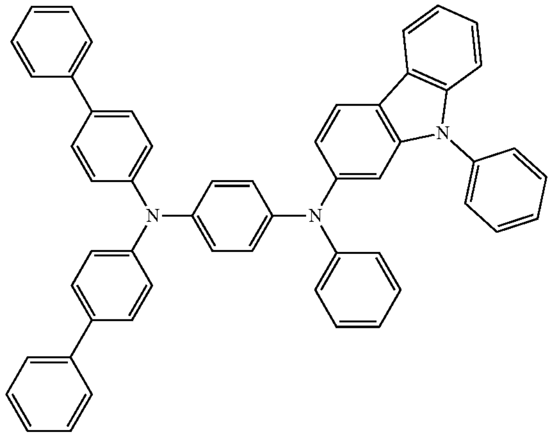
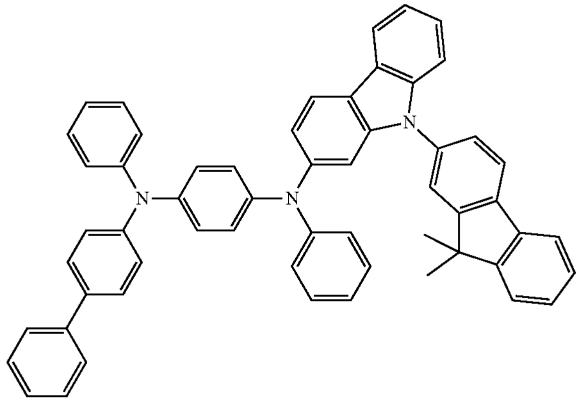

-continued
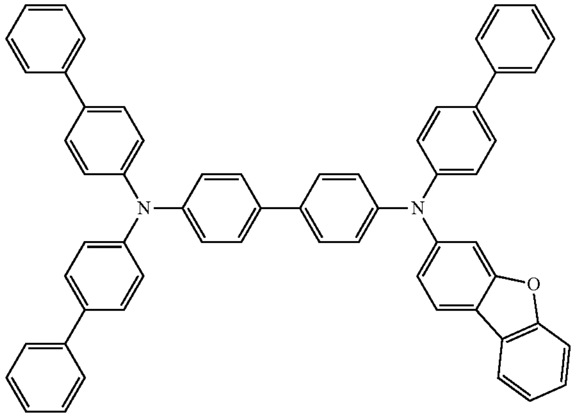
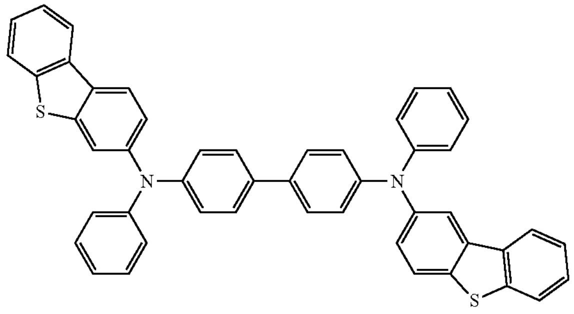
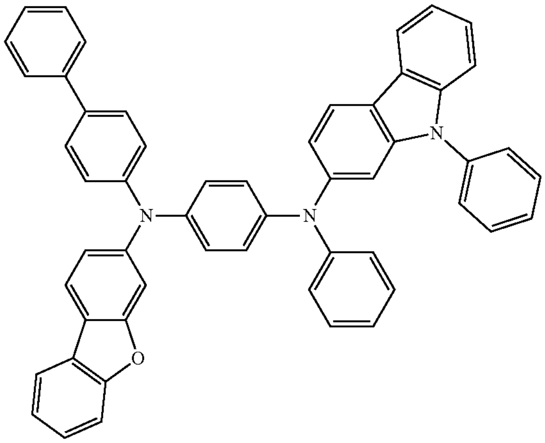
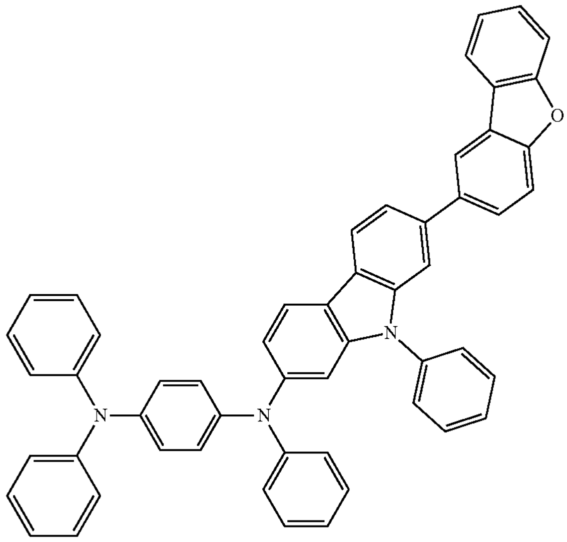
-continued
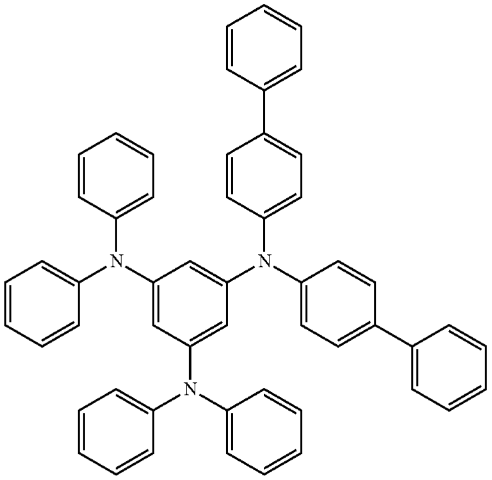
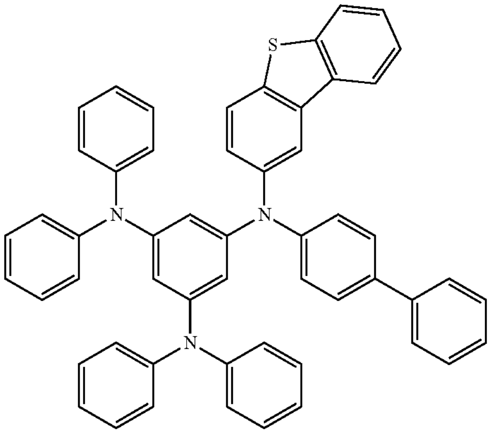
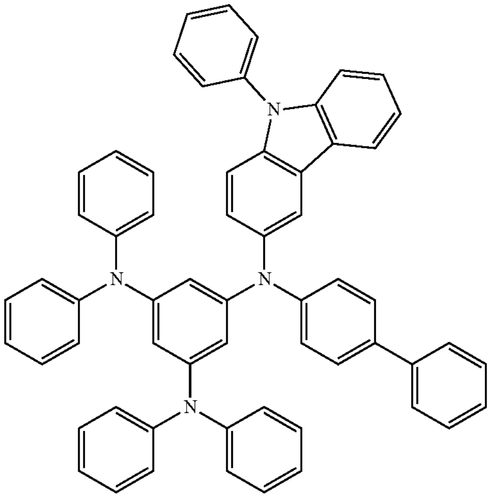

-continued
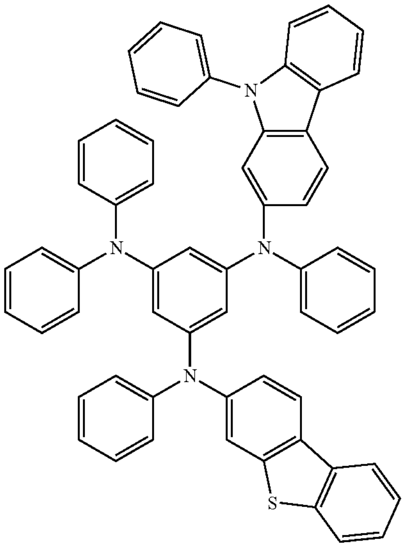
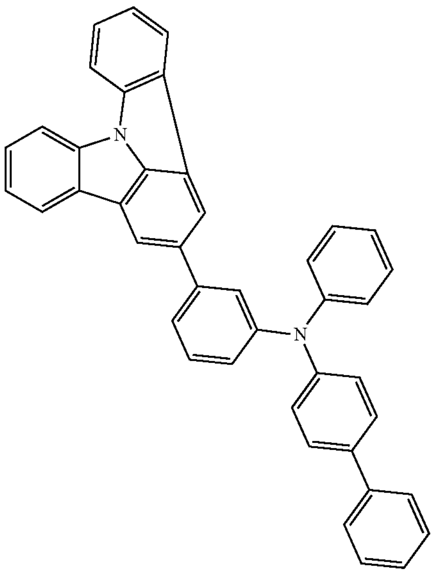
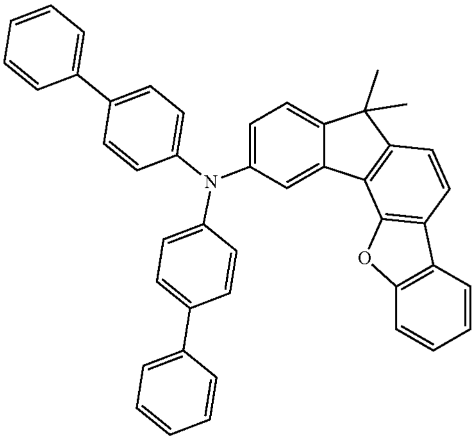
-continued
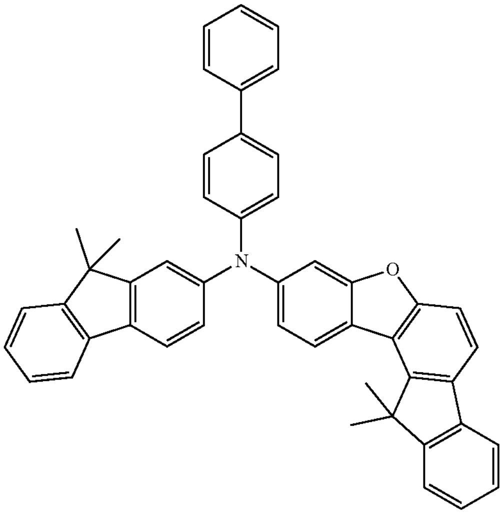
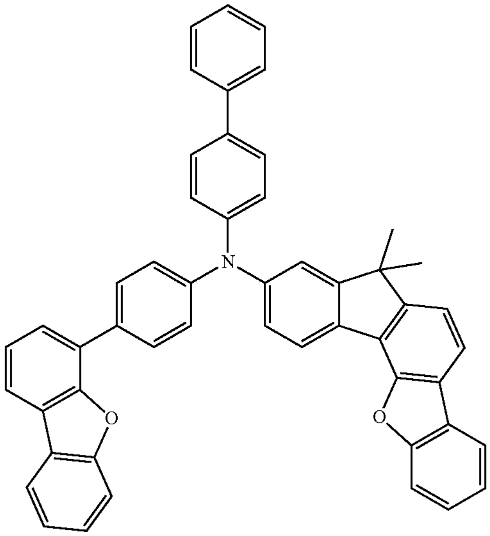
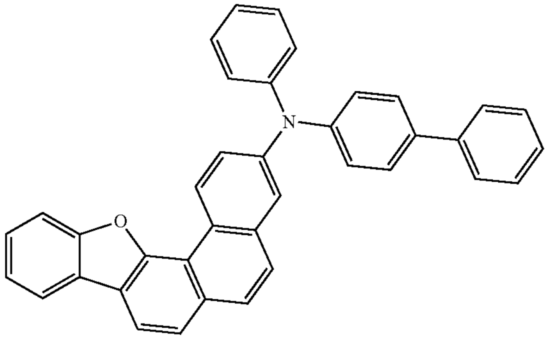

-continued
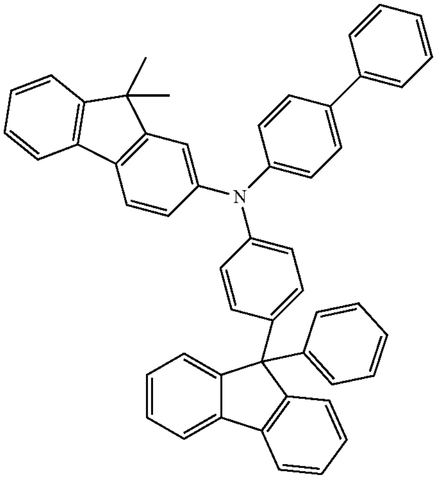
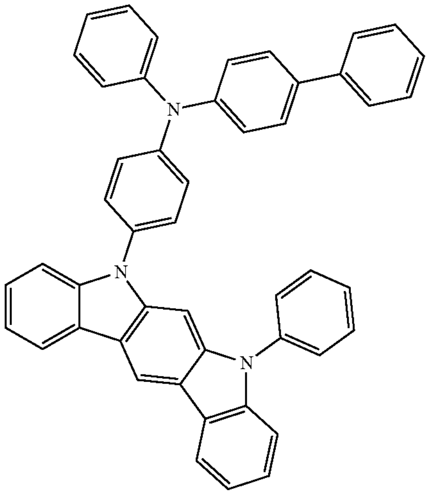
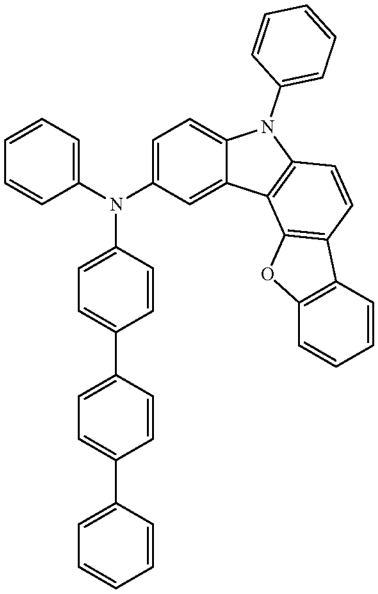
-continued
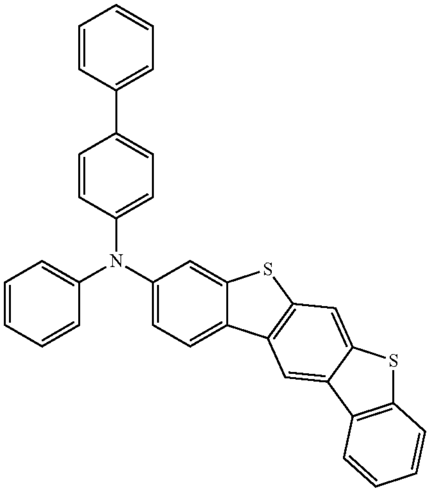
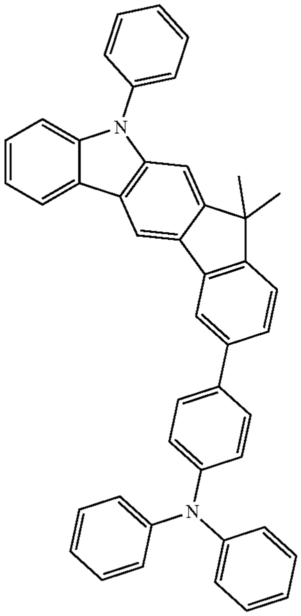
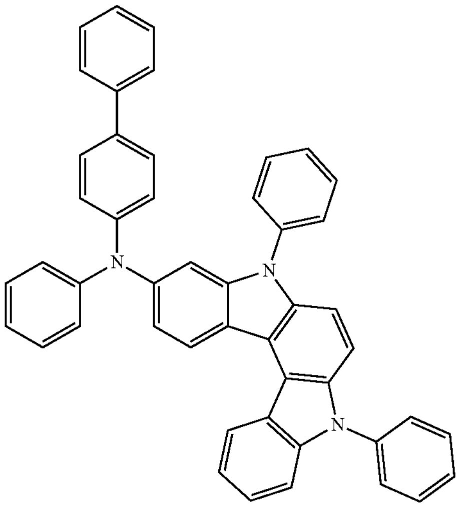

-continued
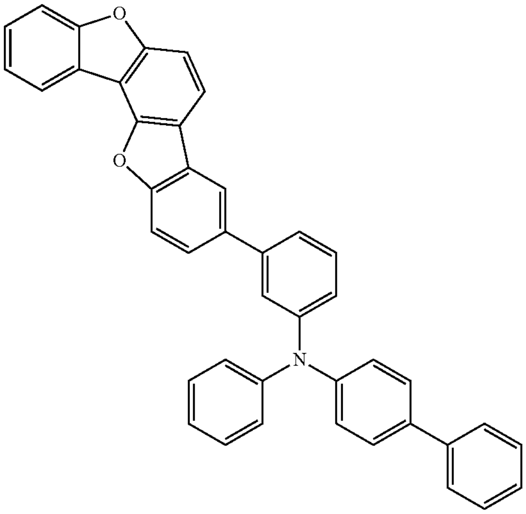
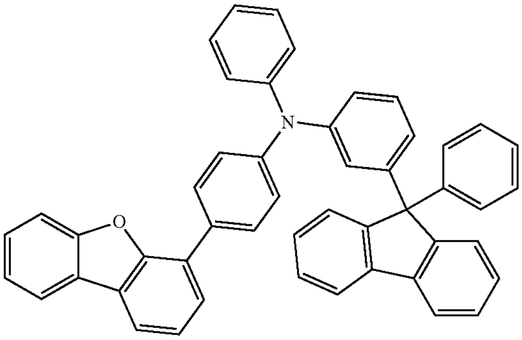
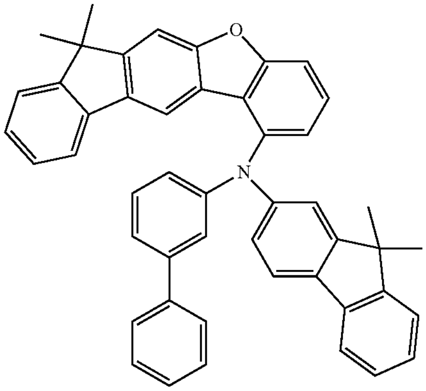
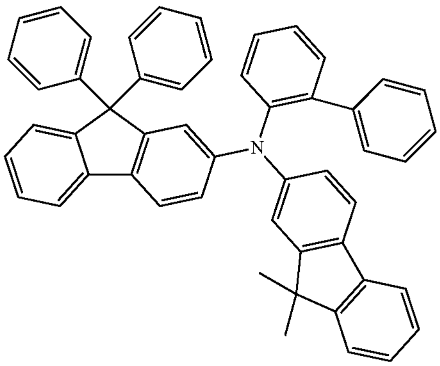
-continued
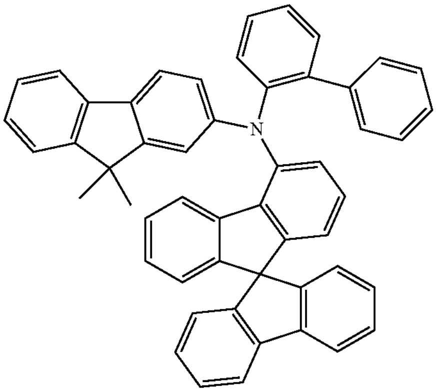
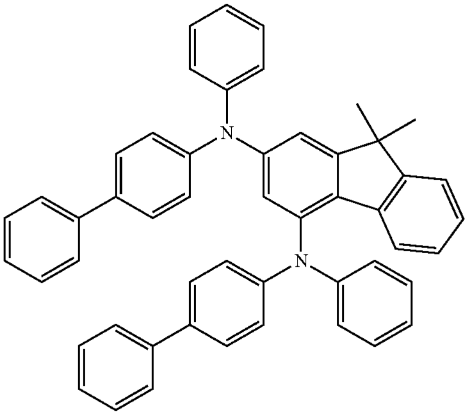
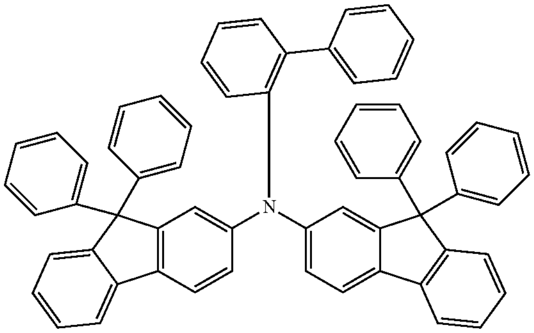
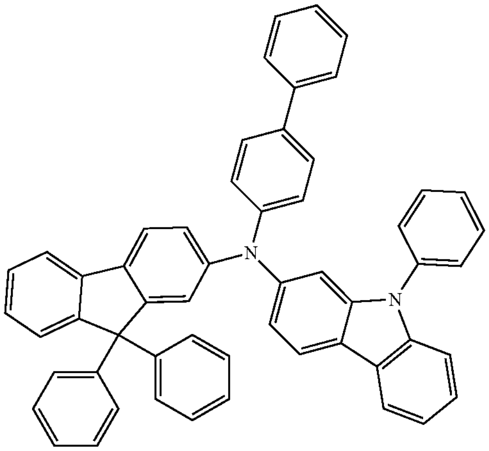

-continued
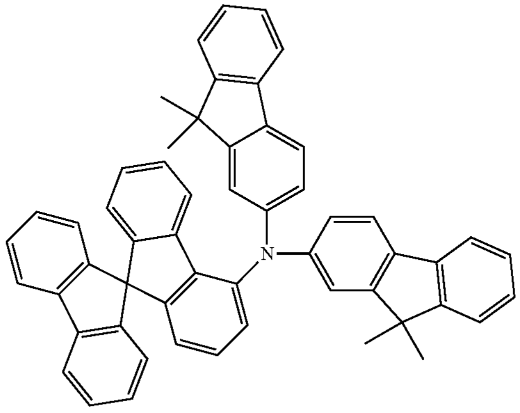
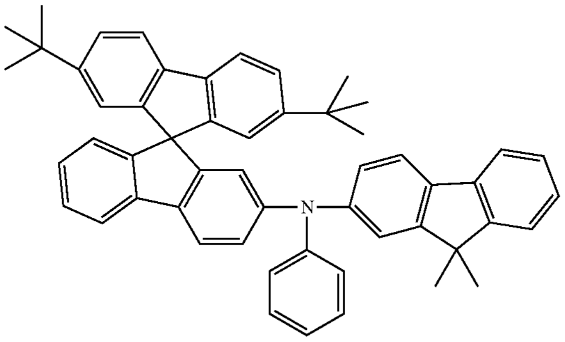
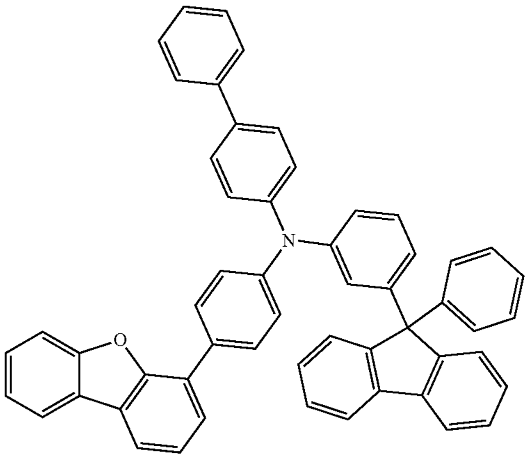
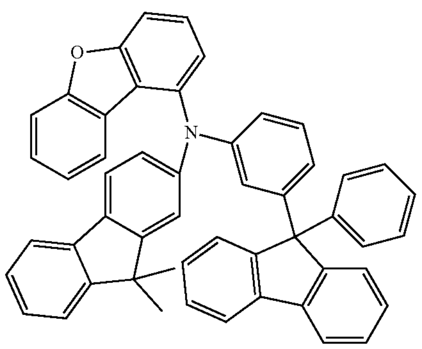
-continued
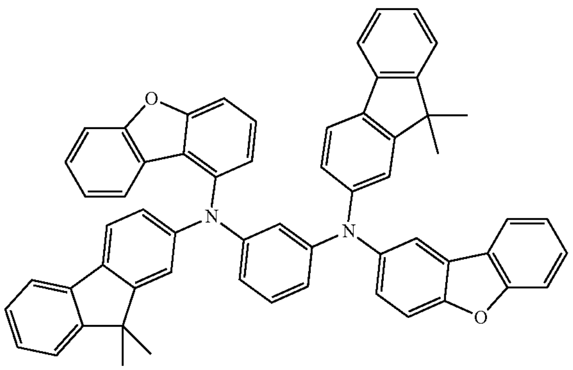
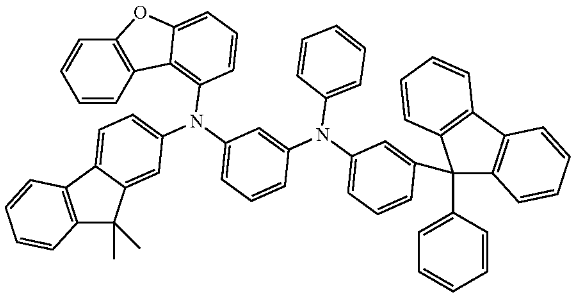
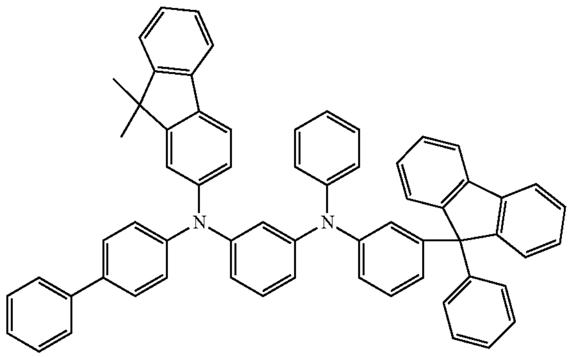
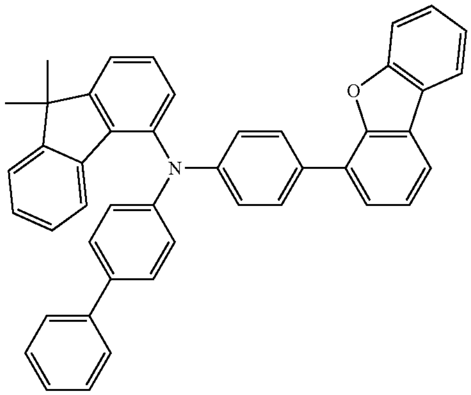

-continued

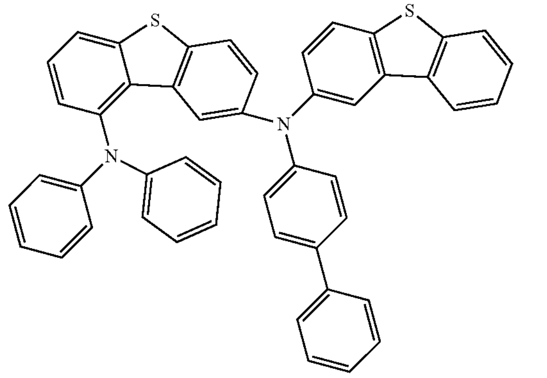

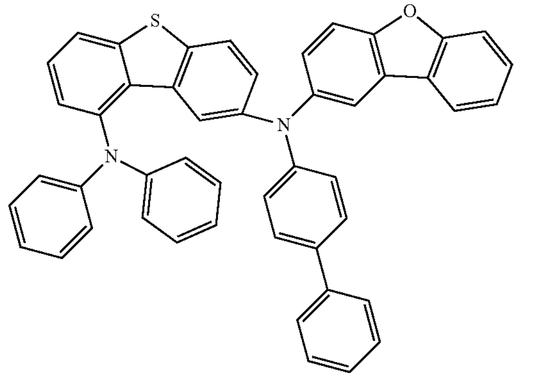

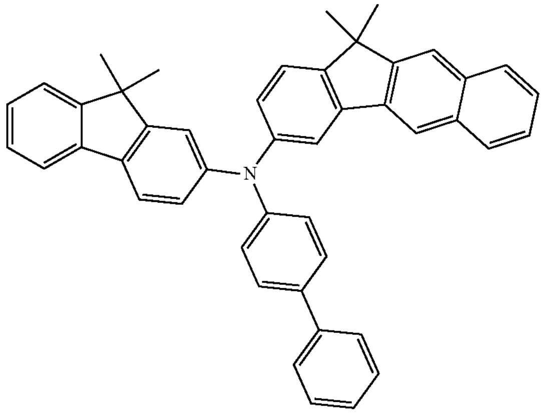

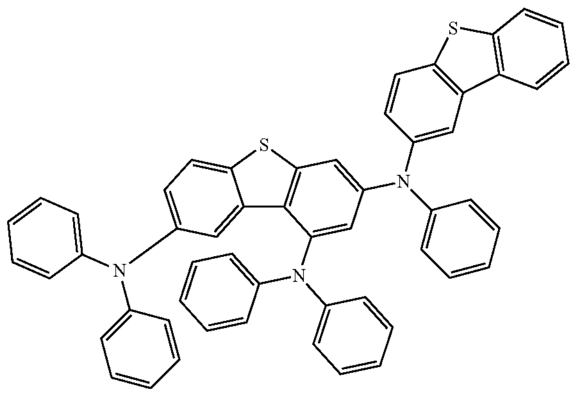

-continued

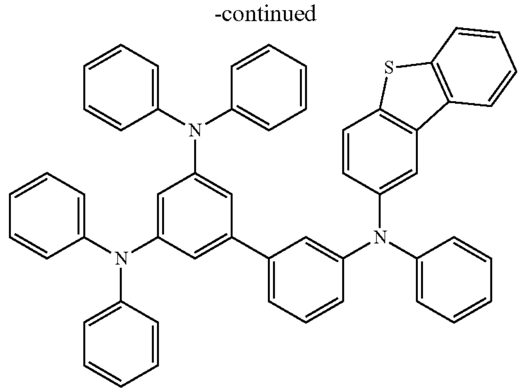

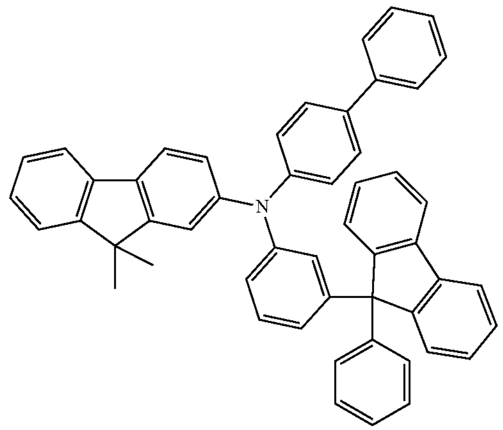

In an implementation, in the hole transport region 140, other suitable compounds may be used in addition to the compound.

In addition, the charge transport region may be, e.g., an electron transport region 150.

The electron transport region 150 may further increase electron injection and/or electron mobility and block holes between the cathode 110 and the light emitting layer 130.

In an implementation, the electron transport region 150 may include an electron transport layer between the cathode 110 and the light emitting layer 130, and an electron transport auxiliary layer between the light emitting layer 130 and the electron transport layer, and at least one of the compounds of Group C may be included in at least one of the electron transport layer and the electron transport auxiliary layer.

[Group C]
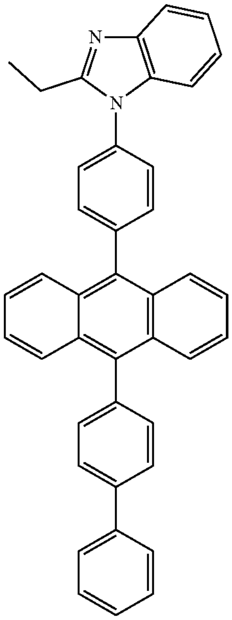
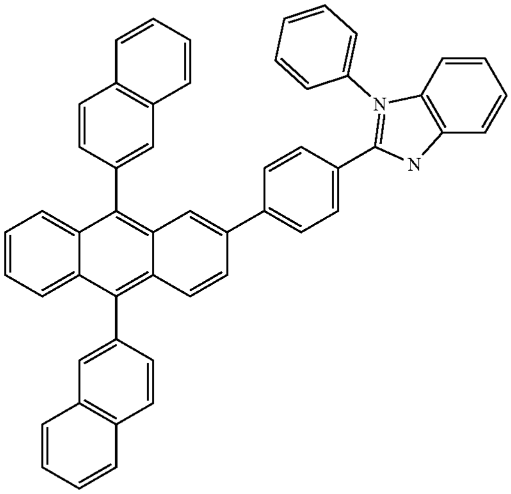
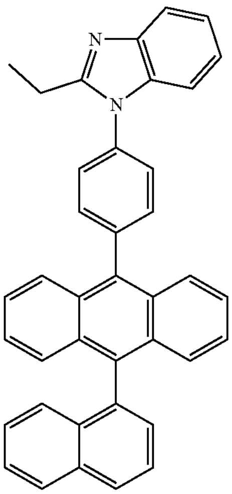
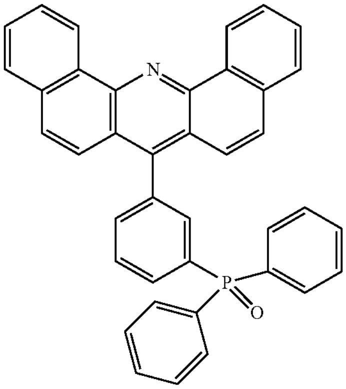
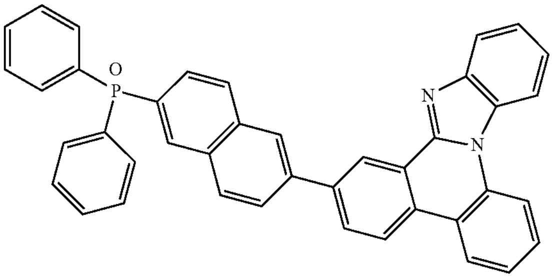
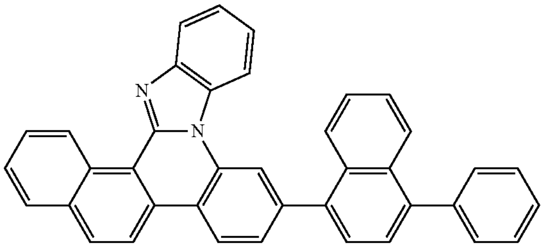
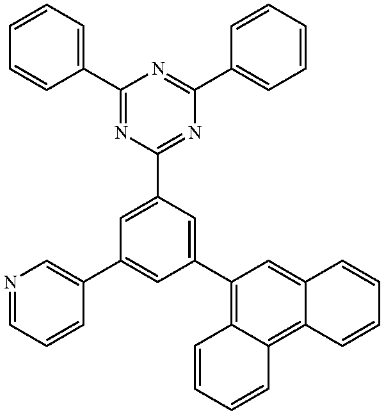

-continued
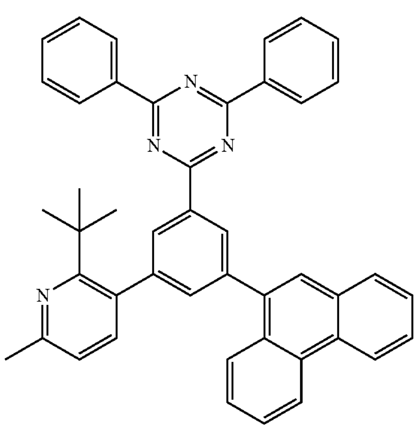
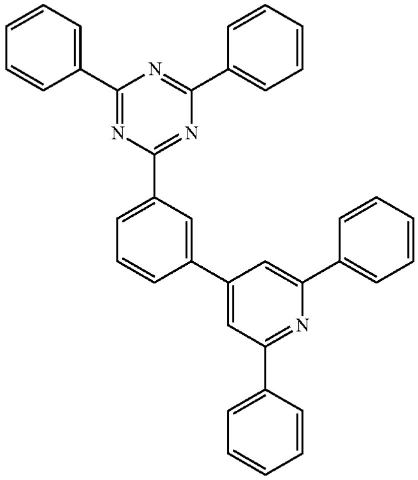
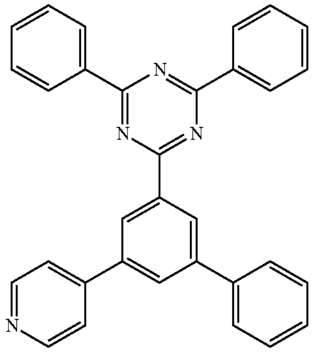
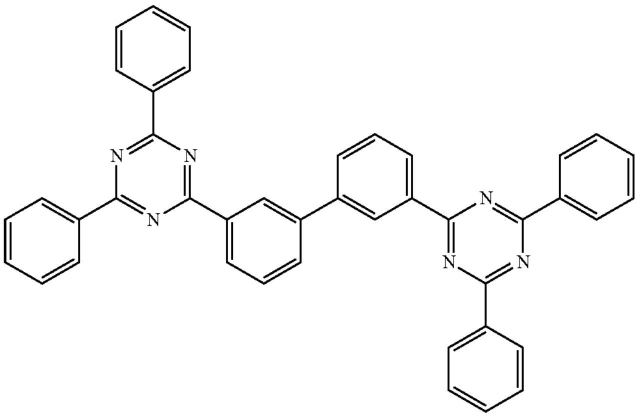
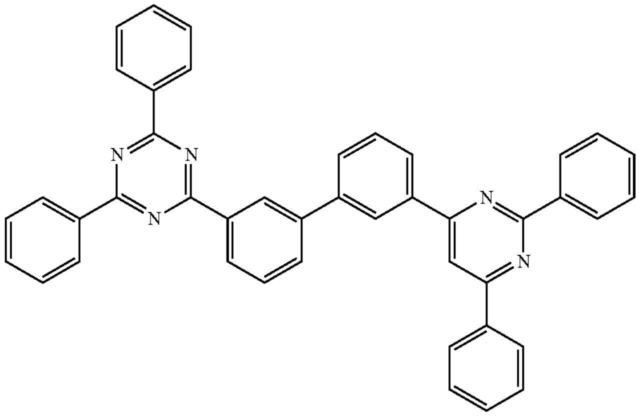
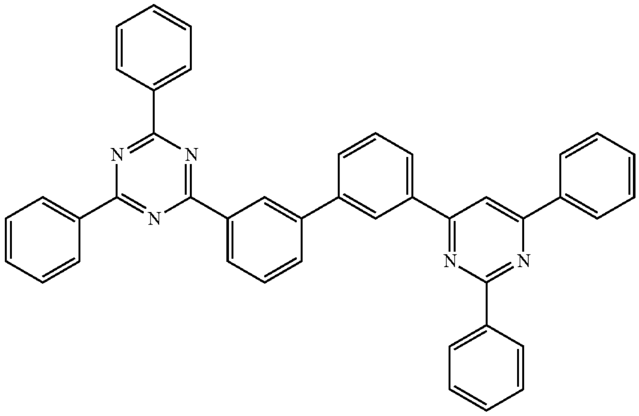

-continued
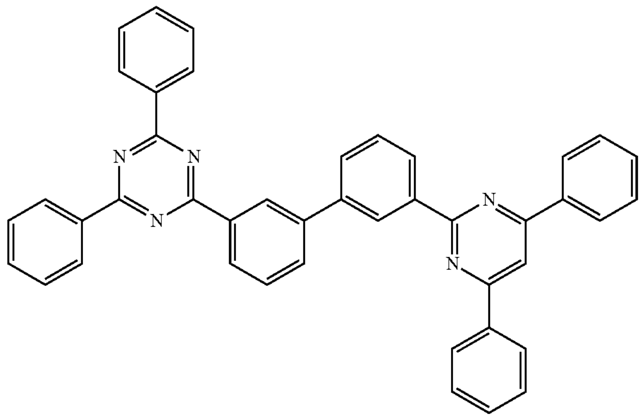
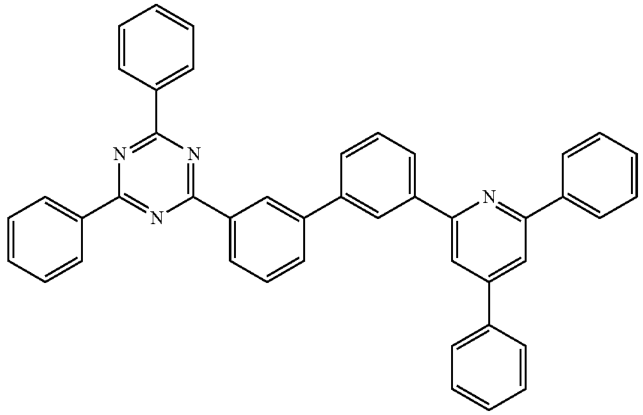
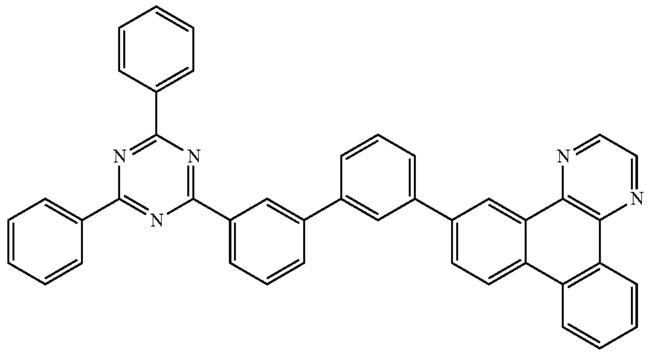
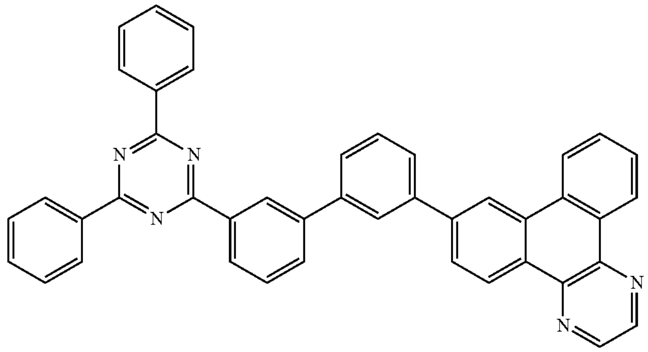

-continued
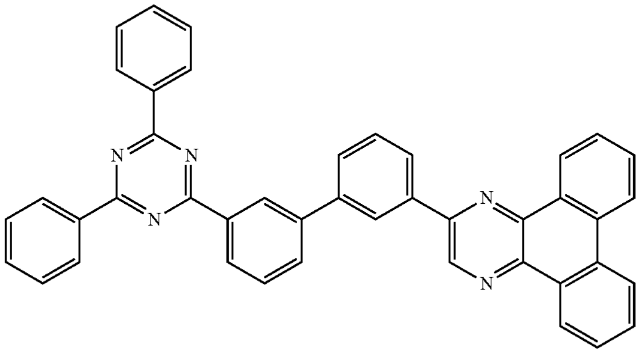
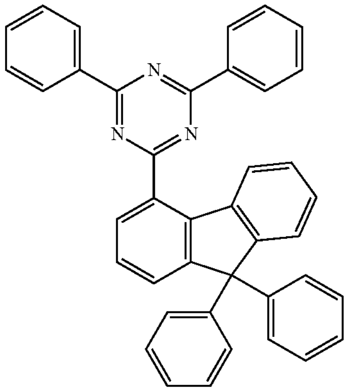
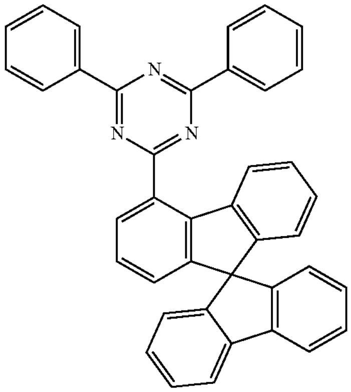
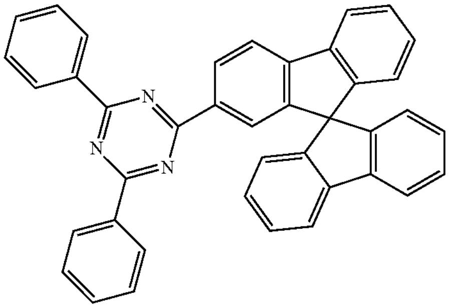
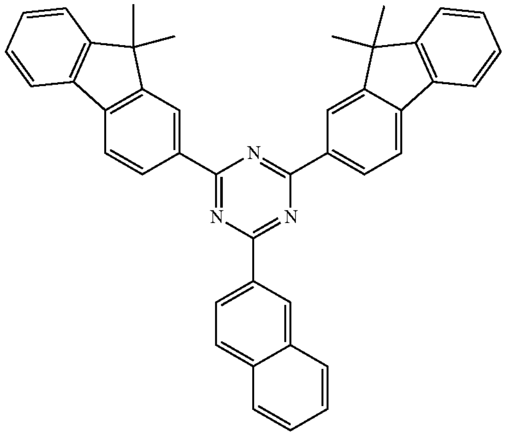
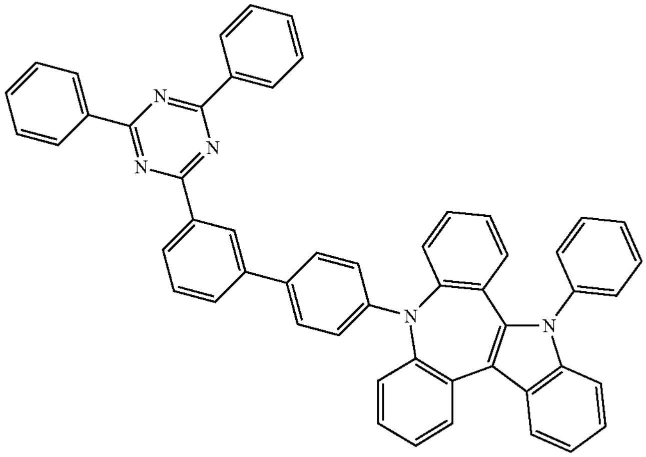

-continued
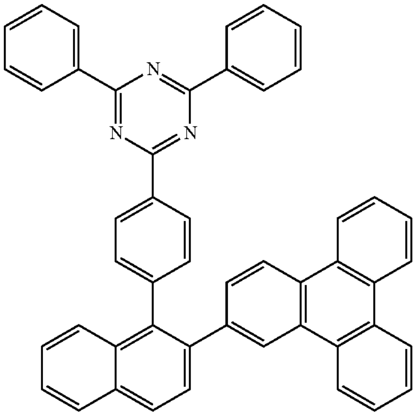
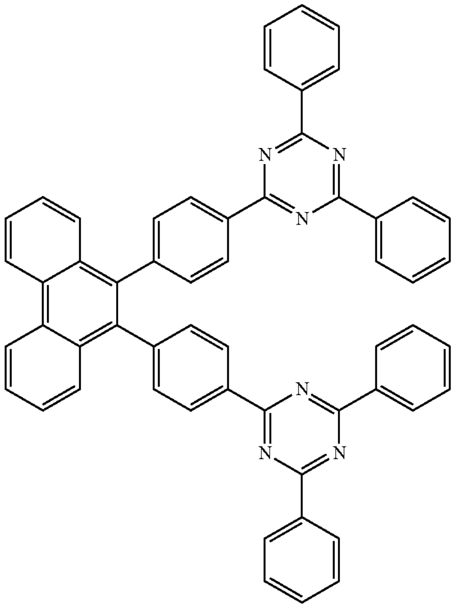
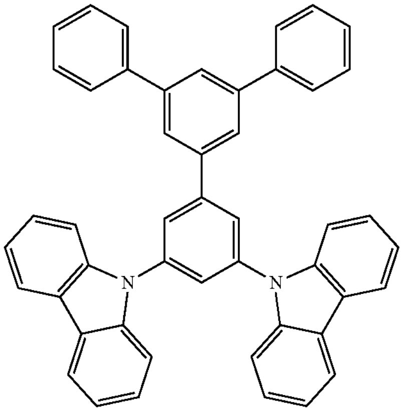
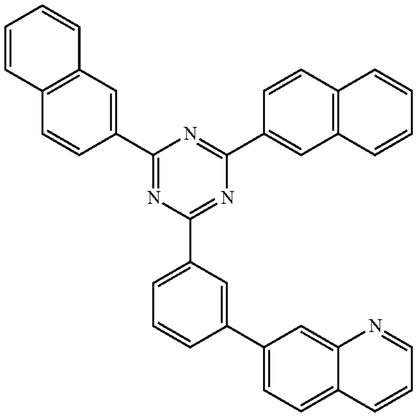
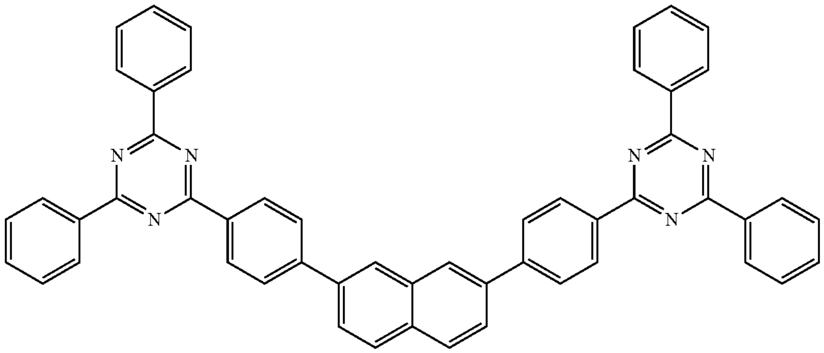
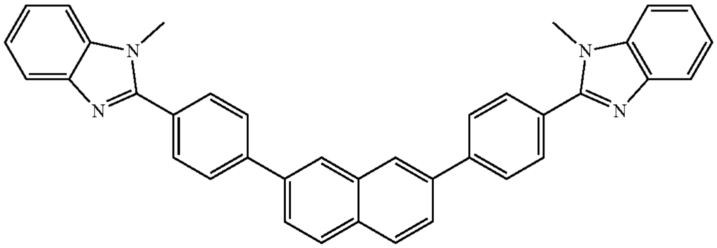

-continued
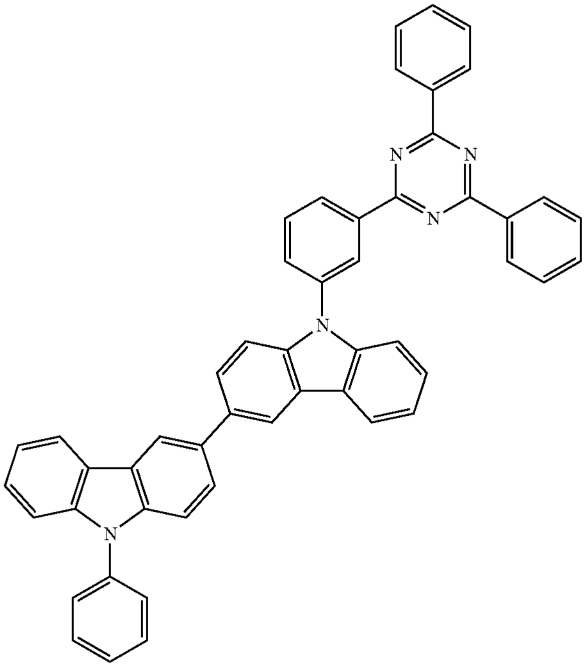
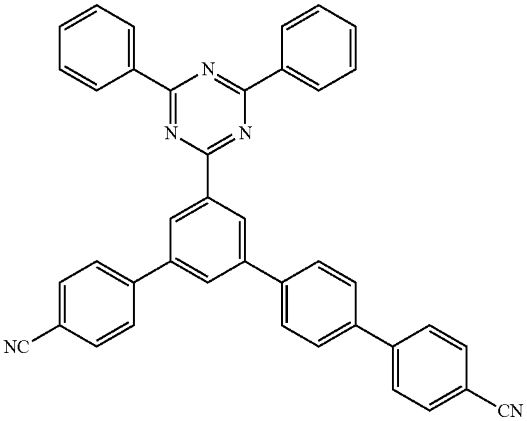
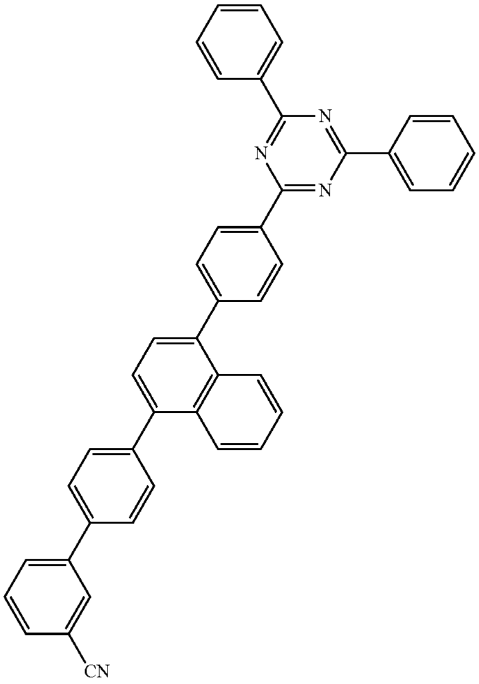

-continued
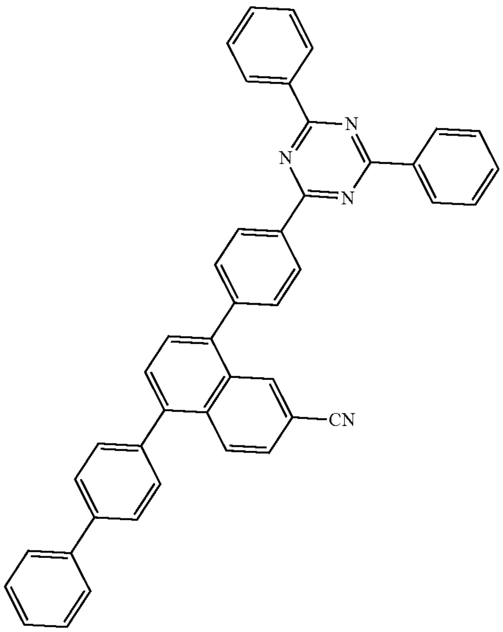
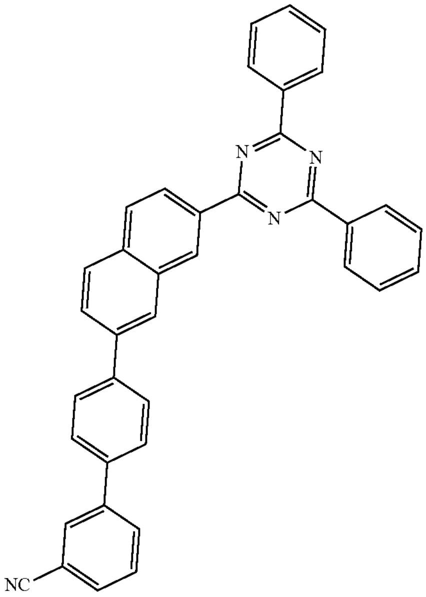
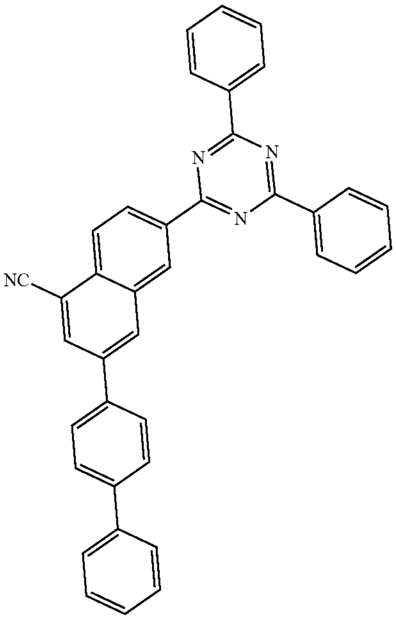
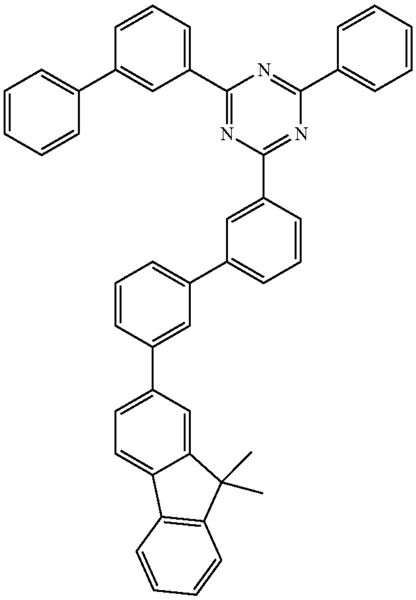

-continued
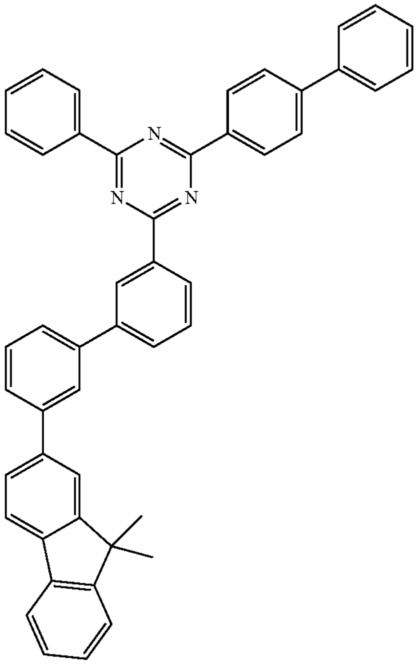
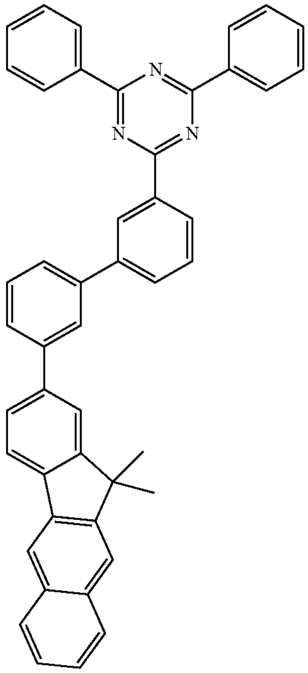
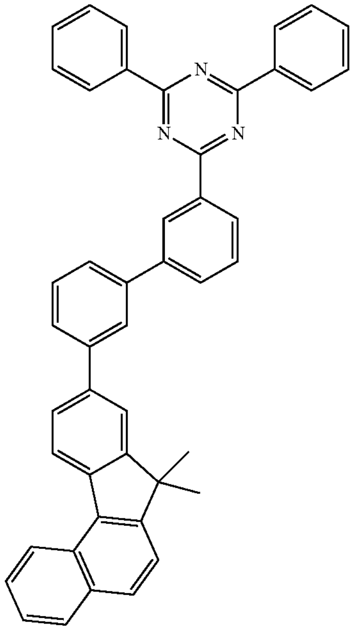
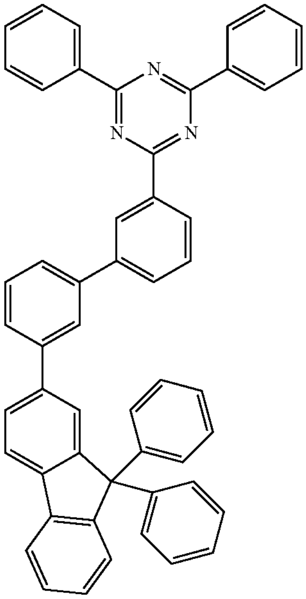
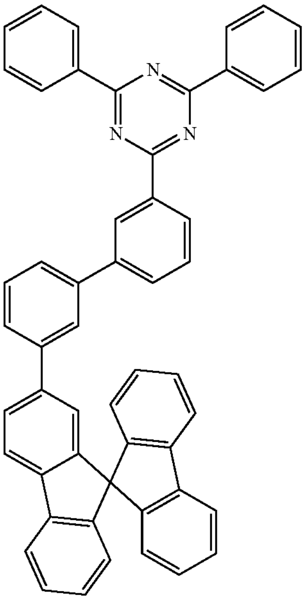

-continued
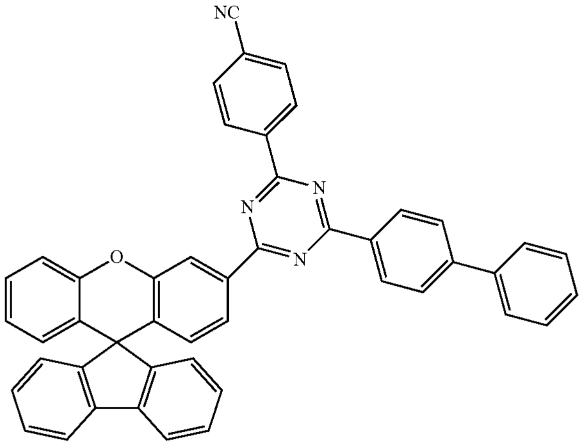
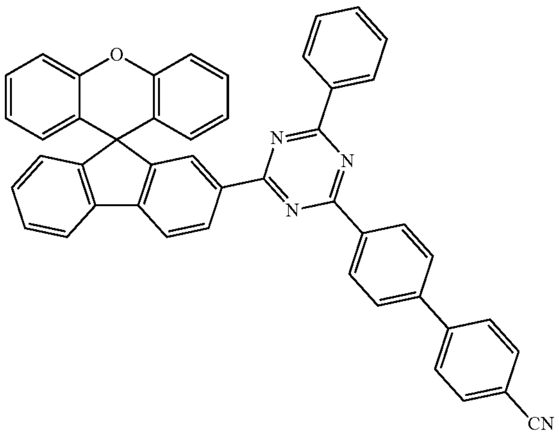
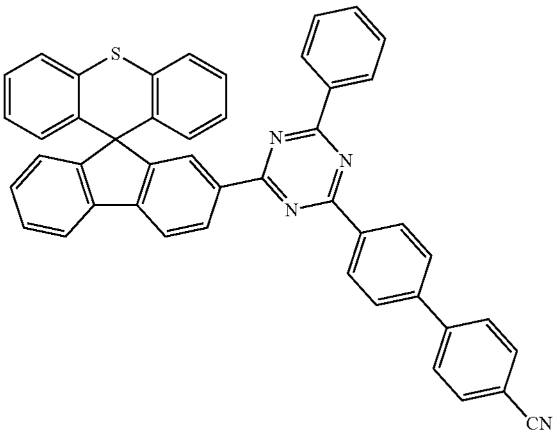
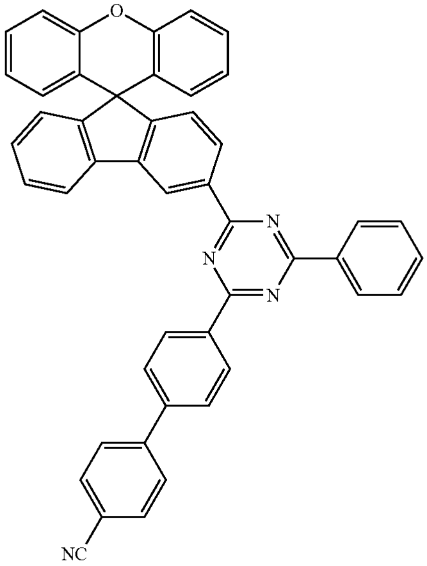
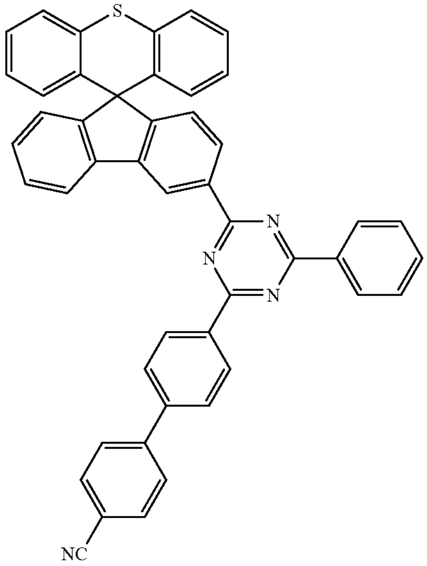

-continued
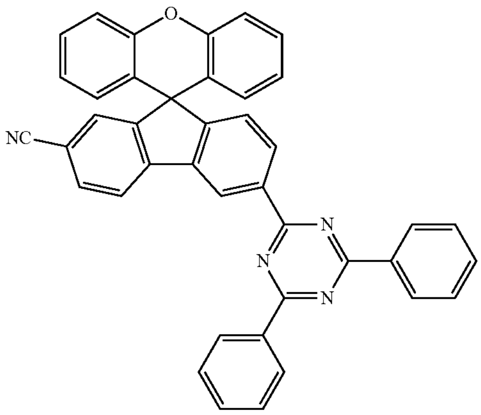
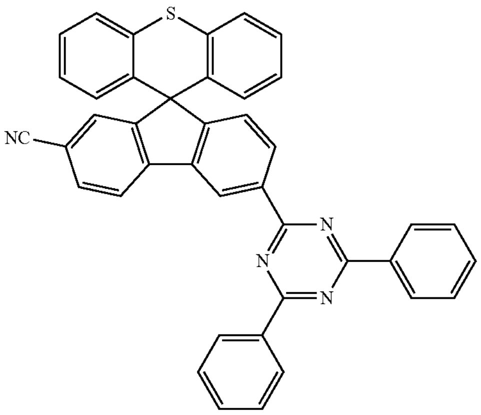
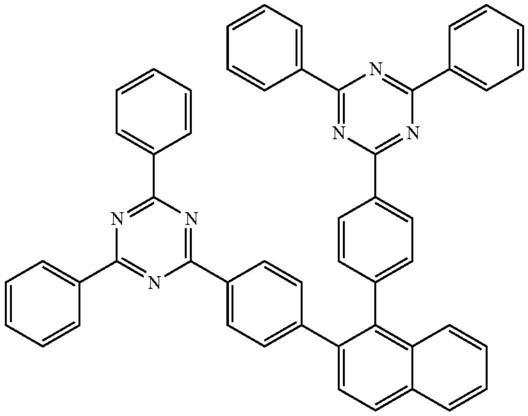
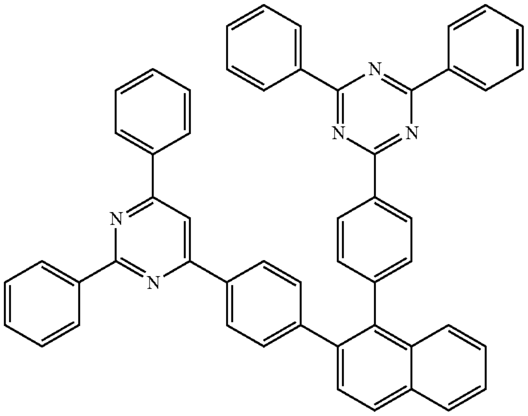
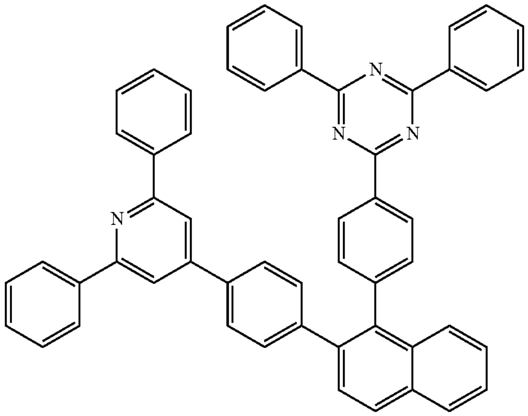
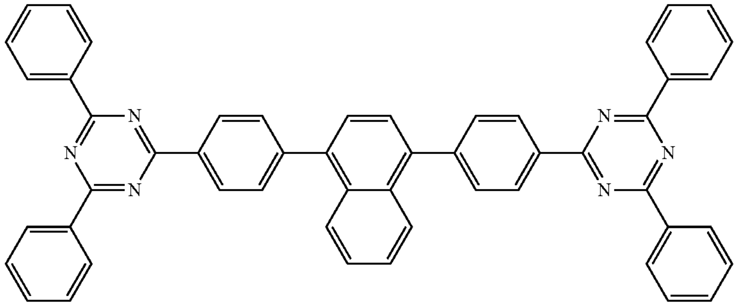

-continued
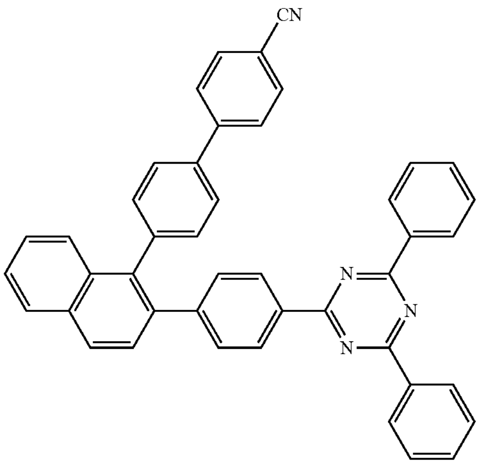
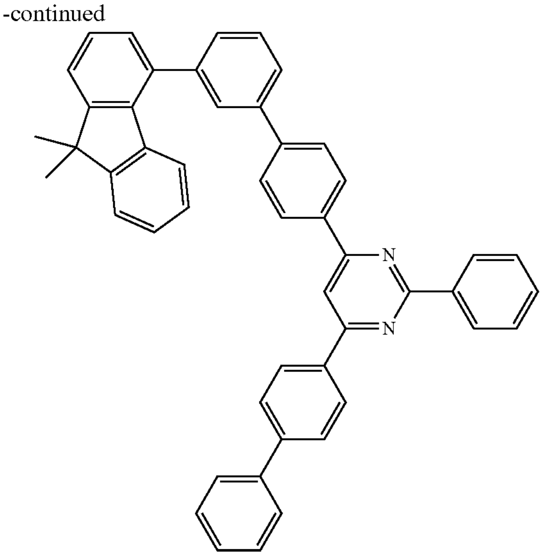
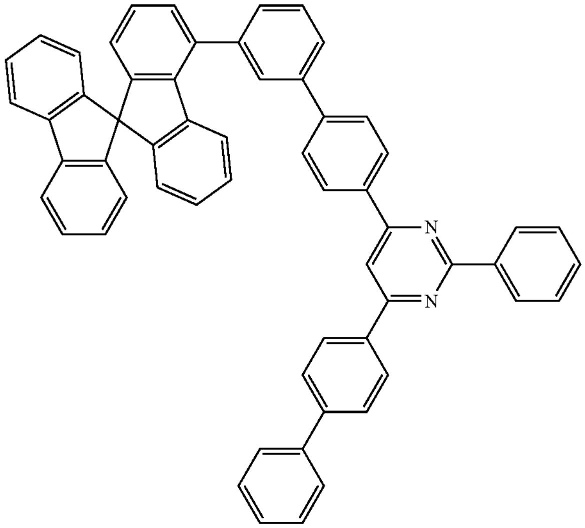
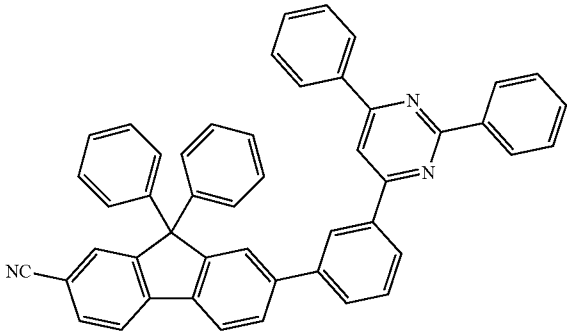
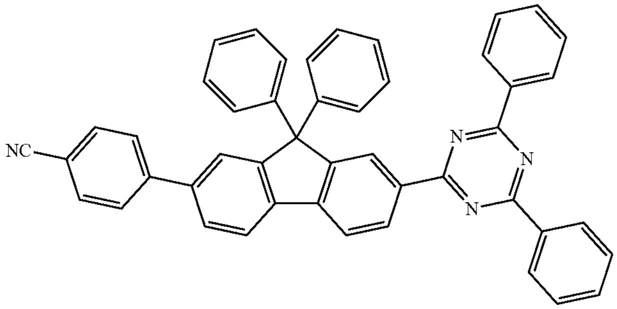

-continued

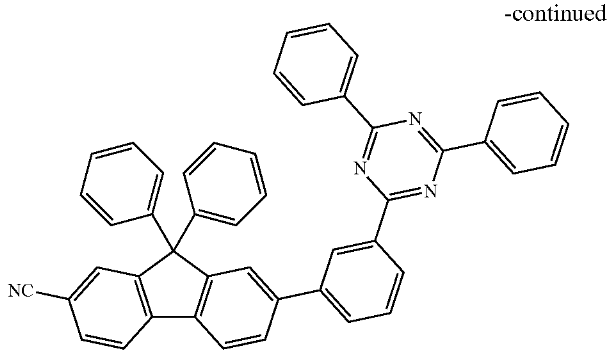

An embodiment may be an organic light emitting diode including a light emitting layer as an organic layer.

Another embodiment may provide an organic light emitting diode including a light emitting layer and a hole transport region as an organic layer.

Another embodiment may provide an organic light emitting diode including a light emitting layer and an electron transport region as an organic layer.

As shown in the FIGURE, the organic light emitting diode according to the embodiment may include a hole transport region 140 and an electron transport region 150 in addition to the light emitting layer 130 as the organic layer 105.

On the other hand, the organic light emitting diode may further include an electron injection layer, a hole injection layer, or the like, in addition to the light emitting layer as the aforementioned organic layer.

The organic light emitting diode 100 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo Chemical Industry, or P&H Tech as far as there in no particular comment or were synthesized by suitable methods.

(Preparation of Compound for Organic Optoelectronic Device)

The compound was synthesized through the following steps.

Synthesis Example 1: Synthesis of Compound A-4

[Reaction Scheme 1]

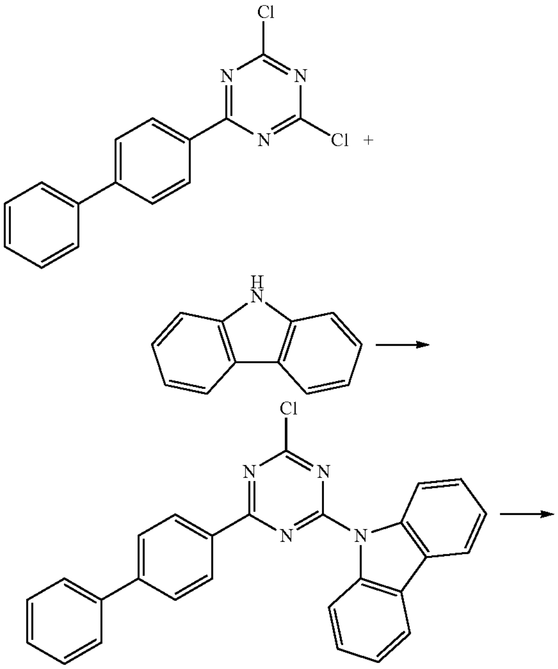

Int-01

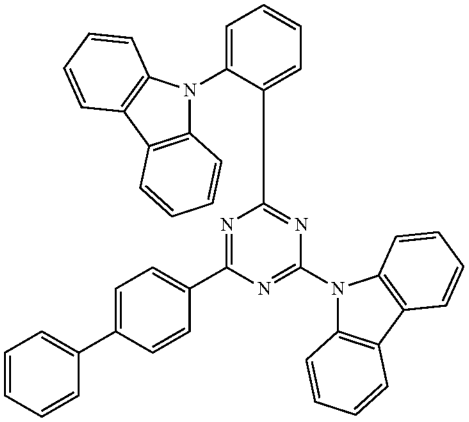

A-4

1st Step: Synthesis of Intermediate Int-01

2,4-dichloro-6-(biphenyl-4-yl)-1,3,5-triazine (39.2 g, 129.78 mmol), carbazole (15.5 g, 92.7 mmol), and sodium tert-butoxide (9.35 g, 97.3 mmol) were put in a round-bottomed flask and stirred with 650 ml of THE at ambient temperature for 12 hours. A solid produced therein was filtered and then, stirred with a water layer for 30 minutes. The resultant was filtered and dried, obtaining 28 g (70%) of Intermediate Int-01.

2nd Step: Synthesis of Compound A-4

15 g (34.65 mmol) of Intermediate Int-01, 9.95 g (34.65 mmol) of 2-(9H-carbazol-9-yl)phenylboronic acid (CAS No. 1189047-28-6), 2 g (1.73 mmol) of $Pd(PPh_3)_4$, 9.58 g (69.3 mmol) of $K_2CO_3$, 400 ml of toluene, and 200 ml of distilled water were put in a flask and stirred under reflux for 12 hours. When a reaction was completed, the resultant was cooled to ambient temperature, and a solid produced therein was filtered, washed with acetone, and dried. 16.4 g (Yield: 74%) of Compound A-4 was obtained.

Synthesis Example 2: Synthesis of Intermediate Int-04

[Reaction Scheme 2]

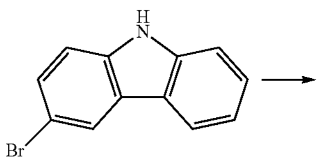

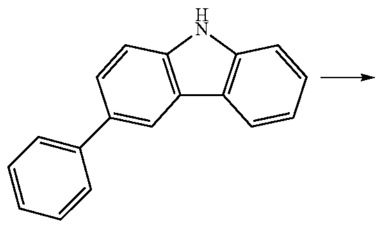

Int-02

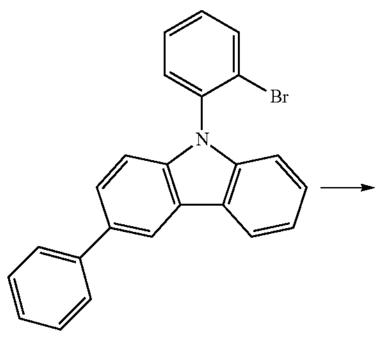

Int-03

-continued

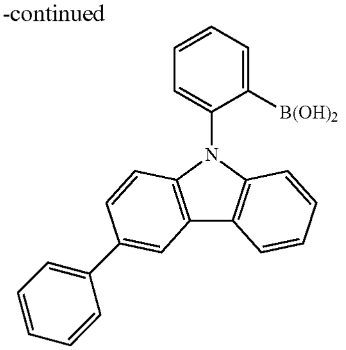

Int-04

1st Step: Synthesis of Intermediate Int-02

3-bromocarbazole (15 g, 60.95 mmol), phenylboronic acid (11.44 g, 73.14 mmol), $K_2CO_3$ (21.06 g, 152.38 mmol), and $Pd(PPh_3)_4$ (3.52 g, 3.05 mmol) were put in a round-bottomed flask and dissolved in 200 ml of THE and 75 ml of distilled water and then, stirred under reflux at 60° C. for 12 hours. When a reaction was completed, after removing an aqueous layer therefrom, the residue was treated through column chromatography (hexane:DCM (20%)), obtaining 12.3 g (83%) of Intermediate Int-02.

2nd Step: Synthesis of Intermediate Int-03

Intermediate Int-02 (50 g, 205.51 mmol), 1-bromo-2-fluorobenzene (36 g, 205.51 mmol), and $K_3PO_4$ (65.44 g, 308.26 mmol) were put in a round-bottomed flask, and 500 ml of DMF was added thereto and then, stirred under reflux at 130° C. for 12 hours. When a reaction was completed, the resultant was treated through column chromatography (hexane:DCM (10%)), obtaining 65.3 g (80%) of Intermediate Int-03.

3rd Step: Synthesis of Intermediate Int-04

Intermediate Int-03 (65 g, 163.2 mmol) was put in a round-bottomed flask, and 500 ml of THE was added thereto and then, cooled to −78° C. Subsequently, n-BuLi (84.86 ml, 212.16 mmol) was added thereto and then, stirred for 30 minutes. Isopropyl borate (48.66 ml, 212.16 mmol) was added thereto at −78° C. and then, stirred for 7 hours, and HCl was added thereto to complete a reaction, and after adding water thereto, an aqueous layer was removed therefrom through extraction. The residue was treated through column chromatography (hexane:DCM (30%)), obtaining 41.6 g (59%) of Intermediate Int-04.

Synthesis Example 3: Synthesis of Compound A-63

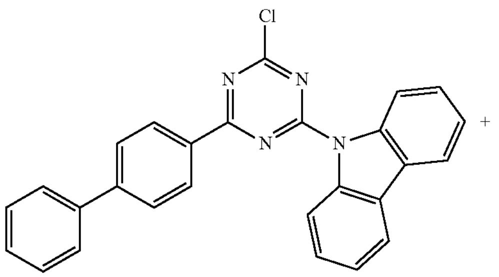

Int-01

-continued

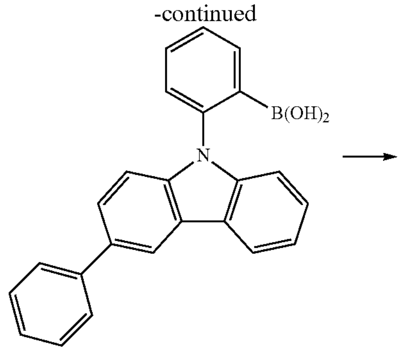

Int-04

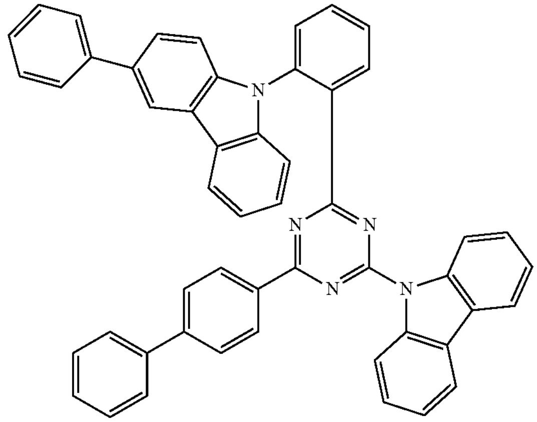

A-63

11.6 g (71%) of Compound A-63 was obtained in the same manner as in the 2nd step of Synthesis Example 1 except that Intermediate Int-04 was used instead of 2-(9H-carbazol-9-yl)phenylboronic acid.

Synthesis Example 4: Synthesis of Intermediate Int-05

[Reaction Scheme 4]

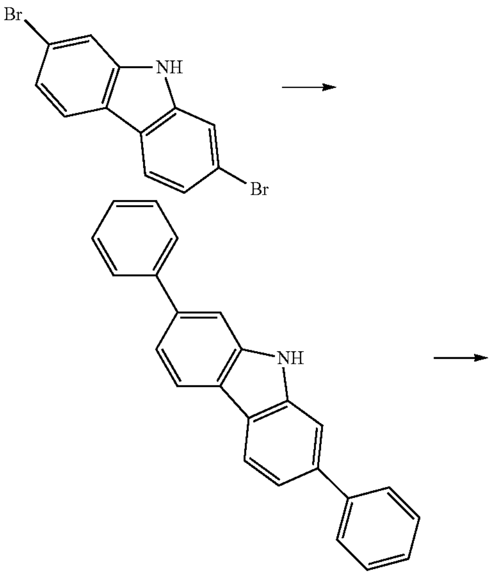

-continued

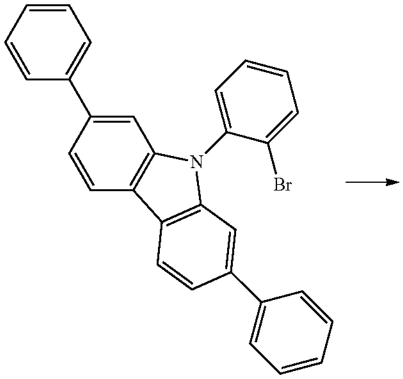

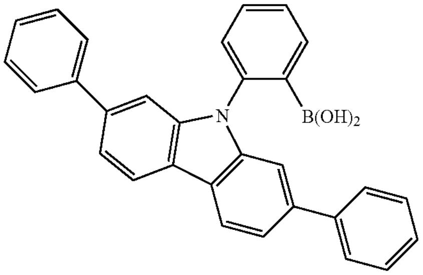

Int-05

56.4 g (52%) of Intermediate Int-05 was obtained in the same manner as in the 1st to 3rd steps of Reaction Scheme 2 except that 2,7-bromocarbazole was used instead of the 3-bromocarbazole in the 1st step of Reaction Scheme 2.

Synthesis Example 5: Synthesis of Compound A-69

[Reaction Scheme 5]

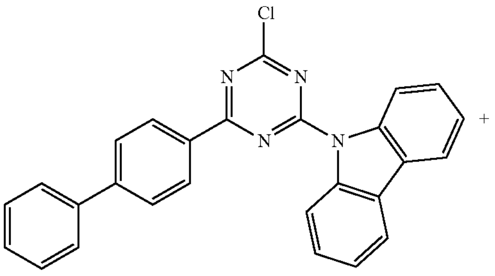

Int-01

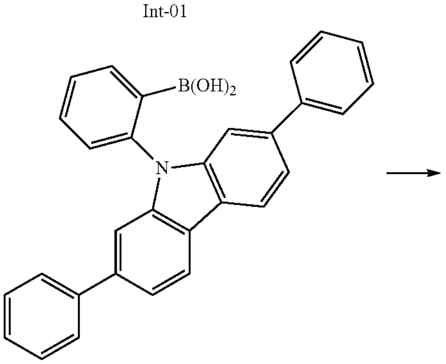

Int-05

-continued

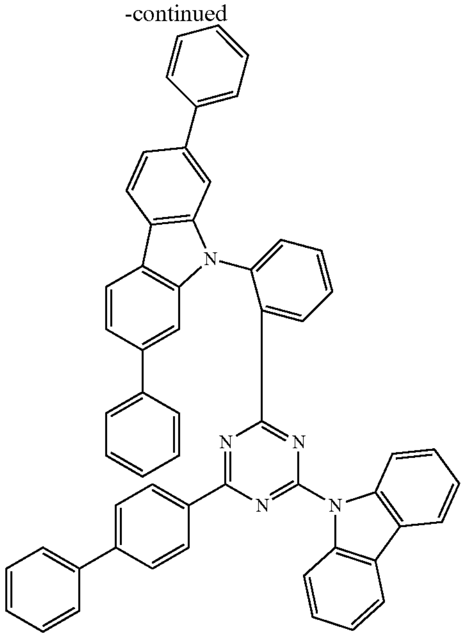

A-69

8.97 g (74%) of Compound A-69 was obtained in the same manner as in the 2nd step of Synthesis Example 1 except that Intermediate Int-05 was used instead of 2-(9H-carbazol-9-yl)phenylboronic acid.

Synthesis Example 6: Synthesis of Intermediate Int-06

[Reaction Scheme 6]

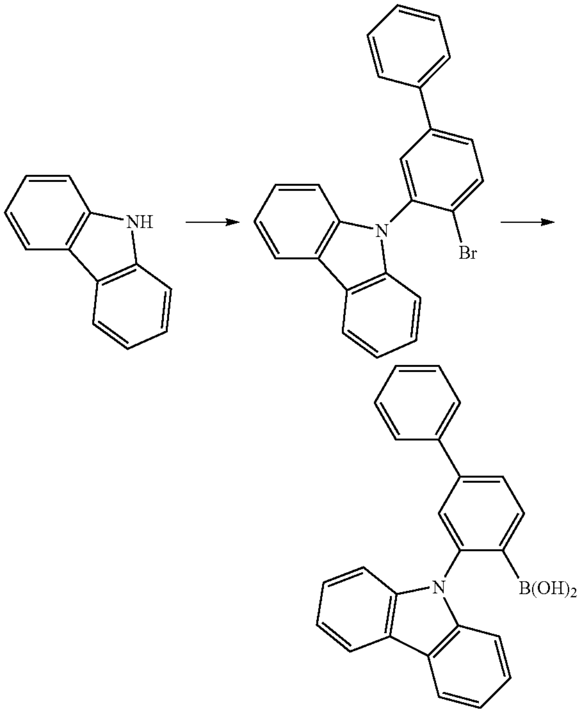

Int-06

35.1 g (54%) of Intermediate Int-06 was obtained in the same manner as in the 2nd to 3rd steps of Reaction Scheme 2 except that carbazole was used instead of Int-02 in the 2nd step of Reaction Scheme 2, and 4-bromo-3-fluoro-1,1'-biphenyl was used instead of the 1-bromo-2-fluorobenzene in the 1st step of Reaction Scheme 2.

Synthesis Example 7: Synthesis of Compound A-98

[Reaction Scheme 7]

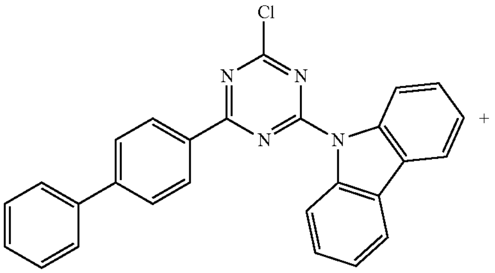

Int-01

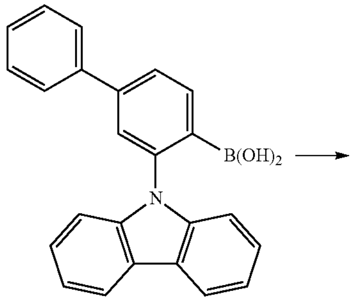

Int-06

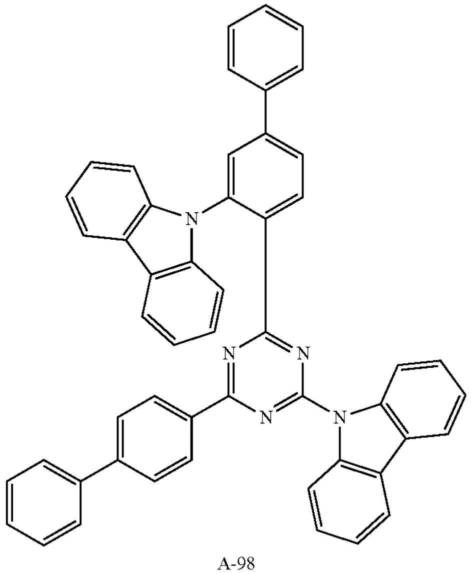

A-98

12.6 g (79%) of Compound A-98 was obtained in the same manner as in the 2nd step of Synthesis Example 1 except that Intermediate Int-06 was used instead of 2-(9H-carbazol-9-yl)phenylboronic acid.

Synthesis Example 8: Synthesis of Compound B-136
B-136
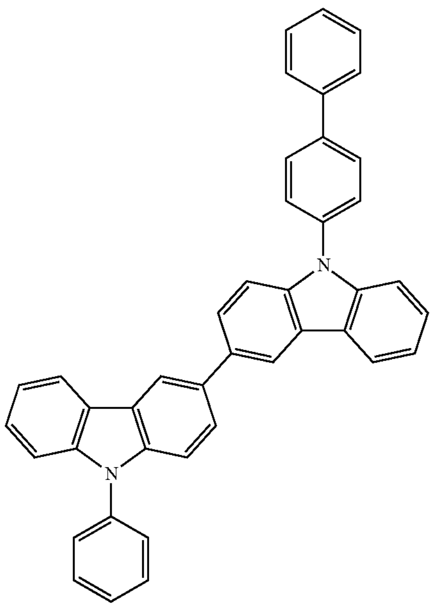
Compound B-136 was synthesized with reference to the synthesis method described in U.S. Pat. No. 10,476,008 B2.
Comparative Synthesis Example 1: Synthesis of Compound Y1
Y1
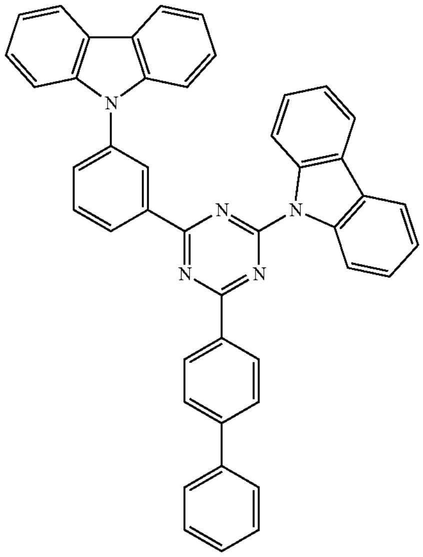
Compound Y1 was synthesized with reference to the synthesis method described in KR 10-2020-0087020 published patent.
Comparative Synthesis Example 2: Synthesis of Compound Y2
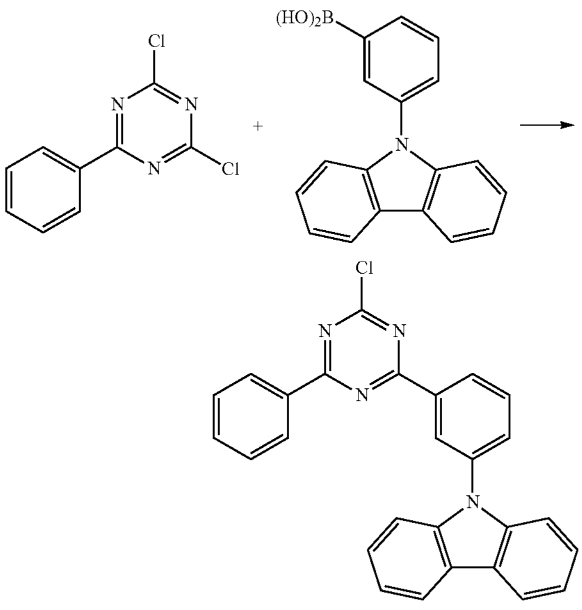
Int-07
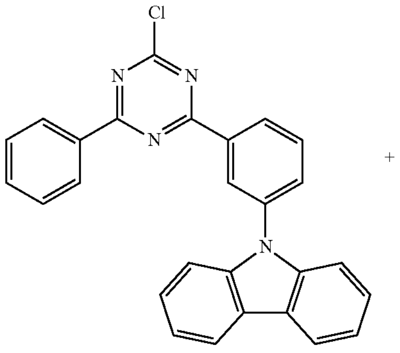
Int-07
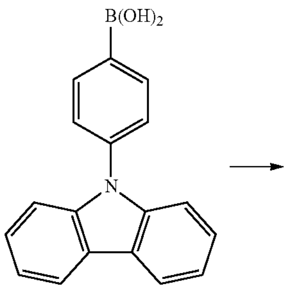

-continued

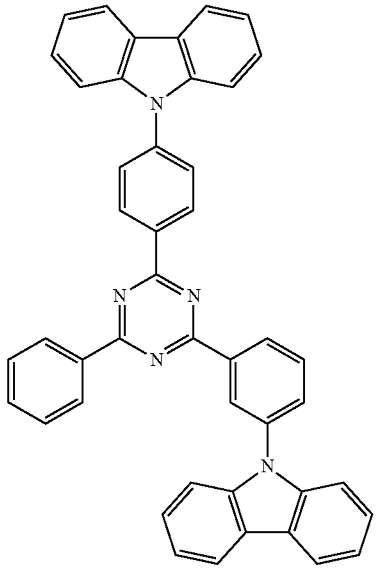

Y2

1st Step: Synthesis of Intermediate Int-07

2,4-dichloro-6-phenyl-1,3,5-triazine (19.5 g, 86.26 mmol), (3-(carbazole-9H)phenyl)pinacol ester (35.04 g, 94.89 mmol), $K_2CO_3$ (23.84 g, 172.52 mmol), and $Pd(PPh_3)_4$ (2.99 g, 2.59 mmol) were put in a round-bottomed flask and dissolved in 250 ml of THE and 85 ml of distilled water and then, stirred under reflux at 60° C. for 12 hours. When a reaction was completed, after removing an aqueous layer therefrom, the residue was treated through column chromatography (hexane:DCM (30%)), obtaining 24.68 g (66%) of Intermediate Int-07.

2nd Step: Synthesis of Compound Y2

Compound Y2 (13.6 g, 81%) was obtained in the same manner as in the 2nd step of Synthesis Example 1 except that Intermediate Int-07 and 4-(9H-carbazol-9-yl)phenyl)boronic acid were used instead of Intermediate Int-01 and 2-(9H-carbazol-9-yl)phenylboronic acid.

Comparative Synthesis Example 3: Synthesis of Compound Y3

[Reaction Scheme 9]

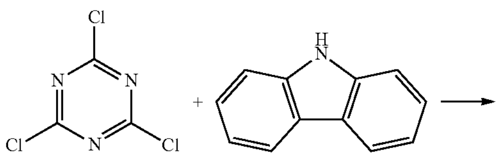

-continued

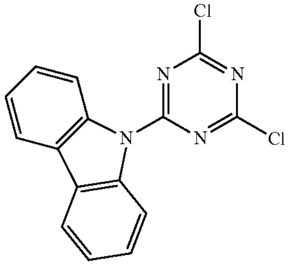

Int-08

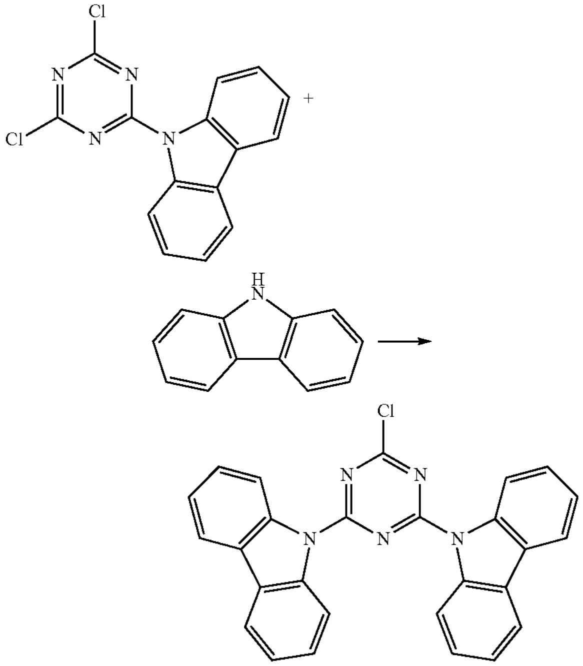

Int-09

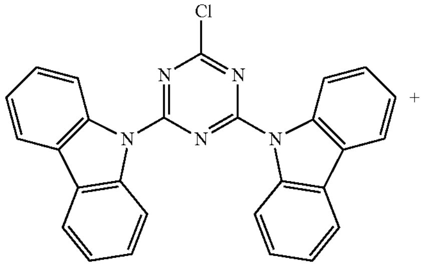

Int-09

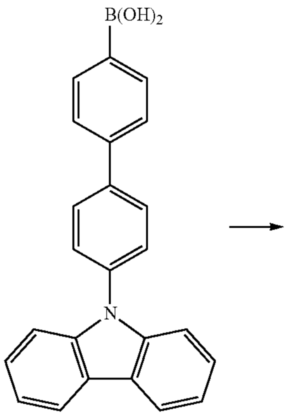

-continued

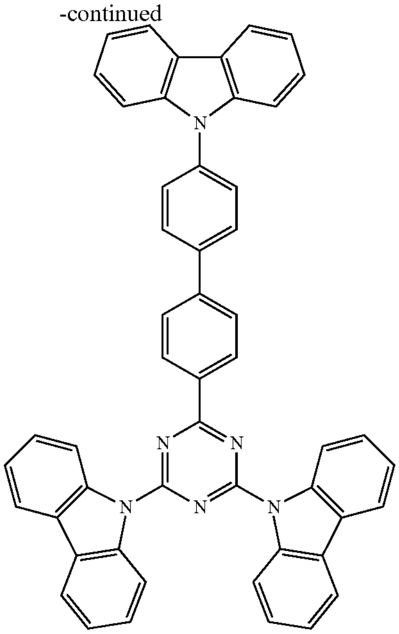

Y3

1 st Step: Synthesis of Intermediate Int-08

28.6 g (170.8 mmol) of carbazole and 180 ml of THF were put in a round flask and then, stirred and cooled in an ice bath to 0° C., and 68.3 ml (170.8 mmol) of a n-BuLi solution (2.5 M in hexane) was slowly added dropwise thereto. The obtained mixture was additionally stirred at ambient temperature for 30 minutes. Subsequently, 30 g (162.7 mmol) of 2,4,6-trichloro-1,3,5-triazine and 180 ml of THF were added thereto under a nitrogen flow and then, stirred, and a Li reagent prepared in advance was slowly added dropwise thereto. Subsequently, the mixture was stirred at ambient temperature for 1 hour. 300 ml of distilled water was added thereto, and a solid precipitated therein was collected by filtration. The solid was dried, obtaining 40.1 g (78%) of Intermediate Int-08.

2nd Step: Synthesis of Intermediate Int-09

Intermediate Int-09 (21.4 g, 68%) was obtained in the same manner as in the 1st step of Synthesis Example 1 except that 2,4-dichloro-6-(biphenyl-4-yl)-1,3,5-triazine was replaced with Int-08 in the 1st step of Reaction Scheme 1.

3rd Step: Synthesis of Compound Y3

(11.7 g, 71%) of Compound Y3 was obtained in the same manner as in the 2nd step of Synthesis Example 1 except that Intermediate Int-09 and 4'-(9H-carbazol-9-yl)-[1,1'-biphenyl]-4-yl)boronic acid were used instead of Intermediate Int-01 and 2-(9H-carbazol-9-yl)phenylboronic acid.

(Manufacture of Organic Light Emitting Diode)

Example 1

A glass substrate coated with a thin film of indium tin oxide (ITO) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 3% NDP-9 (available from Novaled) was vacuum-deposited on the ITO substrate to form a 100 Å-thick hole injection layer, and Compound A was deposited on the hole transport layer to form a 1,350 Å-thick hole transport layer. On the hole transport layer, Compound B was deposited at a thickness of 350 Å to form a hole transport auxiliary layer. On the hole transport auxiliary layer, 400 Å-thick light emitting layer was formed by using Compound A-4 obtained in Synthesis Example 1 and doping 7 wt % of PhGD as a dopant by vacuum-deposition. Subsequently, on the light emitting layer, Compound C was deposited at a thickness of 50 Å to form an electron transport auxiliary layer and Compound D and LiQ were simultaneously vacuum-deposited in a weight ratio of 1:1 to form a 300 Å-thick electron transport layer. On the electron transport layer, LiQ and Al were sequentially vacuum-deposited to be 15 Å-thick and 1,200 Å-thick, manufacturing an organic light emitting diode.

ITO/Compound A (3% NDP-9 doping, 100 Å)/Compound A (1,350 Å)/Compound B (350 Å)/EML [93 wt % of a host (Compound A-4): 7 wt % of PhGD] (400 Å)/Compound C (50 Å)/Compound D:LiQ (300 Å)/LiQ (15 Å)/Al (1,200 Å).

Compound A: N-(biphenyl-4-yl)-9,9-dimethyl-N-(4-(9-phenyl-9H-carbazol-3-yl)phenyl)-9H-fluoren-2-amine Compound B: N-[4-(4-dibenzofuranyl)phenyl]-N-[4-(9-phenyl-9H-fluoren-9-yl)phenyl][1,1'-biphenyl]-4-amine Compound C: 2,4-diphenyl-6-(4', 5', 6'-triphenyl[,1': 2', 1'': 3'', 1''':3''', 1''''-quinquephenyl]-3''''-yl)-1,3,5-triazine Compound D: 2-(1,1'-biphenyl-4-yl)-4-(9,9-diphenyl-9H-fluoren-4-yl)-6-phenyl-1,3,5-triazine

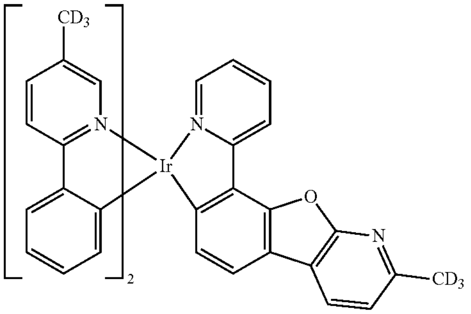

[PhGD]

Example 2

A glass substrate coated with a thin film of ITO (Indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 3% NDP-9 (available from Novaled) was vacuum-deposited on the ITO substrate to form a 100 Å-thick hole injection layer, and Compound A was deposited on the hole transport layer to form a 1,350 Å-thick hole transport layer. On the hole transport layer, Compound E was deposited at a thickness of 350 Å to form a hole transport auxiliary layer. On the hole transport auxiliary layer, 400 Å-thick light emitting layer was formed by using Compound A-63 obtained in Synthesis Example 3 and Compound B-136 obtained in Synthesis Example 8 as a host simultaneously and doping 10 wt % of PhGD as a dopant by vacuum-deposition. Herein Compound A-63 and Compound B-136 were used in a weight ratio of 3:7. Subsequently, on the light emitting layer, Compound F was deposited at a thickness of 50 Å to form an electron transport auxiliary layer and Compound G and LiQ were simultaneously vacuum-deposited in a weight ratio of 1:1 to form a 300 Å-thick electron transport layer. On the electron transport layer, LiQ and Al were sequentially vacuum-deposited to be 15 Å-thick and 1,200 Å-thick, manufacturing an organic light emitting diode.

ITO/Compound A (3% NDP-9 doping, 100 Å)/Compound A (1,350 Å) /Compound E (350 Å)/EML[host (Compound A-63:Compound B-136=3:7):PhGD=90 wt %:10 wt %] (400 Å)/Compound F (50 Å)/Compound G:LiQ (300 Å)/LiQ (15 Å)/Al (1,200 Å).

Compound E: N,N-bis(9,9-dimethyl-9H-fluoren-4-yl)-9,9-spirobi(fluorene)-2-amine

Compound F: 2-[3'-(9,9-dimethyl-9H-fluoren-2-yl)[1,1'-biphenyl]-3-yl]-4,6-diphenyl-1,3,5-triazine Compound G: 2-[4-[4-(4'-cyano-1,1'-biphenyl-4-yl)-1-naphthyl]phenyl]-4,6-diphenyl-1,3,5-triazine

Comparative Examples 1 to 3

Diodes of Comparative Examples 1 to 3 were respectively manufactured according to the same manner as Example 1 except that the host was changed as shown in Table 1.

Example 3 and Comparative Example 4

Diodes of Example 3 and Comparative Example 4 were manufactured in the same manner as in Example 2, except that the host was changed as shown in Table 2.

Evaluations (1) Measurement of Current Density Change Depending on Voltage Change The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

The current efficiency (cd/A) of the same current density (10 mA/cm$^2$) was calculated using the luminance and current density measured from the (1) and (2).

Relative values based on the luminous efficiency of Example 1 are shown in Table 1.

Relative values based on the luminous efficiency of Example 2 are shown in Table 2.

(4) Measurement of Life-Span

T95 life-spans of the diodes were measured as a time when their luminance decreased down to 95% relative to the initial luminance (cd/m$^2$) after emitting light with 24,000 cd/m$^2$ as the initial luminance (cd/m$^2$) and measuring their luminance decreases depending on a time with a Polanonix life-span measurement system.

The relative values based on the T95 life-span of Example 1 are shown in Table 1.

The relative values based on the T95 life-span of Example 2 are shown in Table 2.

(5) Measurement of Driving Voltage

The driving voltage of each diode was measured at 15 mA/cm$^2$ using a current-voltmeter (Keithley 2400), and the results were obtained.

Relative values based on the driving voltage of Example 1 are shown in Table 1.

TABLE 1

| | Host | Driving voltage (%) | Luminous efficiency (%) | Life-span T95 (%) |
|---|---|---|---|---|
| Example 1 | A-4 | 100 | 100 | 100 |
| Comparative Example 1 | Y1 | 102 | 87 | 67 |
| Comparative Example 2 | Y2 | 102 | 98 | 40 |
| Comparative Example 3 | Y3 | 116 | 77 | 4 |

TABLE 2

| | First host | Second host | Luminous efficiency (%) | Life-span T95 (%) |
|---|---|---|---|---|
| Example 2 | A-63 | B-136 | 100 | 100 |
| Example 3 | A-98 | B-136 | 98 | 120 |
| Comparative Example 4 | Y1 | B-136 | 95 | 90 |

Referring to Table 1, the organic light emitting diodes manufactured by applying the compound according to an embodiment exhibited significantly improved driving, efficiency, and life-span characteristics, compared with the organic light emitting diodes according to the Comparative Examples. Referring to Table 2, the organic light emitting diodes manufactured by applying a composition according to an embodiment also exhibited improved efficiency and life-span characteristics, compared with the organic light emitting diode according to the Comparative Example.

One or more embodiments may provide a compound for an organic optoelectronic device capable of realizing a low-driving, high-efficiency and long life-span organic optoelectronic device.

One or more embodiments may provide a composition for an organic optoelectronic device capable of realizing a high-efficiency and long life-span organic optoelectronic device.

A low-driving and high-efficiency long life-span organic optoelectronic device may be realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1:

[Chemical Formula 1]

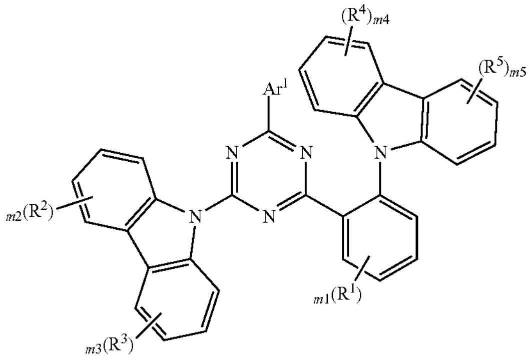

wherein, in Chemical Formula 1, $Ar^1$ is a C6 to C30 non-fused aryl group selected from the substituents of Group I wherein the substituent may be unsubstituted or substituted with deuterium,

[Group I]

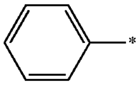

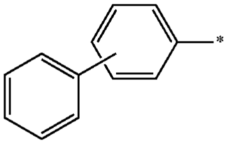

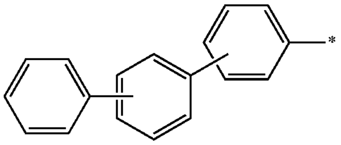

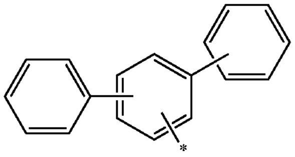

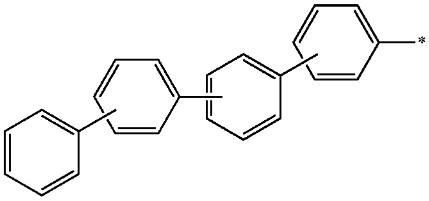

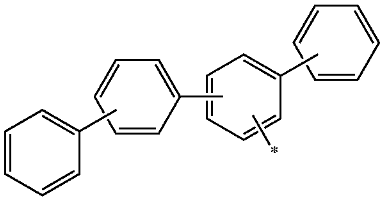

-continued

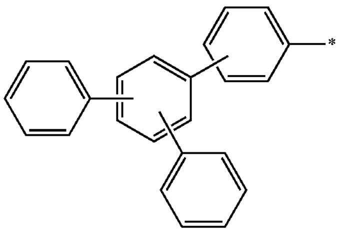

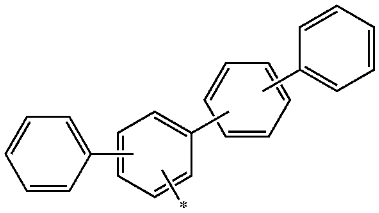

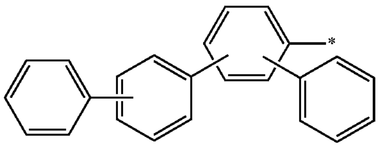

in Group I, * is a linking point, each $R^1$ is independently hydrogen, deuterium, or an unsubstituted C6 to C12 aryl group, $R^2$ to $R^5$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and m1 to m5 are each independently an integer of 1 to 4.

2. The compound as claimed in claim 1, wherein the compound is a compound of Group 1:

[Group 1]

[A-1]

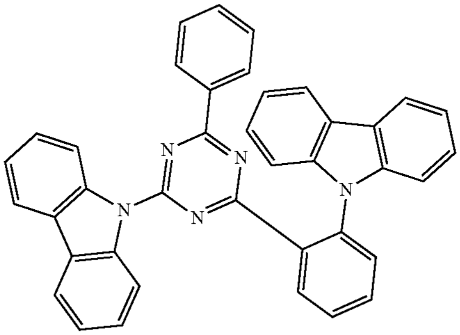

-continued
[A-2]
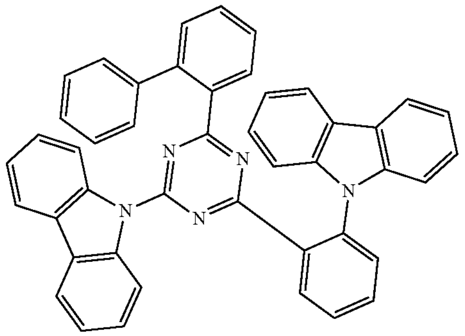
[A-3]
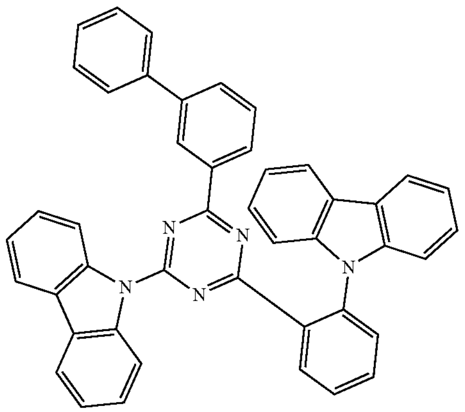
[A-4]
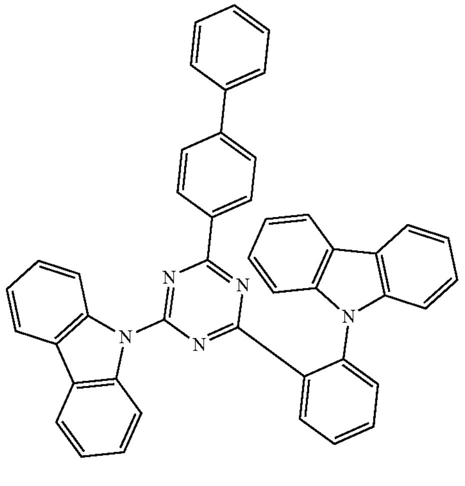
-continued
[A-5]
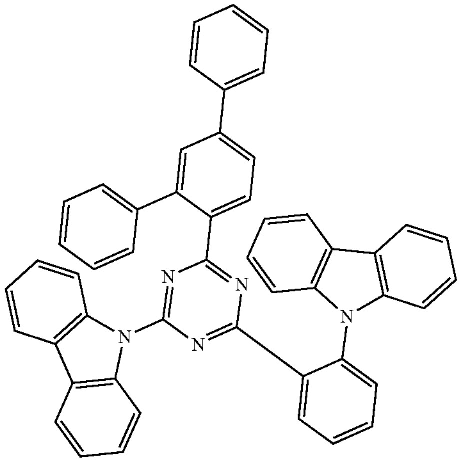
[A-6]
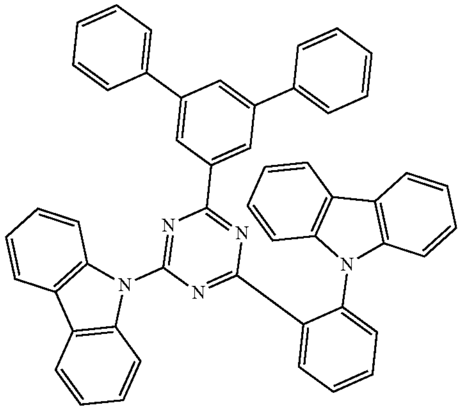
[A-7]
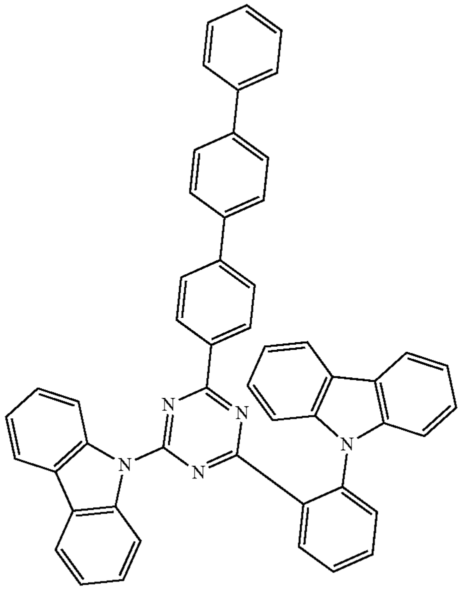

-continued
[A-8]
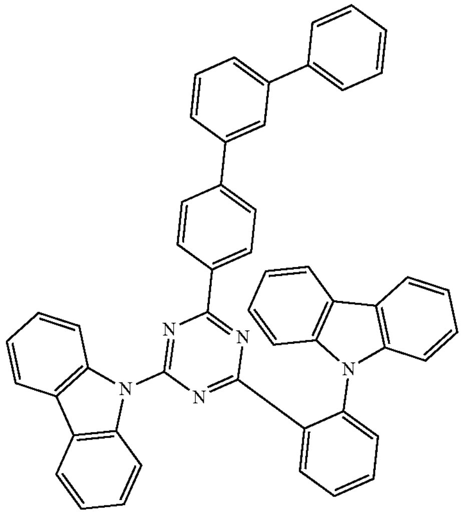
[A-9]
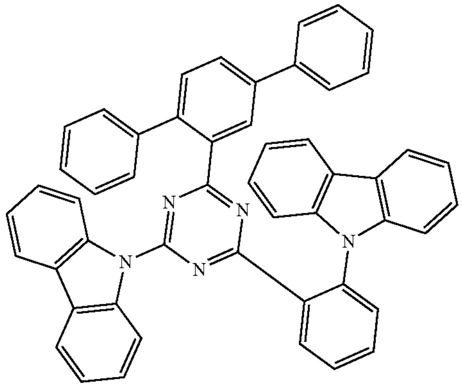
[A-10]
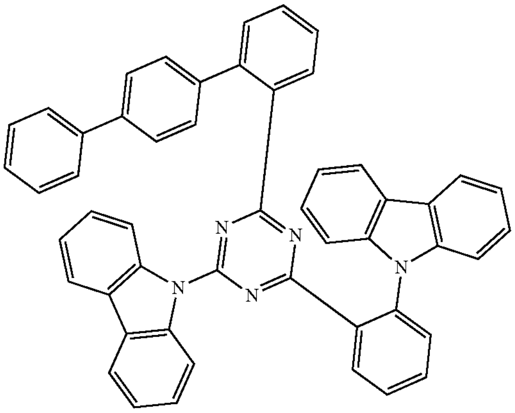
-continued
[A-11]
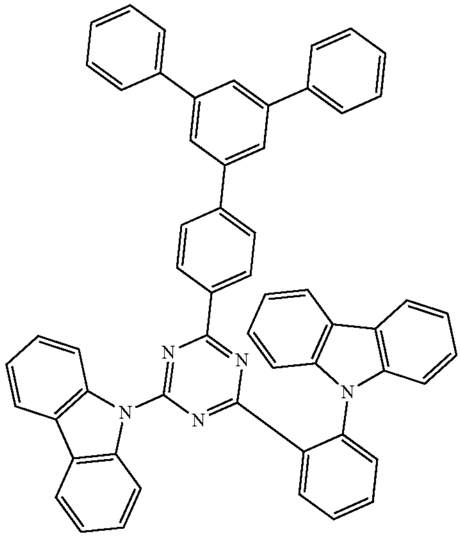
[A-12]
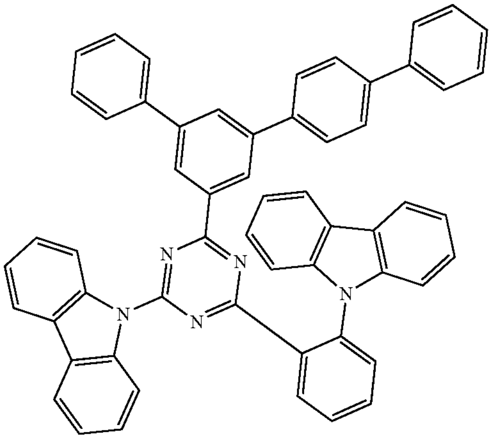
[A-13]
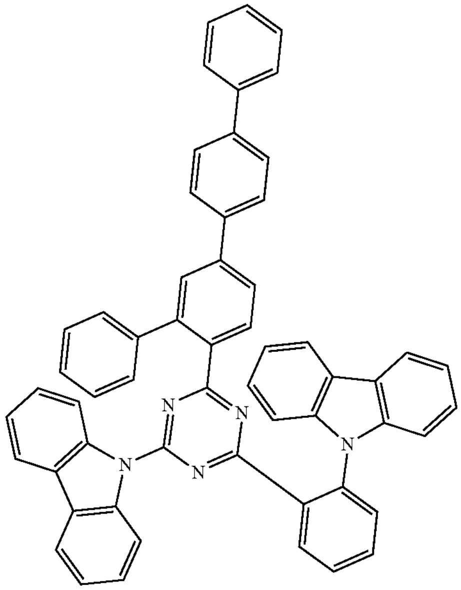

-continued
[A-14]
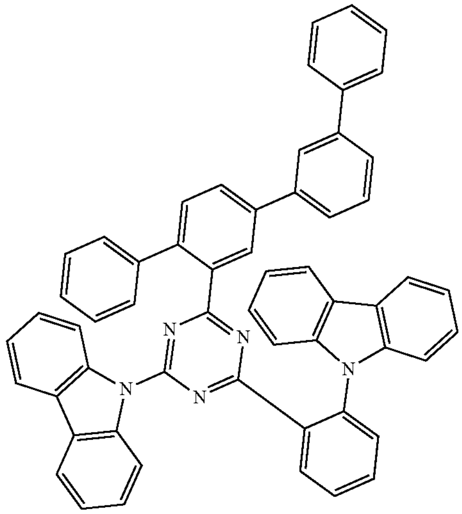
[A-15]
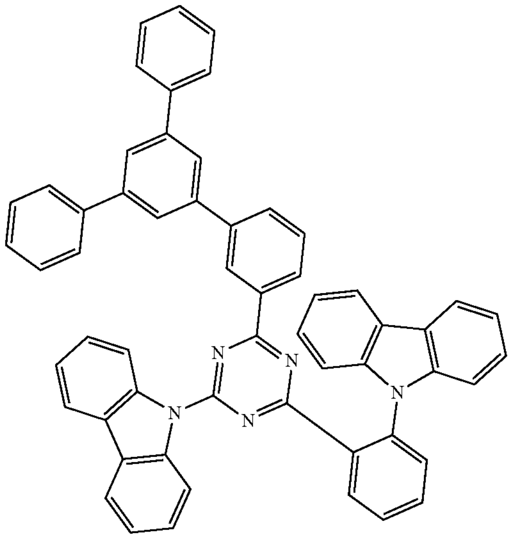
[A-16]
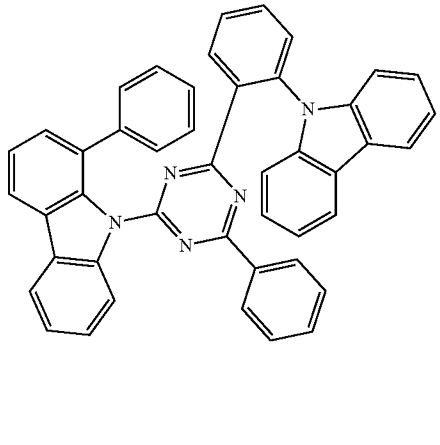
-continued
[A-17]
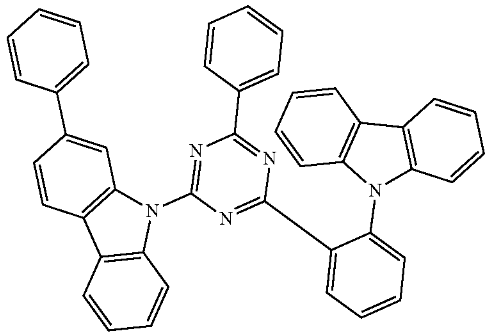
[A-18]
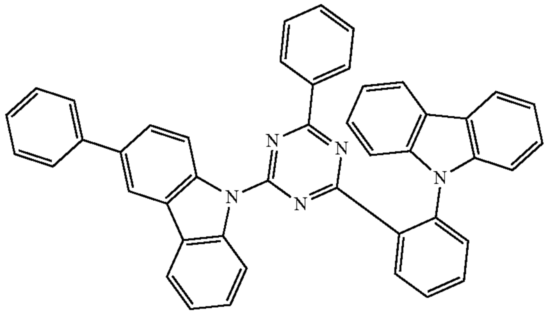
[A-19]
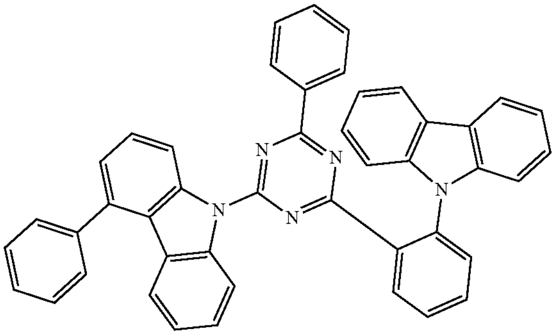
[A-20]
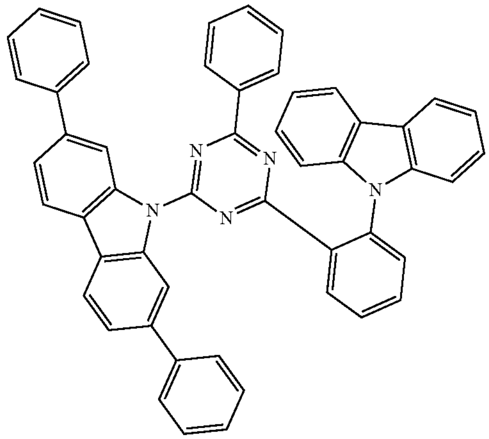

-continued
[A-21]
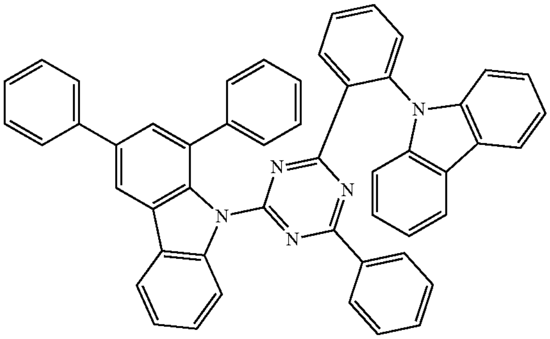
[A-22]
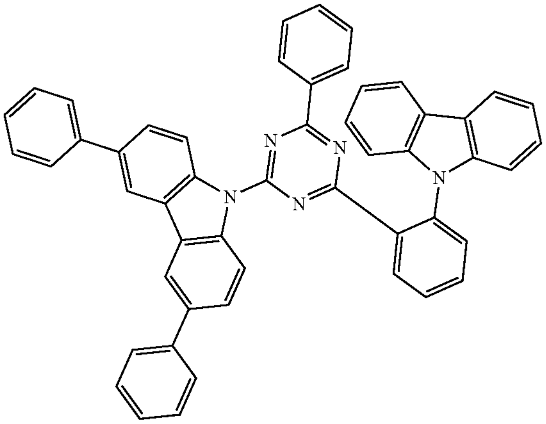
[A-23]
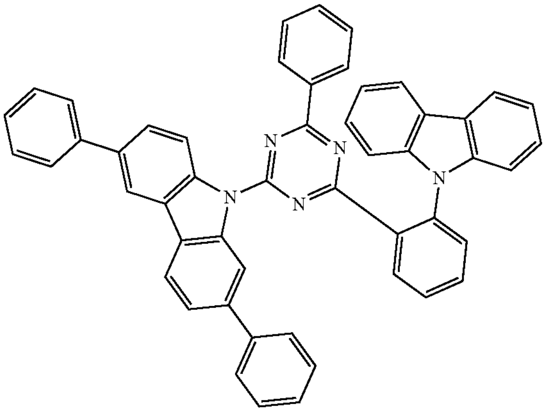
-continued
[A-24]
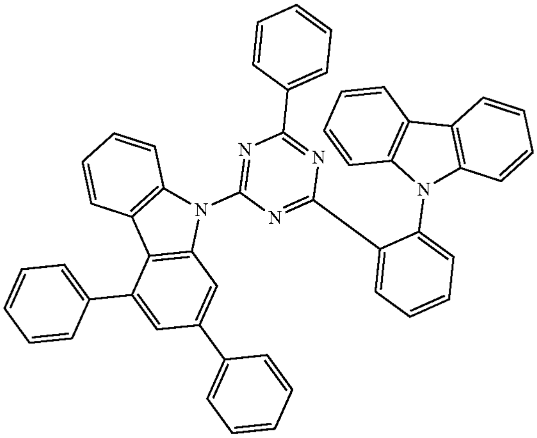
[A-25]
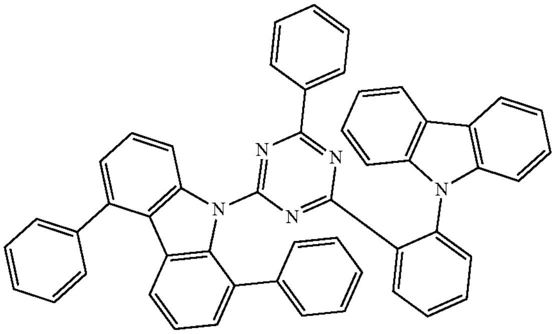
[A-26]
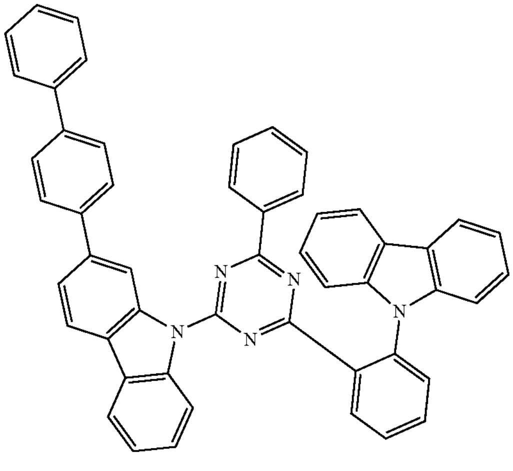
[A-27]
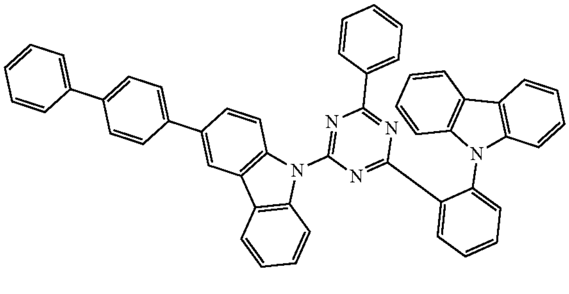

-continued
[A-28]
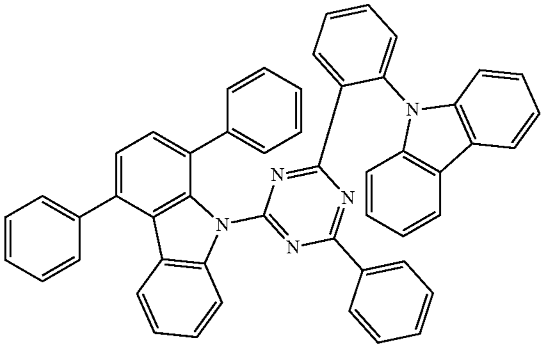
[A-29]
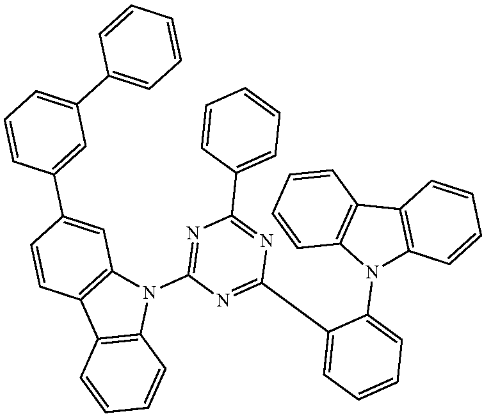
[A-30]
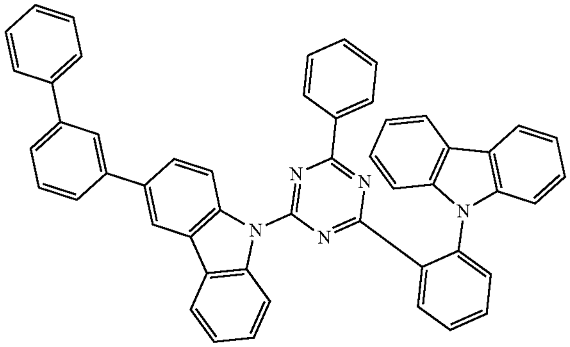
[A-31]
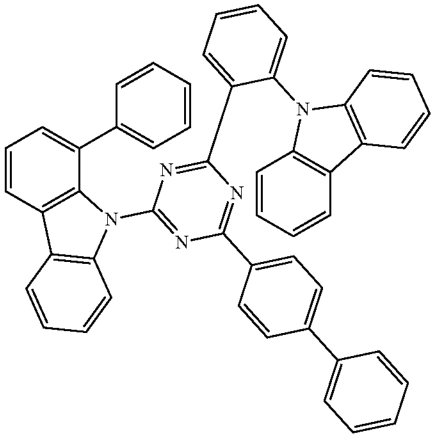
-continued
[A-32]
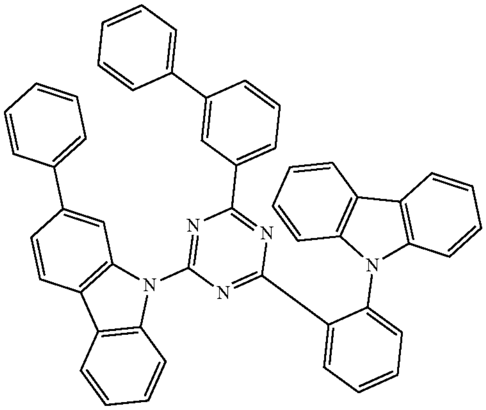
[A-33]
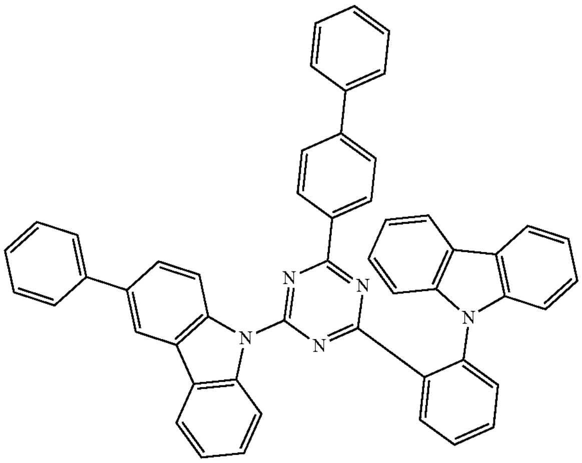
[A-34]
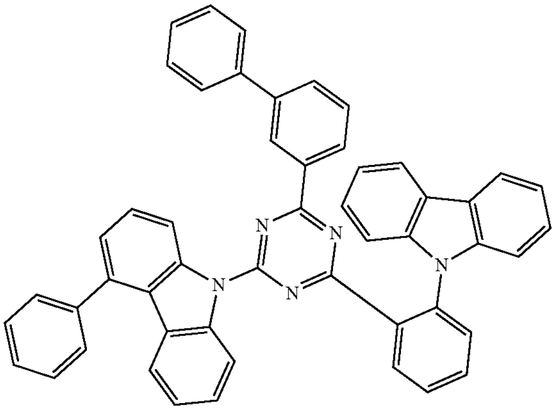

-continued
[A-35]
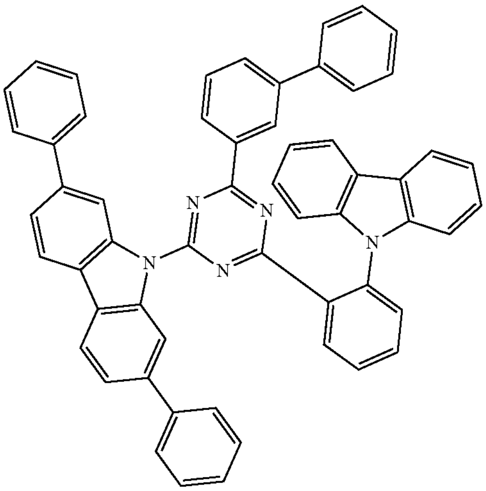
[A-36]
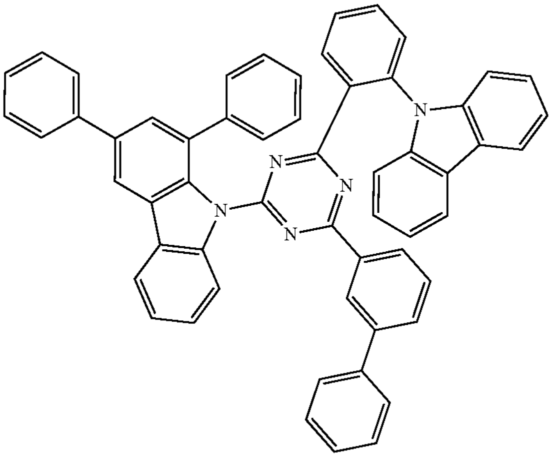
[A-37]
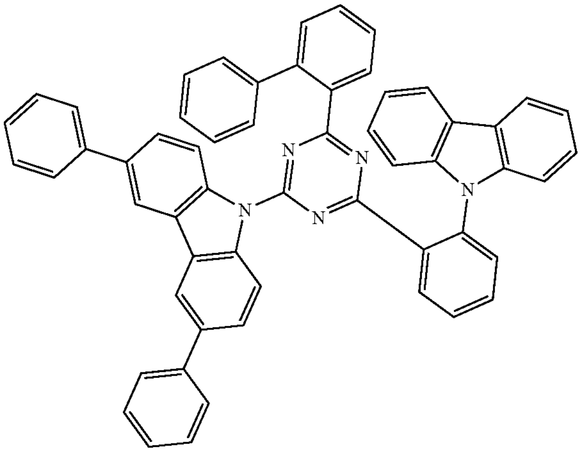
-continued
[A-38]
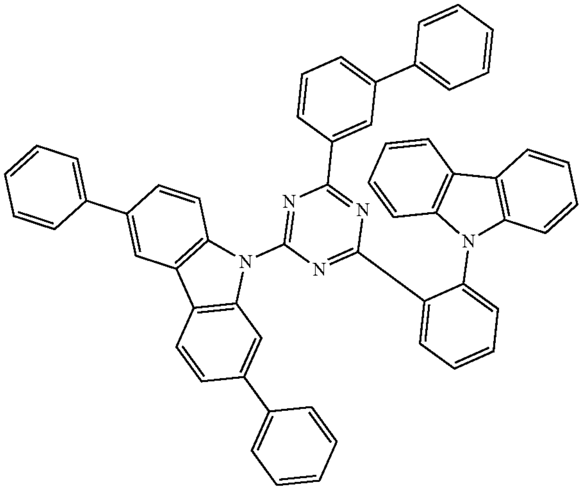
[A-39]
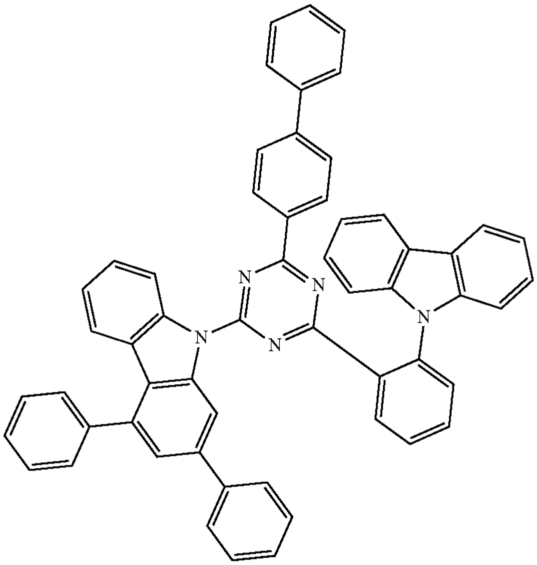
[A-40]
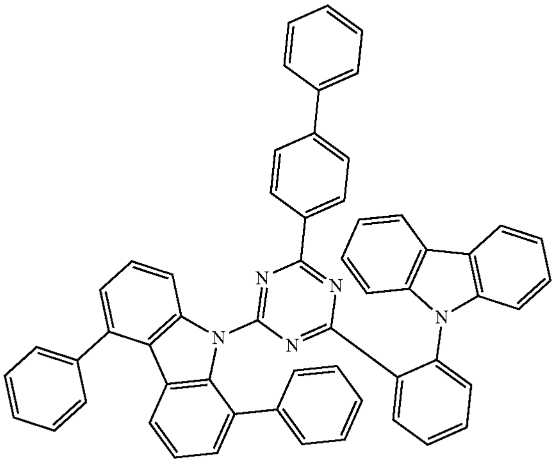

-continued
[A-41]
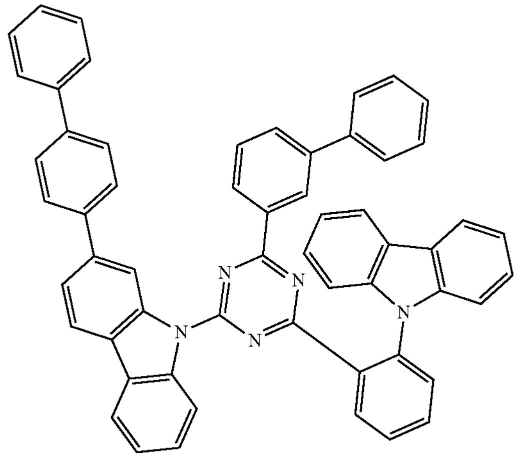
[A-42]
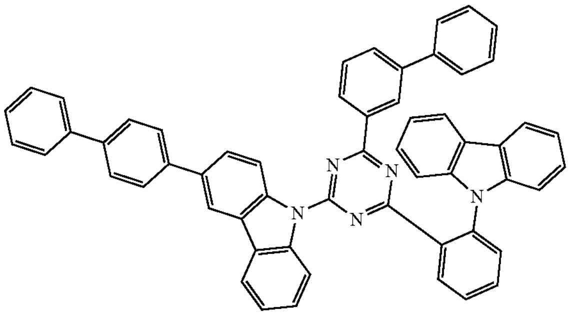
[A-43]
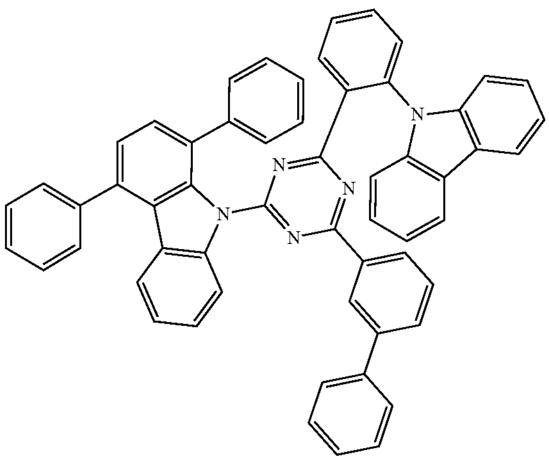
-continued
[A-44]
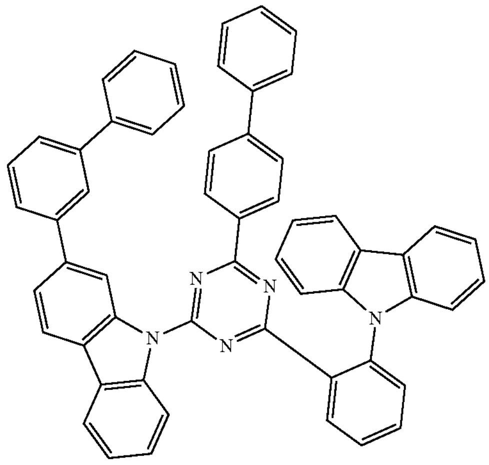
[A-45]
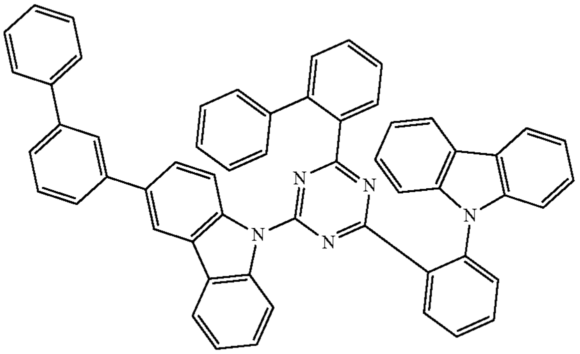
[A-46]
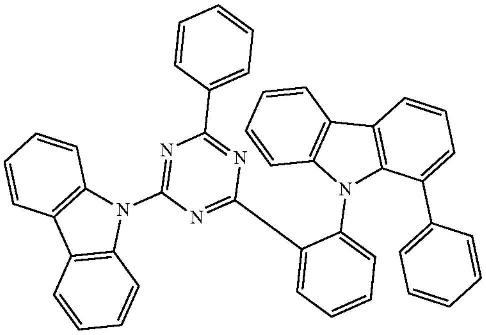
[A-47]
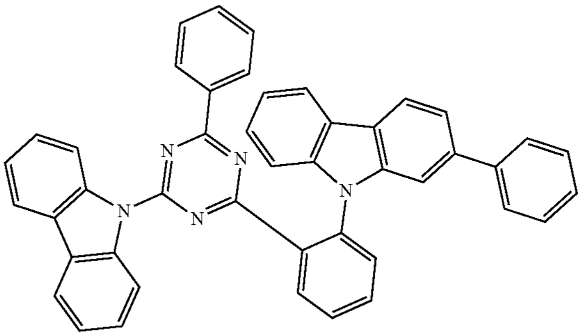

-continued
[A-48]
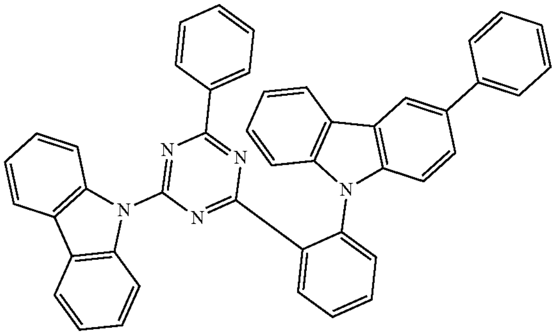
[A-49]
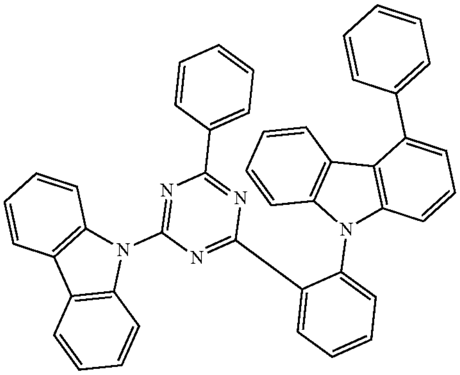
[A-50]
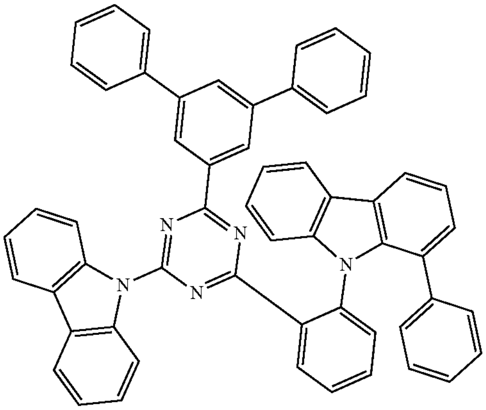
[A-51]
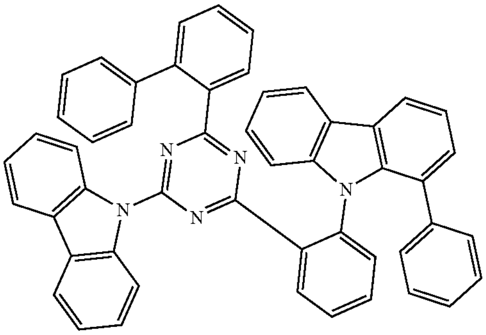
-continued
[A-52]
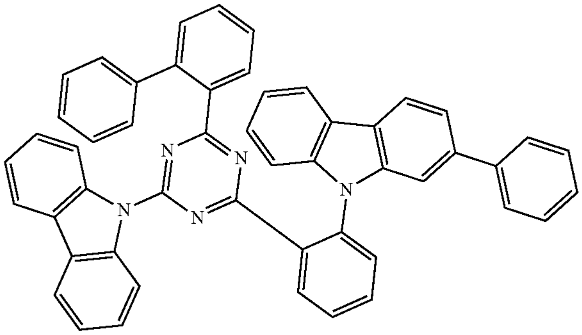
[A-53]
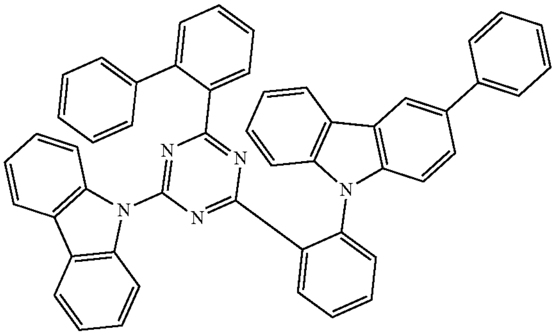
[A-54]
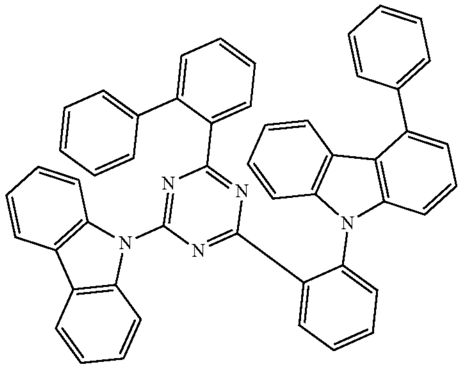
[A-55]
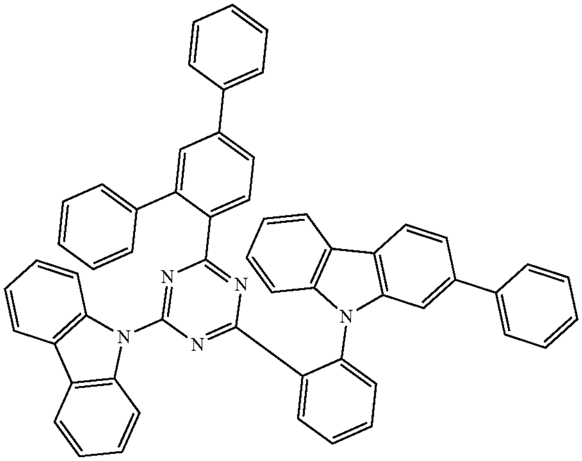

-continued
[A-56]
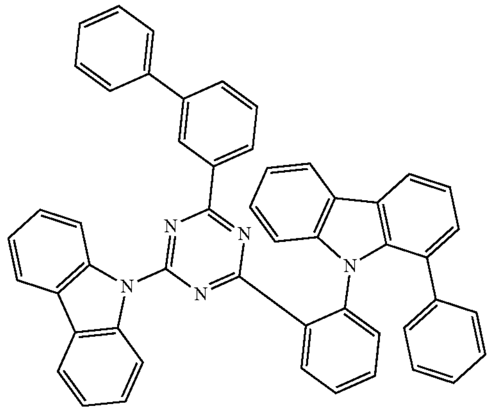
[A-57]
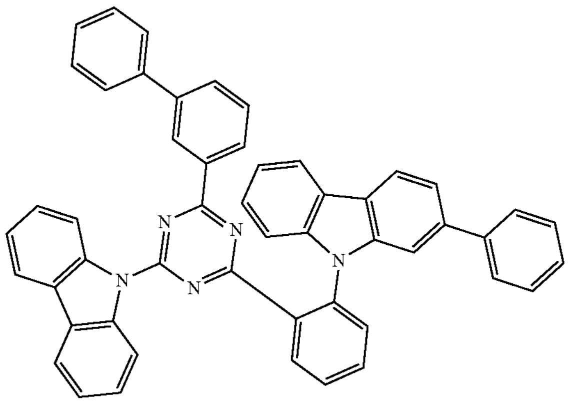
[A-58]
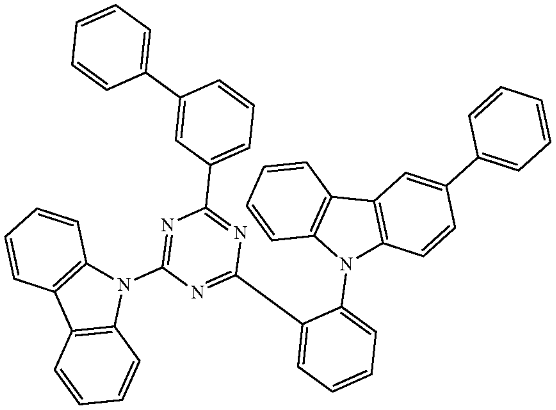
-continued
[A-59]
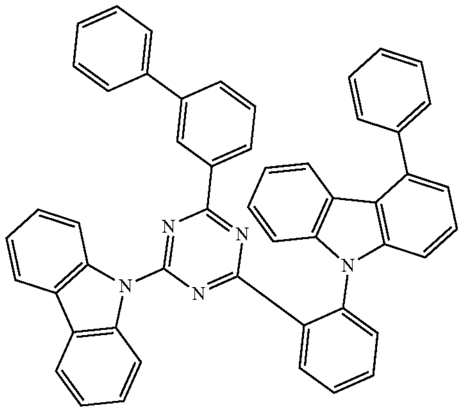
[A-60]
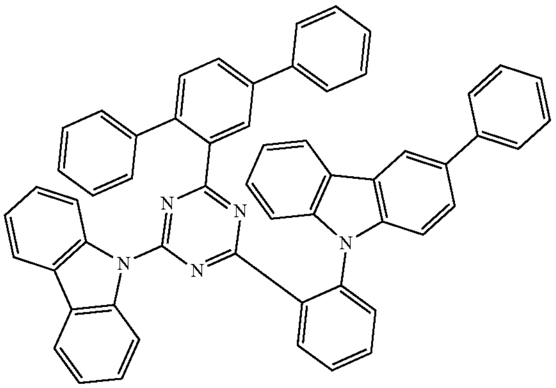
[A-61]
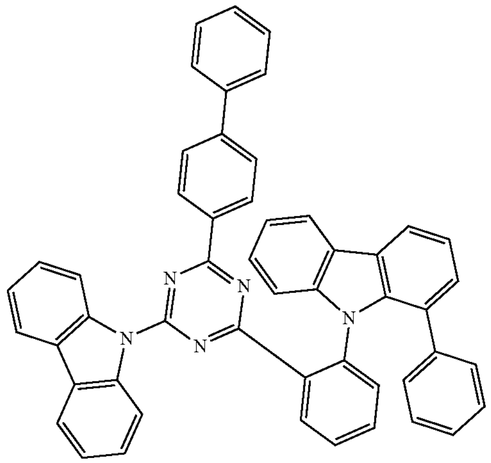

-continued
[A-62]
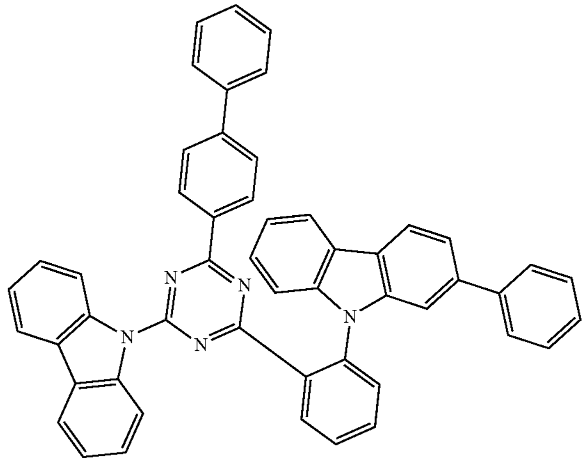
[A-63]
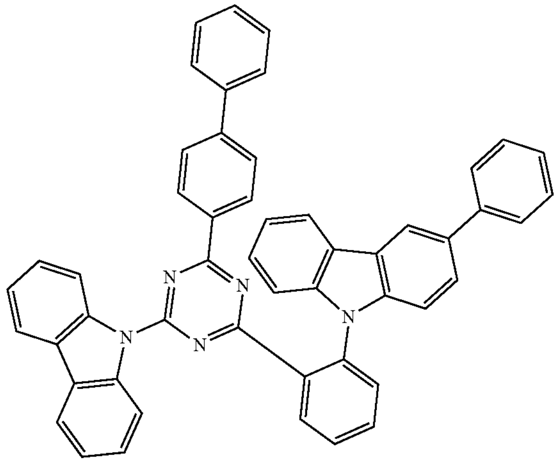
[A-64]
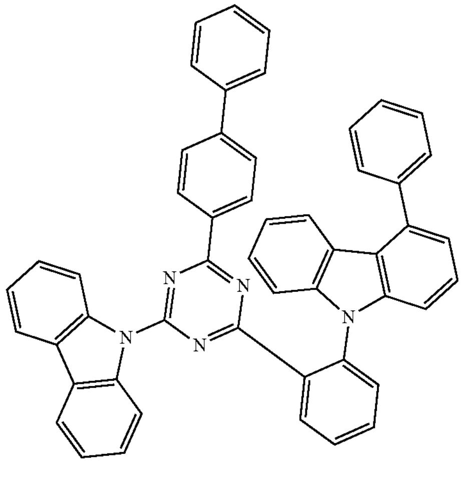
-continued
[A-65]
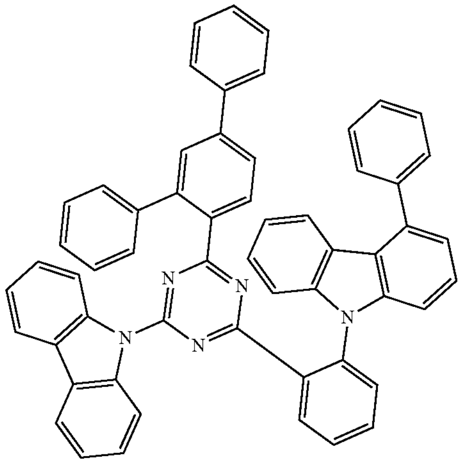
[A-66]
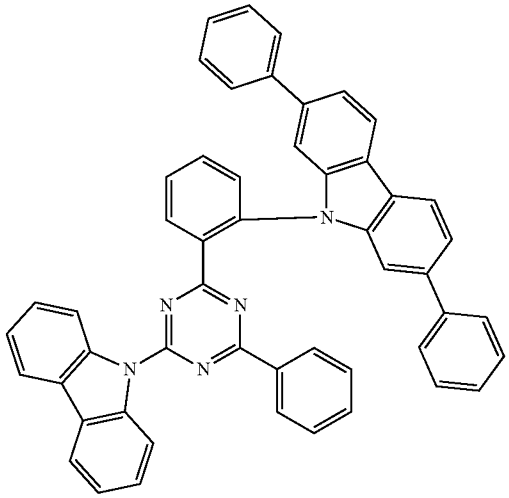
[A-67]
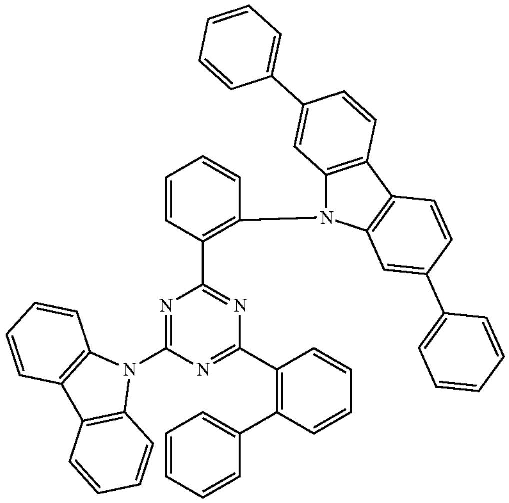

-continued
[A-68]
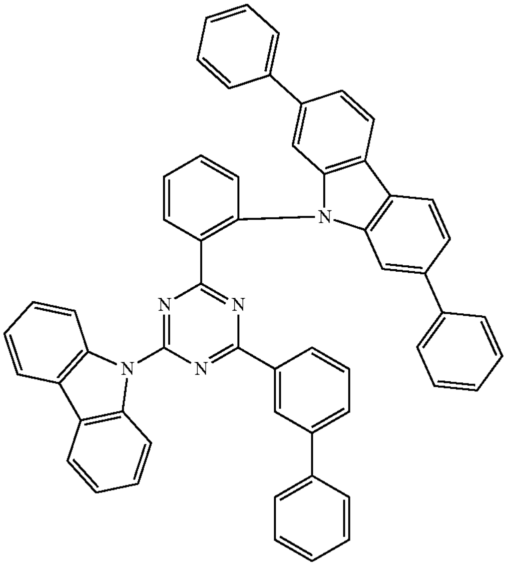
[A-69]
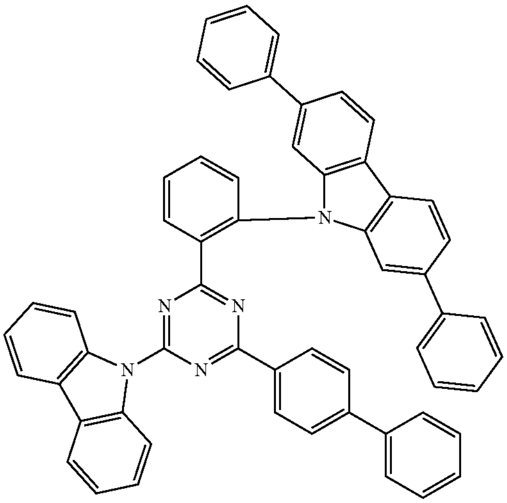
[A-70]
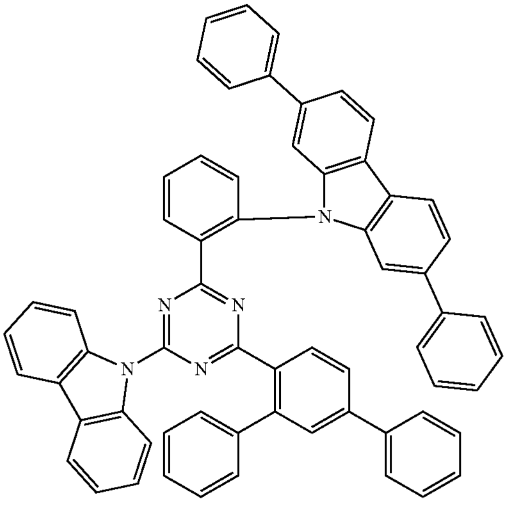
-continued
[A-71]
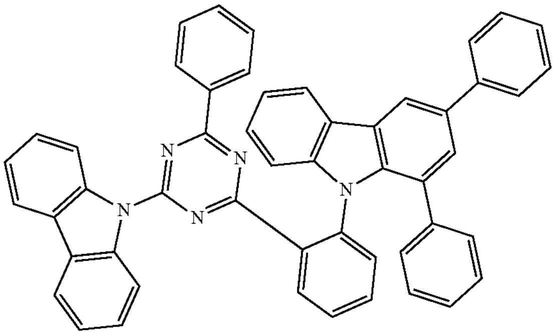
[A-72]
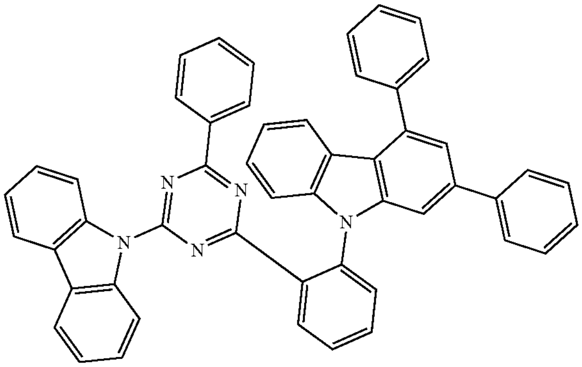
[A-73]
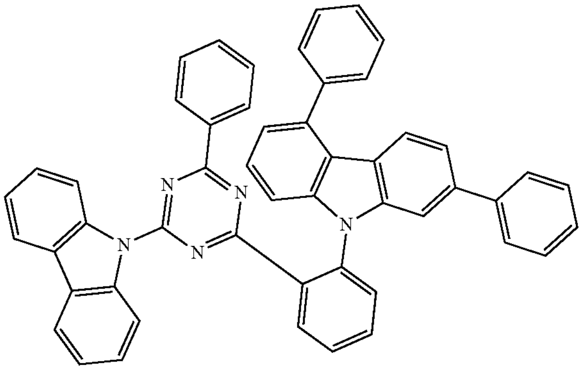
[A-74]
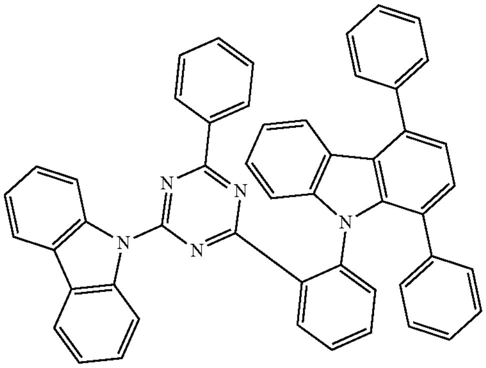

-continued
[A-75]
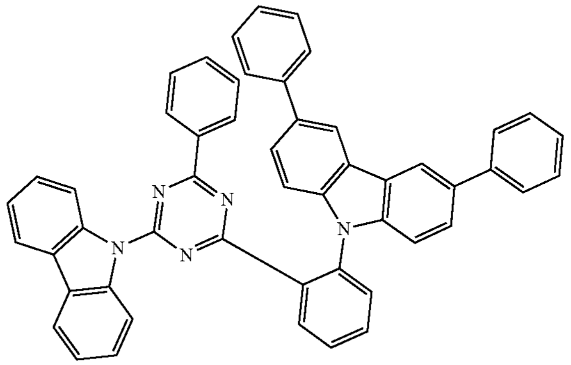
[A-76]
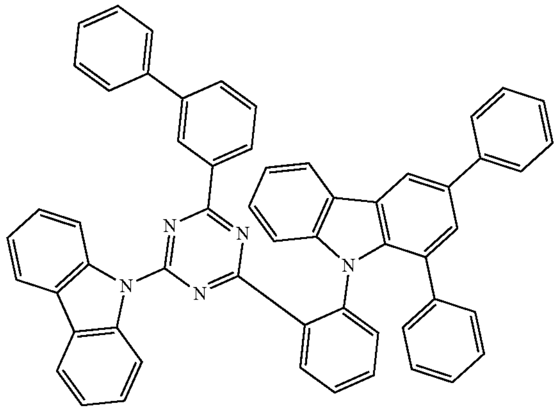
[A-77]
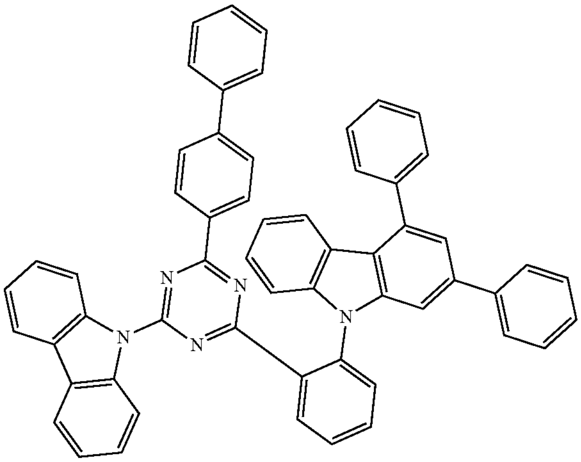
-continued
[A-78]
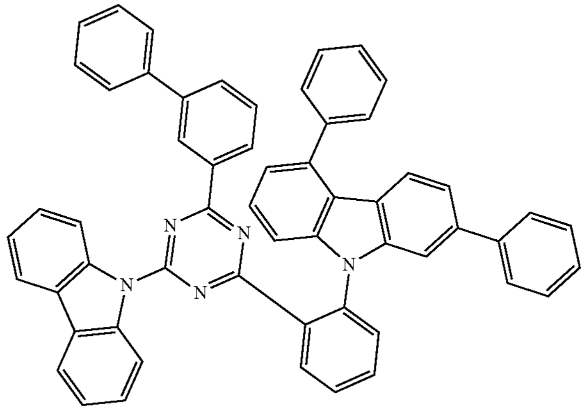
[A-79]
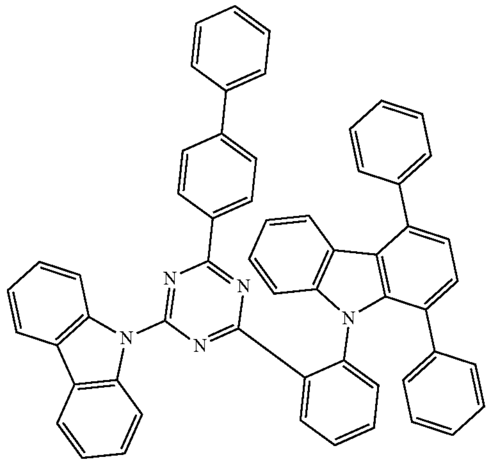
[A-80]
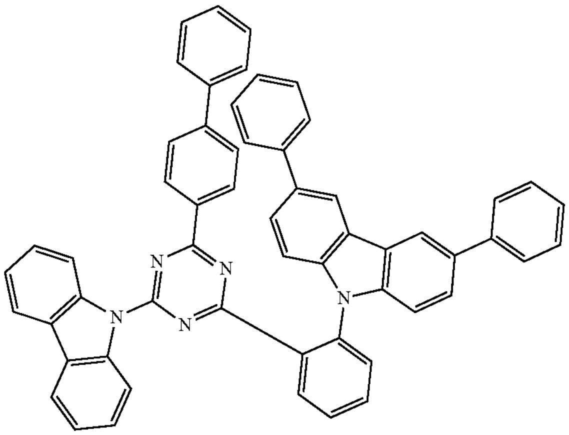

-continued
[A-81]
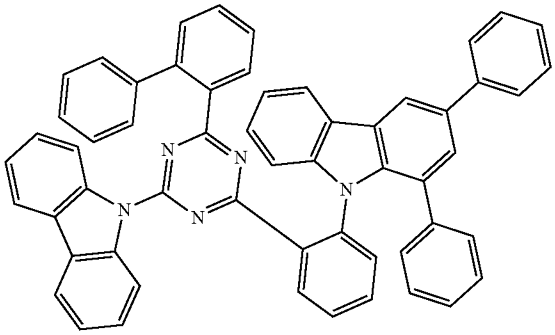
[A-82]
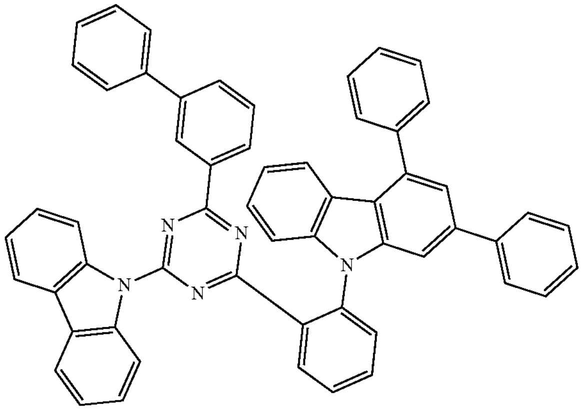
[A-83]
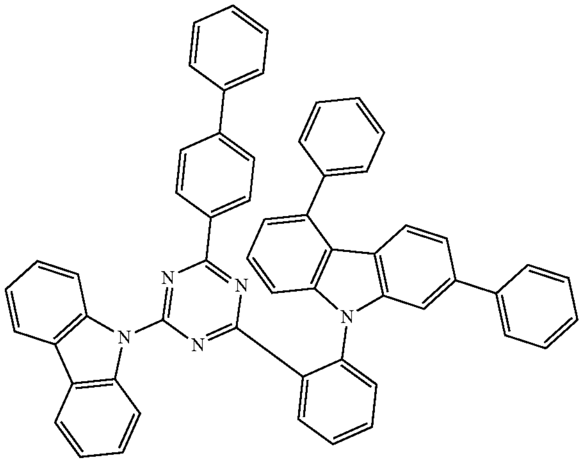
[A-84]
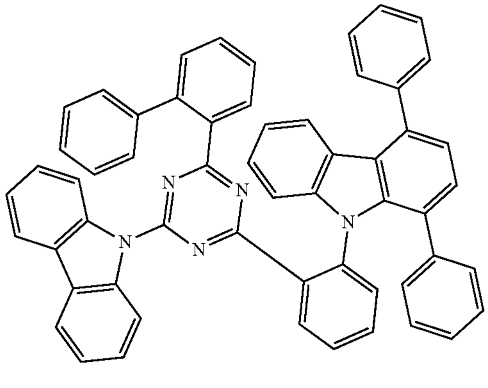
-continued
[A-85]
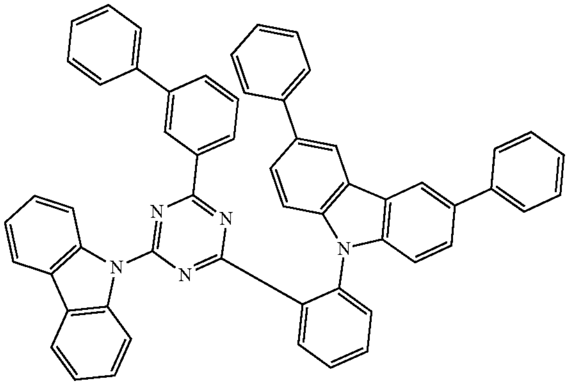
[A-86]
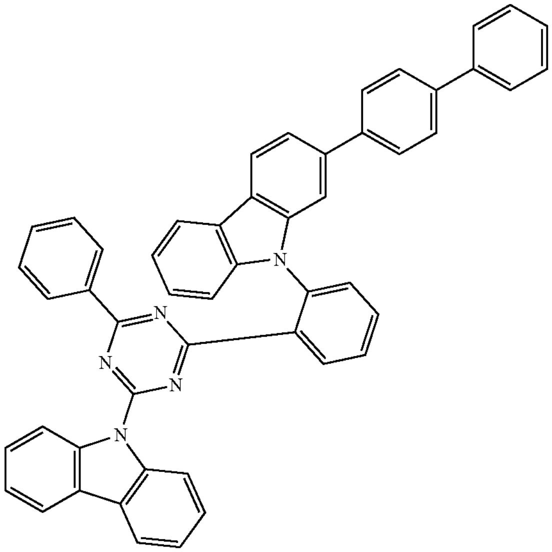
[A-87]
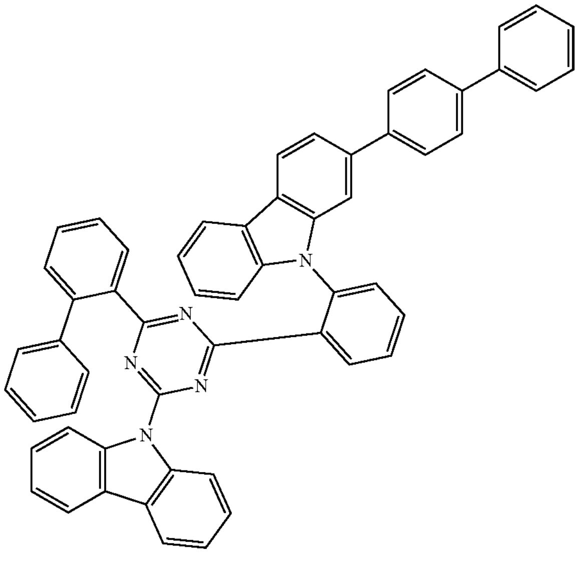

-continued
[A-88]
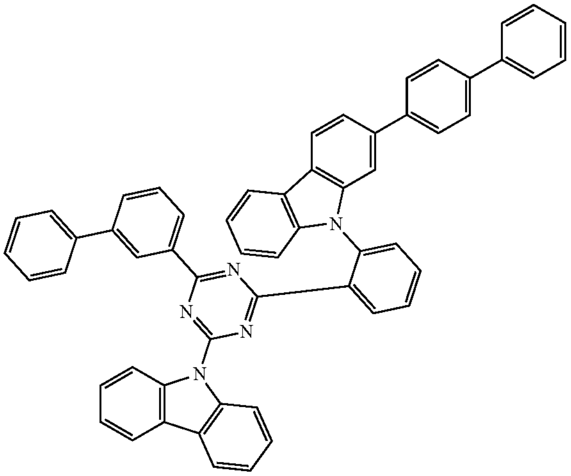
[A-89]
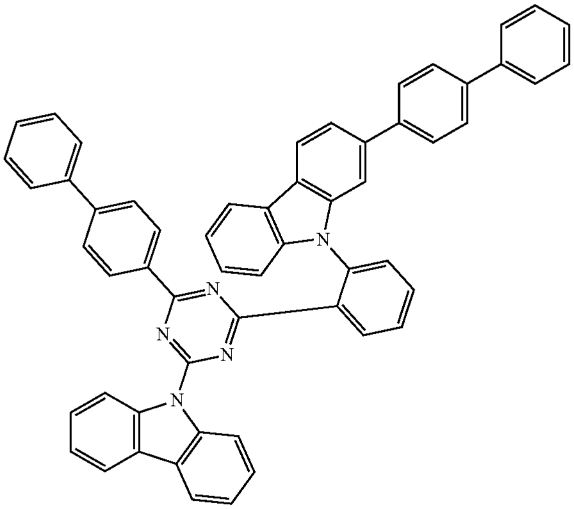
[A-90]
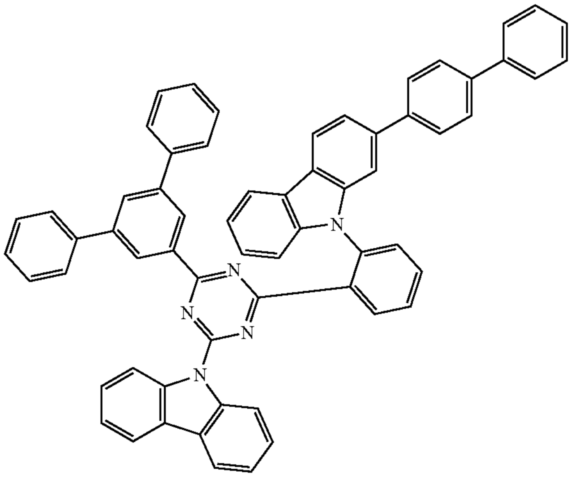
-continued
[A-91]
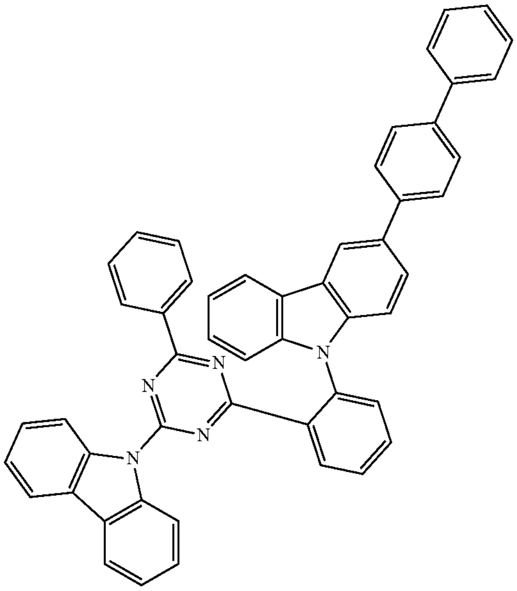
[A-92]
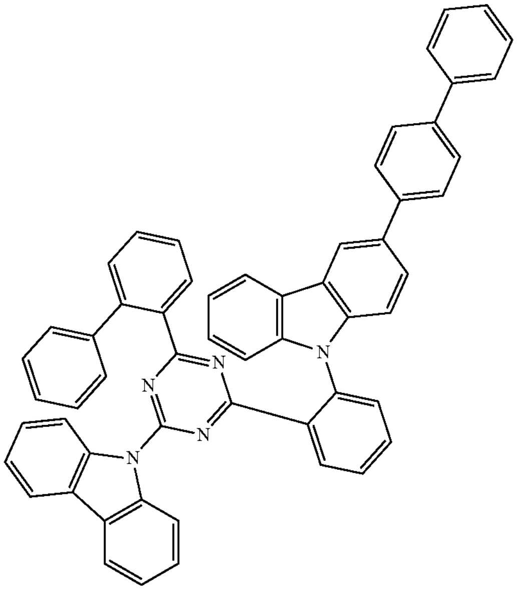

-continued
[A-93]
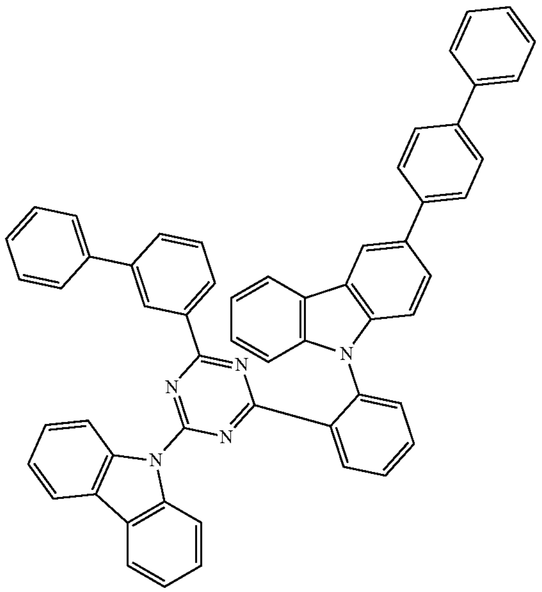
[A-94]
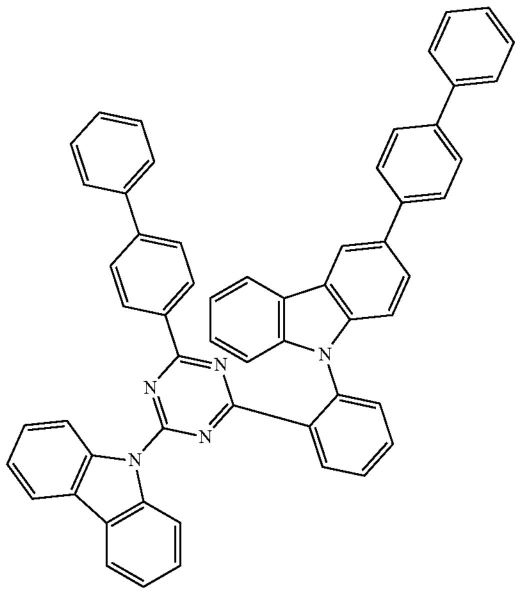
-continued
[A-95]
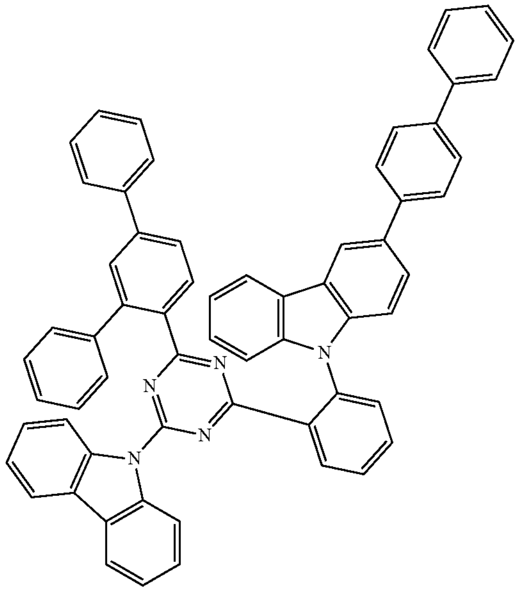
[A-96]
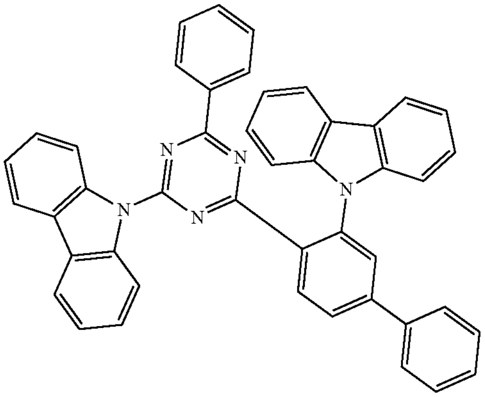
[A-97]
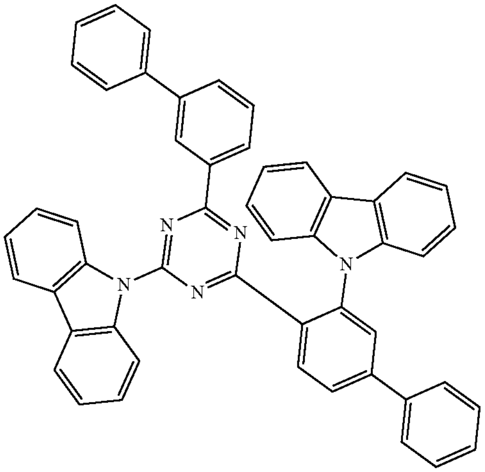

-continued
[A-98]
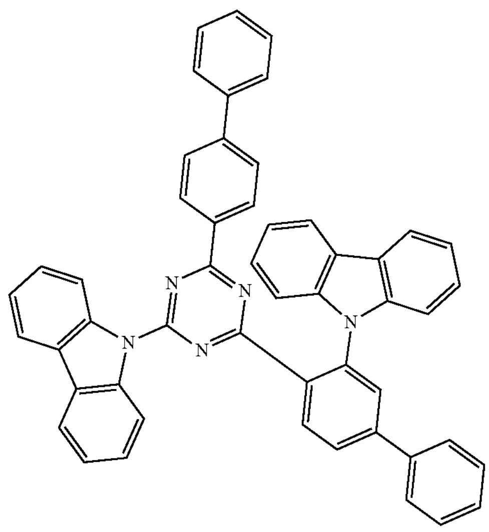
[A-99]
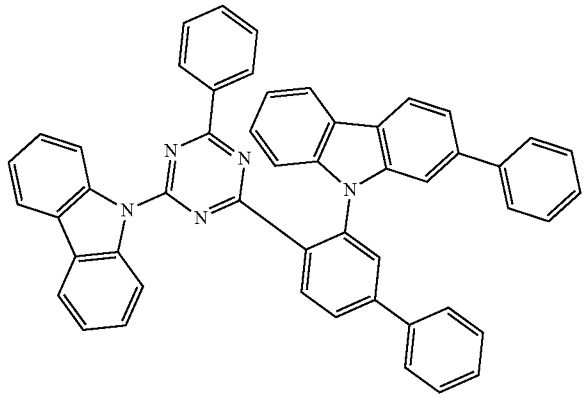
[A-100]
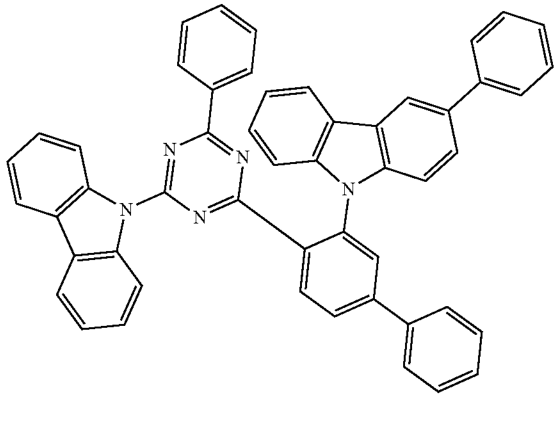
-continued
[A-101]
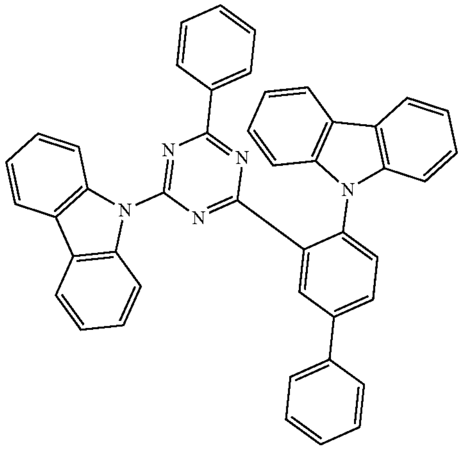
[A-102]
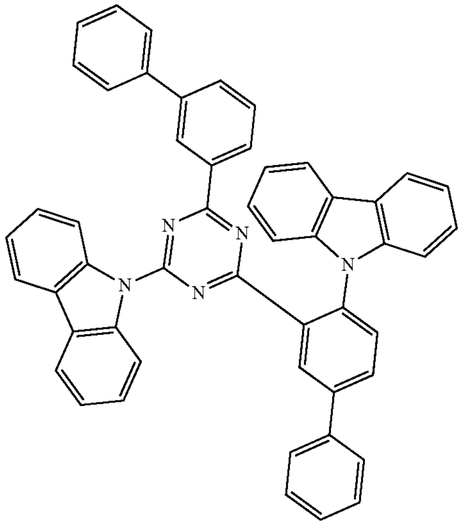
[A-103]
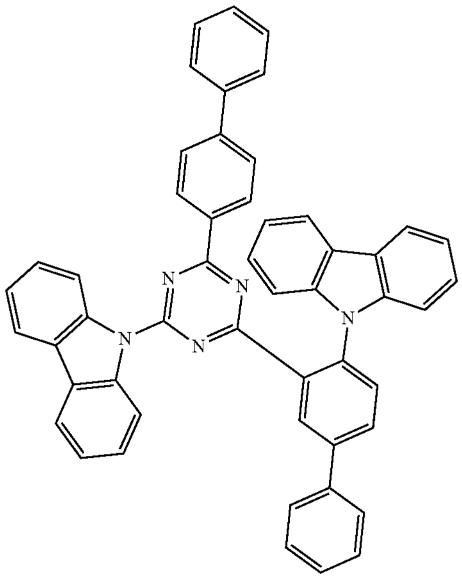

-continued
[A-104]
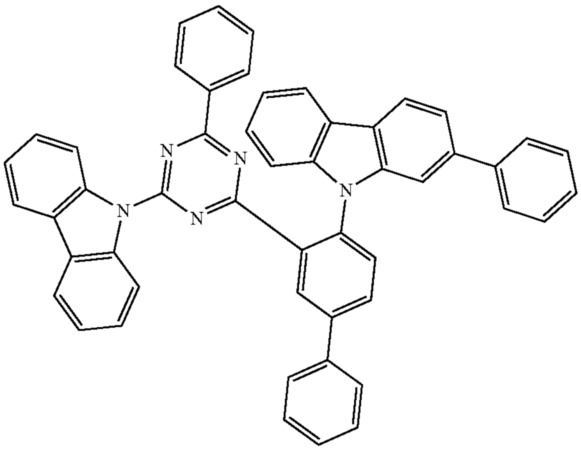
[A-105]
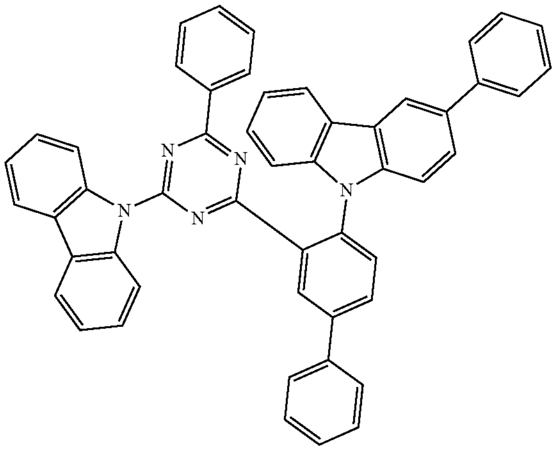
[A-106]
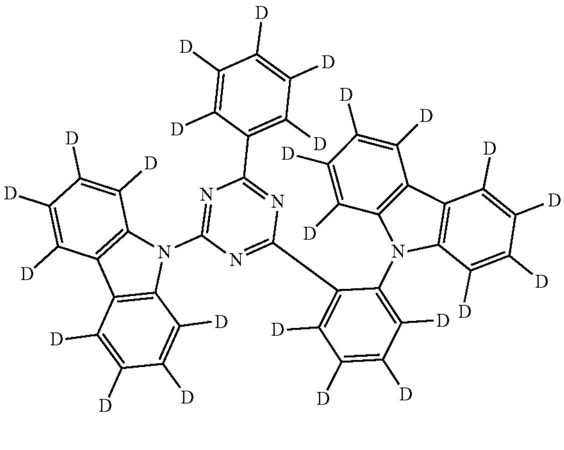
-continued
[A-107]
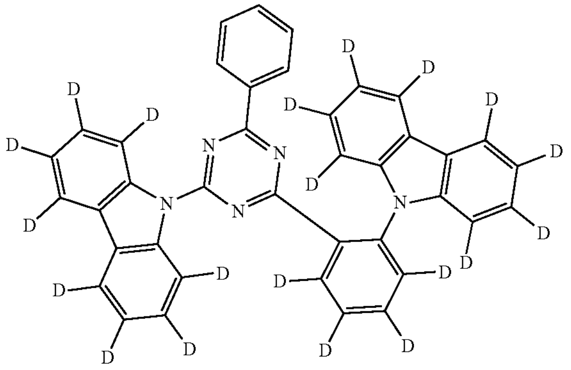
[A-108]
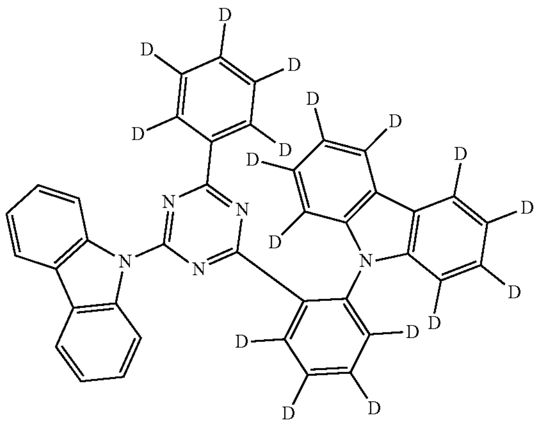
[A-109]
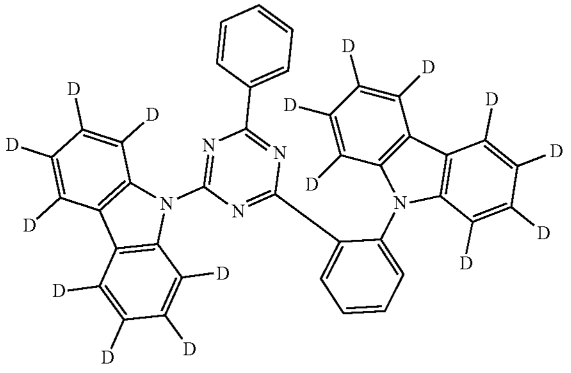

-continued
[A-110]
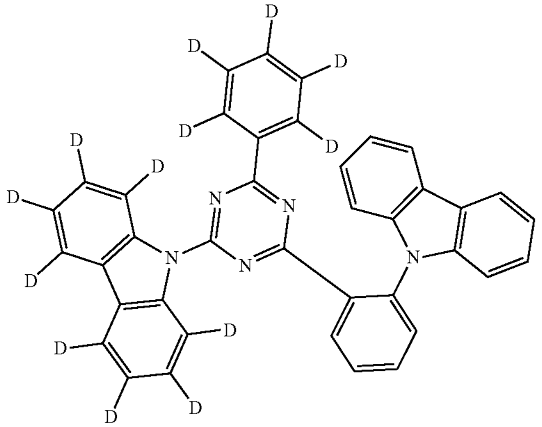
[A-111]
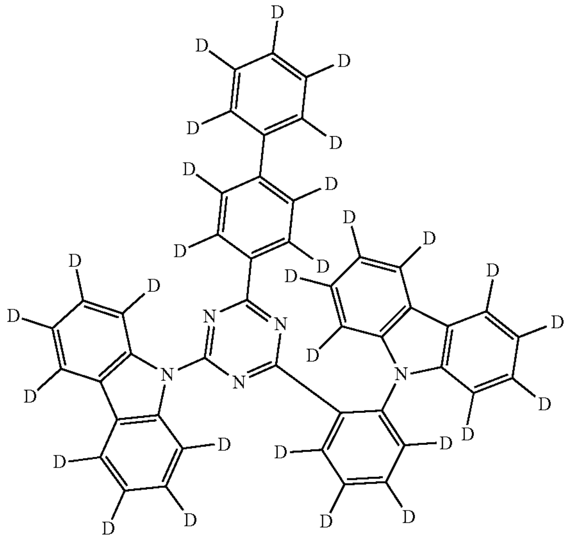
[A-112]
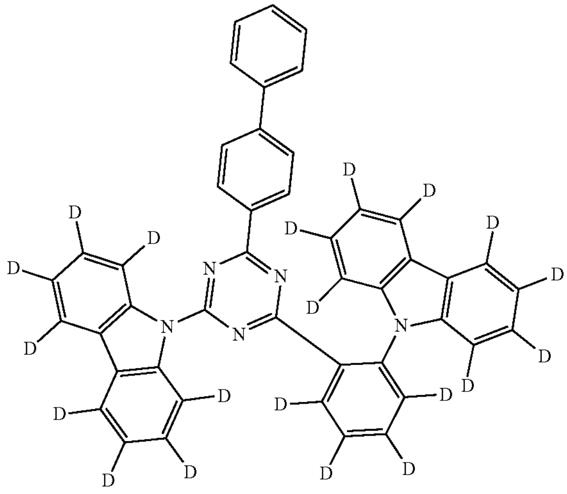
-continued
[A-113]
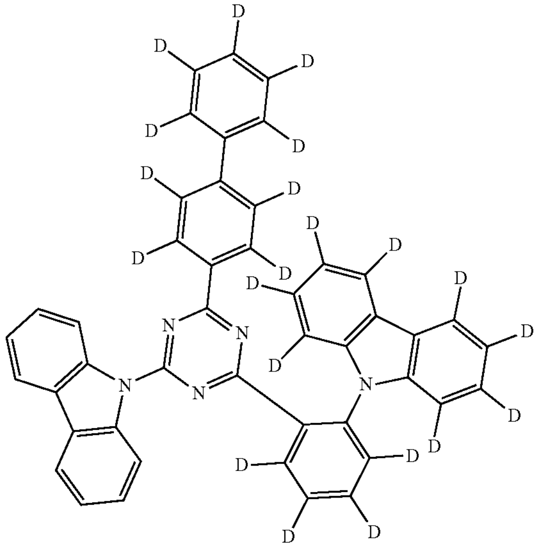
[A-114]
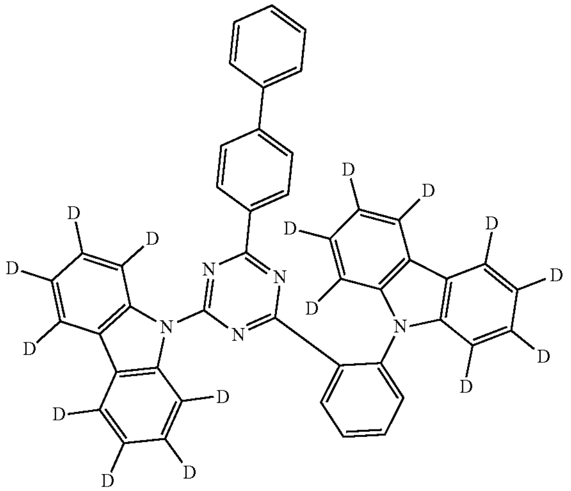
[A-115]
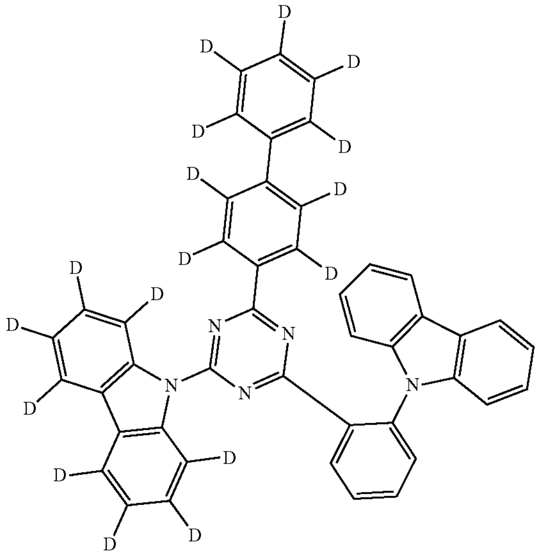

-continued
[A-116]
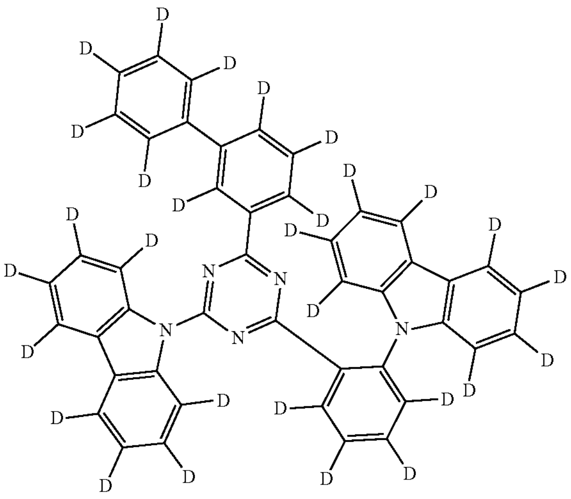
[A-117]
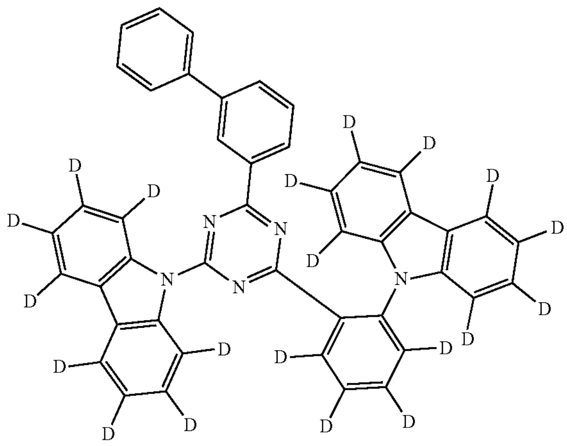
[A-118]
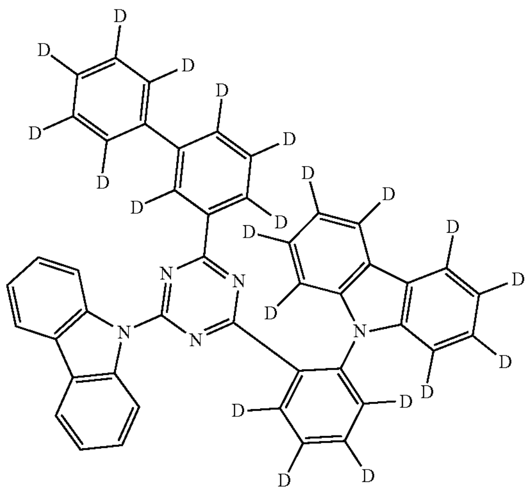
-continued
[A-119]
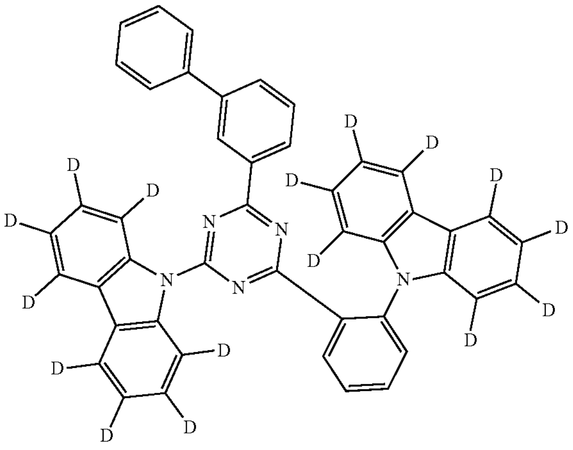
[A-120]
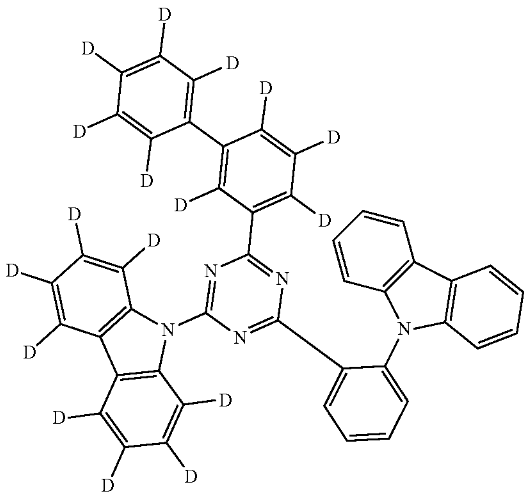
[A-121]
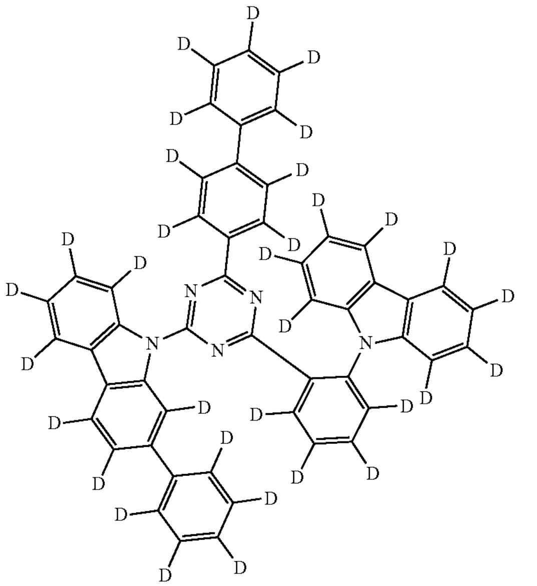

-continued
[A-122]
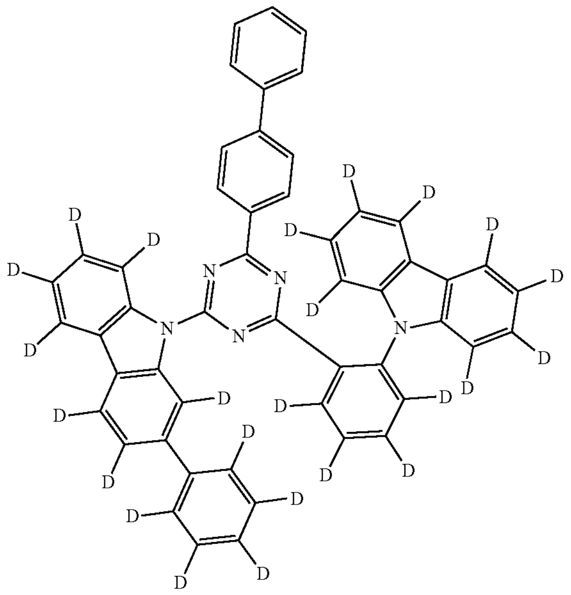
-continued
[A-124]
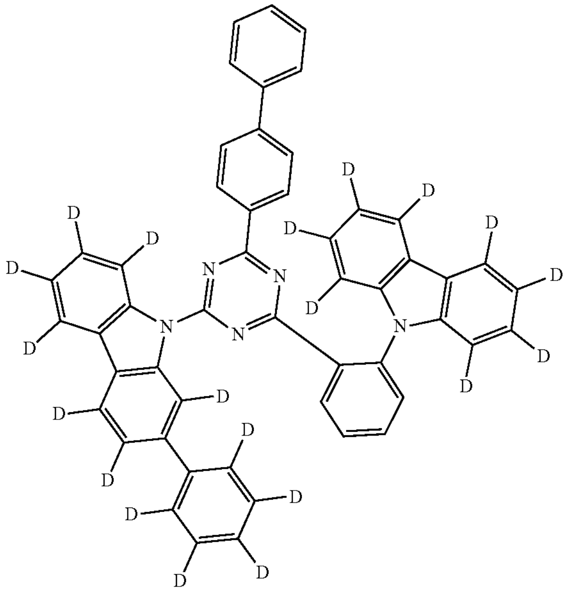
[A-123]
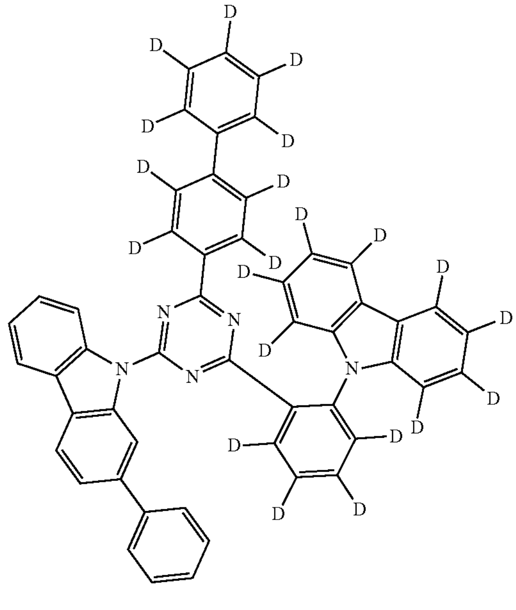
[A-125]
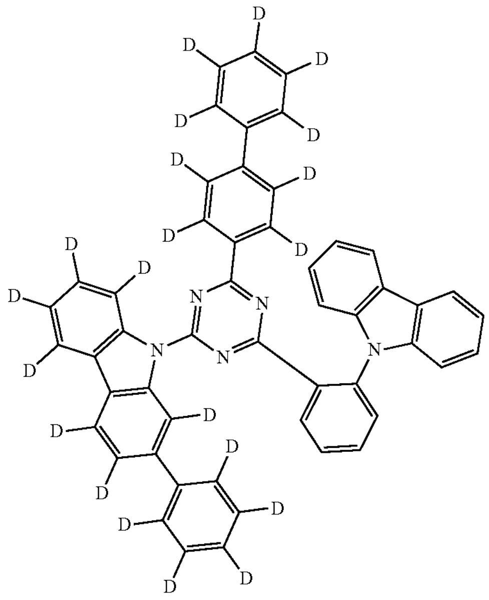

-continued
[A-131]
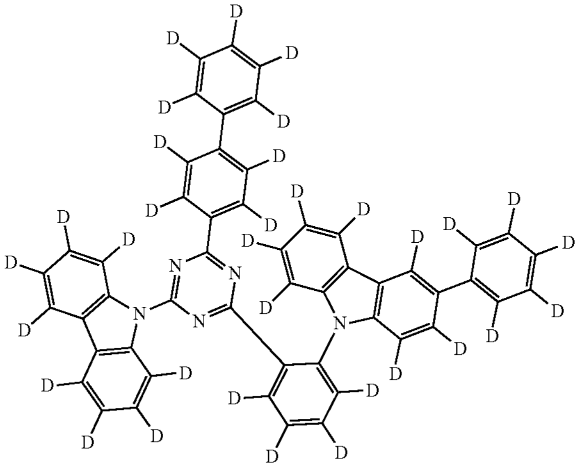
[A-132]
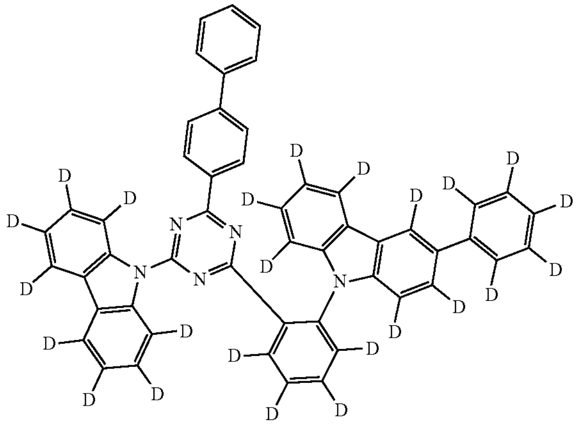
[A-133]
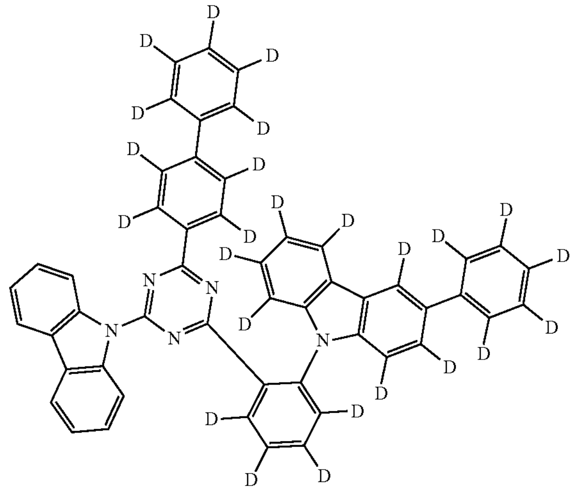
[A-134]
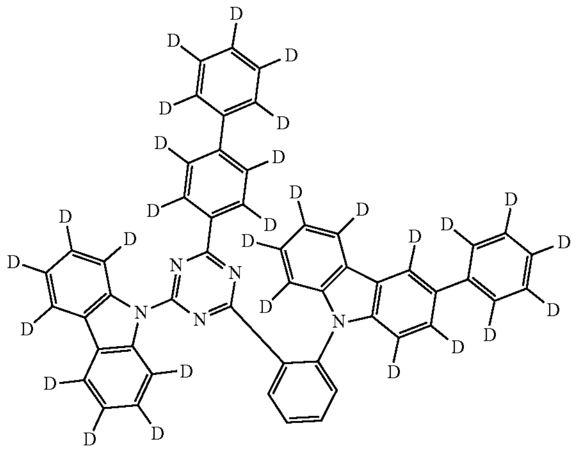
[A-135]
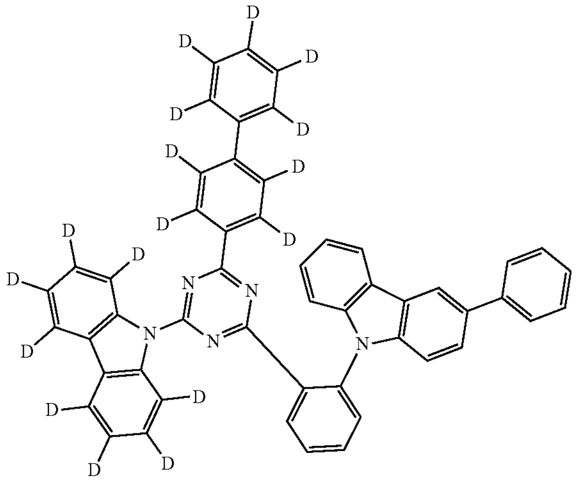
[A-136]
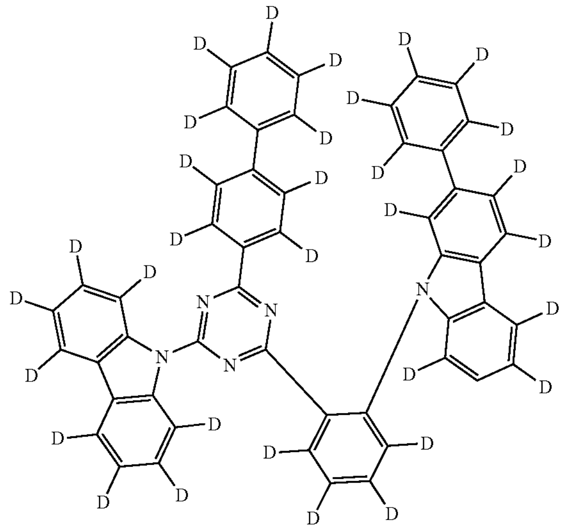

-continued
[A-137]
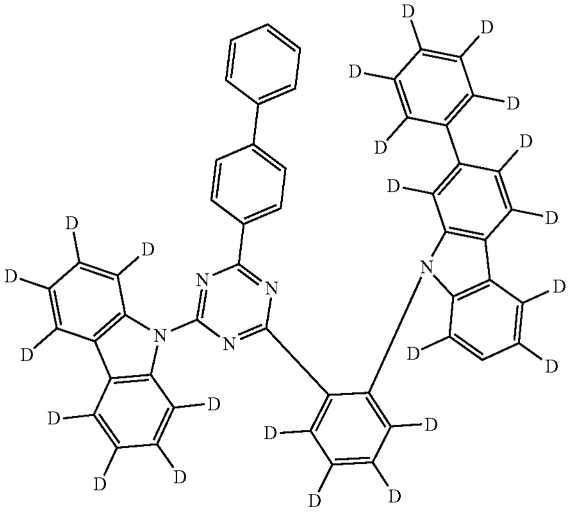
[A-138]
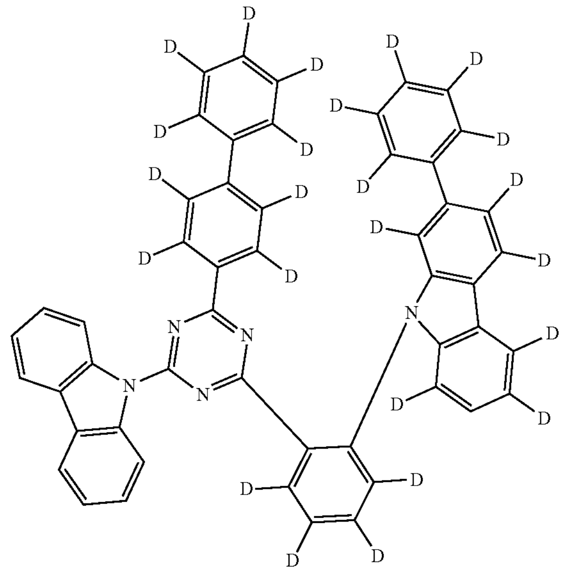
[A-139]
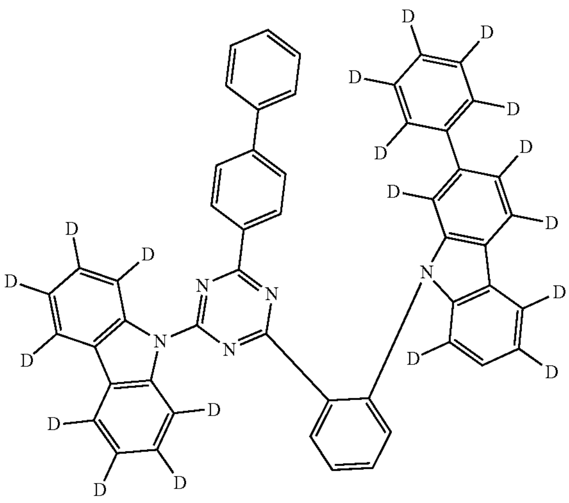
-continued
[A-140]
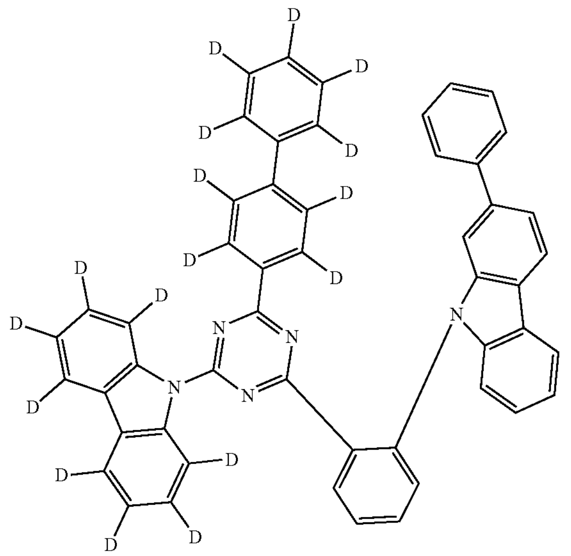
[A-141]
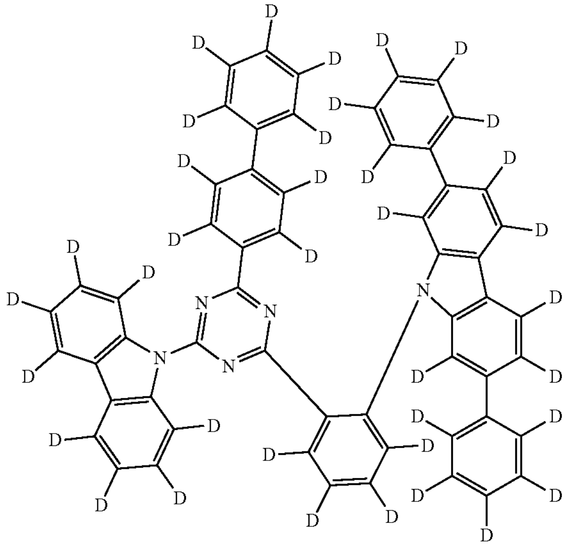

-continued
[A-142]
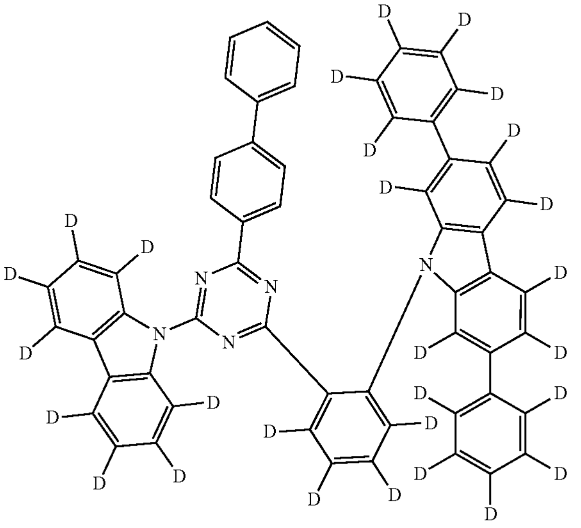
[A-143]
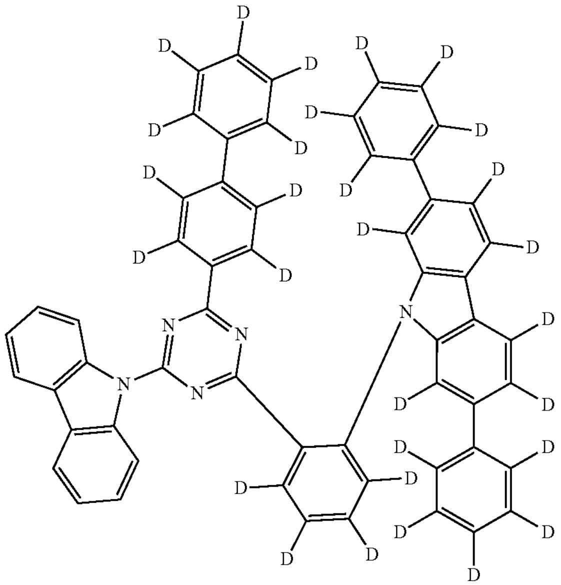
-continued
[A-144]
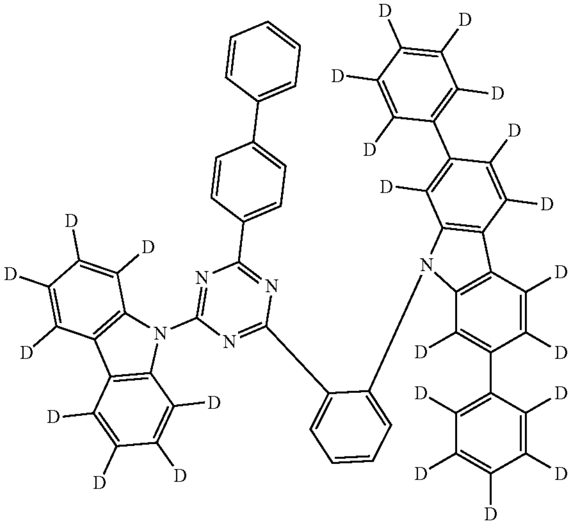
[A-145]
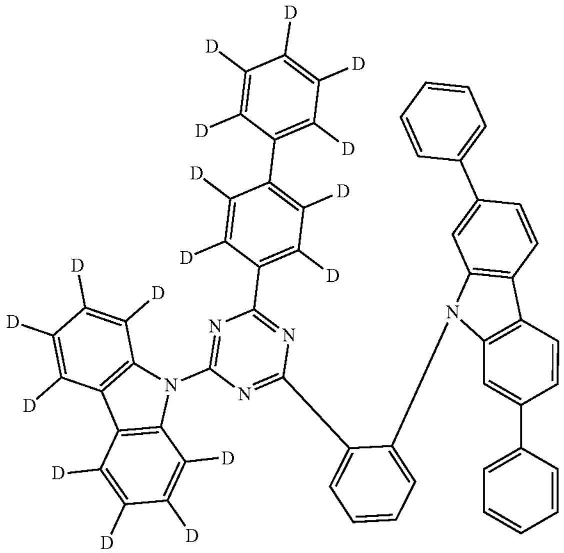

-continued
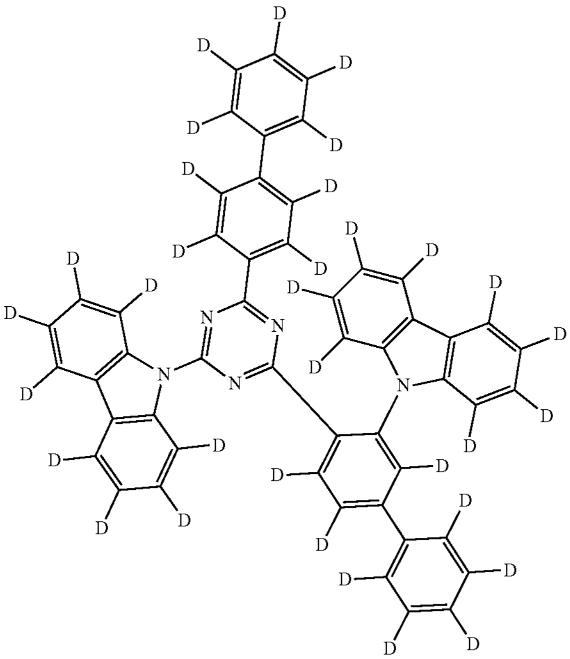
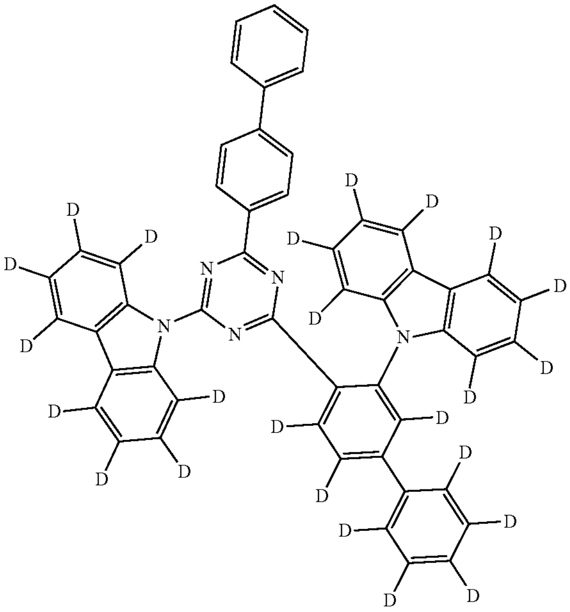
-continued
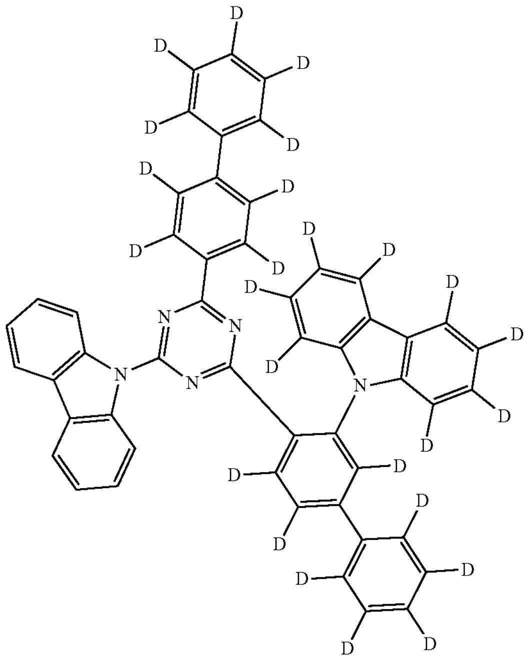
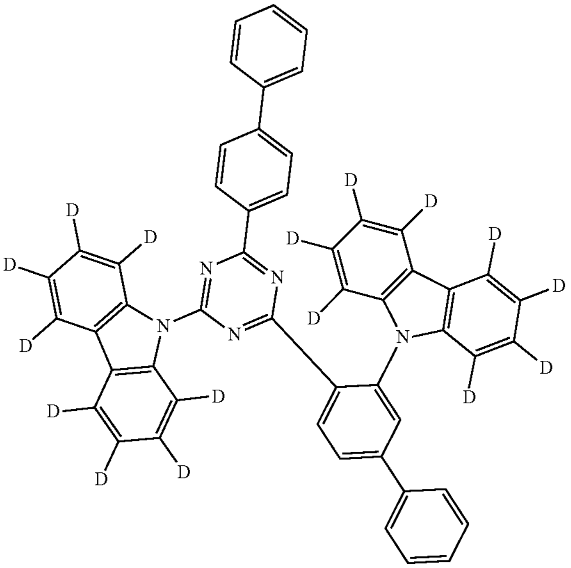

-continued

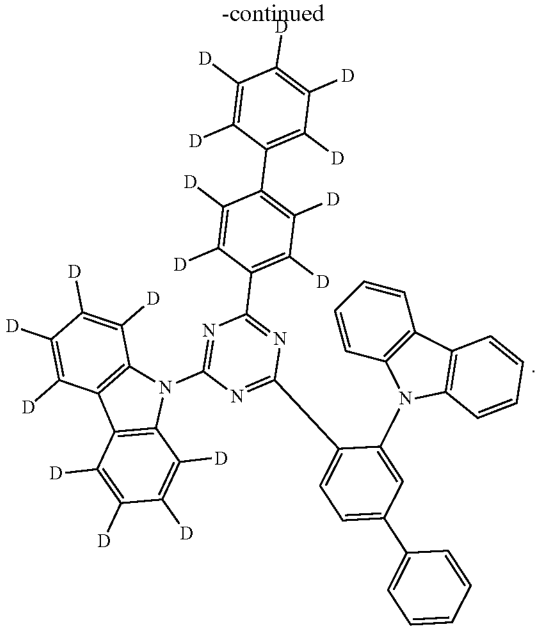

3. A composition for an organic optoelectronic device, the composition comprising:

a first compound; and a second compound, wherein:

the first compound is the compound as claimed in claim 1, and the second compound is represented by:

Chemical Formula 2; or a combination of Chemical Formula 3 and Chemical Formula 4,

[Chemical Formula 2]

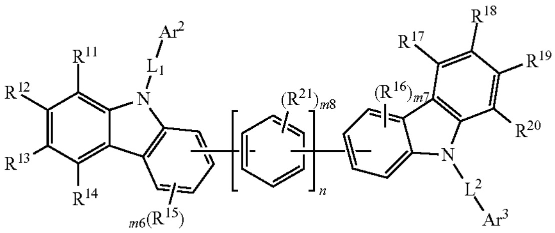

in Chemical Formula 2, $Ar^2$ and $Ar^3$ are each independently a substituted or unsubstituted C6 to C20 aryl group or a substituted or unsubstituted C2 to C30 heterocyclic group, $L^1$ and $L^2$ are each independently a single bond or a substituted or unsubstituted C6 to C20 arylene group, $R^{11}$ to $R^{21}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, m6 and m7 are each independently an integer of 1 to 3, m8 is an integer of 1 to 4, and n is an integer of 0 to 2;

[Chemical Formula 3]

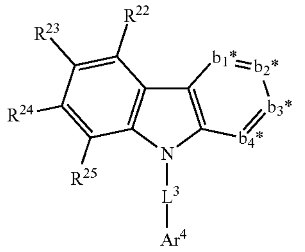

[Chemical Formula 4]

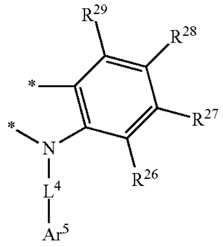

wherein, in Chemical Formulas 3 and 4, $Ar^4$ and $Ar^5$ are each independently a substituted or unsubstituted C6 to C20 aryl group or a substituted or unsubstituted C2 to C30 heterocyclic group, two adjacent ones of $b_1$* to $b_4$* of Chemical Formula 3 are linking carbons linked at * of Chemical Formula 4, the remaining two of $b_1$* to $b_4$* of Chemical Formula 3, not linked at * of Chemical Formula 4, are each independently C-$L^a$-$R^a$, $L^a$, $L^3$, and $L^4$ are each independently a single bond or a substituted or unsubstituted C6 to C20 arylene group, and $R^a$ and $R^{22}$ to $R^{29}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

4. The composition as claimed in claim 3, wherein:

the second compound is represented by Chemical Formula 2,

Chemical Formula 2 is represented by Chemical Formula 2-8,

[Chemical Formula 2-8]

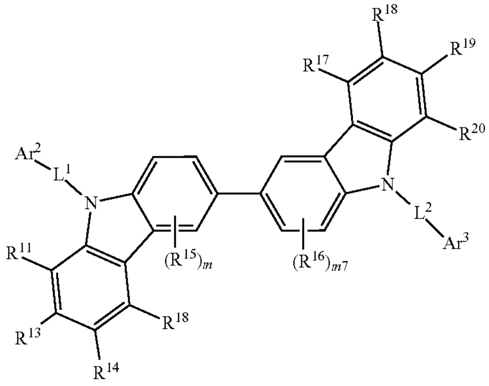

in Chemical Formula 2-8,
$R^{11}$ to $R^{20}$ are each independently hydrogen, deuterium, or a substituted or unsubstituted C6 to C12 aryl group,
m6 and m7 are each independently an integer of 1 to 3, and
moieties $*-L^1-Ar^2$ and $*-L^2-Ar^3$ are each independently a moiety of Group II,
[Group II]
C-1
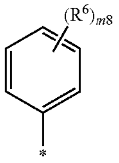
C-2
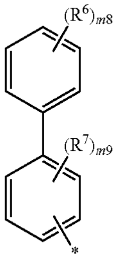
C-3
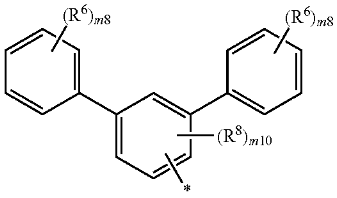
C-4
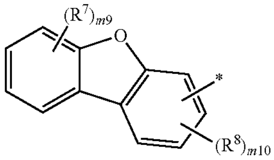
C-5
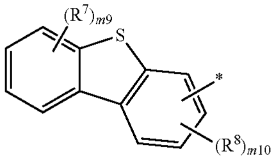
C-6
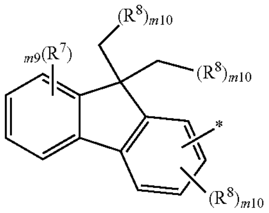
-continued
C-7
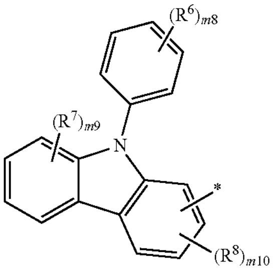
C-8
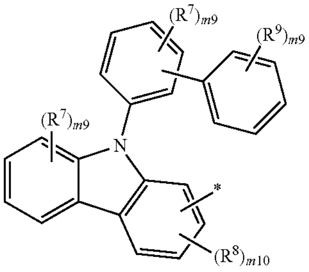
C-9
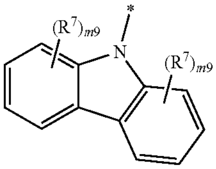
C-10
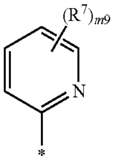
C-11
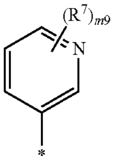
C-12
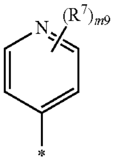
C-13
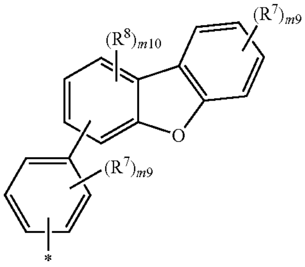

-continued
C-14
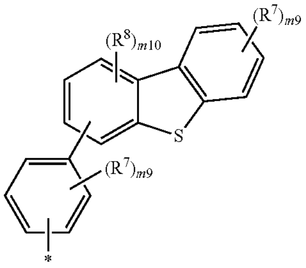
C-15
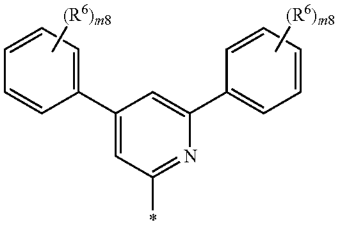
C-16
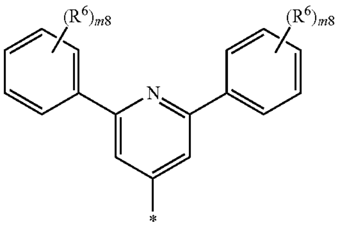
C-17
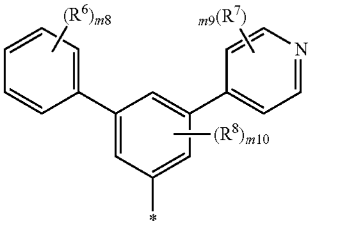
C-18
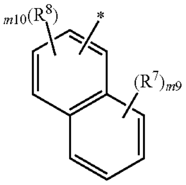
C-19
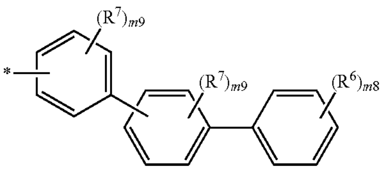
C-20
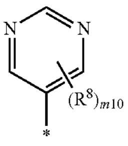
-continued
C-21
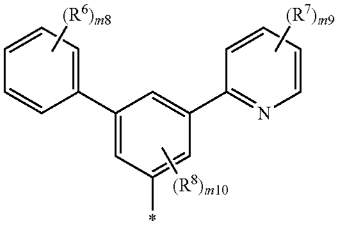
C-22
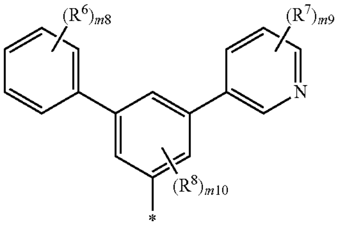
C-23
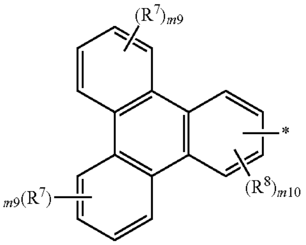
C-24
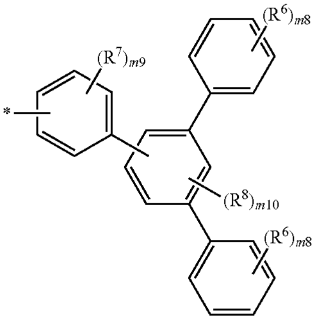
C-25
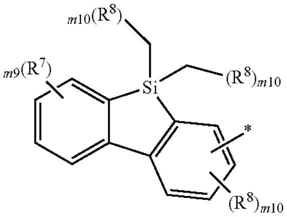
C-26
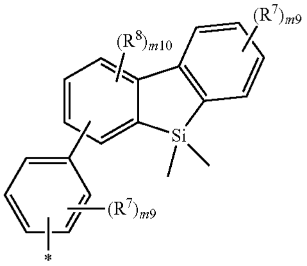
in Group II,
$R^6$ to $R^8$ are each independently hydrogen, deuterium, a substituted or unsubstituted C1 to C4 alkyl group, a substituted or unsubstituted C6 to C18 aryl group, or a substituted or unsubstituted C2 to C30 heteroaryl group, m8 is an integer of 1 to 5, m9 is an integer of 1 to 4, m10 is an integer of 1 to 3, and

* is a linking point.

5. The composition as claimed in claim 3, wherein:

the second compound is represented by the combination of Chemical Formula 3 and Chemical Formula 4, the combination of Chemical Formula 3 and Chemical Formula 4 is represented by Chemical Formula 3C,

[Chemical Formula 3C]

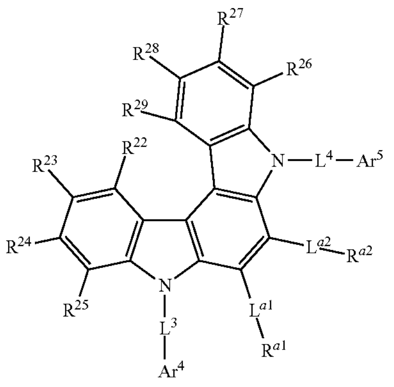

in Chemical Formula 3C, $L^{a1}$ and $L^{a2}$ are each a single bond, $L^3$ and $L^4$ are each independently a single bond or a substituted or unsubstituted C6 to C12 arylene group, $R^{22}$ to $R^{29}$, $R^{a1}$, and $R^{a2}$ are each independently hydrogen, deuterium, or a substituted or unsubstituted C6 to C12 aryl group, and $Ar^4$ and $Ar^5$ are each independently a substituted or unsubstituted phenyl group, a substituted or unsubstituted naphthyl group, or a substituted or unsubstituted biphenyl group.

6. An organic optoelectronic device, comprising:

an anode and a cathode facing each other, and at least one organic layer between the anode and the cathode, wherein the at least one organic layer includes the compound as claimed in claim 1.

7. The organic optoelectronic device as claimed in claim 6, wherein:

the at least one organic layer includes a light emitting layer, and the light emitting layer includes the compound.

8. A display device comprising the organic optoelectronic device as claimed in claim 6.

9. An organic optoelectronic device, comprising:

an anode and a cathode facing each other, and at least one organic layer between the anode and the cathode, wherein the at least one organic layer includes the composition as claimed in claim 3.

10. The organic optoelectronic device as claimed in claim 9, wherein:

the at least one organic layer includes a light emitting layer, and the light emitting layer includes the composition.

11. A display device comprising the organic optoelectronic device as claimed in claim 9.

* * * * *